(12) United States Patent
Reinhard et al.

(10) Patent No.: US 7,867,731 B2
(45) Date of Patent: Jan. 11, 2011

(54) HX2004-6 POLYPEPTIDE EXPRESSED IN CANCEROUS CELLS

(75) Inventors: Christoph Reinhard, Emeryville, CA (US); Anne Bennett Jefferson, Emeryville, CA (US); Vivien W. Chan, Emeryville, CA (US); Joerg Kaufmann, Emeryville, CA (US); Hong Xin, Emeryville, CA (US); Giulia C. Kennedy, Emeryville, CA (US); Greg Harrowe, Emeryville, CA (US); Hamiduddin Khoja, Emeryville, CA (US); Venkatakrishna Shyamala, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1290 days.

(21) Appl. No.: 10/977,087

(22) Filed: Oct. 28, 2004

(65) Prior Publication Data

US 2005/0130926 A1    Jun. 16, 2005

Related U.S. Application Data

(63) Continuation-in-part of application No. 10/081,119, filed on Feb. 21, 2002, now abandoned, said application No. 10/977,087 is a continuation-in-part of application No. 10/763,692, filed on Jan. 22, 2004, now abandoned, which is a continuation of application No. 09/626,301, filed on Jul. 25, 2000, now Pat. No. 6,743,602, said application No. 10/977,087 is a continuation-in-part of application No. 10/698,959, filed on Oct. 30, 2003, now abandoned, which is a continuation of application No. 09/433,360, filed on Nov. 3, 1999, now abandoned.

(60) Provisional application No. 60/271,254, filed on Feb. 21, 2001, provisional application No. 60/145,612, filed on Jul. 26, 1999, provisional application No. 60/148,936, filed on Aug. 13, 1999, provisional application No. 60/107,112, filed on Nov. 4, 1998, provisional application No. 60/114,856, filed on Jan. 6, 1999.

(51) Int. Cl.
*C12P 21/00* (2006.01)
*C12P 21/02* (2006.01)
*C12N 15/09* (2006.01)
*C07K 14/00* (2006.01)
*C07K 14/435* (2006.01)

(52) U.S. Cl. .................. 435/69.1; 435/70.1; 435/70.3; 435/71.1; 530/350

(58) Field of Classification Search ........................ None
See application file for complete search history.

(56) References Cited

U.S. PATENT DOCUMENTS

| 4,889,806 | A | | 12/1989 | Olson et al. |
| 5,721,113 | A | | 2/1998 | Libermann et al. |
| 5,885,577 | A | * | 3/1999 | Alvarez .................. 506/18 |
| 5,932,445 | A | | 8/1999 | Lal et al. |
| 6,566,063 | B1 | | 5/2003 | Kaufmann et al. |
| 6,743,602 | B1 | | 6/2004 | Kennedy et al. |
| 7,501,242 | B2 | | 3/2009 | Reinhard et al. |
| 7,501,243 | B2 | | 3/2009 | Reinhard et al. |
| 7,501,244 | B2 | | 3/2009 | Reinhard et al. |
| 2001/0051344 | A1 | | 12/2001 | Shalon et al. |
| 2003/0045491 | A1 | | 3/2003 | Reinhard et al. |
| 2004/0265928 | A1 | | 12/2004 | Kennedy |
| 2005/0059801 | A1 | | 3/2005 | Kohja et al. |

FOREIGN PATENT DOCUMENTS

| EP | 0839908 A2 | 5/1998 |
| EP | 0 899 332 | 3/1999 |
| WO | WO-98/23782 A2 | 6/1998 |
| WO | WO 99/24463 | 5/1999 |
| WO | WO 99/57144 | 11/1999 |
| WO | WO-00/06589 A1 | 2/2000 |
| WO | WO 00/56756 | 9/2000 |
| WO | WO 00/58473 | 10/2000 |
| WO | WO-01/30964 A2 | 5/2001 |
| WO | WO-01/42472 A2 | 6/2001 |

OTHER PUBLICATIONS

Te Velthuis et al. Insights into the molecular evolution of the PDZ/LIM family and identification of a novel conserved protein motif. PLoS ONE, vol. 2, No. 2, p. e189, Feb. 2007.*

Putalina et al. GenBank Accession No. AAB86592, GI: 2624922, Nov. 19, 1997.*

Mu et al. GenBank Accession No. AAD33924, GI: 4929268, May 20, 1999.*

Bomford. The adjuvant activity of fatty acid esters. The role of acyl chain length and degree of saturation. Immunology, vol. 44, pp. 187-192, 1981.*

(Continued)

*Primary Examiner*—Jennifer Dunston
(74) *Attorney, Agent, or Firm*—Mark Seka; Patricia Tsao

(57) ABSTRACT

The present invention provides polynucleotides, as well as polypeptides encoded thereby, that are differentially expressed in cancer cells. These polynucleotides are useful in a variety of diagnostic and therapeutic methods. The present invention further provides methods of reducing growth of cancer cells. These methods are useful for treating cancer.

13 Claims, 41 Drawing Sheets

OTHER PUBLICATIONS

Alignment of SEQ ID No. 14 of EP Application No. 02709637.9 filed Feb. 21, 2002 to GenBank Accession No. NM_003318, 2 pages, generated Aug. 12, 2008.

Barsky, S. H. et al. (1997). "Evidence of a Dominant Transcriptional Pathway Which Regulates an Undifferentiated and Complete Metastatic Phenotype," *Oncogene* 15: 2077-2091.

Bochert, M. A. et al. (1998). "Molecular Cloning and Expression of Ehf, a New Member of the ets Transcription Factor/Oncoprotein Gene Family," *Biochemical and Biophysical Research Communications* 246:176-181.

Chabert, M. G. et al. (1993). "Cell Culture of Tumors Alters Endogenous Poly(ADPR)Polymerase Expression and Activity," *International Journal of Cancer* 53:837-842.

Chang, C.-H. et al. (1997). "ESX: A Structurally Unique ETS Overexpressed Early During Human Breast Tumorigenesis," *Oncogene* 14:1617-1622.

Cheung, V. G. et al. (Mar. 2003). "Natural Variation in Human Gene Expression Assessed in Lymphoblastoid Cells," *Nature Genetics* 33:422-425.

Choi, S.-G. et al. (Jan. 2, 1998). "A Novel ets-Related Transcription Factor, ERT/ESX/ESE-1, Regulates Expression of the Transforming Growth Factor-β Type II Receptor," *The Journal of Biological Chemistry* 273(1):110-117.

Dermer, G. B. (Mar. 12, 1994). "Another Anniversary for the War on Cancer," *Biotechnology* 12:320.

EMBL-EBI Accession No. AL157372, last updated Nov. 29, 2000, located at <http://www.ebi.ac.uk/cgi-bin/emblfetch?style=html&id=AL157372> visited on Feb. 26, 2009. (38 pages).

EMBL-EBI Accession No. O95238, last updated Feb. 10, 2009, located at <http://www.uniprot.org/uniprot/O95238.txt> visited on Feb. 26, 2009. (4 pages).

GenBank Accession No. A42861, version A42861, last updated Mar. 15, 2004, located at <http://www.ncbi.nlm.nih.gov/protein/346403?report=gpwithparts&log$=seqview> visited Feb. 25, 2009. (2 pages).

GenBank Accession No. A42861, version A42861.1, last updated Mar. 6, 1997, located at <http://www.ncbi.nlm.nih.gov/entrez/viewer.fcgi?db=nuccore&id=2298310> visited Feb. 25, 2009, (1 page).

GenBank Accession No. AA662164, last updated Dec. 3, 1997, located at <http://www.ncbi.nlm.nih.gov/entrez/viewer.fcgi?db=nucest&qty=1&c_start=1&list_uids=2616255&uids=&dopt=gb&dispmax=5&sendto=> visited on Feb. 25, 2009. (2 pages).

GenBank Accession No. AB031549, last updated Jan. 20, 2000, located at <http://www.ncbi.nlm.nih.gov/entrez/viewer.fcgi?6721497:OLD03:63320> visited on Mar. 5, 2009. (2 pages).

GenBank Accession No. AF016294, last updated Jan. 16, 1998, located at <http://www.ncbi.nlm.nih.gov/entrez/viewer.fcgi?db=nuccore&id=2384737> visited on Feb. 25, 2009. (2 pages).

GenBank Accession No. AF016295, last updated Jan. 16, 1998, located at <http://www.ncbi.nlm.nih.gov/entrez/viewer.fcgi?db=nuccore&id=2384739> visited on Feb. 25, 2009. (2 pages).

GenBank Accession No. AF017307, last updated Aug. 21, 1997, located at <http://www.ncbi.nlm.nih.gov/entrez/viewer.fcgi?2338755:OLD02:1112143> visited on Mar. 5, 2009. (2 pages).

GenBank Accession No. AF071538, last updated Dec. 12, 1998, located at <http://www.ncbi.nlm.nih.gov/entrez/viewer.fcgi?4007417:OLD02:495666>. (2 pages).

GenBank Accession No. AF071538, last updated Jan. 10, 2000, located at <http://www.ncbi.nlm.nih.gov/entrez/viewer.fcgi?db=nuccore&id=4007417> visited on Feb. 25, 2009. (2 pages).

GenBank Accession No. AF110184, last updated Jul. 22, 1999, located at <http://www.ncbi.nlm.nih.gov/entrez/viewer.fcgi?db=nuccore&id=5565858> visited on Feb. 25, 2009. (6 pages).

GenBank Accession No. NM_003318, version NM_003318. 3, last updated Feb. 11, 2008, located at <http://www.ncbi.nlm.nih.gov/entrz/viewer.fcgi?34303964:NCBI:20529406>, visited on Mar. 5, 2009. (6 pages).

GenBank Accession No. NM_003318, version NM_003318.1, last updated Mar. 19, 1999, located at <http://www.ncbi.nlm.nih.gov/entrez/viewer.fcgi?db=nuccore&id=4507718> visited on Mar. 5, 2009. (3 pages).

GenBank Accession No. NM_004433, last updated May 7, 1999, located at <http://www.ncbi.nlm.nih.gov/entrez/viewer.fcgi?4758263:OLD02:499282> visited on Mar. 5, 2009. (2 pages).

GenBank Accession No. NM_007921, last updated Jan. 4, 2000, located at <http://www.ncbi.nlm.nih.gov/entrez/viewer.fcgi?6679628:OLD02:1123618> visited on Mar. 5, 2009. (2 pages).

GenBank Accession No. NM_012391, last updated Nov. 2, 2000, located at <http://www.ncbi.nlm.nih.gov/entrez/viewer.fcgi?6912579:OLD03:2758138> visited on Mar. 5, 2009. (3 pages).

GenBank Accession No. P33981, version P33981, last updated May 30, 2000, located at <http://www.ncbi.nlm.nih.gov/entrez/viewer.fcgi?464971:OLD02:1460775> visited on Mar. 5, 2009. (3 pages).

GenBank Accession No. U66894, last updated May 21, 1997, located at <http://www.ncbi.nlm.nih.gov/entrez/viewer.fcgi?db=nuccore&id=1754537> visited on Feb. 25, 2009. (2 pages).

GenBank Accession No. U73843, last updated Aug. 6, 1997, located at <http://www.ncbi.nlm.nih.gov/entrez/viewer.fcgi?db=nuccore&id=1841522> visited on Feb. 25, 2009. (2 pages).

GenBank Accession No. U73844, last updated Aug. 6, 1997, located at <http://www.ncbi.nlm.nih.gov/entrez/viewer.fcgi?db=nuccore&id=1841524> visited on Feb. 25, 2009. (2 pages).

GenBank Accession No. U90654, last updated Nov. 20, 1997, located at <http://www.ncbi.nlm.nih.gov/entrez/viewer.fcgi?db=nuccore&id=2624921>, visited Feb. 25, 2009. (2 pages).

GenBank Accession No. U97156, last updated Dec. 5, 1997, located at <http://www.ncbi.nlm.nih.gov/entrez/viewer.fcgi?db=nuccore&id=2459796> visited on Feb. 25, 2009. (2 pages).

Huang, C.-L. et al. (1998). "Mutations in Exon 7 and 8 of p53 as Poor Prognostic Factors in Patients with Non-Small Cell Lung Cancer," *Oncogene* 16:2469-2477.

Hundt, S. et al. (Oct. 2007). "Blood Markers for Early Detection of Colorectal Cancer: A Systematic Review," *Cancer Epidemiology, Biomarkers and Prevention* 16(10):1935-1953.

International Search Report mailed Apr. 14, 2000 for PCT Application No. PCT/US99/25848 filed Nov. 3, 1999, 3 pages.

International Search Report mailed Dec. 1, 2000 for PCT Application No. PCT/US00/20233 filed Jul. 25, 2000, 3 pages.

International Search Report mailed Jun. 25, 2002, for PCT Application No. PCT/US2002/05278 filed Feb. 21, 2002. 2 pages.

International Search Report mailed Oct. 10, 2000 for PCT Application No. PCT/US00/13173 filed May 12, 2000, 3 pages.

Iwase, T. et al. (Jul. 30, 1993). "Identification of Protein-Tyrosine Kinase Genes Preferentially Expressed in Embryo Stomach and Gastric Cancer," *Biomedical and Biophysical Research Communications* 194(2):698-705.

Liotta, L. A. (Feb. 1992). "Cell Invasion and Metastasis," *Scientific American*, pp. 54-59, 62-63.

Liu, A. Y. et al. (1997). "Identification of Differentially Expressed Prostate Genes: Increased Expression of Transcription Factor ETS-2 in Prostate Cancer," *The Prostate* 30:145-153.

Mishra, L. et al. (1999). "Elf3 Encodes a Novel 200-kD β-Spectrin: Role in Liver Development," *Oncogene* 18:353-364.

Neve, R. et al. (Nov. 1998). "The Epithelium-Specific Ets Transcription Factor ESX is Associated with the Mammary Gland Development and Involution," *The FASEB Journal* 12:1541-1550.

Nozawa, M. et al. (Mar. 1, 2000). "Prostate-Specific Transcription Factor hPSE is Translated Only in Normal Prostate Epithelial Cells," *Cancer Research* 60:1348-1352.

Oettgen, P. et al. (1999). "Genomic Organization of the Human ELF3 (ESE-1/ESX) Gene, a Member of the Ets Transcription Factor Family, and Identification of a Functional Promoter," *Genomics* 55:358-362.

Oettgen, P. et al. (Jan. 14, 2000). "PDEF, a Novel Prostate Epithelium-Specific Ets Transcription Factor, Interacts with the Androgen Receptor and Activates Prostate-Specific Antigen Gene Expression," *Journal of Biological Chemistry* 275(2):1216-1225.

Ottegen, P. et al. (1997), "The Novel Epithelial-Specific Ets Transcription Factor Gene ESX Maps to Human Chromosome 1q32.1," *Genomics* 45:456-457.

Sementchenko, V. I. et al. (1998). "ETS2 Function is Required to Maintain the Transformed State of Human Prostate Cancer Cells," *Oncogene* 17:2883-2888.

Sharrocks, A. D. et al. (1997). "The ETS-Domain Transcription Factor Family," *International Journal of Biochemistry and Cell Biology* 29(12):1371-1387.

Supplementary Partial European Search Report mailed May 27, 2005, for European Application No. 02709637.9 filed on Feb. 21, 2002, 4 pages.

Tymms, M. J. et al. (1997). "A Novel Epithelial-Expressed ETS Gene, ELF3: Human and Murine cDNA Sequences, Murine Genomic Organization, Human Mapping to 1q32.2 and Expression in Tissues and Cancer," *Oncogene* 15:2449-2462.

U.S. Appl. No. 09/433,360, filed Nov. 3, 1999, Khoja et al.

U.S. Appl. No. 10/360,848, filed Feb. 6, 2003, Kaufmann et al.

Welch, D. R. et al. (1994). "Microcell-Mediated Transfer of Chromosome 6 Into Metastatic Human C8161 Melanoma Cells Suppresses Metastasis But Does Not Inhibit Tumorigenicity," *Oncogene* 9:255-262.

Yamada, N. et al. (2000). "Cloning and Expression of the Mouse Pse Gene Encoding a Novel ETS Family Member," *Gene* 241:267-274.

Clonetech. (1996-1997). "PromoterFinderTM DNA Walking Kits," p. 56.

Galderisi, U. et al. (1999). "Antisense Oligonucleotides as Therapeutic Agents," *Journal of Cellular Physiology* 181:251-257.

Japanese Office Action mailed Jun. 26, 2009, for JP Application No. 2002-567954 filed Feb. 21, 2002, 3 pages. (English translation attached, 6 pages).

Okabe, M. (Dec. 1999). "Clinical Development of Monoclonal Antibodies Against Metastatic Tumors," *Biotherapy* 13(12):1193-1199. (English abstract on p. 1193).

Takayama, K. et al. (2000). "Gene Therapy for Lung Cancer Treatment," *Nippon Rinsho* 58:1048-1052. (English abstract on p. 1048).

Agrawal et al., Molecular Medicine Today, 2000, vol. 6, pp. 72-81.

Aiuti et al., "The Chemokine SDF-1 is a Chemoattractant for Human CD34+ Hema-topoietic Progenitor Cells and Provides a New Mechanism to Explain the Mobilization of CD34+ Progenitors to Peripheral Blood", *J. Exp. Med.*, (Jan. 1997), vol. 185(1):111-120.

Alberts Mol. Biol. Cell, 3.sup.rd ed, p. 465, 1994.

Allavena et al. (1994), "Induction of Natural Killer Cell Migration by Monocyte Chemotactic Protein-1, -2, and -3," *Eur. J. Immunol.*, vol. 24:3233-3236.

Berger et al. (1999), "Chemokine Receptors as HIV-1 Coreceptors: roles in Viral Entry, Tropism, and Disease", *Annu. Rev. Immunol.*, vol. 17:657-700.

Bleul et al. (Aug. 1996), "The Lymphocyte Chemoattractant SDF-1 is a Ligand for LESTR/Fusin and Blocks HIV-1 Entry," *Nature*, vol. 382:829-833.

Bork et al. "Go Hunting in sequence databases but watch out for the traps", Trends in Genetics 1996, 12:425-427.

Branch TIBS 1998, vol. 23, p. 45-50.

Brenner et al. "Errors in Genome Annotation", Trends in Genetics 1999, 15:132-133.

Cahill, et al. "Characterization of *MAD2B* and other mitotic spindle checkpoint genes", *Genomics* 1999 vol. 58(2): 181-187.

Carr et al. (Apr. 1994), "Monocyte Chemoattractant Protein 1 Acts as a T-Lymphocyte Chemoattractant," *Proc. Natl. Acad. Sci. USA*, vol. 91:3652-3656.

Carter (1990). "Cancer of the pancreas" Gut, vol. 31: 494-496.

Castor et al. (Feb. 1983), "Structural and Biological Characteristics of Connective Tissue Activat-ing Peptide (CTAP-III), a Major Human Platelet-Derived Growth Factor", *Proc. Natl Acad. Sci. USA*, vol. 80:765-769.

Dahinden et al., (Nov. 1989), "The Neutrophil-Activating Peptide NAF/NAP-1 Induces Histamine and Leukotriene Release by Interleukin 3-Primed Basophils," *J. Exp. Med.*, vol. 170:1787-1793.

Del Villano et al. (1983). "Radioimmunometric assay for a monoclonal antibody-defined tumor marker, CA 19-9" Clin. Chem., vol. 29(3):549-552.

Doerks et al., "Protein annotation: detective work for function prediction". Trends in Genetics. Jun. 1998, vol. 14, No. 6, pp. 248-250.

Fabris et al. (1988). "Serum markers and clinical data in diagnosing pancreatic cancer: A contrastive approach", Am. J. Gastroenterology, vol. 83(5): 549-553.

Fisher (1975). "The pathology of invasive breast cancer", Cancer, vol. 36(1): 1-85.

Frebourg et al. (1988). "The evaluation of CA 19-9 antigen level in the early detection of pancreatic cancer", Cancer, vol. 62(11): 2287-2290.

Fu, EMBO J. 15: 4392-4401, 1996.

GenBank, Accession No. AA005111, May 9, 1997.

GenBank Accession No. AB020665, 1999.

GenBank Accession No. AF144237, Jun. 1, 1999.

GenBank Accession No. AI018075, Aug. 27, 1998.

GenBank Accession No. AI079858, Oct. 1, 1998.

GenBank Accession No. AI355866, Feb. 15, 1999.

GenBank Accession No. M86699, Jan. 14, 1995.

GenBank Accession No. N31885, Jan. 10, 1996.

Graham et al. (Mar. 1990), "Identification and Characterization of an Inhibitor of Haemopoietic Stem Cell Proliferation," *Nature*, vol. 344:442-444.

Hanahan et al. "The hallmarks of cancer", *Cell*, (2000) vol. 100: 57-70.

Haruki, et al. "Molecular analysis of the mitotic checkpoint genes *BUB1*, *BUBBI*, and *BUB3* in human lung cancers", *Cancer Letters* (2001) vol. 162: 201-205.

Hillier, GenBank, Accession No. AA100793 and MPSRCH Search Report p. 5-6, 1997.

Hillier et al. (Oct. 27, 1995) GenBank Accession No. H67224.

Hillier et al. (1996), "Generation and Analysis of 280,000 Human Expressed Sequence Tags," *Genome Research*, vol. 6:807-828.

Hogg, et al. "Cell cycle dependent regulation of the protein kinase TTK", *Oncogene*, 1994 vol. 9: 89-96.

Homma et al. (1991). "The study of the mass screening of person without symptoms and of the screening of outpatients with gastrointestinal complaints or icterus for pancreatic cancer in Japan, using CA 19-9 and Elastase-1 or ultrasonography" Int. J. Pancreatol., vol. 9: 119124.

Jen et al. Stem Cells 2000, vol. 18, pp. 307-319.

Larsen et al. (Mar. 1989), "The Neutrophil-Activating Protein (NAP-1) is Also Chemotactic for T Lymphocytes", Science, vol. 243:1464:1466.

Liao et al. (Nov. 1995), "Human Mig Chemokine: Biochemical and Functional Characterization", *J. Exp. Med.*, vol. 182:1301-1314.

Loetscher et al. (1996), "Activation of NK Cells by CC Chemokines: Chemotaxis, $Ca^2$ Mobilization and Enzyme Release," *J. of Immunol.*, vol. 156:322-327.

Luster et al. (Jul. 1995), "The IP-10 Chemokine Binds to a Specific Cell Surface Heparan Sulfate Site Shared with Platelet Factor 4 and Inhibits Endothelial Cell Proliferation" *J. Exp. Med.*, vol. 182:219-231.

Maione et al. (Jan. 1990), "Inhibition of Angiogenesis by Recombinant Human Platelet Factor- and Related Peptides," *Science*, vol. 247:77-79.

Matsuoka, et al., Identification of novel members of G-protein coupled receptor superfamily expressed in bovine taste tissue. Biochem Biophys Res Commun. Jul. 15, 1993;194(1):504-11.

McClean. Eur. J. Cancer. 29A: 2243-2248, 1993.

Mills, et al. "Expression of TTK, a novel human protein kinase, is associated with cell prolifer-ation", *J. Biol. Chem.*, 1992 vol. 267: 16000-16006.

Mimori et al. *Oncol. Rep.*, (2001) vol. 8: 39-42.

Nagase et al, 1998, Genbank Sequence Database, Accession No. 015462, and MPSRCH search report, 2002, us-09-626-301-4.rspt, pp. 2-3.

Nagase et al. (1998). "Prediction of the coding sequences of unidentified genes. XII. The complete sequencing of 100 new cDNA clones from brain which code for large proteins in vitro" DNA Res., vol. 5: 355-364.

Oberlin et al. (Aug. 1996), "The CXC Chemokine SDF-1 is the Ligand for LESTR/Fusin and Prevents Infection by T-Cell-Line-Adapted HIV-1," *Nature*, vol. 382:833-835.

Olesen, et al. "Mitotic checkpoint genes *hBUB1, hBUB1B, hBUB3,* and *TTK* in human bladder cancer, screening for mutations and loss of heterozygotsity", *Carcinogenesis*, 2001 vol. 22(5): 813-815.

Opalinska et al., Nature Reviews Drug Discovery, 2002, vol. 1, p. 503-514.

Pelchen-Matthews et al. (1999), "Chemokine Receptor Trafficking and Viral Replication", *Immunological Reviews*, vol. 168:33-49.

Putilina et al. (1998) "Analysis of a human cDNA containing a tissue-specific alternatively spliced LIM domain." Biochemical and Biophysical Research Communications, vol. 252 (2):433-439.

Putilina, T. et al, 1998, Genbank Sequence Database, Accession No. JE0325, and MPSRCH search report, 2002, us-09-626-301-4.rpr, p. 1.

Putilina, T. et al, 1997, Genbank Sequence Database, Accession No. 015452, and MPSRCH search report, 2002, us-09-626-301-2.rspt, pp. 2-3.

Putilina, T., GenBank Accession No. U90654 and MPSRCH Search Report p. 5-6, 1997.

Rhodes et al. (1990). "Serum diagnostic tests for pancreatic cancer" Bailliere's Clinical Gastroenterology, vol. 4(4): 833-852.

Ritts et al. (1984). "Initial clinical evaluation of an immunoradiometric assay for CA 19-9 using the NCI serum bank" Int. J. Cancer, vol. 33: 339-345.

Saffery, et al. "Components of the human spindle checkpoint control mechanism localize speci-ically to the active centromere on dicentric chromosomes", *Hum. Genet.*, 2000 vol. 107: 376-384.

Satake et al. (1990). "A clinical evaluation of various tumor markers for the diagnosis of pancreatic cancer" Int. J. Pancreatol., vol. 7: 25-36.

Satake et al. (1991). "Diagnosis of pancreatic cancer" Int. J. Pancreatol., vol. 9: 93-98.

Schmandt, et al. "IL-2-induced expression of TTK, a serine, threonine, tyrosine kinase, correlates with cell cycle progression", *J. Immunol.* (1994) vol. 152: 96-105.

Schröder et al. (Nov. 1987), "Purification and Partial Biochemical Characterization of a Human Monocyte-Derived, Neutrophil-Activating Peptide that Lacks Interleukin 1 Activity," *J. of Immunol.*, vol. 139(10):3474-3483.

Shantz. Intl. J. Biochem & Cell Biol, 31:107-122, 1999.

Shyamala et al. (1998), "Interleukin-8 Receptors R1 and R2 Activate Mitogen-Activated Protein Kinases Induce c-fos, Independent of Ras and Raf-1 in Chinese Hamster Ovary Cells," *Biochemistry*, vol. 37:15918-15924.

Steinberg et al. (1990). "The clinical utility of the CA 19-9 tumor-associated antigen" Am. J. Gastroenterology, vol. 85(4): 350-355.

Thompson et al. (1994), "Clustal W: Improving the Sensitivity of Progressive Multiple Sequence Alignment Through Sequence Weighting, Position-Specific Gap Penalties and Weight Matrix Choice," *Nucleic Acids Research*, vol. 22(22):4673-4680.

Tomizawa, et al. "Tau-tubulin kinase phosphorylates tau at Ser-208 and Ser-210, sites found in paired helical filament-tau", FEBS, (2001) vol. 492: 221-227.

Uguccioni et al. (Actions of the Chemotactic Cytokines MCP-1, MCP-2, MCP-3, RANTES, MIP-1α and MIP-1β on Human Monocytes, *Eur, J. /mmunol.*, vol. 25:64-68, 1995.

Valente et al. (1988), "Purification of a Monocyte Chemotactic Factor Secreted by Nonhuman Primate Vascular Cells in Culture," *Biochemistry*, vol. 27:4162-4168.

Voet et al., 1990. John Wiley & Sons, Inc., pp. 126-128 and 228-234.

Walz et al. (Dec. 1987), "Purification and Amino Acid Sequencing of NAF, A Novel Neutrophil-Activating Factor Produced by Monocytes", *Biochem. and Biophys. Res. Comm.*, vol. 149:755-761.

Wells et al. (1999), "Chemokine Receptors and their Role in Leukocyte Activation", *Immunology Letters*, vol. 65:35-40.

White et al. (1989), "Neutrophil Attractant/Activation Protein-1 (NAP-1) Causes Human Basophil Histamine Release", *Immunology Letters*, vol. 22:151-154.

Yoshimura et al. (Dec. 1987), "Purification of a Human Monocyte-Derived Neutrophil Chemtactic factor that has a Peptide Sequence Similarity to Other Host Defense Cytokines," *Proc. Natl Acad. Sci. USA*, vol. 84:9233-9237.

O'Dowd, et al., "A Novel Gene for a Putative G-protein-coupled receptor with an abundant expression in brain", FEBS Letters, NL, Elsevier Science Publishers, Amsterdam, vol. 394, 1996, pp. 325-329.

Wallin, et al., "Properties of N-terminal tails in G-protein coupled receptors: a statistical study", Protein Engineering, GB, Oxford University Press, Surrey, vol. 8, No. 7, 1995, pp. 693-698.

Jacobs, et al., "A genetic selection for isolating cDNAs encoding secreted proteins", Gene, NL, Elsevier, Amsterdam, vol. 198, 1997, pp. 289-296.

* cited by examiner

FIG. 14A

```
-1380  GATACAGTAGTGCCTGTTAAGCAGTGGTCATTAGTATTAATGCATCAGAATGCTGTGATATAAGCCAGGCTTCTGTGAGAGTGGGGAGG
-1290  AGGGAGGCGTGGCCACCAGAGAAGCAGGCACAAAAACGCACTCTAGGGAAGAGATCCACCTGAAAACGCAGCGTGTCTTTCTTTATTG
-1200  ACCCTGGAGGGCTGGACCATTGGGATTAGGAGTGGTCGAGTGTACCATTCAGGACCTTGTGTTACCTCCCCTGTTCCTCCGCTCCATCCT
-1110  CCCTCAACCTTCTCTGGGAATGACTGATAACTGAGTCCTCAACCAAGGTGCCAGTGACGATAACAGCCAAGTACAGGGCTCCCTGGGGT
-1020  GCAAAGTGCAACCTTACGTTGGAGAATGTGGGTATTGGGTATTGTGAAGGTGAGGGCTAGTTCTAAAGGCCTTGGGATCCCCTGCAGCCCAGAA
-930   TCCTCATGCTCTCGGCAGTTACACAGTTCCTGAAACAAGAGAAAATCAGCATTATCTAGAACTTTCTCCCGTCAGAATGGAGTAG
-840   CAGGTACGTGGAGCCCTTCTGAGATGATTTGGAGAAAGGAAGCCCAGCTCCAGGGACAACTCTCAGCCCACCTGGCAGGACATGGAGG
-750   AAGCCAAAAGCTGGACTGTGTGCCCCCAGGGCTCAAGGAGGTGGAGGTCTATGGGGAGAGCAAGTTGCTGCTGACTGGCCCCCGATTACAGGCTGTGGTGGTATCTCTGTCC
-660   TGCATGGCATCCCCTGCCATCACCGCCACTGTGTGGGGCACAGAGAACACAGTTCCCACCAGTCGCGGTTGG
-570   AGGAGTCCTTCCTCACCCTCACCGCCACTGTGTGGGGCACAGAGAACACAGTTCCCACCAGTCGCGGTTGG
-480   CCCACAAGCCTCGGGATCCCTCCCCAGGGTTCTCTGAAGCTCTCCCTGGCCTGGGCATGGGTGGTTCTGGATCTCCACTGCTCTC
-390   CTCAACTGATTTCGTCTCTGGCCCCTCAGCTGATCCATCTTAGAACCCCATCCCCAGCCTCTGCCCTTGCACTGTCAGGGCATGGATCCCCAGCA
-300   ACTTGTCTGTCTCTGGCCCCTCAGCTGATCCATCTTAGAACCCCATCCCCAGCCTCTGCCCTTGCACTGTCAGGGCATGGATCCCCAGCA
-210   AGCTGAGTGGCTATGCAGCAACAATGAACGAGTGAATGAGCGAGTGAATGAGTCCCCTAGCTGTCAGGGCATGGATCCCCAGCA
-120   AGGAGGGAGACCTGCAAGGGTTAATCAGAGACCTGCCTGTGTCTGAGGTAAGCAAGGAGTGTATTGTTCAGTAAATAAGGAAGGA
       TATAA                                                                          +1
-30    TTACTTATATAATGGGAAATCAGGCCCTGACCAACTCTTCATCTCGCGCTGTCTGACTTCCTCCCAGCACATTCCTGCACTCTGCCGTGTC
+61    CACACTGCCCCACAGACCCAGTCCTCCAAGCCTGCTGCGCAGCCCTCAGGTTGGGCCTTGCACGGTGCCAGCAGGCAG
+151   CCCTGGGCTGGGGTAGGGACTCCGCCACAGGCACTCCAGACCCTGAGACCTCAGAGGGCCACCCTTGAGGTGCCAGCCCCCAGTGGC
+241   CAACCTGAGTGCTGCCTCTGCCACCAGCCCTGCTGGCCCCCTGGTTCCGCTGGCCTGCCTGGCTGAGACACCGCCAGTGGCCTCA
+331   GCTGCCCACACCTCTTCCCGGCCACTGGCACTGGCACTGCAGCAGACAGCTCCTGGGCACTGCCAGCAGCCCCCTGGGCACTGCCAGCAGACAGCTCCTGGGCACTGCCAGC
```

FIG. 14B

```
                M   G   S   A   S   P   G   L   S   S   V   S   P   S   H   L   L   L   P   P   D   T   V   S   R>
 +421  CAAACAGCAGCGGGCATGGGCAGCGCCAGCCCGGGTCTGAGCAGTGTCTCCCCCAGCCACCTCCTGCTGCCCCCAGACACGGTGTCGCGGA
        T   G   L   E   K   A   A   G   A   V   G   L   E   R   R   D   W   S   P   P   A   T   P   E   Q   G   L>
 +511  CAGGCTTGGAGAAGGCCGCAGGGGCGGGGCTGGAGCGTCGAGACGACTGGAGTCCCAGTCCACCGCCGAGCCCGAGCAGGGCCTGT
        S   A   F   Y   L   S   Y   F   D   M   L   Y   P   E   D   S   S   W   A   A   K   A   P   G   A   S   S   R   E   E>
 +601  CCGGCCTTCTACCTCTCCTACTTTGACATGCTGTACCCTGAGGACAGCAGCTGGGCAGCCAAGGCCCCTGGGGCCAGTAGCCGGGAGGAGC
        P   P   E   E   P   E   Q   C   P   V   I   D   S   Q   A   P   A   G   S   L   D   L   V   P   G   G   L   T   L   E>
 +691  CACCTGAGGAGCCTGAGCAGTGCCCGGTGCCCCGGTGCCATTGACAGCCAAGCCCCAGCGGGCAGCCTGGACTTGGTGCCCGGGGCTGACCTTGGAGG
        E   H   S   L   E   Q   V   Q   S   M   V   V   G   E   V   L   K   D   I   E   T   A   C   K   L   N   I   T   A>
 +781  AGCACTCGCTGGAACGTCAGAGCATGGTGGTGGGCGAAGTGCTCAAGGACATCGAGACGGCCTGCAAGCTGAACATCACCGCAG
        D   P   M   D   W   S   P   S   N   V   Q   K   W   L   L   W   T   E   H   Q   Y   R   L   P   P   M   G   K   A   F>
 +871  ATCCCATGGACTGGAGCCCCAGCAATGTGCAGAAGTGGCTCCTGTGGACAGAGCACCAATACCGGCTGCCCCCCATGGGCAAGGCCTTCC
        Q   E   L   A   G   K   E   L   C   A   M   S   E   E   Q   F   R   Q   R   S   P   L   G   G   D   V   L   H   A   H>
 +961  AGGAGCTGGCCGGGAAGGAGCTGTGCGCCATGTCGGAGGAGCAGTTCCGCCAGCGCTCGCCCCTGGGTGGAGATGTGCTGCACGCCCACC
        L   D   I   W   K   S   A   W   M   K   E   R   T   S   P   G   A   I   H   Y   C   A   S   T   S   E   E   S   W>
+1051  TGGACATCTGGAAGTCAGCGGCCTGGATGAAAGAGCGGACTTCACCTGTGCCCTGACCAGTGAGGAGAGCTGGA
        T   D   S   E   V   D   S   S   C   S   G   Q   P   I   H   L   W   Q   F   L   K   E   L   L   L   K   P   H   S   Y>
+1141  CCGACAGCGAGGTGGACTCATCATGCTCCGGGCAGCCCATCCACCTGTGGCAGTTCCTCAAGGAGTTGCTACTCAAGCCCCACAGCTATG
        G   R   F   I   R   W   L   N   K   E   K   G   I   F   K   I   E   D   S   A   Q   V   A   R   L   W   G   I   R   K>
+1231  GCCGCTTCATTAGGTGGCTCAACAAGGAGAAGGGCATCTTCAAAATTGAGGACTCAGCCCAGGTGGCCCGGCTGTGGGGCATCCGCAAGA
        N   R   P   A   M   N   Y   D   K   L   S   R   S   I   R   Q   Y   Y   K   G   I   I   R   K   P   D   I   S   Q>
+1321  ACCGTCCCGCCATGAACTACGACAAGCTGAGCCGCTCCATCCGCCAGTATTACAAGAAGGGCATCATCCGGAAGCCAGACATCTCCCAGC
        R   L   V   Y   Q   F   V   H   P   I   *
+1411  GCCTCGTCTACCAGTTCGTGCACCCCATCTGAGTGCCTGGCCTGCCCTCTCCTGCCCTGCC
+1501  TCAGCCAGGCCCTGAGATGGGGGAAAACGGGCCTTCCAGAGCCCTGACCTTCAGGAGGGCCAACCAACTG
+1591  CCCCAGGGGATATGGTCCTTCGGAGCCTCCCAACACCTGCTTCCTCCAGGGTGCTCCCCTGGACAGA
+1681  GGGAGACAGGGCTGCTCCCCAACACCTGCTTCCTCCAGCCCTGACCATTCCAGAGCCAGAGCATTTCTGACCACTGGGGACAAAGGCCAC
+1771  AGCCAGTCCAGGCCTGAGCCATGGTGCAGGAGACATCTGCACCCCTGAG
+1861  TTGGGCAGCCAGGAGAGTGCCCCCGGAATGGATAATAGAGATACTAGAGAACTGAAAAAAAAAAAAAAAAAAAAA  +1938
```

 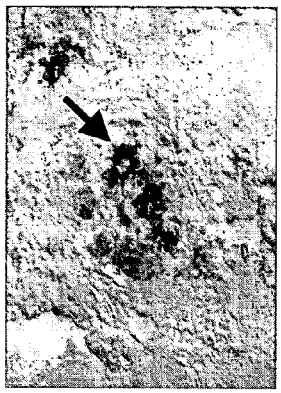 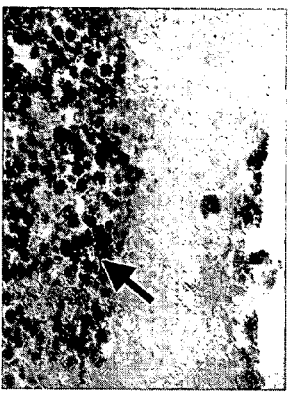
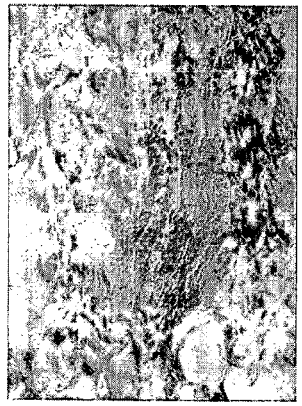  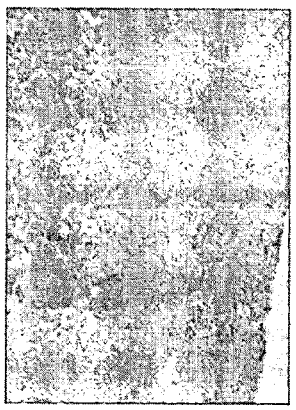
19B GSEF / H&E — breast normal, breast normal, in situ carcinoma FIG. 23
SK-BR-3
MDA-MB-435-GSEF (Cl.48)
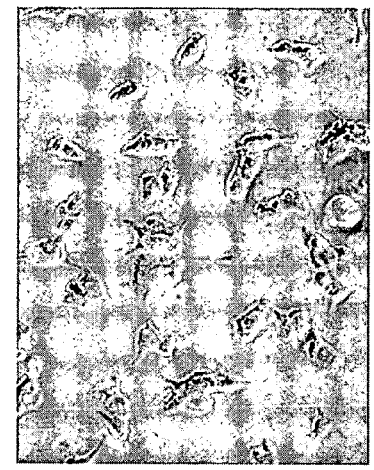
MDA-MB-435-GSEF (Cl.46)
Parental MDA-MB-435
MDA-MB-435-E1AF (Cl.43)

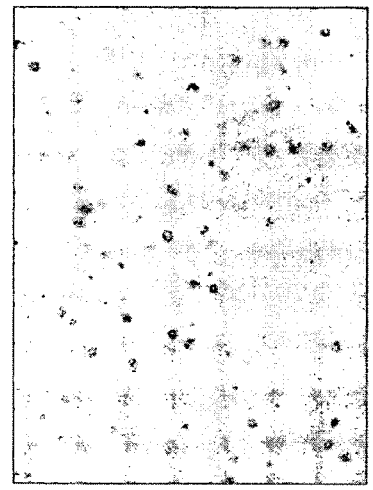
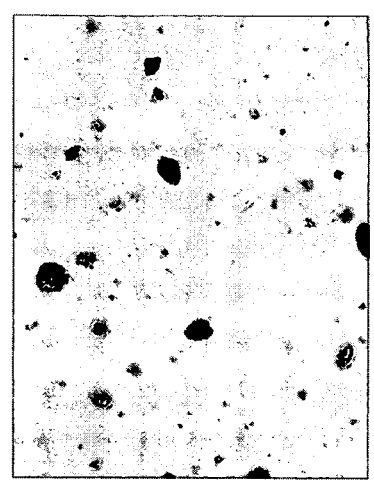
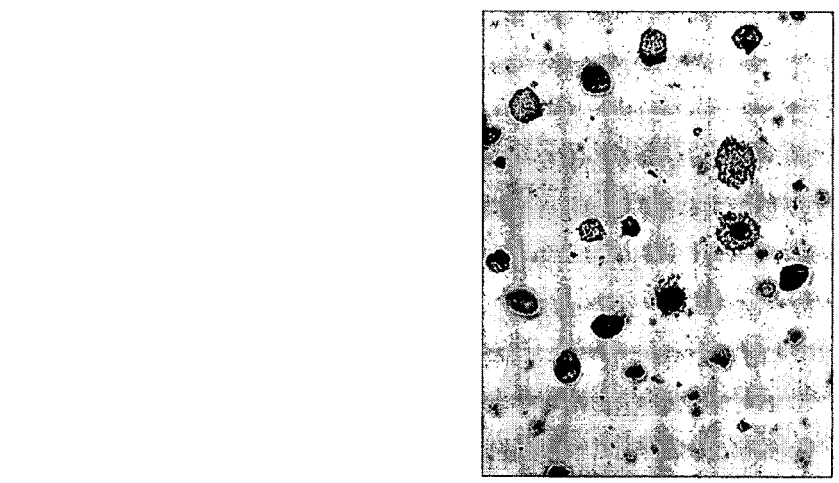
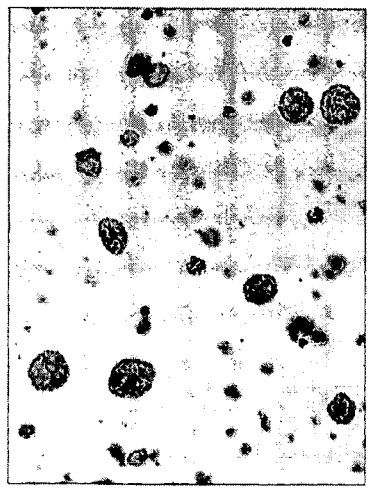
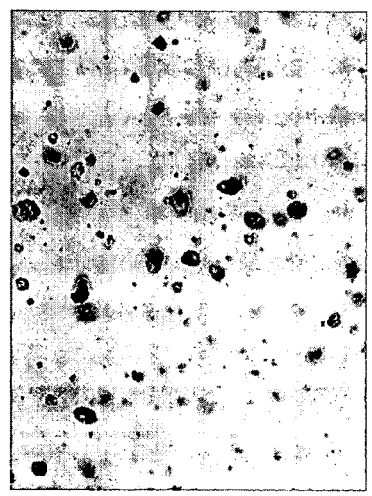
FIG. 24

Differential Display Sequencing Gel Autoradiograph
Primer Pair: Arp1/Ap2

Cancer}
Dysplasia}
Pancreatitis}
Normal}

← 2004-6

```
ATAGCACGACTGTGTATGCTCTGGAGGACTGAAAGGCTGTACAAGCCCTATGTATTTTTT
TTCAAATATACATATGCATGGGTCTTGCTGCTGCCTCTTTTGCTGACTGTAATTGGACTT
TGAAGCTTCGAAGTTATATCATAAAAATTTGTAACCTTTGTCTGAGAGAGAGCTCAGCTA
AGCAATCACTTTCCACTTCTTTTCACAGGATAATATAAACGTTTTCTTGAAAGCTTGTGA
ACAGATTGGATTGAAAGAAGCCCAGCTTTTCCATCCTGGAGATCTACAGGATTTATCAAA
TCGAGTCACTGTCAAGCAAGAAGAGACTGACAGGAGAGTGAAAAATGTTTTGATAACATT
GTACTGGCTGGGAAGAAAAGCACAAAGCAACCCGTACTATAATGGTCCCCATCTTAATTT
GAAAGCGTTTGAGAATCTTTTAGGACAAGCACTGACGAAGGCACTCGAAGACTCCAGCTT
CCTGAAAAGAAGTGGCAGGGACAGTGGCTACGGTGACATCTGGTGTCCTGAACGTGGAGA
ATTTCTTGCTCCTCCAAGGCACCATAAGAGAGAAGATTCCTTTGAAAGCTTGGACTCTTT
GGGCTCGAGGTCATTGACAAGCTGCTCCTCTGATATCACGTTGAGAGGGGGCGTGAAGG
TTTTGAAAGTGACACAGATTCGGAATTTACATTCAAGATGCAGGATTATAATAAAGATGA
TATGTCGTATCGAAGGATTTCGGCTGTTGAGCCAAGACTGCGTTACCCTTCAATCGTTT
TTTACCCAACAAAAGTAGACAGCCATCCTATGTACCAGCACCTCTGAGAAAGAAAAAGCC
AGACAAACATGAGGATAACAGAAGAAGTTGGGCAAGCCCGGTTTATACAGAAGCAGATGG
AACATTTTCAAGGAGTAAGTCCATGAGTGATGTCAGCGCAGAAGATGTTCAAAACTTGCG
TCAGCTGCGTTACGAGGAGATGCAGAAAATAAAATCACAATTAAAAGAACAAGATCAGAA
ATGGCAGGATGACCTTGCAAAATGGAAAGATCGTCGAAAAGTTACACTTCAGATCTGCA
GAAGAAAAAGAAGAGAGAAGAAATTGAAAAGCAGGCACTTGAGAAGTCTAAGAGAAG
CTCTAAGACGTTTAAGGAAATGCTGCAGGACAGGGAATCCCAAAATCAAAAGTCTACAGT
TCCGTCAAGAAGGAGAATGTATTCTTTTGATGATGTGCTGGAGGAAGGAAAGCGACCCCC
TACAATGACTGTGTCAGAAGCAAGTTACCAGAGTGAGAGAGTAGAAGAGAAGGGAGCAAC
TTATCCTTCAGAAATTCCCAAAGAAGATTCTACCACTTTTGCAAAAAGAGAGGACCGTGT
AACAACTGAAATTCAGCTTCCTTCTCAAAGTCCTGTGGAAGAACAAAGCCCAGCCTCTTT
GTCTTCTCTGCGTTCACGGAGCACACAAATGGAATCAACTCGTGTTTCAGCTTCTCTCCC
CAGAAGTTACCGGAAAACTGATACAGTCAGGTTAACATCTGTGGTCACACCAAGACCCTT
TGGCTCTCAGACAAGGGGAATCTCATCACTCCCCAGATCTTACACGATGGATGATGCTTG
GAAGTATAATGGAGATGTTGAAGACATTAAGAGAACTCCAAACAATGTGGTCAGCACCCC
TGCACCAAGCCCGGACGCAAGCCAACTGGCTTCAAGCTTATCTAGCCAGAAAGAGGTAGC
AGCAACAGAAGAAGATGTGACAAGGCTGCCCTCTCCTACATCCCCCTTCTCATCTCTTTC
CCAAGACCAGGCTGCCACTTCTAAAGCCACATTGTCTTCCACATCTGGTCTTGATTTAAT
GTCTGAATCTGGAGAAGGGGAAATCTCCCCACAAAGAGAAGTCTCAAGATCCCAGGATCA
GTTCAGTGATATGAGAATCAGCATAAACCAGACGCCTGGGAAGAGTCTTGACTTTGGGTT
TACAATAAAATGGGATATTCCTGGGATCTTCGTAGCATCAGTTGAAGCAGGTAGCCCAGC
AGAATTTTCTCAGCTACAAGTAGATGATGAAATTATTGCTATTAACAACACCAAGTTTTC
ATATAACGATTCAAAAGAGTGGGAGGAAGCCATGGCTAAGGCTCAAGAAACTGGACACCT
AGTGATGGATGTGAGGCGCTATGGAAAGGCTGGTTCACCTGAAACAAAGTGGATTGATGC
AACTTCTGGAATTTACAACTCAGAAAAATCTTCAAATCTATCTGTAACAACTGATTTCTC
CGAAAGCCTTCAGAGTTCTAATATTGAATCCAAGAAATCAATGGAATTCATGATGAAAG
CAATGCTTTTGAATCAAAAGCATCTGAATCCATTTCTTTGAAAAACTTAAAAAGGCGATC
ACAATTTTTTGAACAAGGAAGCTCTGATTCGGTGGTTCCTGATCTTCCAGTTCCAACCAT
```

FIG. 27

```
CAGTGCCCCGAGTCGCTGGGTGTGGGATCAAGAGGAGGAGCGGAAGCGGCAGGAGAGGTG
GCAGAAGGAGCAGGACCGCCTACTGCAGGAAAAATATCAACGTGAGCAGGAGAAACTGAG
GGAAGAGTGGCAAAGGGCCAAACAGGAGGCAGAGAGAGAGAATTCCAAGTACTTGGATGA
GGAACTGATGGTCCTAAGCTCAAACAGCATGTCTCTGACCACACGGGAGCCCTCTCTTGC
CACCTGGGAAGCTACCTGGAGTGAAGGGTCCAAGTCTTCAGACAGAGAAGGAACCCGAGC
AGGAGAAGAGGAGAGGAGACAGCCACAAGAGGAAGTTGTTCATGAGGACCAAGGAAAGAA
GCCGCAGGATCAGCTTGTTATTGAGAGAGAGAGGAAATGGGAGCAACAGCTTCAGGAAGA
GCAAGAGCAAAAGCGGCTTCAGGCTGAGGCTGAGGAGCAGAAGCGTCCTGCGGAGGAGCA
GAAGCGCCAGGCAGAGATAGAGCGGGAAACATCAGTCAGAATATACCAGTACAGGAGGCC
TGTTGATTCCTATGATATACCAAAGACAGAAGAAGCATCTTCAGGTTTTCTTCCTGGTGA
CAGGAATAAATCCAGATCTACTACTGAACTGGATGATTACTCCACAAATAAAAATGGAAA
CAATAAATATTTAGACCAAATTGGGAACACGACCTCTTCACAGAGGAGATCCAAGAAAGA
ACAAGTACCATCAGGAGCAGAATTGGAGAGGCAACAAATCCTTCAGGAAATGAGGAAGAG
AACACCCCTTCACAATGACAACAGCTGGATCCGACAGCGCAGTGCCAGTGTCAACAAAGA
GCCTGTTAGTCTTCCTGGGATCATGAGAAGAGGCGAATCTTTAGATAACCTGGACTCCCC
CCGATCCAATTCTTGGAGACAGCCTCCTTGGCTCAATCAGCCCACAGGATTCTATGCTTC
TTCCTCTGTGCAAGACTTTAGTCGCCCACCACCTCAGCTGGTGTCCACATCAAACCGTGC
CTACATGCGGAACCCCTCCTCCAGCGTGCCCCCACCTTCAGCTGGCTCCGTGAAGACCTC
CACCACAGGTGTGGCCACCACACAGTCCCCCACCCCGAGAAGCCATTCCCCTTCAGCTTC
ACAGTCAGGCTCTCAGCTGCGTAACAGGTCAGTCAGTGGGAAGCGCATATGCTCCTACTG
CAATAACATTCTGGGCAAAGGAGCCGCCATGATCATCGAGTCCCTGGGTCTTTGTTATCA
TTTGCATTGTTTTAAGTGTGTTGCCTGTGAGTGTGACCTCGGAGGCTCTTCCTCAGGAGC
TGAAGTCAGGATCAGAAACCACCAACTGTACTGCAACGACTGCTATCTCAGATTCAAATC
TGGACGGCCAACCGCCATGTGATGTAAGCCTCCATACGAAAGCACTGTTGCAGATAGAAG
AAGAGGTGGTTGCTGCTCATGTAGATCTATAAATATGTGTTGTATGTCTTTTTTGCTTTT
TTTTTAAAAAAAAGAATAACTTTTTTTGCCTCTTTAGATTACATAGAAGCATTGTAGTCT
TGGTAGAACCAGTATTTTTGTTGTTTATTTATAAGGTAATTGTGTGTGGGAAAAGTGCA
GTATTTACCTGTTGAATTCAGCATCTTGAGAGCACAAGGGAAAAAATAAGAACCTACGAA
TATTTTGAGGCAGATAATGATCTAGTTTGACTTTCTAGTTAGTGGTGTTTGAAGAGGG
TATTTTATTGTTTTTTAAAAAAAGGTTCTTAAACATTATTTGAAATAGTTAATATAAATA
CATAATTGCATTTGCTCTGTTTATTGTAATGTATTCTAAATTAATGCAGAACCATATGGA
AAATTTCATTAAAATCTATCCCCAAATGTGCTTTCTGTATCCTTCCTTCTACCTATTATT
CTGATTTTAAAAATGCAGTTAATGTACCATTTATTTGCTTGATGAAGGGAGCTCTATTT
TCTTTACCAGAAATGTTGCTAAGTAATTCCCAATAGAAAGCTGCTTATTTTCATTAATGA
AAAATAACCATGGTTTGTATACTAGAAGTCTTCTTCAGAAACTGGTGAGCCTTTCTGTTC
AATTGCATTTGTAAATAAACTTGCTGATGCATTTAAAAAAAAAAAAAAAAAAA
```

FIG. 27 (cont'd)

```
ATAGCACGACTGTGTATGCTCTGGAGGACTGAAAGGCTGTACAAGCCCTATGTATTTTTT
TTCAAATATACATATGCATGGGTCTTGCTGCTGCCTCTTTTGCTGACTGTAATTGGACTT
TGAAGCTTCGAAGTTATATCATAAAAATTTGTAACCTTTGTCTGAGAGAGAGCTCAGCTA
AGCAATCACTTTCCACTTCTTTTCACAGGATAATATAAACGTTTTCTTGAAAGCTTGTGA
ACAGATTGGATTGAAAGAAGCCCAGCTTTTCCATCCTGGAGATCTACAGGATTTATCAAA
TCGAGTCACTGTCAAGCAAGAAGAGACTGACAGGAGAGTGAAAAATGTTTTGATAACATT
GTACTGGCTGGGAAGAAAAGCACAAAGCAACCCGTACTATAATGGTCCCCATCTTAATTT
GAAAGCGTTTGAGAATCTTTTAGGACAAGCACTGACGAAGGCACTCGAAGACTCCAGCTT
CCTGAAAAGAAGTGGCAGGGACAGTGGCTACGGTGACATCTGGTGTCCTGAACGTGGAGA
ATTTCTTGCTCCTCCAAGGCACCATAAGAGAGAAGATTCCTTTGAAAGCTTGGACTCTTT
GGGCTCGAGGTCATTGACAAGCTGCTCCTCTGATATCACGTTGAGAGGGGGCGTGAAGG
TTTGAAAGTGACACAGATTCGGAATTTACATTCAAGATGCAGGATTATAATAAAGATGA
TATGTCGTATCGAAGGATTTCGGCTGTTGAGCCAAAGACTGCGTTACCCTTCAATCGTTT
TTTACCCAACAAAAGTAGACAGCCATCCTATGTACCAGCACCTCTGAGAAAGAAAAAGCC
AGACAAACATGAGGATAACAGAAGAAGTTGGGCAAGCCCGGTTTATACAGAAGCAGATGG
AACATTTTCAAGactctttcaaaagatttatggtgagaatggGAGTAAGTCCATGAGTGA
TGTCAGCGCAGAAGATGTTCAAAACTTGCGTCAGCTGCGTTACGAGGAGATGCAGAAAAT
AAAATCACAATTAAAAGAACAAGATCAGAAATGGCAGGATGACCTTGCAAAATGGAAAGA
TCGTCGAAAAAGTTACACTTCAGATCTGCAGAAGAAAAAGAAGAGAGAGAAGAAATTGA
AAAGCAGGCACTTGAGAAGTCTAAGAGAAGCTCTAAGACGTTTAAGGAAATGCTGCAGGA
CAGGGAATCCCAAAATCAAAAGTCTACAGTTCCGTCAAGAAGGAGAATGTATTCTTTTGA
TGATGTGCTGGAGGAAGGAAAGCGACCCCCTACAATGACTGTGTCAGAAGCAAGTTACCA
GAGTGAGAGAGTAGAAGAGAAGGGAGCAACTTATCCTTCAGAAATTCCCAAAGAAGATTC
TACCACTTTTGCAAAAAGAGAGGACCGTGTAACAACTGAAATTCAGCTTCCTTCTCAAAG
TCCTGTGGAAGAACAAAGCCCAGCCTCTTTGTCTTCTCTGCGTTCACGGAGCACACAAAT
GGAATCAACTCGTGTTTCAGCTTCTCTCCCCAGAAGTTACCGGAAAACTGATACAGTCAG
GTTAACATCTGTGGTCACACCAAGACCCTTTGGCTCTCAGACAAGGGGAATCTCATCACT
CCCCAGATCTTACACGATGGATGATGCTTGGAAGTATAATGGAGATGTTGAAGACATTAA
GAGAACTCCAAACAATGTGGTCAGCACCCCTGCACCAAGCCCGGACGCAAGCCAACTGGC
TTCAAGCTTATCTAGCCAGAAAGAGGTAGCAGCAACAGAAGAAGATGTGACAAGGCTGCC
CTCTCCTACATCCCCCTTCTCATCTCTTTCCCAAGACCAGGCTGCCACTTCTAAAGCCAC
ATTGTCTTCCACATCTGGTCTTGATTTAATGTCTGAATCTGGAGAAGGGGAAATCTCCCC
ACAAAGAGAAGTCTCAAGATCCCAGGATCAGTTCAGTGATATGAGAATCAGCATAAACCA
GACGCCTGGGAAGAGTCTTGACTTTGGGTTTACAATAAAATGGGATATTCCTGGGATCTT
CGTAGCATCAGTTGAAGCAGGTAGCCCAGCAGAATTTTCTCAGCTACAAGTAGATGATGA
AATTATTGCTATTAACAACACCAAGTTTTCATATAACGATTCAAAAGAGTGGGAGGAAGC
CATGGCTAAGGCTCAAGAAACTGGACACCTAGTGATGGATGTGAGGCGCTATGGAAAGGC
TGGTTCACCTGAAACAAAGTGGATTGATGCAACTTCTGGAATTTACAACTCAGAAAAATC
TTCAAATCTATCTGTAACAACTGATTTCTCCGAAAGCCTTCAGAGTTCTAATATTGAATC
CAAAGAAATCAATGGAATTCATGATGAAAGCAATGCTTTTGAATCAAAAGCATCTGAATC
```

FIG. 28

```
CATTTCTTTGAAAAACTTAAAAAGGCGATCACAATTTTTTGAACAAGGAAGCTCTGATTC
GGTGGTTCCTGATCTTCCAGTTCCAACCATCAGTGCCCCGAGTCGCTGGGTGTGGGATCA
AGAGGAGGAGCGGAAGCGGCAGGAGAGGTGGCAGAAGGAGCAGGACCGCCTACTGCAGGA
AAAATATCAACGTGAGCAGGAGAAACTGAGGGAAGAGTGGCAAAGGGCCAAACAGGAGGC
AGAGAGAGAGAATTCCAAGTACTTGGATGAGGAACTGATGGTCCTAAGCTCAAACAGCAT
GTCTCTGACCACACGGGAGCCCTCTCTTGCCACCTGGGAAGCTACCTGGAGTGAAGGGTC
CAAGTCTTCAGACAGAGAAGGAACCCGAGCAGGAGAAGAGGAGAGGAGACAGCCACAAGA
GGAAGTTGTTCATGAGGACCAAGGAAAGAAGCCGCAGGATCAGCTTGTTATTGAGAGAGA
GAGGAAATGGGAGCAACAGCTTCAGGAAGAGCAAGAGCAAAAGCGGCTTCAGGCTGAGGC
TGAGGAGCAGAAGCGTCCTGCGGAGGAGCAGAAGCGCCAGGCAGAGATAGAGCGGGAAAC
ATCAGTCAGAATATACCAGTACAGGAGGCCTGTTGATTCCTATGATATACCAAAGACAGA
AGAAGCATCTTCAGGTTTTCTTCCTGGTGACAGGAATAAATCCAGATCTACTACTGAACT
GGATGATTACTCCACAAATAAAAATGGAAACAATAAATATTTAGACCAAATTGGGAACAC
GACCTCTTCACAGAGGAGATCCAAGAAAGAACAAGTACCATCAGGAGCAGAATTGGAGAG
GCAACAAATCCTTCAGGAAATGAGGAAGAGAACACCCCTTCACAATGACAACAGCTGGAT
CCGACAGCGCAGTGCCAGTGTCAACAAAGAGCCTGTTAGTCTTCCTGGGATCATGAGAAG
AGGCGAATCTTTAGATAACCTGGACTCCCCCCGATCCAATTCTTGGAGACAGCCTCCTTG
GCTCAATCAGCCCACAGGATTCTATGCTTCTTCCTCTGTGCAAGACTTTAGTCGCCCACC
ACCTCAGCTGGTGTCCACATCAAACCGTGCCTACATGCGGAACCCCTCCTCCAGCGTGCC
CCCACCTTCAGCTGGCTCCGTGAAGACCTCCACCACAGGTGTGGCCACCACACAGTCCCC
CACCCCGAGAAGCCATTCCCCTTCAGCTTCACAGTCAGGCTCTCAGCTGCGTAACAGGTC
AGTCAGTGGGAAGCGCATATGCTCCTACTGCAATAACATTCTGGGCAAAGGAGCCGCCAT
GATCATCGAGTCCCTGGGTCTTTGTTATCATTTGCATTGTTTTAAGTGTGTTGCCTGTGA
GTGTGACCTCGGAGGCTCTTCCTCAGGAGCTGAAGTCAGGATCAGAAACCACCAACTGTA
CTGCAACGACTGCTATCTCAGATTCAAATCTGGACGGCCAACCGCCATGTGATGTAAGCC
TCCATACGAAAGCACTGTTGCAGATAGAAGAAGAGGTGGTTGCTGCTCATGTAGATCTAT
AAATATGTGTTGTATGTCTTTTTTGCTTTTTTTTAAAAAAAAGAATAACTTTTTTTGCC
TCTTTAGATTACATAGAAGCATTGTAGTCTTGGTAGAACCAGTATTTTGTTGTTTATTT
ATAAGGTAATTGTGTGTGGGGAAAAGTGCAGTATTTACCTGTTGAATTCAGCATCTTGAG
AGCACAAGGGAAAAATAAGAACCTACGAATATTTTGAGGCAGATAATGATCTAGTTTG
ACTTTCTAGTTAGTGGTGTTTTGAAGAGGGTATTTTATTGTTTTTAAAAAAAGGTTCTT
AAACATTATTTGAAATAGTTAATATAAATACATAATTGCATTTGCTCTGTTTATTGTAAT
GTATTCTAAATTAATGCAGAACCATATGGAAAATTTCATTAAAATCTATCCCCAAATGTG
CTTTCTGTATCCTTCCTTCTACCTATTATTCTGATTTTTAAAAATGCAGTTAATGTACCA
TTTATTTGCTTGATGAAGGGAGCTCTATTTTCTTTACCAGAAATGTTGCTAAGTAATTCC
CAATAGAAAGCTGCTTATTTTCATTAATGAAAAATAACCATGGTTTGTATACTAGAAGTC
TTCTTCAGAAACTGGTGAGCCTTTCTGTTCAATTGCATTTGTAAATAAACTTGCTGATGC
ATTTAAAAAAAAAAAAAAAAAAA
```

FIG. 28 (cont'd)

Probe: 2004-6

SEQUENCE LISTING

```
<160> NUMBER OF SEQ ID NOS: 96

<210> SEQ ID NO 1
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 1
cggaatcaag tcttctagct                                         20

<210> SEQ ID NO 2
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 2
ggttgctcaa aagttggtat g                                       21

<210> SEQ ID NO 3
<211> LENGTH: 24
<212> TYPE: DNA
<213> ORGANISM: Artificial Sequence
<220> FEATURE:
<223> OTHER INFORMATION: synthesized oligonucleotide
```

<400> SEQUENCE: 3
cgggaaatcg tgcgtgacat taag                                    24

<210> SEQ ID NO 4
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 4
tgatctcctt ctgcatcctg tcgg                                    24

<210> SEQ ID NO 5
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 5
gggactcttc caaatgggca tgact                                   25

<210> SEQ ID NO 6
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 6
tccagtaact cttgcgttcc catgg                                   25

<210> SEQ ID NO 7
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 7
tcagtacggg taaaccttct caggg                                   25

<210> SEQ ID NO 8
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 8
ggtacccttg cgttctcaat gacct                                   25

<210> SEQ ID NO 9
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 9
taggtctttg gccggtgatg ggtcg                                   25

<210> SEQ ID NO 10

```
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 10
gctgggtagt ggccggtttc tggat                                           25

<210> SEQ ID NO 11
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 11
actcatctgg ctgggctatg gtggt                                           25

<210> SEQ ID NO 12
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 12
tggtggtatc gggtcggtct actca                                           25

<210> SEQ ID NO 13
<211> LENGTH: 3866
<212> TYPE: DNA
<213> ORGANISM: Homo sapiens
<220> FEATURE:
<221> NAME/KEY: CDS
<222> LOCATION: (1026)...(3551)
<221> NAME/KEY: misc_feature
<222> LOCATION: (0)...(0)
<223> OTHER INFORMATION: TTK

<400> SEQUENCE: 13
ggaattcctt tttttttttt tttgagatgg agtttcactc ttgttggcca ggctggagtg     60
caatggcaca atctcagctt actgcaacct ccgcctcccg ggttcaagcg attctcctgc    120
ctcagcctct caagtagctg ggattacagg catgtgccac cacccctggc taactaattt    180 ctttttctatt tagtagagat ggggtttcac catgttggtc aggctggtct tgaactcctg    240
acctcaggtg atccacttgc cttggcctcc caaagtgcta ggattacagc cgtgaaactg    300
tgcctggctg attcttttttt tgttgttgga tttttgaaac agggtctccc ttggtcgccc    360
aggctggagt gcagtggtgc gatcttggct cactataacc tccacctcct ggtttcaagt    420
gatcctccca ctttagcctc ctgagtagct gtgattacag gcgtgcacca ccacacccgg    480 ctaattttttg tattttttatt agagacaggg tttcaccatg ttggccaggc tgttctcaaa    540
ctcctggact caagggatcc gcctgcctcc acttcccaaa gtcccgagat tacaggtgtg    600
agtcaccatg cctgacccta taattcttaa gtcattttttt ctggtccatt tcttccttag    660
ggtcctcaca acaaatctgc attaggcggt acaataatcc ttaacttcat gattcacaaa    720
aggaagatga agtgattcat gatttagaaa gggaagtag taagcccact gcacactcct    780
ggatgatgat cctaaatcca gatacagtaa aaatgggggta tgggaaggta gaatacaaaa    840
tttggtttaa attaattatc taaatatcta aaaacattttt tggatacatt gttgatgtga    900
atgtaagact gtacagactt cctagaaaac agtttgggtt ccatctttttc atttccccag    960
```

-continued

```
tgcagttttc tgtagaaatg gaatccgagg atttaagtgg cagagaattg acaattgatt    1020
```

| ccata | atg<br>Met<br>1 | aac<br>Asn | aaa<br>Lys | gtg<br>Val | aga<br>Arg<br>5 | gac<br>Asp | att<br>Ile | aaa<br>Lys | aat<br>Asn | aag<br>Lys<br>10 | ttt<br>Phe | aaa<br>Lys | aat<br>Asn | gaa<br>Glu | gac<br>Asp<br>15 | 1070 |
|---|---|---|---|---|---|---|---|---|---|---|---|---|---|---|---|---|
| | ctt<br>Leu | act<br>Thr | gat<br>Asp | gaa<br>Glu<br>20 | cta<br>Leu | agc<br>Ser | ttg<br>Leu | aat<br>Asn | aaa<br>Lys<br>25 | att<br>Ile | tct<br>Ser | gct<br>Ala | gat<br>Asp | act<br>Thr<br>30 | aca<br>Thr | gat<br>Asp | 1118 |
| | aac<br>Asn | tcg<br>Ser | gga<br>Gly | act<br>Thr<br>35 | gtt<br>Val | aac<br>Asn | caa<br>Gln | att<br>Ile | atg<br>Met<br>40 | atg<br>Met | atg<br>Met | gca<br>Ala | aac<br>Asn | aac<br>Asn<br>45 | cca<br>Pro | gag<br>Glu | 1166 |
| | gac<br>Asp | tgg<br>Trp | ttg<br>Leu | agt<br>Ser<br>50 | ttg<br>Leu | ttg<br>Leu | ctc<br>Leu | aaa<br>Lys | cta<br>Leu<br>55 | gag<br>Glu | aaa<br>Lys | aac<br>Asn | agt<br>Ser | gtt<br>Val<br>60 | ccg<br>Pro | cta<br>Leu | 1214 |
| | agt<br>Ser | gat<br>Asp | gct<br>Ala | ctt<br>Leu<br>65 | tta<br>Leu | aat<br>Asn | aaa<br>Lys | ttg<br>Leu | att<br>Ile<br>70 | ggt<br>Gly | cgt<br>Arg | tac<br>Tyr | agt<br>Ser | caa<br>Gln<br>75 | gca<br>Ala | att<br>Ile | 1262 |
| | gaa<br>Glu<br>80 | gcg<br>Ala | ctt<br>Leu | ccc<br>Pro | cca<br>Pro | gat<br>Asp<br>85 | aaa<br>Lys | tat<br>Tyr | ggc<br>Gly | caa<br>Gln | aat<br>Asn<br>90 | gag<br>Glu | agt<br>Ser | ttt<br>Phe | gct<br>Ala | aga<br>Arg<br>95 | 1310 |
| | att<br>Ile | caa<br>Gln | gtg<br>Val | aga<br>Arg<br>100 | ttt<br>Phe | gct<br>Ala | gaa<br>Glu | tta<br>Leu | aaa<br>Lys<br>105 | gct<br>Ala | att<br>Ile | caa<br>Gln | gag<br>Glu | cca<br>Pro<br>110 | gat<br>Asp | gat<br>Asp | 1358 |
| | gca<br>Ala | cgt<br>Arg | gac<br>Asp | tac<br>Tyr<br>115 | ttt<br>Phe | caa<br>Gln | atg<br>Met | gcc<br>Ala | aga<br>Arg<br>120 | gca<br>Ala | aac<br>Asn | tgc<br>Cys | aag<br>Lys | aaa<br>Lys<br>125 | ttt<br>Phe | gct<br>Ala | 1406 |
| | ttt<br>Phe | gtt<br>Val | cat<br>His | ata<br>Ile<br>130 | tct<br>Ser | ttt<br>Phe | gca<br>Ala | caa<br>Gln | ttt<br>Phe<br>135 | gaa<br>Glu | ctg<br>Leu | tca<br>Ser | caa<br>Gln | ggt<br>Gly<br>140 | aat<br>Asn | gtc<br>Val | 1454 |
| | aaa<br>Lys | aaa<br>Lys | agt<br>Ser | aaa<br>Lys<br>145 | caa<br>Gln | ctt<br>Leu | ctt<br>Leu | caa<br>Gln | aaa<br>Lys<br>150 | gct<br>Ala | gta<br>Val | gaa<br>Glu | cgt<br>Arg | gga<br>Gly<br>155 | gca<br>Ala | gta<br>Val | 1502 |
| | cca<br>Pro<br>160 | cta<br>Leu | gaa<br>Glu | atg<br>Met | ctg<br>Leu | gaa<br>Glu<br>165 | att<br>Ile | gcc<br>Ala | ctg<br>Leu | cgg<br>Arg | aat<br>Asn<br>170 | tta<br>Leu | aac<br>Asn | ctc<br>Leu | caa<br>Gln | aaa<br>Lys<br>175 | 1550 |
| | aag<br>Lys | cag<br>Gln | ctg<br>Leu | ctt<br>Leu | tca<br>Ser<br>180 | gag<br>Glu | gag<br>Glu | gaa<br>Glu | aag<br>Lys | aag<br>Lys<br>185 | aat<br>Asn | tta<br>Leu | tca<br>Ser | gca<br>Ala | tct<br>Ser<br>190 | acg<br>Thr | | 1598 |
| | gta<br>Val | tta<br>Leu | act<br>Thr | gcc<br>Ala<br>195 | caa<br>Gln | gaa<br>Glu | tca<br>Ser | ttt<br>Phe | tcc<br>Ser<br>200 | ggt<br>Gly | tca<br>Ser | ctt<br>Leu | ggg<br>Gly | cat<br>His<br>205 | tta<br>Leu | cag<br>Gln | 1646 |
| | aat<br>Asn | agg<br>Arg | aac<br>Asn | aac<br>Asn<br>210 | agt<br>Ser | tgt<br>Cys | gat<br>Asp | tcc<br>Ser | aga<br>Arg<br>215 | gga<br>Gly | cag<br>Gln | act<br>Thr | act<br>Thr | aaa<br>Lys<br>220 | gcc<br>Ala | agg<br>Arg | 1694 |
| | ttt<br>Phe | tta<br>Leu | tat<br>Tyr | gga<br>Gly<br>225 | gag<br>Glu | aac<br>Asn | atg<br>Met | cca<br>Pro | cca<br>Pro<br>230 | caa<br>Gln | gat<br>Asp | gca<br>Ala | gaa<br>Glu | ata<br>Ile<br>235 | ggt<br>Gly | tac<br>Tyr | 1742 |
| | cgg<br>Arg<br>240 | aat<br>Asn | tca<br>Ser | ttg<br>Leu | aga<br>Arg | caa<br>Gln<br>245 | act<br>Thr | aac<br>Asn | aaa<br>Lys | act<br>Thr | aaa<br>Lys<br>250 | cag<br>Gln | tca<br>Ser | tgc<br>Cys | cca<br>Pro | ttt<br>Phe<br>255 | 1790 |
| | gga<br>Gly | aga<br>Arg | gtc<br>Val | cca<br>Pro<br>260 | gtt<br>Val | aac<br>Asn | ctt<br>Leu | cta<br>Leu | aat<br>Asn<br>265 | agc<br>Ser | cca<br>Pro | gat<br>Asp | tgt<br>Cys | gat<br>Asp<br>270 | gtg<br>Val | aag<br>Lys | 1838 |
| | aca<br>Thr | gat<br>Asp | gat<br>Asp | tca<br>Ser<br>275 | gtt<br>Val | gta<br>Val | cct<br>Pro | tgt<br>Cys | ttt<br>Phe<br>280 | atg<br>Met | aaa<br>Lys | aga<br>Arg | caa<br>Gln | acc<br>Thr<br>285 | tct<br>Ser | aga<br>Arg | 1886 |
| | tca<br>Ser | gaa<br>Glu | tgc<br>Cys | cga<br>Arg<br>290 | gat<br>Asp | ttg<br>Leu | gtt<br>Val | gtg<br>Val | cct<br>Pro<br>295 | gga<br>Gly | tct<br>Ser | aaa<br>Lys | cca<br>Pro | agt<br>Ser<br>300 | gga<br>Gly | aat<br>Asn | 1934 |

-continued

| | |
|---|---|
| gat tcc tgt gaa tta aga aat tta aag tct gtt caa aat agt cat ttc<br>Asp Ser Cys Glu Leu Arg Asn Leu Lys Ser Val Gln Asn Ser His Phe<br>305     310     315 | 1982 |
| aag gaa cct ctg gtg tca gat gaa aag agt tct gaa ctt att att act<br>Lys Glu Pro Leu Val Ser Asp Glu Lys Ser Ser Glu Leu Ile Ile Thr<br>320    325     330     335 | 2030 |
| gat tca ata acc ctg aag aat aaa acg gaa tca agt ctt cta gct aaa<br>Asp Ser Ile Thr Leu Lys Asn Lys Thr Glu Ser Ser Leu Leu Ala Lys<br>    340     345     350 | 2078 |
| tta gaa gaa act aaa gag tat caa gaa cca gag gtt cca gag agt aac<br>Leu Glu Glu Thr Lys Glu Tyr Gln Glu Pro Glu Val Pro Glu Ser Asn<br>355     360     365 | 2126 |
| cag aaa cag tgg caa gct aag aga aag tca gag tgt att aac cag aat<br>Gln Lys Gln Trp Gln Ala Lys Arg Lys Ser Glu Cys Ile Asn Gln Asn<br>370     375     380 | 2174 |
| cct gct gca tct tca aat cac tgg cag att ccg gag tta gcc cga aaa<br>Pro Ala Ala Ser Ser Asn His Trp Gln Ile Pro Glu Leu Ala Arg Lys<br>385     390     395 | 2222 |
| gtt aat aca gag cag aaa cat acc act ttt gag caa cct gtc ttt tca<br>Val Asn Thr Glu Gln Lys His Thr Thr Phe Glu Gln Pro Val Phe Ser<br>400     405     410     415 | 2270 |
| gtt tca aaa cag tca cca cca ata tca aca tct aaa tgg ttt gac cca<br>Val Ser Lys Gln Ser Pro Pro Ile Ser Thr Ser Lys Trp Phe Asp Pro<br>    420     425     430 | 2318 |
| aaa tct att tgt aag aca cca agc agc aat acc ttg gat gat tac atg<br>Lys Ser Ile Cys Lys Thr Pro Ser Ser Asn Thr Leu Asp Asp Tyr Met<br>435     440     445 | 2366 |
| agc tgt ttt aga act cca gtt gta aag aat gac ttt cca cct gct tgt<br>Ser Cys Phe Arg Thr Pro Val Val Lys Asn Asp Phe Pro Pro Ala Cys<br>450     455     460 | 2414 |
| cag ttg tca aca cct tat ggc caa cct gcc tgt ttc cag cag caa cag<br>Gln Leu Ser Thr Pro Tyr Gly Gln Pro Ala Cys Phe Gln Gln Gln Gln<br>465     470     475 | 2462 |
| cat caa ata ctt gcc act cca ctt caa aat tta cag gtt tta gca tct<br>His Gln Ile Leu Ala Thr Pro Leu Gln Asn Leu Gln Val Leu Ala Ser<br>480     485     490     495 | 2510 |
| tct tca gca aat gaa tgc att tcg gtt aaa gga aga att tat tcc ata<br>Ser Ser Ala Asn Glu Cys Ile Ser Val Lys Gly Arg Ile Tyr Ser Ile<br>    500     505     510 | 2558 |
| tta aag cag ata gga agt gga ggt tca agc aag gta ttt cag gtg tta<br>Leu Lys Gln Ile Gly Ser Gly Gly Ser Ser Lys Val Phe Gln Val Leu<br>515     520     525 | 2606 |
| aat gaa aag aaa cag ata tat gct ata aaa tat gtg aac tta gaa gaa<br>Asn Glu Lys Lys Gln Ile Tyr Ala Ile Lys Tyr Val Asn Leu Glu Glu<br>530     535     540 | 2654 |
| gca gat aac caa act ctt gat agt tac cgg aac gaa ata gct tat ttg<br>Ala Asp Asn Gln Thr Leu Asp Ser Tyr Arg Asn Glu Ile Ala Tyr Leu<br>545     550     555 | 2702 |
| aat aaa cta caa caa cac agt gat aag atc atc cga ctt tat gat tat<br>Asn Lys Leu Gln Gln His Ser Asp Lys Ile Ile Arg Leu Tyr Asp Tyr<br>560     565     570     575 | 2750 |
| gaa atc acg gac cag tac atc tac atg gta atg gag tgt gga aat att<br>Glu Ile Thr Asp Gln Tyr Ile Tyr Met Val Met Glu Cys Gly Asn Ile<br>    580     585     590 | 2798 |
| gat ctt aat agt tgg ctt aaa aag aaa aaa tcc att gat cca tgg gaa<br>Asp Leu Asn Ser Trp Leu Lys Lys Lys Lys Ser Ile Asp Pro Trp Glu<br>595     600     605 | 2846 |
| cgc aag agt tac tgg aaa aat atg tta gag gca gtt cac aca atc cat<br>Arg Lys Ser Tyr Trp Lys Asn Met Leu Glu Ala Val His Thr Ile His<br>610     615     620 | 2894 |

```
caa cat ggc att gtt cac agt gat ctt aaa cca gct aac ttt ctg ata    2942
Gln His Gly Ile Val His Ser Asp Leu Lys Pro Ala Asn Phe Leu Ile
    625                 630                 635 gtt gat gga atg cta aag cta att gat ttt ggg att gca aac caa atg    2990
Val Asp Gly Met Leu Lys Leu Ile Asp Phe Gly Ile Ala Asn Gln Met
640                 645                 650                 655 caa cca gat aca aca agt gtt gtt aaa gat tct cag gtt ggc aca gtt    3038
Gln Pro Asp Thr Thr Ser Val Val Lys Asp Ser Gln Val Gly Thr Val
                660                 665                 670 aat tat atg cca cca gaa gca atc aaa gat atg tct tcc aga gag        3086
Asn Tyr Met Pro Pro Glu Ala Ile Lys Asp Met Ser Ser Ser Arg Glu
            675                 680                 685 aat ggg aaa tct aag tca aag ata agc ccc aaa agt gat gtt tgg tcc    3134
Asn Gly Lys Ser Lys Ser Lys Ile Ser Pro Lys Ser Asp Val Trp Ser
        690                 695                 700 tta gga tgt att ttg tac tat atg act tac ggg aaa aca cca ttt cag    3182
Leu Gly Cys Ile Leu Tyr Tyr Met Thr Tyr Gly Lys Thr Pro Phe Gln
    705                 710                 715 cag ata att aat cag att tct aaa tta cat gcc ata att gat cct aat    3230
Gln Ile Ile Asn Gln Ile Ser Lys Leu His Ala Ile Ile Asp Pro Asn
720                 725                 730                 735 cat gaa att gaa ttt ccc gat att cca gag aaa gat ctt caa gat gtg    3278
His Glu Ile Glu Phe Pro Asp Ile Pro Glu Lys Asp Leu Gln Asp Val
                740                 745                 750 tta aag tgt tgt tta aaa agg gac cca aaa cag agg ata tcc att cct    3326
Leu Lys Cys Cys Leu Lys Arg Asp Pro Lys Gln Arg Ile Ser Ile Pro
            755                 760                 765 gag ctc ctg gct cat cca tat gtt caa att caa act cat cca gtt aac    3374
Glu Leu Leu Ala His Pro Tyr Val Gln Ile Gln Thr His Pro Val Asn
        770                 775                 780 caa atg gcc aag gga acc act gaa gaa atg aaa tat gtt ctg ggc caa    3422
Gln Met Ala Lys Gly Thr Thr Glu Glu Met Lys Tyr Val Leu Gly Gln
    785                 790                 795 ctt gtt ggt ctg aat tct cct aac tcc att ttg aaa gct gct aaa act    3470
Leu Val Gly Leu Asn Ser Pro Asn Ser Ile Leu Lys Ala Ala Lys Thr
800                 805                 810                 815 tta tat gaa cac tat agt ggt ggt gaa agt cat aat tct tca tcc tcc    3518
Leu Tyr Glu His Tyr Ser Gly Gly Glu Ser His Asn Ser Ser Ser Ser
                820                 825                 830 aag act ttt gaa aaa aaa agg gga aaa aaa tga tttgcagtta ttcgtaatgt  3571
Lys Thr Phe Glu Lys Lys Arg Gly Lys Lys  *
            835                 840 cagataggag gtataaaata tattggactg ttatactctt gaatccctgt ggaaatctac  3631
atttgaagac aacatcactc tgaagtgtta tcagcaaaaa aaattcagtg agattatctt  3691
taaaagaaaa ctgtaaaaat agcaaccact tatggcactg tatatattgt agacttgttt  3751
tctctgtttt atgctcttgt gtaatctact tgacatcatt ttactcttgg aatagtgggt  3811
ggatagcaag tatattctaa aaaactttgt aaataaagtt ttgtggctaa aatga        3866

<210> SEQ ID NO 14
<211> LENGTH: 841
<212> TYPE: PRT
<213> ORGANISM: Homo sapiens

<400> SEQUENCE: 14

Met Asn Lys Val Arg Asp Ile Lys Asn Lys Phe Lys Asn Glu Asp Leu
1               5                   10                  15

Thr Asp Glu Leu Ser Leu Asn Lys Ile Ser Ala Asp Thr Thr Asp Asn
```

-continued

```
                20                  25                  30
Ser Gly Thr Val Asn Gln Ile Met Met Ala Asn Asn Pro Glu Asp
            35                  40                  45

Trp Leu Ser Leu Leu Leu Lys Leu Glu Lys Asn Ser Val Pro Leu Ser
 50                  55                  60

Asp Ala Leu Leu Asn Lys Leu Ile Gly Arg Tyr Ser Gln Ala Ile Glu
 65                  70                  75                  80

Ala Leu Pro Pro Asp Lys Tyr Gly Gln Asn Glu Ser Phe Ala Arg Ile
                85                  90                  95

Gln Val Arg Phe Ala Glu Leu Lys Ala Ile Gln Glu Pro Asp Asp Ala
                100                 105                 110

Arg Asp Tyr Phe Gln Met Ala Arg Ala Asn Cys Lys Lys Phe Ala Phe
                115                 120                 125

Val His Ile Ser Phe Ala Gln Phe Glu Leu Ser Gln Gly Asn Val Lys
                130                 135                 140

Lys Ser Lys Gln Leu Leu Gln Lys Ala Val Glu Arg Gly Ala Val Pro
145                 150                 155                 160

Leu Glu Met Leu Glu Ile Ala Leu Arg Asn Leu Asn Leu Gln Lys Lys
                165                 170                 175

Gln Leu Leu Ser Glu Glu Lys Lys Asn Leu Ser Ala Ser Thr Val
                180                 185                 190

Leu Thr Ala Gln Glu Ser Phe Ser Gly Ser Leu Gly His Leu Gln Asn
                195                 200                 205

Arg Asn Asn Ser Cys Asp Ser Arg Gly Gln Thr Thr Lys Ala Arg Phe
                210                 215                 220

Leu Tyr Gly Glu Asn Met Pro Pro Gln Asp Ala Glu Ile Gly Tyr Arg
225                 230                 235                 240

Asn Ser Leu Arg Gln Thr Asn Lys Thr Lys Gln Ser Cys Pro Phe Gly
                245                 250                 255

Arg Val Pro Val Asn Leu Leu Asn Ser Pro Asp Cys Asp Val Lys Thr
                260                 265                 270

Asp Asp Ser Val Val Pro Cys Phe Met Lys Arg Gln Thr Ser Arg Ser
                275                 280                 285

Glu Cys Arg Asp Leu Val Val Pro Gly Ser Lys Pro Ser Gly Asn Asp
                290                 295                 300

Ser Cys Glu Leu Arg Asn Leu Lys Ser Val Gln Asn Ser His Phe Lys
305                 310                 315                 320

Glu Pro Leu Val Ser Asp Glu Lys Ser Ser Glu Leu Ile Ile Thr Asp
                325                 330                 335

Ser Ile Thr Leu Lys Asn Lys Thr Glu Ser Ser Leu Leu Ala Lys Leu
                340                 345                 350

Glu Glu Thr Lys Glu Tyr Gln Glu Pro Glu Val Pro Glu Ser Asn Gln
                355                 360                 365

Lys Gln Trp Gln Ala Lys Arg Lys Ser Glu Cys Ile Asn Gln Asn Pro
                370                 375                 380

Ala Ala Ser Ser Asn His Trp Gln Ile Pro Glu Leu Ala Arg Lys Val
385                 390                 395                 400

Asn Thr Glu Gln Lys His Thr Thr Phe Glu Gln Pro Val Phe Ser Val
                405                 410                 415

Ser Lys Gln Ser Pro Pro Ile Ser Thr Ser Lys Trp Phe Asp Pro Lys
                420                 425                 430

Ser Ile Cys Lys Thr Pro Ser Ser Asn Thr Leu Asp Asp Tyr Met Ser
                435                 440                 445
```

```
Cys Phe Arg Thr Pro Val Val Lys Asn Asp Phe Pro Pro Ala Cys Gln
    450                 455                 460

Leu Ser Thr Pro Tyr Gly Gln Pro Ala Cys Phe Gln Gln Gln His
465                 470                 475                 480

Gln Ile Leu Ala Thr Pro Leu Gln Asn Leu Gln Val Leu Ala Ser Ser
                    485                 490                 495

Ser Ala Asn Glu Cys Ile Ser Val Lys Gly Arg Ile Tyr Ser Ile Leu
                500                 505                 510

Lys Gln Ile Gly Ser Gly Gly Ser Ser Lys Val Phe Gln Val Leu Asn
            515                 520                 525

Glu Lys Lys Gln Ile Tyr Ala Ile Lys Tyr Val Asn Leu Glu Glu Ala
        530                 535                 540

Asp Asn Gln Thr Leu Asp Ser Tyr Arg Asn Glu Ile Ala Tyr Leu Asn
545                 550                 555                 560

Lys Leu Gln Gln His Ser Asp Lys Ile Ile Arg Leu Tyr Asp Tyr Glu
                    565                 570                 575

Ile Thr Asp Gln Tyr Ile Tyr Met Val Met Glu Cys Gly Asn Ile Asp
                580                 585                 590

Leu Asn Ser Trp Leu Lys Lys Lys Ser Ile Asp Pro Trp Glu Arg
            595                 600                 605

Lys Ser Tyr Trp Lys Asn Met Leu Glu Ala Val His Thr Ile His Gln
        610                 615                 620

His Gly Ile Val His Ser Asp Leu Lys Pro Ala Asn Phe Leu Ile Val
625                 630                 635                 640

Asp Gly Met Leu Lys Leu Ile Asp Phe Gly Ile Ala Asn Gln Met Gln
                    645                 650                 655

Pro Asp Thr Thr Ser Val Val Lys Asp Ser Gln Val Gly Thr Val Asn
                660                 665                 670

Tyr Met Pro Pro Glu Ala Ile Lys Asp Met Ser Ser Ser Arg Glu Asn
            675                 680                 685

Gly Lys Ser Lys Ser Lys Ile Ser Pro Lys Ser Asp Val Trp Ser Leu
        690                 695                 700

Gly Cys Ile Leu Tyr Tyr Met Thr Tyr Gly Lys Thr Pro Phe Gln Gln
705                 710                 715                 720

Ile Ile Asn Gln Ile Ser Lys Leu His Ala Ile Asp Pro Asn His
                    725                 730                 735

Glu Ile Glu Phe Pro Asp Ile Pro Glu Lys Asp Leu Gln Asp Val Leu
                740                 745                 750

Lys Cys Cys Leu Lys Arg Asp Pro Lys Gln Arg Ile Ser Ile Pro Glu
            755                 760                 765

Leu Leu Ala His Pro Tyr Val Gln Ile Gln Thr His Pro Val Asn Gln
        770                 775                 780

Met Ala Lys Gly Thr Thr Glu Glu Met Lys Tyr Val Leu Gly Gln Leu
785                 790                 795                 800

Val Gly Leu Asn Ser Pro Asn Ser Ile Leu Lys Ala Ala Lys Thr Leu
                    805                 810                 815

Tyr Glu His Tyr Ser Gly Gly Glu Ser His Asn Ser Ser Ser Ser Lys
                820                 825                 830

Thr Phe Glu Lys Lys Arg Gly Lys Lys
            835                 840

<210> SEQ ID NO 15
<211> LENGTH: 2735
```

```
<212> TYPE: DNA
<213> ORGANISM: Saccharomyces cerevisiae
<220> FEATURE:
<221> NAME/KEY: CDS
<222> LOCATION: (34)...(2499)

<400> SEQUENCE: 15
agaaaagata gtgttacaca acatcaacta aaa atg gaa aat att aca caa ccc        54
                                     Met Glu Asn Ile Thr Gln Pro
                                      1               5 aca cag caa tcc acg cag gct act caa agg ttt ttg att gag aag ttt        102
Thr Gln Gln Ser Thr Gln Ala Thr Gln Arg Phe Leu Ile Glu Lys Phe
         10                  15                  20 tct caa gaa cag atc ggc gaa aac att gtg tgc agg gtc att tgt acc        150
Ser Gln Glu Gln Ile Gly Glu Asn Ile Val Cys Arg Val Ile Cys Thr
 25                  30                  35 acg ggt caa att ccc atc cga gat ttg tca gct gat att tca caa gtg        198
Thr Gly Gln Ile Pro Ile Arg Asp Leu Ser Ala Asp Ile Ser Gln Val
 40                  45                  50                  55 ctt aag gaa aaa cga tcc ata aag aaa gtt tgg aca ttt ggt aga aac        246
Leu Lys Glu Lys Arg Ser Ile Lys Lys Val Trp Thr Phe Gly Arg Asn
                 60                  65                  70 cca gcc tgt gac tat cat tta gga aac att tca aga ctg tca aat aag        294
Pro Ala Cys Asp Tyr His Leu Gly Asn Ile Ser Arg Leu Ser Asn Lys
             75                  80                  85 cat ttc caa ata cta cta gga gaa gac ggt aac ctt tta ttg aat gac        342
His Phe Gln Ile Leu Leu Gly Glu Asp Gly Asn Leu Leu Leu Asn Asp
         90                  95                 100 att tcc act aat ggg acc tgg tta aat ggg caa aaa gtc gag aag aac        390
Ile Ser Thr Asn Gly Thr Trp Leu Asn Gly Gln Lys Val Glu Lys Asn
    105                 110                 115 agc aat cag tta ctg tct caa ggt gat gaa ata acc gtt ggt gta ggc        438
Ser Asn Gln Leu Leu Ser Gln Gly Asp Glu Ile Thr Val Gly Val Gly
120                 125                 130                 135 gtg gaa tca gat att tta tct ctg gtc att ttc ata aac gac aaa ttt        486
Val Glu Ser Asp Ile Leu Ser Leu Val Ile Phe Ile Asn Asp Lys Phe
                140                 145                 150 aag cag tgc ctc gag cag aac aaa gtt gat cgc ata aga tct aac ctg        534
Lys Gln Cys Leu Glu Gln Asn Lys Val Asp Arg Ile Arg Ser Asn Leu
            155                 160                 165 aaa aat acc tct aaa ata gct tct cct ggt ctt aca tca tct act gca        582
Lys Asn Thr Ser Lys Ile Ala Ser Pro Gly Leu Thr Ser Ser Thr Ala
        170                 175                 180 tca tca atg gtg gcc aac aag act ggt att ttt aag gat ttt tcg att        630
Ser Ser Met Val Ala Asn Lys Thr Gly Ile Phe Lys Asp Phe Ser Ile
    185                 190                 195 att gac gaa gtg gtg ggc cag ggt gca ttt gcc aca gta aag aaa gcc        678
Ile Asp Glu Val Val Gly Gln Gly Ala Phe Ala Thr Val Lys Lys Ala
200                 205                 210                 215 att gaa aga act act ggg aaa aca ttc gcg gtg aag att ata agt aaa        726
Ile Glu Arg Thr Thr Gly Lys Thr Phe Ala Val Lys Ile Ile Ser Lys
                220                 225                 230 cgc aaa gta ata ggc aat atg gat ggt gtg aca aga gag tta gaa gta        774
Arg Lys Val Ile Gly Asn Met Asp Gly Val Thr Arg Glu Leu Glu Val
            235                 240                 245 ttg caa aag ctc aat cat cca agg ata gta cga ttg aaa gga ttt tat        822
Leu Gln Lys Leu Asn His Pro Arg Ile Val Arg Leu Lys Gly Phe Tyr
        250                 255                 260 gaa gat act gag agt tat tat atg gtg atg gag ttc gtt tct ggt ggt        870
Glu Asp Thr Glu Ser Tyr Tyr Met Val Met Glu Phe Val Ser Gly Gly
    265                 270                 275
```

```
gac tta atg gat ttt gtt gct gct cat ggt gcg gtt gga gaa gat gct      918
Asp Leu Met Asp Phe Val Ala Ala His Gly Ala Val Gly Glu Asp Ala
280                 285                 290                 295 ggg agg gag ata tcc agg cag ata ctc aca gca ata aaa tac att cac      966
Gly Arg Glu Ile Ser Arg Gln Ile Leu Thr Ala Ile Lys Tyr Ile His
                300                 305                 310 tct atg ggc atc agc cat cgt gac cta aag ccc gat aat att ctt att     1014
Ser Met Gly Ile Ser His Arg Asp Leu Lys Pro Asp Asn Ile Leu Ile
            315                 320                 325 gaa caa gac gat cct gta ttg gta aag ata acc gac ttt ggt ctg gca     1062
Glu Gln Asp Asp Pro Val Leu Val Lys Ile Thr Asp Phe Gly Leu Ala
        330                 335                 340 aaa gta caa gga aat ggg tct ttt atg aaa acc ttc tgt ggc act ttg     1110
Lys Val Gln Gly Asn Gly Ser Phe Met Lys Thr Phe Cys Gly Thr Leu
    345                 350                 355 gca tat gtg gca cct gaa gtc atc aga ggt aaa gat aca tcc gta tct     1158
Ala Tyr Val Ala Pro Glu Val Ile Arg Gly Lys Asp Thr Ser Val Ser
360                 365                 370                 375 cct gat gaa tac gaa gaa agg aat gag tac tct tcg tta gtg gat atg     1206
Pro Asp Glu Tyr Glu Glu Arg Asn Glu Tyr Ser Ser Leu Val Asp Met
                380                 385                 390 tgg tca atg gga tgt ctt gtg tat gtt atc cta acg ggc cac tta cct     1254
Trp Ser Met Gly Cys Leu Val Tyr Val Ile Leu Thr Gly His Leu Pro
            395                 400                 405 ttt agt ggt agc aca cag gac caa tta tat aaa cag att gga aga ggc     1302
Phe Ser Gly Ser Thr Gln Asp Gln Leu Tyr Lys Gln Ile Gly Arg Gly
        410                 415                 420 tca tat cat gaa ggg ccc ctc aaa gat ttc cgg ata tct gaa gaa gca     1350
Ser Tyr His Glu Gly Pro Leu Lys Asp Phe Arg Ile Ser Glu Glu Ala
    425                 430                 435 aga gat ttc ata gat tca ttg tta cag gtg gat cca aat aat agg tcg     1398
Arg Asp Phe Ile Asp Ser Leu Leu Gln Val Asp Pro Asn Asn Arg Ser
440                 445                 450                 455 aca gct gca aaa gcc ttg aat cat ccc tgg atc aag atg agt cca ttg     1446
Thr Ala Ala Lys Ala Leu Asn His Pro Trp Ile Lys Met Ser Pro Leu
                460                 465                 470 ggc tca caa tca tat ggt gat ttt tca caa ata tcc tta tca caa tcg     1494
Gly Ser Gln Ser Tyr Gly Asp Phe Ser Gln Ile Ser Leu Ser Gln Ser
            475                 480                 485 ttg tcg cag cag aaa tta tta gaa aat atg gac gat gct caa tac gaa     1542
Leu Ser Gln Gln Lys Leu Leu Glu Asn Met Asp Asp Ala Gln Tyr Glu
        490                 495                 500 ttt gtc aaa gcg caa agg aaa tta caa atg gag caa caa ctt caa gaa     1590
Phe Val Lys Ala Gln Arg Lys Leu Gln Met Glu Gln Gln Leu Gln Glu
    505                 510                 515 cag gat cag gaa gac caa gat gga aaa att caa gga ttt aaa ata ccc     1638
Gln Asp Gln Glu Asp Gln Asp Gly Lys Ile Gln Gly Phe Lys Ile Pro
520                 525                 530                 535 gca cac gcc cct att cga tat aca cag ccc aaa agc att gaa gca gaa     1686
Ala His Ala Pro Ile Arg Tyr Thr Gln Pro Lys Ser Ile Glu Ala Glu
                540                 545                 550 act aga gaa caa aaa ctt tta cat tcc aat aat act gag aat gtc aag     1734
Thr Arg Glu Gln Lys Leu Leu His Ser Asn Asn Thr Glu Asn Val Lys
            555                 560                 565 agc tca aag aaa aag ggt aat ggt agg ttt tta act tta aaa cca ttg     1782
Ser Ser Lys Lys Lys Gly Asn Gly Arg Phe Leu Thr Leu Lys Pro Leu
        570                 575                 580 cct gac agc att att caa gaa agc ctg gag att cag caa ggt gtg aat     1830
Pro Asp Ser Ile Ile Gln Glu Ser Leu Glu Ile Gln Gln Gly Val Asn
```

-continued

```
                585                 590                 595
cca ttt ttc att ggt aga tcc gag gat tgc aat tgt aaa att gaa gac    1878
Pro Phe Phe Ile Gly Arg Ser Glu Asp Cys Asn Cys Lys Ile Glu Asp
600                 605                 610                 615 aat agg ttg tct cga gtt cat tgc ttc att ttc aaa aag agg cat gct    1926
Asn Arg Leu Ser Arg Val His Cys Phe Ile Phe Lys Lys Arg His Ala
                620                 625                 630 gta ggc aaa agc atg tat gaa tct ccg gca caa ggt tta gat gat att    1974
Val Gly Lys Ser Met Tyr Glu Ser Pro Ala Gln Gly Leu Asp Asp Ile
            635                 640                 645 tgg tat tgc cac acc gga act aac gtg agc tat tta aat aat aac cgc    2022
Trp Tyr Cys His Thr Gly Thr Asn Val Ser Tyr Leu Asn Asn Asn Arg
        650                 655                 660 atg ata cag ggt acg aaa ttc ctt tta caa gac gga gat gaa atc aag    2070
Met Ile Gln Gly Thr Lys Phe Leu Leu Gln Asp Gly Asp Glu Ile Lys
    665                 670                 675 atc att tgg gat aaa aac aat aaa ttt gtc att ggc ttt aaa gtg gaa    2118
Ile Ile Trp Asp Lys Asn Asn Lys Phe Val Ile Gly Phe Lys Val Glu
680                 685                 690                 695 att aac gat act aca ggt ctg ttt aac gag gga tta ggt atg tta caa    2166
Ile Asn Asp Thr Thr Gly Leu Phe Asn Glu Gly Leu Gly Met Leu Gln
                700                 705                 710 gaa caa aga gta gta ctt aag caa aca gcc gaa gaa aaa gat ttg gtg    2214
Glu Gln Arg Val Val Leu Lys Gln Thr Ala Glu Glu Lys Asp Leu Val
            715                 720                 725 aaa aag tta acc cag atg atg gca gct caa cgt gca aat caa ccc tcg    2262
Lys Lys Leu Thr Gln Met Met Ala Ala Gln Arg Ala Asn Gln Pro Ser
        730                 735                 740 gct tct tct tca tca atg tcg gct aag aag ccg cca gtt agc gat aca    2310
Ala Ser Ser Ser Ser Met Ser Ala Lys Lys Pro Pro Val Ser Asp Thr
    745                 750                 755 aat aat aac ggc aat aat tcg gta cta aac gac ttg gta gag tca ccg    2358
Asn Asn Asn Gly Asn Asn Ser Val Leu Asn Asp Leu Val Glu Ser Pro
760                 765                 770                 775 att aat gcg aat acg ggg aac att ttg aag aga ata cat tcg gta agt    2406
Ile Asn Ala Asn Thr Gly Asn Ile Leu Lys Arg Ile His Ser Val Ser
                780                 785                 790 tta tcg caa tca caa att gat cct agt aag aag gtt aaa agg gca aaa    2454
Leu Ser Gln Ser Gln Ile Asp Pro Ser Lys Lys Val Lys Arg Ala Lys
            795                 800                 805 ttg gac caa acc tca aaa ggc ccc gag aat ttg caa ttt tcg taa        2499
Leu Asp Gln Thr Ser Lys Gly Pro Glu Asn Leu Gln Phe Ser *
        810                 815                 820 ccaaggacaa atacccatag aaaatgctgc ccctttttaa gagagaagat ggtagatacc   2559
aatactcaga attcccagta caaagaacca atatcggagt caataaacag tatgatgaac   2619
ttgctttcgc aaataaaaga tatcactcag aagcacccag taataaagga tgcagatagc   2679
tcgagatttg gtaaggttga gtttagggac ttttatgacg aagtttcacg gaattc       2735

<210> SEQ ID NO 16
<211> LENGTH: 821
<212> TYPE: PRT
<213> ORGANISM: Saccharomyces cerevisiae

<400> SEQUENCE: 16

Met Glu Asn Ile Thr Gln Pro Thr Gln Gln Ser Thr Gln Ala Thr Gln
1               5                   10                  15

Arg Phe Leu Ile Glu Lys Phe Ser Gln Glu Gln Ile Gly Glu Asn Ile
            20                  25                  30
```

-continued

```
Val Cys Arg Val Ile Cys Thr Thr Gly Gln Ile Pro Ile Arg Asp Leu
             35                  40                  45

Ser Ala Asp Ile Ser Gln Val Leu Lys Glu Lys Arg Ser Ile Lys Lys
 50                  55                  60

Val Trp Thr Phe Gly Arg Asn Pro Ala Cys Asp Tyr His Leu Gly Asn
 65                  70                  75                  80

Ile Ser Arg Leu Ser Asn Lys His Phe Gln Ile Leu Leu Gly Glu Asp
             85                  90                  95

Gly Asn Leu Leu Leu Asn Asp Ile Ser Thr Asn Gly Thr Trp Leu Asn
            100                 105                 110

Gly Gln Lys Val Glu Lys Asn Ser Asn Gln Leu Leu Ser Gln Gly Asp
            115                 120                 125

Glu Ile Thr Val Gly Val Gly Val Glu Ser Asp Ile Leu Ser Leu Val
            130                 135                 140

Ile Phe Ile Asn Asp Lys Phe Lys Gln Cys Leu Glu Gln Asn Lys Val
145                 150                 155                 160

Asp Arg Ile Arg Ser Asn Leu Lys Asn Thr Ser Lys Ile Ala Ser Pro
                165                 170                 175

Gly Leu Thr Ser Ser Thr Ala Ser Ser Met Val Ala Asn Lys Thr Gly
            180                 185                 190

Ile Phe Lys Asp Phe Ser Ile Ile Asp Glu Val Val Gly Gln Gly Ala
            195                 200                 205

Phe Ala Thr Val Lys Lys Ala Ile Glu Arg Thr Thr Gly Lys Thr Phe
            210                 215                 220

Ala Val Lys Ile Ile Ser Lys Arg Lys Val Ile Gly Asn Met Asp Gly
225                 230                 235                 240

Val Thr Arg Glu Leu Glu Val Leu Gln Lys Leu Asn His Pro Arg Ile
                245                 250                 255

Val Arg Leu Lys Gly Phe Tyr Glu Asp Thr Glu Ser Tyr Tyr Met Val
                260                 265                 270

Met Glu Phe Val Ser Gly Gly Asp Leu Met Asp Phe Val Ala Ala His
            275                 280                 285

Gly Ala Val Gly Glu Asp Ala Gly Arg Glu Ile Ser Arg Gln Ile Leu
            290                 295                 300

Thr Ala Ile Lys Tyr Ile His Ser Met Gly Ile Ser His Arg Asp Leu
305                 310                 315                 320

Lys Pro Asp Asn Ile Leu Ile Glu Gln Asp Asp Pro Val Leu Val Lys
                325                 330                 335

Ile Thr Asp Phe Gly Leu Ala Lys Val Gln Gly Asn Gly Ser Phe Met
            340                 345                 350

Lys Thr Phe Cys Gly Thr Leu Ala Tyr Val Ala Pro Glu Val Ile Arg
            355                 360                 365

Gly Lys Asp Thr Ser Val Ser Pro Asp Glu Tyr Glu Glu Arg Asn Glu
            370                 375                 380

Tyr Ser Ser Leu Val Asp Met Trp Ser Met Gly Cys Leu Val Tyr Val
385                 390                 395                 400

Ile Leu Thr Gly His Leu Pro Phe Ser Gly Ser Thr Gln Asp Gln Leu
                405                 410                 415

Tyr Lys Gln Ile Gly Arg Gly Ser Tyr His Glu Gly Pro Leu Lys Asp
            420                 425                 430

Phe Arg Ile Ser Glu Glu Ala Arg Asp Phe Ile Asp Ser Leu Leu Gln
            435                 440                 445
```

```
Val Asp Pro Asn Asn Arg Ser Thr Ala Ala Lys Ala Leu Asn His Pro
    450                 455                 460

Trp Ile Lys Met Ser Pro Leu Gly Ser Gln Ser Tyr Gly Asp Phe Ser
465                 470                 475                 480

Gln Ile Ser Leu Ser Gln Ser Leu Ser Gln Lys Leu Leu Glu Asn
                485                 490                 495

Met Asp Asp Ala Gln Tyr Glu Phe Val Lys Ala Gln Arg Lys Leu Gln
            500                 505                 510

Met Glu Gln Gln Leu Gln Glu Gln Asp Gln Glu Asp Gln Asp Gly Lys
        515                 520                 525

Ile Gln Gly Phe Lys Ile Pro Ala His Ala Pro Ile Arg Tyr Thr Gln
    530                 535                 540

Pro Lys Ser Ile Glu Ala Glu Thr Arg Glu Gln Lys Leu Leu His Ser
545                 550                 555                 560

Asn Asn Thr Glu Asn Val Lys Ser Ser Lys Lys Gly Asn Gly Arg
                565                 570                 575

Phe Leu Thr Leu Lys Pro Leu Pro Asp Ser Ile Ile Gln Glu Ser Leu
            580                 585                 590

Glu Ile Gln Gln Gly Val Asn Pro Phe Phe Ile Gly Arg Ser Glu Asp
        595                 600                 605

Cys Asn Cys Lys Ile Glu Asp Asn Arg Leu Ser Arg Val His Cys Phe
    610                 615                 620

Ile Phe Lys Lys Arg His Ala Val Gly Lys Ser Met Tyr Glu Ser Pro
625                 630                 635                 640

Ala Gln Gly Leu Asp Asp Ile Trp Tyr Cys His Thr Gly Thr Asn Val
                645                 650                 655

Ser Tyr Leu Asn Asn Asn Arg Met Ile Gln Gly Thr Lys Phe Leu Leu
            660                 665                 670

Gln Asp Gly Asp Glu Ile Lys Ile Ile Trp Asp Lys Asn Asn Lys Phe
        675                 680                 685

Val Ile Gly Phe Lys Val Glu Ile Asn Asp Thr Thr Gly Leu Phe Asn
    690                 695                 700

Glu Gly Leu Gly Met Leu Gln Glu Gln Arg Val Val Leu Lys Gln Thr
705                 710                 715                 720

Ala Glu Glu Lys Asp Leu Val Lys Lys Leu Thr Gln Met Met Ala Ala
                725                 730                 735

Gln Arg Ala Asn Gln Pro Ser Ala Ser Ser Ser Met Ser Ala Lys
            740                 745                 750

Lys Pro Pro Val Ser Asp Thr Asn Asn Gly Asn Asn Ser Val Leu
        755                 760                 765

Asn Asp Leu Val Glu Ser Pro Ile Asn Ala Asn Thr Gly Asn Ile Leu
    770                 775                 780

Lys Arg Ile His Ser Val Ser Leu Ser Gln Ser Gln Ile Asp Pro Ser
785                 790                 795                 800

Lys Lys Val Lys Arg Ala Lys Leu Asp Gln Thr Ser Lys Gly Pro Glu
                805                 810                 815

Asn Leu Gln Phe Ser
            820

<210> SEQ ID NO 17
<211> LENGTH: 2525
<212> TYPE: DNA
<213> ORGANISM: Homo sapiens
<220> FEATURE:
<221> NAME/KEY: CDS
```

<222> LOCATION: (289)...(1230)

<400> SEQUENCE: 17

| | |
|---|---:|
| tcctgccccg cggcgctgcc gcacgagccc cacgagccgc tcaccccgcc gttctcagcg | 60 |
| ctgcccgacc ccgctggcgc gccctcccgc cgccagtccc ggcagcgccc tcagttgtcc | 120 |
| tccgactcgc cctcggcctt ccgcgccagc cgcagccaca gccgcaacgc caccgcagc | 180 |
| cacagccaca gccacagccc caggcatagc cttcggcaca gccccggctc cggctcctgc | 240 |
| ggcagctcct ctgggcaccg tccctgcgcc gacatcctgg aggttggg atg ctc ttg | 297 |
|                                                                                                                               Met Leu Leu | |
|                                                                                                                                1 | |
| tcc aaa atc aac tcg ctt gcc cac ctg cgc gcc gcg ccc tgc aac gac | 345 |
| Ser Lys Ile Asn Ser Leu Ala His Leu Arg Ala Ala Pro Cys Asn Asp | |
|   5                       10                      15 | |
| ctg cac gcc acc aag ctg gcg ccc ggc aag gag aag gag ccc ctg gag | 393 |
| Leu His Ala Thr Lys Leu Ala Pro Gly Lys Glu Lys Glu Pro Leu Glu | |
| 20                       25                      30                      35 | |
| tcg cag tac cag gtg ggc ccg cta ctg ggc agc ggc ggc ttc ggc tcg | 441 |
| Ser Gln Tyr Gln Val Gly Pro Leu Leu Gly Ser Gly Gly Phe Gly Ser | |
|                  40                      45                      50 | |
| gtc tac tca ggc atc cgc gtc tcc gac aac ttg ccg gtg gcc atc aaa | 489 |
| Val Tyr Ser Gly Ile Arg Val Ser Asp Asn Leu Pro Val Ala Ile Lys | |
|          55                      60                      65 | |
| cac gtg gag aag gac cgg att tcc gac tgg gga gag ctg cct aat ggc | 537 |
| His Val Glu Lys Asp Arg Ile Ser Asp Trp Gly Glu Leu Pro Asn Gly | |
|         70                     75                      80 | |
| act cga gtg ccc atg gaa gtg gtc ctg ctg aag aag gtg agc tcg ggt | 585 |
| Thr Arg Val Pro Met Glu Val Val Leu Leu Lys Lys Val Ser Ser Gly | |
| 85                       90                      95 | |
| ttc tcc ggc gtc att agg ctc ctg gac tgg ttc gag agg ccc gac agt | 633 |
| Phe Ser Gly Val Ile Arg Leu Leu Asp Trp Phe Glu Arg Pro Asp Ser | |
| 100                    105                  110                115 | |
| ttc gtc ctg atc ctg gag agg ccc gag ccg gtg caa gat ctc ttc gac | 681 |
| Phe Val Leu Ile Leu Glu Arg Pro Glu Pro Val Gln Asp Leu Phe Asp | |
|                  120                  125                130 | |
| ttc atc acg gaa agg gga gcc ctg caa gag gag ctc gcc cgc agc ttc | 729 |
| Phe Ile Thr Glu Arg Gly Ala Leu Gln Glu Glu Leu Ala Arg Ser Phe | |
|              135                  140                145 | |
| ttc tgg cag gtg ctg gag gcc gtg cgg cac tgc cac aac tgc ggg gtg | 777 |
| Phe Trp Gln Val Leu Glu Ala Val Arg His Cys His Asn Cys Gly Val | |
|          150                     155                  160 | |
| ctc cac cgc gac atc aag gac gaa aac atc ctt atc gac ctc aat cgc | 825 |
| Leu His Arg Asp Ile Lys Asp Glu Asn Ile Leu Ile Asp Leu Asn Arg | |
| 165                    170                  175 | |
| ggc gag ctc aag ctc atc gac ttc ggg tcg ggg gcg ctg ctc aaa gac | 873 |
| Gly Glu Leu Lys Leu Ile Asp Phe Gly Ser Gly Ala Leu Leu Lys Asp | |
| 180                    185                  190                195 | |
| acc gtc tac acg gac ttc gat ggg acc cga gtg tat agc cct cca gag | 921 |
| Thr Val Tyr Thr Asp Phe Asp Gly Thr Arg Val Tyr Ser Pro Pro Glu | |
|                200                  205                210 | |
| tgg atc cgc tac cat cgc tac cat ggc agg tcg gcg gca gtc tgg tcc | 969 |
| Trp Ile Arg Tyr His Arg Tyr His Gly Arg Ser Ala Ala Val Trp Ser | |
|              215                  220                225 | |
| ctg ggg atc ctg ctg tat gat atg gtg tgt gga gat att cct ttc gag | 1017 |
| Leu Gly Ile Leu Leu Tyr Asp Met Val Cys Gly Asp Ile Pro Phe Glu | |
|          230                     235                  240 | |
| cat gac gaa gag atc atc agg ggc cag gtt ttc ttc agg cag agg gtc | 1065 |
| His Asp Glu Glu Ile Ile Arg Gly Gln Val Phe Phe Arg Gln Arg Val | |
|          245                     250                  255 | |

```
tct tca gaa tgt cag cat ctc att aga tgg tgc ttg gcc ctg aga cca    1113
Ser Ser Glu Cys Gln His Leu Ile Arg Trp Cys Leu Ala Leu Arg Pro
260                 265                 270                 275 tca gat agg cca acc ttc gaa gaa atc cag aac cat cca tgg atg caa    1161
Ser Asp Arg Pro Thr Phe Glu Glu Ile Gln Asn His Pro Trp Met Gln
                280                 285                 290 gat gtt ctc ctg ccc cag gaa act gct gag atc cac ctc cac agc ctg    1209
Asp Val Leu Leu Pro Gln Glu Thr Ala Glu Ile His Leu His Ser Leu
            295                 300                 305 tcg ccg ggg ccc agc aaa tag cagcctttct ggcaggtcct ccctctctt       1260
Ser Pro Gly Pro Ser Lys *
        310 gtcagatgcc cgagggaggg gaagcttctg tctccagctt cccgagtacc agtgacacgt  1320
ctcgccaagc aggacagtgc ttgatacagg aacaacattt acaactcatt ccagatccca  1380
ggcccctgga ggctgcctcc aacagtgag gaagagtgac tctccagggg tcctaggcct   1440
caactcctcc catagatact ctcttcttct cataggtgtc cagcattgct ggactgctga  1500
aatatcccgg gggtgggggg tggggtgggg tcagaaccct gccatggaac tgtttccttc  1560
atcatgagtt ctgctgaatg ccgcgatggg tcaggtaggg gggaaacagg ttgggatggg  1620
ataggactag caccatttta agtccctgtc acctcttccg actctttctg agtgccttct  1680
gtggggactc cggctgtgct gggagaaata cttgaacttg cctcttttac ctgctgcttc  1740
tccaaaaatc tgcctgggtt tgttcccta ttttctctc ctgtcctccc tcacccctc    1800
cttcatatga aggtgccat ggaagaggct acagggccaa acgctgagcc acctgccctt   1860
ttttctgcct cctttagtaa aactccgagt gaactggtct tccttttgg tttttactta  1920
actgtttcaa agccaagacc tcacacacag aaaaaatgca caaacaatgc aatcaacaga  1980
aaagctgtaa atgtgtgtac agttggcatg gtagtataca aaaagattgt agtggatcta  2040
atttttcaga aattttgcct ttaagttatt ttacctgttt tgtttcttg ttttgaaaga   2100
tgcgcattct aacctggagg tcaatgttat gtatttattt atttatttat ttggttccct  2160
tcctattcca agcttccata gctgctgccc tagttttctt tcctcctttc ctcctctgac  2220
ttggggacct tttggggag ggctgcgacg cttgctctgt ttgtggggtg acgggactca   2280
ggcgggacag tgctgcagct ccctggcttc tgtggggccc ctcacctact tacccaggtg  2340
ggtcccggct ctgtgggtga tggggagggg cattgctgac tgtgtatata ggataattat  2400
gaaaagcagt tctggatggt gtgccttcca gatcctctct ggggctgtgt tttgagcagc  2460
aggtagcctg gctggtttta tctgagtgaa atactgtaca ggggaataaa agagatctta  2520
ttttt                                                              2525

<210> SEQ ID NO 18
<211> LENGTH: 313
<212> TYPE: PRT
<213> ORGANISM: Homo sapiens

<400> SEQUENCE: 18

Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
            20                  25                  30

Pro Leu Glu Ser Gln Tyr Gln Val Gly Pro Leu Leu Gly Ser Gly Gly
        35                  40                  45

Phe Gly Ser Val Tyr Ser Gly Ile Arg Val Ser Asp Asn Leu Pro Val
```

```
                 50                  55                  60
Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Ser Ser Gly Phe Ser Gly Val Ile Arg Leu Leu Asp Trp Phe Glu Arg
                100                 105                 110

Pro Asp Ser Phe Val Leu Ile Leu Glu Arg Pro Glu Pro Val Gln Asp
                115                 120                 125

Leu Phe Asp Phe Ile Thr Glu Arg Gly Ala Leu Gln Glu Glu Leu Ala
130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
                180                 185                 190

Leu Lys Asp Thr Val Tyr Thr Asp Phe Asp Gly Thr Arg Val Tyr Ser
                195                 200                 205

Pro Pro Glu Trp Ile Arg Tyr His Arg Tyr His Gly Arg Ser Ala Ala
                210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
                260                 265                 270

Leu Arg Pro Ser Asp Arg Pro Thr Phe Glu Glu Ile Gln Asn His Pro
                275                 280                 285

Trp Met Gln Asp Val Leu Leu Pro Gln Glu Thr Ala Glu Ile His Leu
                290                 295                 300

His Ser Leu Ser Pro Gly Pro Ser Lys
305                 310

<210> SEQ ID NO 19
<211> LENGTH: 3401
<212> TYPE: DNA
<213> ORGANISM: Saccharomyces cerevisiae
<220> FEATURE:
<221> NAME/KEY: CDS
<222> LOCATION: (789)...(2795)

<400> SEQUENCE: 19
atcgatacaa ctccccagaa atatcactgt tgagagttca tgtcaagacg tagtatagta      60
ttgcaacagg aaaaaaaaat cttattgcgt agcactctgt atctatttta tatatctgtt     120
tctatatttg attaatctct tgttatcttg gtgatgatcg cacaagtatg tactcctgta     180
tctgcaagaa tatctgtttt aaactttca agcaaggaa accccgtctt atataggtta      240
tccgcaaagg tcacattttc ttgcaaatag aagaaaaagc acccacaagc acactaacac     300
agtgccagag caaaactata tcctttgcat ccgatctcaa acgctgttct tatcgcatct     360
gtcttcgtcc tttcatctgc atttaccttt tcttttcat cctctatttg ccttttcatt     420
agtggcaatt tttccagttt tttccctctg cgtcccgttg cacctgaaag gatctttcta     480
acgtgtgttg tctactagtg agcgattcg tgagccatac acgttctata gaaaattgaa      540
```

-continued

```
taaactttac ttcaaaggga tctggacaca gagataactg cttacctgct tgccggaaga    600
aaagaattac taaaaagaa gacaagggta gctgctattg tgggtacacg tttcacagaa    660 ctacttttc cttgtccttc tccagacatc aacgtcatac aactaaaact gataaagtac    720 ccgttttcc gtacatttct atagatacat tattatatta agcagatcga gacgttaatt    780 tctcaaag atg gaa gac aag ttt gct aac ctc agt ctc cat gag aaa act    830
         Met Glu Asp Lys Phe Ala Asn Leu Ser Leu His Glu Lys Thr
           1               5                  10 ggt aag tca tct atc caa tta aac gag caa aca ggc tca gat aat ggc    878
Gly Lys Ser Ser Ile Gln Leu Asn Glu Gln Thr Gly Ser Asp Asn Gly
 15              20                  25                  30 tct gct gtc aag aga aca tct tcg acg tcc tcg cac tac aat aac atc    926
Ser Ala Val Lys Arg Thr Ser Ser Thr Ser Ser His Tyr Asn Asn Ile
                 35                  40                  45 aac gct gac ctt cat gct cgt gta aaa gct ttt caa gaa caa cgt gca    974
Asn Ala Asp Leu His Ala Arg Val Lys Ala Phe Gln Glu Gln Arg Ala
             50                  55                  60 ttg aaa agg tct gcc agc gtg ggc agt aat caa agc gag caa gac aaa   1022
Leu Lys Arg Ser Ala Ser Val Gly Ser Asn Gln Ser Glu Gln Asp Lys
         65                  70                  75 ggc agt tca caa tca cct aaa cat att cag cag att gtt aat aag cca   1070
Gly Ser Ser Gln Ser Pro Lys His Ile Gln Gln Ile Val Asn Lys Pro
 80                  85                  90 ttg ccg cct ctt ccc gta gca gga agt tct aag gtt tca caa aga atg   1118
Leu Pro Pro Leu Pro Val Ala Gly Ser Ser Lys Val Ser Gln Arg Met
 95                 100                 105                 110 agt agc caa gtc gtg caa gcg tcc tcc aag agc act ctt aag aac gtt   1166
Ser Ser Gln Val Val Gln Ala Ser Ser Lys Ser Thr Leu Lys Asn Val
                115                 120                 125 ctg gac aat caa gaa aca caa aac att acc gac gta aat att aac atc   1214
Leu Asp Asn Gln Glu Thr Gln Asn Ile Thr Asp Val Asn Ile Asn Ile
            130                 135                 140 gat aca acc aaa att acc gcc aca aca att ggt gta aat act ggc cta   1262
Asp Thr Thr Lys Ile Thr Ala Thr Thr Ile Gly Val Asn Thr Gly Leu
        145                 150                 155 cct gct act gac att acg ccg tca gtt tct aat act gca tca gca aca   1310
Pro Ala Thr Asp Ile Thr Pro Ser Val Ser Asn Thr Ala Ser Ala Thr
160                 165                 170 cat aag gcg caa ttg ctg aat cct aac aga agg gca cca aga agg ccg   1358
His Lys Ala Gln Leu Leu Asn Pro Asn Arg Arg Ala Pro Arg Arg Pro
175                 180                 185                 190 ctt tct acc cag cac cct aca aga cca aat gtt gcc ccg cat aag gcc   1406
Leu Ser Thr Gln His Pro Thr Arg Pro Asn Val Ala Pro His Lys Ala
                195                 200                 205 cct gct ata atc aac aca cca aaa caa agt tta agt gcc cgt cga ggg   1454
Pro Ala Ile Ile Asn Thr Pro Lys Gln Ser Leu Ser Ala Arg Arg Gly
            210                 215                 220 ctc aaa tta cca cca gga gga atg tca tta aaa atg ccc act aaa aca   1502
Leu Lys Leu Pro Pro Gly Gly Met Ser Leu Lys Met Pro Thr Lys Thr
        225                 230                 235 gct caa cag ccg cag cag ttt gcc cca agc cct tca aac aaa aaa cat   1550
Ala Gln Gln Pro Gln Gln Phe Ala Pro Ser Pro Ser Asn Lys Lys His
240                 245                 250 ata gaa acc tta tca aac agc aaa gtt gtt gaa ggg aaa aga tcg aat   1598
Ile Glu Thr Leu Ser Asn Ser Lys Val Val Glu Gly Lys Arg Ser Asn
255                 260                 265                 270 ccg ggt tct ttg ata aat ggt gtg caa agc aca tcc acc tca tca agt   1646
Pro Gly Ser Leu Ile Asn Gly Val Gln Ser Thr Ser Thr Ser Ser Ser
                275                 280                 285
```

```
acc gaa ggc cca cat gac act gta ggc act aca ccc aga act gga aac      1694
Thr Glu Gly Pro His Asp Thr Val Gly Thr Thr Pro Arg Thr Gly Asn
            290                 295                 300 agc aac aac tct tca aat tct ggt agt agt ggt ggt ggt ggt ctt ttc      1742
Ser Asn Asn Ser Ser Asn Ser Gly Ser Ser Gly Gly Gly Gly Leu Phe
                305                 310                 315 gca aat ttc tcg aaa tac gtg gat atc aaa tcc ggc tct ttg aat ttt      1790
Ala Asn Phe Ser Lys Tyr Val Asp Ile Lys Ser Gly Ser Leu Asn Phe
320                 325                 330 gca ggc aaa cta tcg cta tcc tct aaa gga ata gat ttc agc aat ggt      1838
Ala Gly Lys Leu Ser Leu Ser Ser Lys Gly Ile Asp Phe Ser Asn Gly
335                 340                 345                 350 tct agt tcg aga att aca ttg gac gaa cta gaa ttt ttg gat gaa ctg      1886
Ser Ser Ser Arg Ile Thr Leu Asp Glu Leu Glu Phe Leu Asp Glu Leu
                355                 360                 365 ggt cat ggt aac tat ggt aac gtc tca aag gta ctg cat aag ccc aca      1934
Gly His Gly Asn Tyr Gly Asn Val Ser Lys Val Leu His Lys Pro Thr
                370                 375                 380 aat gtt att atg gcg acg aag gaa gtc cgt ttg gag cta gat gag gct      1982
Asn Val Ile Met Ala Thr Lys Glu Val Arg Leu Glu Leu Asp Glu Ala
                385                 390                 395 aaa ttt aga caa att tta atg gaa cta gaa gtt ttg cat aaa tgc aat      2030
Lys Phe Arg Gln Ile Leu Met Glu Leu Glu Val Leu His Lys Cys Asn
400                 405                 410 tct ccc tat att gtg gat ttt tat ggt gca ttc ttt att gag ggc gcc      2078
Ser Pro Tyr Ile Val Asp Phe Tyr Gly Ala Phe Phe Ile Glu Gly Ala
415                 420                 425                 430 gtc tac atg tgt atg gaa tac atg gat ggt ggt tcc ttg gat aaa ata      2126
Val Tyr Met Cys Met Glu Tyr Met Asp Gly Gly Ser Leu Asp Lys Ile
                435                 440                 445 tac gac gaa tca tct gaa atc ggc ggc att gat gaa cct cag cta gcg      2174
Tyr Asp Glu Ser Ser Glu Ile Gly Gly Ile Asp Glu Pro Gln Leu Ala
                450                 455                 460 ttt att gcc aat gct gtc att cat gga cta aaa gaa ctc aaa gag cag      2222
Phe Ile Ala Asn Ala Val Ile His Gly Leu Lys Glu Leu Lys Glu Gln
                465                 470                 475 cat aat atc ata cac aga gat gtc aaa cca aca aat att tta tgt tca      2270
His Asn Ile Ile His Arg Asp Val Lys Pro Thr Asn Ile Leu Cys Ser
480                 485                 490 gcc aac caa ggc acc gta aag ctg tgc gat ttc ggt gtt tct ggt aat      2318
Ala Asn Gln Gly Thr Val Lys Leu Cys Asp Phe Gly Val Ser Gly Asn
495                 500                 505                 510 ttg gtg gca tct tta gcg aag act aat att ggt tgt cag tca tac atg      2366
Leu Val Ala Ser Leu Ala Lys Thr Asn Ile Gly Cys Gln Ser Tyr Met
                515                 520                 525 gca cct gaa cga atc aaa tcg ttg aat cca gat aga gcc acc tat acc      2414
Ala Pro Glu Arg Ile Lys Ser Leu Asn Pro Asp Arg Ala Thr Tyr Thr
                530                 535                 540 gta cag tca gac atc tgg tct tta ggt tta agc att ctg gaa atg gca      2462
Val Gln Ser Asp Ile Trp Ser Leu Gly Leu Ser Ile Leu Glu Met Ala
                545                 550                 555 cta ggt aga tat ccg tat cca cca gaa aca tac gac aac att ttc tct      2510
Leu Gly Arg Tyr Pro Tyr Pro Pro Glu Thr Tyr Asp Asn Ile Phe Ser
                560                 565                 570 caa ttg agc gct att gtt gat ggg ccg ccg aga tta cct tca gat          2558
Gln Leu Ser Ala Ile Val Asp Gly Pro Pro Arg Leu Pro Ser Asp
575                 580                 585                 590 aaa ttc agt tct gac gca caa gat ttt gtt tct tta tgt cta caa aag      2606
Lys Phe Ser Ser Asp Ala Gln Asp Phe Val Ser Leu Cys Leu Gln Lys
```

-continued

```
                    595                 600                 605
att ccg gaa aga aga cct aca tac gca gct tta aca gag cat cct tgg     2654
Ile Pro Glu Arg Arg Pro Thr Tyr Ala Ala Leu Thr Glu His Pro Trp
            610                 615                 620 tta gta aaa tac aga aac cag gat gtc cac atg agt gag tat atc act     2702
Leu Val Lys Tyr Arg Asn Gln Asp Val His Met Ser Glu Tyr Ile Thr
        625                 630                 635 gaa cga tta gaa agg cgc aac aaa atc tta cgg gaa cgt ggt gag aat     2750
Glu Arg Leu Glu Arg Arg Asn Lys Ile Leu Arg Glu Arg Gly Glu Asn
    640                 645                 650 ggt tta tct aaa aat gta ccg gca tta cat atg ggt ggt tta tag         2795
Gly Leu Ser Lys Asn Val Pro Ala Leu His Met Gly Gly Leu  *
655                 660                 665 cgttaatatc caaataaaag caaacaggca cgtgaatata caacaaaaa  aaaagcagac   2855 gaaaagctac tgtggaaatg atgcggcgaa tacaaaaaaa ccttacatat acatatgttt   2915
attgtaataa acttgcatta tactcgttat agacatatat atatatatat attcatatat   2975
atatatcgtc tgacttcctt ttgtcgaacc taaaaaaggg cacgaattat gacagagtat   3035
tgaggggatg ttatttcaag caccggcaag tgaagcgatg tggacgtcaa tatattgtgt   3095
tattcgatta ttgctacggc catcgactcc tcgaaattat ttacgttcgg ggctgacaac   3155
gcaagaaaga aaaatgctc tggaattgtc tgatggtttt tccgctcttt acggctcaag    3215
gctaggaaag aaaaaaaagt ccaaaatcat cgagaaaata aaggtgtttt gaaagttca    3275 aatccacgtt attgagagta gatgtggagt ctggaccagg aactatacct gtatcttacc   3335
ctaacttcta aattttgcta ctttcacgga aaacagtaaa taattaccta tcaagataaa   3395
gagctc                                                              3401

<210> SEQ ID NO 20
<211> LENGTH: 668
<212> TYPE: PRT
<213> ORGANISM: Saccharomyces cerevisiae

<400> SEQUENCE: 20

Met Glu Asp Lys Phe Ala Asn Leu Ser Leu His Glu Lys Thr Gly Lys
1               5                   10                  15

Ser Ser Ile Gln Leu Asn Glu Gln Thr Gly Ser Asp Asn Gly Ser Ala
            20                  25                  30

Val Lys Arg Thr Ser Ser Thr Ser Ser His Tyr Asn Asn Ile Asn Ala
        35                  40                  45

Asp Leu His Ala Arg Val Lys Ala Phe Gln Glu Gln Arg Ala Leu Lys
    50                  55                  60

Arg Ser Ala Ser Val Gly Ser Asn Gln Ser Glu Gln Asp Lys Gly Ser
65                  70                  75                  80

Ser Gln Ser Pro Lys His Ile Gln Gln Ile Val Asn Lys Pro Leu Pro
                85                  90                  95

Pro Leu Pro Val Ala Gly Ser Ser Lys Val Ser Gln Arg Met Ser Ser
            100                 105                 110

Gln Val Val Gln Ala Ser Ser Lys Ser Thr Leu Lys Asn Val Leu Asp
        115                 120                 125

Asn Gln Glu Thr Gln Asn Ile Thr Asp Val Asn Ile Asn Ile Asp Thr
    130                 135                 140

Thr Lys Ile Thr Ala Thr Thr Ile Gly Val Asn Thr Gly Leu Pro Ala
145                 150                 155                 160

Thr Asp Ile Thr Pro Ser Val Ser Asn Thr Ala Ser Ala Thr His Lys
```

-continued

```
                165                 170                 175
Ala Gln Leu Leu Asn Pro Asn Arg Arg Ala Pro Arg Arg Pro Leu Ser
                    180                 185                 190

Thr Gln His Pro Thr Arg Pro Asn Val Ala Pro His Lys Ala Pro Ala
                    195                 200                 205

Ile Ile Asn Thr Pro Lys Gln Ser Leu Ser Ala Arg Arg Gly Leu Lys
                    210                 215                 220

Leu Pro Pro Gly Gly Met Ser Leu Lys Met Pro Thr Lys Thr Ala Gln
225                 230                 235                 240

Gln Pro Gln Gln Phe Ala Pro Ser Pro Ser Asn Lys Lys His Ile Glu
                    245                 250                 255

Thr Leu Ser Asn Ser Lys Val Val Glu Gly Lys Arg Ser Asn Pro Gly
                    260                 265                 270

Ser Leu Ile Asn Gly Val Gln Ser Thr Ser Thr Ser Ser Ser Thr Glu
                    275                 280                 285

Gly Pro His Asp Thr Val Gly Thr Thr Pro Arg Thr Gly Asn Ser Asn
                    290                 295                 300

Asn Ser Ser Asn Ser Gly Ser Ser Gly Gly Gly Leu Phe Ala Asn
305                 310                 315                 320

Phe Ser Lys Tyr Val Asp Ile Lys Ser Gly Ser Leu Asn Phe Ala Gly
                    325                 330                 335

Lys Leu Ser Leu Ser Ser Lys Gly Ile Asp Phe Ser Asn Gly Ser Ser
                    340                 345                 350

Ser Arg Ile Thr Leu Asp Glu Leu Glu Phe Leu Asp Glu Leu Gly His
                    355                 360                 365

Gly Asn Tyr Gly Asn Val Ser Lys Val Leu His Lys Pro Thr Asn Val
                    370                 375                 380

Ile Met Ala Thr Lys Glu Val Arg Leu Glu Leu Asp Glu Ala Lys Phe
385                 390                 395                 400

Arg Gln Ile Leu Met Glu Leu Glu Val Leu His Lys Cys Asn Ser Pro
                    405                 410                 415

Tyr Ile Val Asp Phe Tyr Gly Ala Phe Phe Ile Glu Gly Ala Val Tyr
                    420                 425                 430

Met Cys Met Glu Tyr Met Asp Gly Gly Ser Leu Asp Lys Ile Tyr Asp
                    435                 440                 445

Glu Ser Ser Glu Ile Gly Gly Ile Asp Glu Pro Gln Leu Ala Phe Ile
                    450                 455                 460

Ala Asn Ala Val Ile His Gly Leu Lys Glu Leu Lys Glu Gln His Asn
465                 470                 475                 480

Ile Ile His Arg Asp Val Lys Pro Thr Asn Ile Leu Cys Ser Ala Asn
                    485                 490                 495

Gln Gly Thr Val Lys Leu Cys Asp Phe Gly Val Ser Gly Asn Leu Val
                    500                 505                 510

Ala Ser Leu Ala Lys Thr Asn Ile Gly Cys Gln Ser Tyr Met Ala Pro
                    515                 520                 525

Glu Arg Ile Lys Ser Leu Asn Pro Asp Arg Ala Thr Tyr Thr Val Gln
                    530                 535                 540

Ser Asp Ile Trp Ser Leu Gly Leu Ser Ile Leu Glu Met Ala Leu Gly
545                 550                 555                 560

Arg Tyr Pro Tyr Pro Pro Glu Thr Tyr Asp Asn Ile Phe Ser Gln Leu
                    565                 570                 575

Ser Ala Ile Val Asp Gly Pro Pro Arg Leu Pro Ser Asp Lys Phe
                    580                 585                 590
```

```
Ser Ser Asp Ala Gln Asp Phe Val Ser Leu Cys Leu Gln Lys Ile Pro
        595                 600                 605

Glu Arg Arg Pro Thr Tyr Ala Ala Leu Thr Glu His Pro Trp Leu Val
    610                 615                 620

Lys Tyr Arg Asn Gln Asp Val His Met Ser Glu Tyr Ile Thr Glu Arg
625                 630                 635                 640

Leu Glu Arg Arg Asn Lys Ile Leu Arg Glu Arg Gly Glu Asn Gly Leu
                645                 650                 655

Ser Lys Asn Val Pro Ala Leu His Met Gly Gly Leu
            660                 665

<210> SEQ ID NO 21
<211> LENGTH: 1883
<212> TYPE: DNA
<213> ORGANISM: Homo sapiens
<220> FEATURE:
<221> NAME/KEY: CDS
<222> LOCATION: (121)...(1203)

<400> SEQUENCE: 21
gtgagccacc gcccccagcc tggcctggca tttctttgag ttcaggaagt gtgacaagga      60
tttggacacc cagaaataag cgtgtcgaga agagcacaag cagaggatcc agcgctcggc     120 atg gcg gag cca gat ctg gag tgc gag cag atc cgt ctg aag tgt att      168
Met Ala Glu Pro Asp Leu Glu Cys Glu Gln Ile Arg Leu Lys Cys Ile
1               5                   10                  15 cgt aag gag ggc ttc ttc acg gtg cct ccg gaa cac agg ctg gga cga      216
Arg Lys Glu Gly Phe Phe Thr Val Pro Pro Glu His Arg Leu Gly Arg
            20                  25                  30 tgc cgg agt gtg aag gag ttt gag aag ctg aac cgc att gga gag ggt      264
Cys Arg Ser Val Lys Glu Phe Glu Lys Leu Asn Arg Ile Gly Glu Gly
        35                  40                  45 acc tac ggc att gtg tat cgg gcc cgg gac acc cag aca gat gag att      312
Thr Tyr Gly Ile Val Tyr Arg Ala Arg Asp Thr Gln Thr Asp Glu Ile
    50                  55                  60 gtc gca ctg aag aag gtg cgg atg gac aag gag aag gat ggc atc ccc      360
Val Ala Leu Lys Lys Val Arg Met Asp Lys Glu Lys Asp Gly Ile Pro
65                  70                  75                  80 atc agc agc ttg cgg gag atc acg ctg ctc cgc ctg cgt cat ccg          408
Ile Ser Ser Leu Arg Glu Ile Thr Leu Leu Arg Leu Arg His Pro
                85                  90                  95 aac atc gtg gag ctg aag gag gtg gtt gtg ggg aac cac ctg gag agc      456
Asn Ile Val Glu Leu Lys Glu Val Val Val Gly Asn His Leu Glu Ser
            100                 105                 110 atc ttc ctg gtg atg ggt tac tgt gag cag gac ctg gcc agc ctc ctg      504
Ile Phe Leu Val Met Gly Tyr Cys Glu Gln Asp Leu Ala Ser Leu Leu
        115                 120                 125 gag aat atg cca aca ccc ttc tcg gag gct cag gtc aag tgc atc gtg      552
Glu Asn Met Pro Thr Pro Phe Ser Glu Ala Gln Val Lys Cys Ile Val
    130                 135                 140 ctg cag gtg ctc cgg ggc ctc cag tat ctg cac agg aac ttc att atc      600
Leu Gln Val Leu Arg Gly Leu Gln Tyr Leu His Arg Asn Phe Ile Ile
145                 150                 155                 160 cac agg gac ctg aag gtt tcc aac ttg ctc atg acc gac aag ggt tgt      648
His Arg Asp Leu Lys Val Ser Asn Leu Leu Met Thr Asp Lys Gly Cys
                165                 170                 175 gtg aag aca gcg gat ttc ggc ctg gcc cgg gcc tat ggt gtc cca gta      696
Val Lys Thr Ala Asp Phe Gly Leu Ala Arg Ala Tyr Gly Val Pro Val
            180                 185                 190
```

```
aag cca atg acc ccc aag gtg gtc act ctc tgg tac cga gcc cct gaa    744
Lys Pro Met Thr Pro Lys Val Val Thr Leu Trp Tyr Arg Ala Pro Glu
        195                 200                 205 ctg ctg ttg gga acc acc acg cag acc acc agc atc gac atg tgg gct    792
Leu Leu Leu Gly Thr Thr Thr Gln Thr Thr Ser Ile Asp Met Trp Ala
    210                 215                 220 gtg ggc tgc ata ctg gcc gag ctg ctg gcg cac agg cct ctt ctc ccc    840
Val Gly Cys Ile Leu Ala Glu Leu Leu Ala His Arg Pro Leu Leu Pro
225                 230                 235                 240 ggc act tcc gag atc cac cag atc gac ttg atc gtg cag ctg ctg ggc    888
Gly Thr Ser Glu Ile His Gln Ile Asp Leu Ile Val Gln Leu Leu Gly
                245                 250                 255 acg ccc agt gag aac atc tgg ccg ggc ttt tcc aag ctg cca ctg gtc    936
Thr Pro Ser Glu Asn Ile Trp Pro Gly Phe Ser Lys Leu Pro Leu Val
            260                 265                 270 ggc cag tac agc ctc cgg aag cag ccc tac aac aac ctg aag cac aag    984
Gly Gln Tyr Ser Leu Arg Lys Gln Pro Tyr Asn Asn Leu Lys His Lys
        275                 280                 285 ttc cca tgg ctg tcg gag gcc ggg ctg cgc ctg ctg cac ttc ctg ttc   1032
Phe Pro Trp Leu Ser Glu Ala Gly Leu Arg Leu Leu His Phe Leu Phe
    290                 295                 300 atg tac gac cct aag aaa agg gcg acg gcc ggg gac tgc ctg gag agc   1080
Met Tyr Asp Pro Lys Lys Arg Ala Thr Ala Gly Asp Cys Leu Glu Ser
305                 310                 315                 320 tcc tat ttc aag gag aag ccc cta ccc tgt gag ccg gag ctc atg ccg   1128
Ser Tyr Phe Lys Glu Lys Pro Leu Pro Cys Glu Pro Glu Leu Met Pro
                325                 330                 335 acc ttt ccc cac cac cgc aac aag cgg gcc gcc cca gcc acc tcc gag   1176
Thr Phe Pro His His Arg Asn Lys Arg Ala Ala Pro Ala Thr Ser Glu
            340                 345                 350 ggc cag agc aag cgc tgt aaa ccc tga cggtgggcct ggcacacgcc          1223
Gly Gln Ser Lys Arg Cys Lys Pro *
        355                 360 tgtattccca caccaggtct tccgatcagt ggtgtctgtg aagggtgccg cgagccaggc  1283
tgaccaggcg cccgggatcc agctcatccc cttggctggg aacatcctcc actgacttcc  1343
tcccactgtc tgccctgaac ccactgctgc ccccagaaaa aggccgggtg acaccggggg  1403
ctcccagccc gtgcaccctg gaagggcagg tctggcggct ccatccgtgg ctgcaggggt  1463
ctcatgtggt cctcctcgct atgttggaaa tgtgcaacca ctgcttcttg ggaggagtgg  1523
tgggtgcagt cccccgctg tctttgagtt gtggtggacc gctggcctgg gatgagaggg    1583
cccagaagac cttcgtatcc cctctcagtc gcccggggct gtcccgtgca tgggttggct  1643
gtggggaccc caggtgggcc tggcaggact ccagatgagg acaagaggga caaggtatgg  1703
ggtgggagcc acaattgagg ataccccgag ctaccaggag agccctgggc tggaggctga  1763
gctggatccc tgctccccac acggaggacc caacaggagg ccgtggctct gatgctgagc  1823
gaagctatag gctcttgttg gataaaagct tttttaacag aaaaaaaaaa aaaaaaaaa   1883

<210> SEQ ID NO 22
<211> LENGTH: 360
<212> TYPE: PRT
<213> ORGANISM: Homo sapiens

<400> SEQUENCE: 22

Met Ala Glu Pro Asp Leu Glu Cys Glu Gln Ile Arg Leu Lys Cys Ile
1               5                   10                  15

Arg Lys Glu Gly Phe Phe Thr Val Pro Pro Glu His Arg Leu Gly Arg
            20                  25                  30
```

```
Cys Arg Ser Val Lys Glu Phe Glu Lys Leu Asn Arg Ile Gly Glu Gly
         35                  40                  45

Thr Tyr Gly Ile Val Tyr Arg Ala Arg Asp Thr Gln Thr Asp Glu Ile
     50                  55                  60

Val Ala Leu Lys Lys Val Arg Met Asp Lys Glu Lys Asp Gly Ile Pro
 65                  70                  75                  80

Ile Ser Ser Leu Arg Glu Ile Thr Leu Leu Arg Leu Arg His Pro
                 85                  90                  95

Asn Ile Val Glu Leu Lys Glu Val Val Gly Asn His Leu Glu Ser
                100                 105                 110

Ile Phe Leu Val Met Gly Tyr Cys Glu Gln Asp Leu Ala Ser Leu Leu
                115                 120                 125

Glu Asn Met Pro Thr Pro Phe Ser Glu Ala Gln Val Lys Cys Ile Val
        130                 135                 140

Leu Gln Val Leu Arg Gly Leu Gln Tyr Leu His Arg Asn Phe Ile Ile
145                 150                 155                 160

His Arg Asp Leu Lys Val Ser Asn Leu Leu Met Thr Asp Lys Gly Cys
                165                 170                 175

Val Lys Thr Ala Asp Phe Gly Leu Ala Arg Ala Tyr Gly Val Pro Val
                180                 185                 190

Lys Pro Met Thr Pro Lys Val Val Thr Leu Trp Tyr Arg Ala Pro Glu
        195                 200                 205

Leu Leu Leu Gly Thr Thr Thr Gln Thr Thr Ser Ile Asp Met Trp Ala
210                 215                 220

Val Gly Cys Ile Leu Ala Glu Leu Leu Ala His Arg Pro Leu Leu Pro
225                 230                 235                 240

Gly Thr Ser Glu Ile His Gln Ile Asp Leu Ile Val Gln Leu Leu Gly
                245                 250                 255

Thr Pro Ser Glu Asn Ile Trp Pro Gly Phe Ser Lys Leu Pro Leu Val
                260                 265                 270

Gly Gln Tyr Ser Leu Arg Lys Gln Pro Tyr Asn Asn Leu Lys His Lys
        275                 280                 285

Phe Pro Trp Leu Ser Glu Ala Gly Leu Arg Leu Leu His Phe Leu Phe
290                 295                 300

Met Tyr Asp Pro Lys Lys Arg Ala Thr Ala Gly Asp Cys Leu Glu Ser
305                 310                 315                 320

Ser Tyr Phe Lys Glu Lys Pro Leu Pro Cys Glu Pro Glu Leu Met Pro
                325                 330                 335

Thr Phe Pro His His Arg Asn Lys Arg Ala Ala Pro Ala Thr Ser Glu
                340                 345                 350

Gly Gln Ser Lys Arg Cys Lys Pro
        355                 360

<210> SEQ ID NO 23
<211> LENGTH: 2299
<212> TYPE: DNA
<213> ORGANISM: Mus musculus
<220> FEATURE:
<221> NAME/KEY: CDS
<222> LOCATION: (142)...(1698)

<400> SEQUENCE: 23
ccggacttcc atgggcagca gcagcggcag ggaacggagg gcgaatagat ttcagagcct      60
gcacctgaag tacaattcga atcctgctcc agggagcgag ccactgtccg gatccagaaa    120
```

-continued

| | | |
|---|---|---|
| ctttggccac tgggaggaaa a atg gcc agt gat acc cca ggt ttc tac atg<br>                                           Met Ala Ser Asp Thr Pro Gly Phe Tyr Met<br>                                             1                 5                          10 | 171 |
| gac aaa ctt aat aaa tac cgc cag atg cac gga gta gcc att acg tat<br>Asp Lys Leu Asn Lys Tyr Arg Gln Met His Gly Val Ala Ile Thr Tyr<br>                15                     20                        25 | 219 |
| aaa gaa ctt agt act tcg gga cct cca cat gac aga agg ttt aca ttt<br>Lys Glu Leu Ser Thr Ser Gly Pro Pro His Asp Arg Arg Phe Thr Phe<br>         30                    35                     40 | 267 |
| caa gtt tta ata gat gag aag gaa ttt gga gaa gcc aaa ggt aga tca<br>Gln Val Leu Ile Asp Glu Lys Glu Phe Gly Glu Ala Lys Gly Arg Ser<br>              45                   50                    55 | 315 |
| aag acg gag gca aga aac gct gca gcc aaa tta gct gtt gat ata ctt<br>Lys Thr Glu Ala Arg Asn Ala Ala Ala Lys Leu Ala Val Asp Ile Leu<br>       60                    65                     70 | 363 |
| gat aac gaa aac aag gtg gat tgt cac acg agt gca tgt gag caa ggc<br>Asp Asn Glu Asn Lys Val Asp Cys His Thr Ser Ala Cys Glu Gln Gly<br>75                    80                    85                     90 | 411 |
| ttg ttc gtt ggt aac tac ata ggc ctt gtc aat agc ttt gcc cag aag<br>Leu Phe Val Gly Asn Tyr Ile Gly Leu Val Asn Ser Phe Ala Gln Lys<br>                95                   100                  105 | 459 |
| aaa aag ctg tct gta aat tat gaa cag tgt gag ccc aac tct gag ttg<br>Lys Lys Leu Ser Val Asn Tyr Glu Gln Cys Glu Pro Asn Ser Glu Leu<br>             110                  115                  120 | 507 |
| cct caa aga ttt att tgt aaa tgc aaa att ggg cag aca atg tat ggt<br>Pro Gln Arg Phe Ile Cys Lys Cys Lys Ile Gly Gln Thr Met Tyr Gly<br>          125                   130                  135 | 555 |
| act ggt tca ggt gtc acc aaa cag gag gca aag cag ttg gct gcg aaa<br>Thr Gly Ser Gly Val Thr Lys Gln Glu Ala Lys Gln Leu Ala Ala Lys<br>140                   145                  150 | 603 |
| gaa gcc tat cag aag ctg tta aag agc ccg ccg aaa act gcc gga aca<br>Glu Ala Tyr Gln Lys Leu Leu Lys Ser Pro Pro Lys Thr Ala Gly Thr<br>155                   160                  165                  170 | 651 |
| tcc tct agc gtt gtc aca tct aca ttc agt ggc ttt tcc agc agc tcg<br>Ser Ser Ser Val Val Thr Ser Thr Phe Ser Gly Phe Ser Ser Ser Ser<br>             175                  180                  185 | 699 |
| tct atg aca agt aat ggt gtt tcc cag tca gca cct gga agt ttt tcc<br>Ser Met Thr Ser Asn Gly Val Ser Gln Ser Ala Pro Gly Ser Phe Ser<br>          190                   195                  200 | 747 |
| tca gag aac gtg ttt acg aac ggt ctc gga gaa aat aaa agg aaa tca<br>Ser Glu Asn Val Phe Thr Asn Gly Leu Gly Glu Asn Lys Arg Lys Ser<br>             205                  210                  215 | 795 |
| gga gta aaa gta tcc cct gat gat gtg caa aga aat aaa tat acc ttg<br>Gly Val Lys Val Ser Pro Asp Asp Val Gln Arg Asn Lys Tyr Thr Leu<br>220                   225                  230 | 843 |
| gac gcc agg ttt aac agc gat ttt gaa gac ata gaa gaa att ggc tta<br>Asp Ala Arg Phe Asn Ser Asp Phe Glu Asp Ile Glu Glu Ile Gly Leu<br>235                   240                  245                  250 | 891 |
| ggt gga ttt ggt caa gtt ttc aaa gcg aaa cac aga att gat gga aag<br>Gly Gly Phe Gly Gln Val Phe Lys Ala Lys His Arg Ile Asp Gly Lys<br>             255                  260                  265 | 939 |
| aga tac gct att aag cgc gtt aaa tat aac acg gag aag gcg gag cac<br>Arg Tyr Ala Ile Lys Arg Val Lys Tyr Asn Thr Glu Lys Ala Glu His<br>          270                   275                  280 | 987 |
| gaa gta caa gcg ctg gca gaa ctc aat cac gtc aac att gtc caa tac<br>Glu Val Gln Ala Leu Ala Glu Leu Asn His Val Asn Ile Val Gln Tyr<br>         285                   290                  295 | 1035 |
| cat agt tgt tgg gag gga gtt gac tat gat cct gag cac agc atg agt<br>His Ser Cys Trp Glu Gly Val Asp Tyr Asp Pro Glu His Ser Met Ser<br>300                   305                  310 | 1083 |

```
gat aca agt cga tac aaa acc cgg tgc ctc ttt att caa atg gaa ttc    1131
Asp Thr Ser Arg Tyr Lys Thr Arg Cys Leu Phe Ile Gln Met Glu Phe
315                 320                 325                 330 tgt gat aaa gga act ttg gag caa tgg atg aga aac aga aat cag agt    1179
Cys Asp Lys Gly Thr Leu Glu Gln Trp Met Arg Asn Arg Asn Gln Ser
                335                 340                 345 aaa gtg gac aaa gct ttg att ttg gac tta tat gaa caa atc gtg acc    1227
Lys Val Asp Lys Ala Leu Ile Leu Asp Leu Tyr Glu Gln Ile Val Thr
        350                 355                 360 gga gtg gag tat ata cac tcg aaa ggg tta att cac aga gat ctt aag    1275
Gly Val Glu Tyr Ile His Ser Lys Gly Leu Ile His Arg Asp Leu Lys
                365                 370                 375 cca ggt aat ata ttt tta gta gat gaa aga cac att aag atc gga gac    1323
Pro Gly Asn Ile Phe Leu Val Asp Glu Arg His Ile Lys Ile Gly Asp
380                 385                 390 ttt ggc ctt gca aca gcc ctg gaa aat gat gga aaa tcc cga aca agg    1371
Phe Gly Leu Ala Thr Ala Leu Glu Asn Asp Gly Lys Ser Arg Thr Arg
395                 400                 405                 410 aga aca gga act ctt caa tac atg agt cca gaa cag tta ttt tta aag    1419
Arg Thr Gly Thr Leu Gln Tyr Met Ser Pro Glu Gln Leu Phe Leu Lys
                415                 420                 425 cac tat gga aaa gaa gtg gac atc ttt gct ttg ggc ctt att cta gct    1467
His Tyr Gly Lys Glu Val Asp Ile Phe Ala Leu Gly Leu Ile Leu Ala
                430                 435                 440 gaa ctt ctt cac acg tgc ttc acg gag tca gag aaa ata aag ttt ttc    1515
Glu Leu Leu His Thr Cys Phe Thr Glu Ser Glu Lys Ile Lys Phe Phe
                445                 450                 455 gaa agt cta aga aaa ggc gac ttc tct aat gat ata ttc gac aac aaa    1563
Glu Ser Leu Arg Lys Gly Asp Phe Ser Asn Asp Ile Phe Asp Asn Lys
460                 465                 470 gaa aaa agc ctt cta aaa aaa cta ctc tca gag aaa ccc aag gac cga    1611
Glu Lys Ser Leu Leu Lys Lys Leu Leu Ser Glu Lys Pro Lys Asp Arg
475                 480                 485                 490 cct gag aca tct gaa atc ctg aag acc ttg gct gaa tgg agg aac atc    1659
Pro Glu Thr Ser Glu Ile Leu Lys Thr Leu Ala Glu Trp Arg Asn Ile
                495                 500                 505 tca gag aaa gaa aag aaa cac atg tta ggg cct ttc tga gaaaacattc    1708
Ser Glu Lys Glu Lys Lys His Met Leu Gly Pro Phe *
                510                 515 cttctgccgt ggtttccctt taacgatctg cagtctgagg ggagtatcag tgaatattat   1768
ccttcttttc ttaataccac tctcccagac aggttttggt tagggtgacc cacagacatt   1828
gtatttatta ggctatgaaa agtatgccc atttcctcaa ttgttaattg ctgggcctgt    1888
ggctggctag ctagccaaat atgtaaatgc ttgtttctcg tctgcccaaa gagaaaggca   1948
ggctcctgtg tgggaagtca cagagccccc aaagccaact ggatgaggaa ggactctggc   2008
ttttggcata aaaagagct ggtagtcaga gctggggcag aaggtcctgc agacagacag   2068
acagacagac agacagagac acaaagacat ggactagaat ggaggaggga gggaggaagg   2128
gagggaggga gagagagaga gagaaagaaa gagagagaga ggacatggag acaaaatggc   2188
ttaagttagc tgggctacct gagagactgt cccagaaaac aggccaacaa ccttccttat   2248
gctatataga tgtctcagtg tctttatcat taaacaccaa gcaggagtgc t            2299

<210> SEQ ID NO 24
<211> LENGTH: 518
<212> TYPE: PRT
<213> ORGANISM: Mus musculus
```

```
<400> SEQUENCE: 24

Met Ala Ser Asp Thr Pro Gly Phe Tyr Met Asp Lys Leu Asn Lys Tyr
 1               5                  10                  15

Arg Gln Met His Gly Val Ala Ile Thr Tyr Lys Glu Leu Ser Thr Ser
            20                  25                  30

Gly Pro Pro His Asp Arg Arg Phe Thr Phe Gln Val Leu Ile Asp Glu
        35                  40                  45

Lys Glu Phe Gly Glu Ala Lys Gly Arg Ser Lys Thr Glu Ala Arg Asn
    50                  55                  60

Ala Ala Ala Lys Leu Ala Val Asp Ile Leu Asp Asn Glu Asn Lys Val
65                  70                  75                  80

Asp Cys His Thr Ser Ala Cys Glu Gln Gly Leu Phe Val Gly Asn Tyr
                85                  90                  95

Ile Gly Leu Val Asn Ser Phe Ala Gln Lys Lys Leu Ser Val Asn
            100                 105                 110

Tyr Glu Gln Cys Glu Pro Asn Ser Glu Leu Pro Gln Arg Phe Ile Cys
            115                 120                 125

Lys Cys Lys Ile Gly Gln Thr Met Tyr Gly Thr Gly Ser Gly Val Thr
        130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Ser Val Val Thr
                165                 170                 175

Ser Thr Phe Ser Gly Phe Ser Ser Ser Ser Met Thr Ser Asn Gly
            180                 185                 190

Val Ser Gln Ser Ala Pro Gly Ser Phe Ser Ser Glu Asn Val Phe Thr
            195                 200                 205

Asn Gly Leu Gly Glu Asn Lys Arg Lys Ser Gly Val Lys Val Ser Pro
        210                 215                 220

Asp Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
                245                 250                 255

Phe Lys Ala Lys His Arg Ile Asp Gly Lys Arg Tyr Ala Ile Lys Arg
            260                 265                 270

Val Lys Tyr Asn Thr Glu Lys Ala Glu His Glu Val Gln Ala Leu Ala
        275                 280                 285

Glu Leu Asn His Val Asn Ile Val Gln Tyr His Ser Cys Trp Glu Gly
    290                 295                 300

Val Asp Tyr Asp Pro Glu His Ser Met Ser Asp Thr Ser Arg Tyr Lys
305                 310                 315                 320

Thr Arg Cys Leu Phe Ile Gln Met Glu Phe Cys Asp Lys Gly Thr Leu
                325                 330                 335

Glu Gln Trp Met Arg Asn Arg Asn Gln Ser Lys Val Asp Lys Ala Leu
            340                 345                 350

Ile Leu Asp Leu Tyr Glu Gln Ile Val Thr Gly Val Gly Tyr Ile His
        355                 360                 365

Ser Lys Gly Leu Ile His Arg Asp Leu Lys Pro Gly Asn Ile Phe Leu
    370                 375                 380

Val Asp Glu Arg His Ile Lys Ile Gly Asp Phe Gly Leu Ala Thr Ala
385                 390                 395                 400

Leu Glu Asn Asp Gly Lys Ser Arg Arg Thr Gly Thr Leu Gln
                405                 410                 415
```

```
Tyr Met Ser Pro Glu Gln Leu Phe Leu Lys His Tyr Gly Lys Glu Val
        420                 425                 430
Asp Ile Phe Ala Leu Gly Leu Ile Leu Ala Glu Leu Leu His Thr Cys
        435                 440                 445
Phe Thr Glu Ser Glu Lys Ile Lys Phe Phe Glu Ser Leu Arg Lys Gly
        450                 455                 460
Asp Phe Ser Asn Asp Ile Phe Asp Asn Lys Glu Lys Ser Leu Leu Lys
465                 470                 475                 480
Lys Leu Leu Ser Glu Lys Pro Lys Asp Arg Pro Glu Thr Ser Glu Ile
                485                 490                 495
Leu Lys Thr Leu Ala Glu Trp Arg Asn Ile Ser Glu Lys Glu Lys Lys
                500                 505                 510
His Met Leu Gly Pro Phe
                515

<210> SEQ ID NO 25
<211> LENGTH: 2055
<212> TYPE: DNA
<213> ORGANISM: Homo sapiens
<220> FEATURE:
<221> NAME/KEY: CDS
<222> LOCATION: (211)...(1632)

<400> SEQUENCE: 25
caggaagact ctgagtccga cgttggccta cccagtcgga aggcagagct gcaatctagt      60
taactacctc ctttccccta gatttccttt cattctgctc aagtcttcgc ctgtgtccga     120
tccctatcta ctttctctcc tcttgtagca agcctcagac tccaggcttg agctaggttt     180 tgttttctc ctggtgagaa ttcgaagacc atg tct acg gaa ctc ttc tca tcc      234
                                Met Ser Thr Glu Leu Phe Ser Ser
                                  1               5 aca aga gag gaa gga agc tct ggc tca gga ccc agt ttt agg tct aat      282
Thr Arg Glu Glu Gly Ser Ser Gly Ser Gly Pro Ser Phe Arg Ser Asn
        10                  15                  20 caa agg aaa atg tta aac ctg ctc ctg gag aga gac act tcc ttt acc      330
Gln Arg Lys Met Leu Asn Leu Leu Leu Glu Arg Asp Thr Ser Phe Thr
25                  30                  35                  40 gtc tgt cca gat gtc cct aga act cca gtg ggc aaa ttt ctt ggt gat      378
Val Cys Pro Asp Val Pro Arg Thr Pro Val Gly Lys Phe Leu Gly Asp
                    45                  50                  55 tct gca aac cta agc att ttg tct gga gga acc cca aaa tgt tgc ctc      426
Ser Ala Asn Leu Ser Ile Leu Ser Gly Gly Thr Pro Lys Cys Cys Leu
            60                  65                  70 gat ctt tcg aat ctt agc agt ggg gag ata act gcc act cag ctt acc      474
Asp Leu Ser Asn Leu Ser Ser Gly Glu Ile Thr Ala Thr Gln Leu Thr
        75                  80                  85 act tct gca gac ctt gat gaa act ggt cac ctg gat tct tca gga ctt      522
Thr Ser Ala Asp Leu Asp Glu Thr Gly His Leu Asp Ser Ser Gly Leu
        90                  95                 100 cag gaa gtg cat tta gct ggg atg aat cat gac cag cac cta atg aaa      570
Gln Glu Val His Leu Ala Gly Met Asn His Asp Gln His Leu Met Lys
105                 110                 115                 120 tgt agc cca gca cag ctt ctt tgt agc act ccg aat ggt ttg gac cgt      618
Cys Ser Pro Ala Gln Leu Leu Cys Ser Thr Pro Asn Gly Leu Asp Arg
                125                 130                 135 ggc cat aga aag aga gat gca atg tgt agt tca tct gca aat aaa gaa      666
Gly His Arg Lys Arg Asp Ala Met Cys Ser Ser Ser Ala Asn Lys Glu
            140                 145                 150
```

```
                                                        -continued aat gac aat gga aac ttg gtg gac agt gaa atg aaa tat ttg ggc agt      714
Asn Asp Asn Gly Asn Leu Val Asp Ser Glu Met Lys Tyr Leu Gly Ser
            155                 160                 165 ccc att act act gtt cca aaa ttg gat aaa aat cca aac cta gga gaa      762
Pro Ile Thr Thr Val Pro Lys Leu Asp Lys Asn Pro Asn Leu Gly Glu
        170                 175                 180 gac cag gca gaa gag att tca gat gaa tta atg gag ttt tcc ctg aaa      810
Asp Gln Ala Glu Glu Ile Ser Asp Glu Leu Met Glu Phe Ser Leu Lys
185                 190                 195                 200 gat caa gaa gca aag gtg agc aga agt ggc cta tat cgc tcc ccg tcg      858
Asp Gln Glu Ala Lys Val Ser Arg Ser Gly Leu Tyr Arg Ser Pro Ser
                205                 210                 215 atg cca gag aac ttg aac agg cca aga ctg aag cag gtg gaa aaa ttc      906
Met Pro Glu Asn Leu Asn Arg Pro Arg Leu Lys Gln Val Glu Lys Phe
            220                 225                 230 aag gac aac aca ata cca gat aaa gtt aaa aaa aag tat ttt tct ggc      954
Lys Asp Asn Thr Ile Pro Asp Lys Val Lys Lys Lys Tyr Phe Ser Gly
        235                 240                 245 caa gga aag ctc agg aag ggc tta tgt tta aag aag aca gtc tct ctg     1002
Gln Gly Lys Leu Arg Lys Gly Leu Cys Leu Lys Lys Thr Val Ser Leu
250                 255                 260 tgt gac att act atc act cag atg ctg gag gaa gat tct aac cag ggg     1050
Cys Asp Ile Thr Ile Thr Gln Met Leu Glu Glu Asp Ser Asn Gln Gly
265                 270                 275                 280 cac ctg att ggt gat ttt tcc aag gta tgt gcg ctg cca acc gtg tca     1098
His Leu Ile Gly Asp Phe Ser Lys Val Cys Ala Leu Pro Thr Val Ser
                285                 290                 295 ggg aaa cac caa gat ctg aag tat gtc aac cca gaa aca gtg gct gcc     1146
Gly Lys His Gln Asp Leu Lys Tyr Val Asn Pro Glu Thr Val Ala Ala
            300                 305                 310 tta ctg tcg ggg aag ttc cag ggt ctg att gag aag ttt tat gtc att     1194
Leu Leu Ser Gly Lys Phe Gln Gly Leu Ile Glu Lys Phe Tyr Val Ile
        315                 320                 325 gat tgt cgc tat cca tat gag tat ctg gga gga cac atc cag gga gcc     1242
Asp Cys Arg Tyr Pro Tyr Glu Tyr Leu Gly Gly His Ile Gln Gly Ala
330                 335                 340 tta aac tta tat agt cag gaa gaa ctg ttt aac ttc ttt ctg aag aag     1290
Leu Asn Leu Tyr Ser Gln Glu Glu Leu Phe Asn Phe Phe Leu Lys Lys
345                 350                 355                 360 ccc atc gtc cct ttg gac acc cag aag aga ata atc gtg ttc cac         1338
Pro Ile Val Pro Leu Asp Thr Gln Lys Arg Ile Ile Val Phe His
                365                 370                 375 tgt gaa ttc tcc tca gag agg ggc ccc cga atg tgc cgc tgt ctg cgt     1386
Cys Glu Phe Ser Ser Glu Arg Gly Pro Arg Met Cys Arg Cys Leu Arg
        380                 385                 390 gaa gag gac agg tct ctg aac cag tat cct gca ttg tac tac cca gag     1434
Glu Glu Asp Arg Ser Leu Asn Gln Tyr Pro Ala Leu Tyr Tyr Pro Glu
395                 400                 405 cta tat atc ctt aaa ggc ggc tac aga gac ttc ttt cca gaa tat atg     1482
Leu Tyr Ile Leu Lys Gly Gly Tyr Arg Asp Phe Phe Pro Glu Tyr Met
            410                 415                 420 gaa ctg tgt gaa cca cag agc tac tgc cct atg cat cat cag gac cac     1530
Glu Leu Cys Glu Pro Gln Ser Tyr Cys Pro Met His His Gln Asp His
425                 430                 435                 440 aag act gag ttg ctg agg tgt cga agc cag agc aaa gtg cag gaa ggg     1578
Lys Thr Glu Leu Leu Arg Cys Arg Ser Gln Ser Lys Val Gln Glu Gly
                445                 450                 455 gag cgg cag ctg cgg gag cag att gcc ctt ctg gtg aag gac atg agc     1626
Glu Arg Gln Leu Arg Glu Gln Ile Ala Leu Leu Val Lys Asp Met Ser
        460                 465                 470
```

-continued

```
cca tga taacattcca gccactggct gctaacaagt caccaaaaag acactgcaga    1682
Pro * aaccctgagc agaaagaggc cttctggatg gccaaaccca agattattaa aagatgtctc    1742
tgcaaaccaa caggctacca acttgtatcc aggcctggga atggattagg tttcagcaga    1802
gctgaaagct ggtggcagag tcctggagct ggctctataa ggcagccttg agttgcatag    1862
agatttgtat tggttcaggg aactctggca ttccttttcc caactcctca tgtcttctca    1922
caagccagcc aactctttct ctctgggctt cgggctatgc aagagcgttg tctaccttct    1982
ttctttgtat tttccttctt tgtttccccc tctttctttt ttaaaaatgg aaaaataaac    2042
actacagaat gag    2055
```

<210> SEQ ID NO 26
<211> LENGTH: 473
<212> TYPE: PRT
<213> ORGANISM: Homo sapiens

<400> SEQUENCE: 26

```
Met Ser Thr Glu Leu Phe Ser Ser Thr Arg Glu Glu Gly Ser Ser Gly
 1               5                  10                  15

Ser Gly Pro Ser Phe Arg Ser Asn Gln Arg Lys Met Leu Asn Leu Leu
                20                  25                  30

Leu Glu Arg Asp Thr Ser Phe Thr Val Cys Pro Asp Val Pro Arg Thr
            35                  40                  45

Pro Val Gly Lys Phe Leu Gly Asp Ser Ala Asn Leu Ser Ile Leu Ser
        50                  55                  60

Gly Gly Thr Pro Lys Cys Cys Leu Asp Leu Ser Asn Leu Ser Ser Gly
 65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
    130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Ser Met Pro Glu Asn Leu Asn Arg Pro
    210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
        275                 280                 285
```

-continued

Val Cys Ala Leu Pro Thr Val Ser Gly Lys His Gln Asp Leu Lys Tyr
        290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
        355                 360                 365

Lys Arg Ile Ile Ile Val Phe His Cys Glu Phe Ser Ser Glu Arg Gly
    370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415

Arg Asp Phe Phe Pro Glu Tyr Met Glu Leu Cys Glu Pro Gln Ser Tyr
            420                 425                 430

Cys Pro Met His His Gln Asp His Lys Thr Glu Leu Leu Arg Cys Arg
        435                 440                 445

Ser Gln Ser Lys Val Gln Glu Gly Glu Arg Gln Leu Arg Glu Gln Ile
    450                 455                 460

Ala Leu Leu Val Lys Asp Met Ser Pro
465                 470

<210> SEQ ID NO 27
<211> LENGTH: 21
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Biotinylated Ser
<220> FEATURE:
<221> NAME/KEY: VARIANT
<222> LOCATION: 21
<223> OTHER INFORMATION: Xaa = Aminated Arginine

<400> SEQUENCE: 27

Xaa Gly Ser Gly Ser Gly Leu Tyr Arg Ser Pro Ser Met Pro Glu Asn
1               5                   10                  15

Leu Asn Arg Pro Xaa
            20

<210> SEQ ID NO 28
<211> LENGTH: 18
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Biotinylated Gly
<220> FEATURE:
<221> NAME/KEY: VARIANT
<222> LOCATION: 18
<223> OTHER INFORMATION: Xaa = Hydroxylated Lysine

<400> SEQUENCE: 28

Xaa Gly Gly Gly Leu Tyr Arg Ser Pro Ser Met Pro Glu Asn Leu Asn
1               5                   10                  15

Arg Xaa

<210> SEQ ID NO 29
<211> LENGTH: 2295
<212> TYPE: DNA
<213> ORGANISM: Saccharomyces cerevisiae
<220> FEATURE:
<221> NAME/KEY: CDS
<222> LOCATION: (1)...(2295)

<400> SEQUENCE: 29

| | | | | | | | | | | | | | | | | |
|---|---|---|---|---|---|---|---|---|---|---|---|---|---|---|---|---|
| atg | tca | aca | aac | tca | ttc | cat | gat | tat | gtg | gat | tta | aaa | tcg | aga | act | 48 |
| Met | Ser | Thr | Asn | Ser | Phe | His | Asp | Tyr | Val | Asp | Leu | Lys | Ser | Arg | Thr | |
| 1 | | | | 5 | | | | | 10 | | | | | 15 | | |
| aat | aca | cga | cag | ttt | tca | gat | gac | gaa | gag | ttc | act | acg | cct | cca | aaa | 96 |
| Asn | Thr | Arg | Gln | Phe | Ser | Asp | Asp | Glu | Glu | Phe | Thr | Thr | Pro | Pro | Lys | |
| | | | 20 | | | | | 25 | | | | | 30 | | | |
| cta | agc | aat | ttc | gga | tca | gct | tta | ctt | tcc | cac | aca | gaa | aaa | act | tca | 144 |
| Leu | Ser | Asn | Phe | Gly | Ser | Ala | Leu | Leu | Ser | His | Thr | Glu | Lys | Thr | Ser | |
| | | 35 | | | | | 40 | | | | | 45 | | | | |
| gca | tca | gag | ata | tta | tca | agt | cat | aat | aat | gac | aag | atc | gca | aat | cga | 192 |
| Ala | Ser | Glu | Ile | Leu | Ser | Ser | His | Asn | Asn | Asp | Lys | Ile | Ala | Asn | Arg | |
| | 50 | | | | | 55 | | | | | 60 | | | | | |
| tta | gaa | gaa | atg | gac | agg | agt | tca | tca | agg | agt | cac | ccc | cca | ccg | tca | 240 |
| Leu | Glu | Glu | Met | Asp | Arg | Ser | Ser | Ser | Arg | Ser | His | Pro | Pro | Pro | Ser | |
| 65 | | | | | 70 | | | | | 75 | | | | | 80 | |
| atg | ggc | aat | ttg | aca | tcc | ggt | cat | act | agt | acc | tca | tcg | cat | tca | acc | 288 |
| Met | Gly | Asn | Leu | Thr | Ser | Gly | His | Thr | Ser | Thr | Ser | Ser | His | Ser | Thr | |
| | | | | 85 | | | | | 90 | | | | | 95 | | |
| ttg | ttc | gga | cga | tat | ctg | aga | aat | aat | cac | cag | act | agc | atg | acg | acg | 336 |
| Leu | Phe | Gly | Arg | Tyr | Leu | Arg | Asn | Asn | His | Gln | Thr | Ser | Met | Thr | Thr | |
| | | | 100 | | | | | 105 | | | | | 110 | | | |
| atg | aac | act | agt | gac | ata | gag | ata | aat | gtt | gga | aat | agt | ctt | gat | aag | 384 |
| Met | Asn | Thr | Ser | Asp | Ile | Glu | Ile | Asn | Val | Gly | Asn | Ser | Leu | Asp | Lys | |
| | | 115 | | | | | 120 | | | | | 125 | | | | |
| agt | ttt | gaa | agg | ata | agg | aat | ttg | cga | caa | aat | atg | aaa | gaa | gat | att | 432 |
| Ser | Phe | Glu | Arg | Ile | Arg | Asn | Leu | Arg | Gln | Asn | Met | Lys | Glu | Asp | Ile | |
| | 130 | | | | | 135 | | | | | 140 | | | | | |
| acg | gca | aag | tat | gct | gaa | agg | aga | agt | aag | aga | ttt | tta | ata | tcc | aat | 480 |
| Thr | Ala | Lys | Tyr | Ala | Glu | Arg | Arg | Ser | Lys | Arg | Phe | Leu | Ile | Ser | Asn | |
| 145 | | | | | 150 | | | | | 155 | | | | | 160 | |
| agg | aca | acg | aag | ctg | ggt | cct | gca | aag | aga | gcg | atg | act | ttg | aca | aat | 528 |
| Arg | Thr | Thr | Lys | Leu | Gly | Pro | Ala | Lys | Arg | Ala | Met | Thr | Leu | Thr | Asn | |
| | | | | 165 | | | | | 170 | | | | | 175 | | |
| atc | ttt | gat | gag | gat | gtg | cct | aac | tct | cca | aac | cag | cca | ata | aat | gca | 576 |
| Ile | Phe | Asp | Glu | Asp | Val | Pro | Asn | Ser | Pro | Asn | Gln | Pro | Ile | Asn | Ala | |
| | | | 180 | | | | | 185 | | | | | 190 | | | |
| agg | gag | aca | gtg | gaa | tta | cca | ctt | gag | gat | tct | cac | caa | aca | aac | ttt | 624 |
| Arg | Glu | Thr | Val | Glu | Leu | Pro | Leu | Glu | Asp | Ser | His | Gln | Thr | Asn | Phe | |
| | | 195 | | | | | 200 | | | | | 205 | | | | |
| aaa | gaa | cga | aga | gag | aat | acg | gat | tat | gat | tca | att | gat | ttt | gga | gat | 672 |
| Lys | Glu | Arg | Arg | Glu | Asn | Thr | Asp | Tyr | Asp | Ser | Ile | Asp | Phe | Gly | Asp | |
| | 210 | | | | | 215 | | | | | 220 | | | | | |
| ttg | aat | cct | atc | cag | tat | att | aaa | aaa | cat | aat | ctt | ccc | aca | agt | gac | 720 |
| Leu | Asn | Pro | Ile | Gln | Tyr | Ile | Lys | Lys | His | Asn | Leu | Pro | Thr | Ser | Asp | |
| 225 | | | | | 230 | | | | | 235 | | | | | 240 | |
| ctt | cca | cta | ata | tct | caa | atc | tac | ttt | gat | aaa | caa | aga | gaa | gaa | aat | 768 |
| Leu | Pro | Leu | Ile | Ser | Gln | Ile | Tyr | Phe | Asp | Lys | Gln | Arg | Glu | Glu | Asn | |
| | | | | 245 | | | | | 250 | | | | | 255 | | |
| aga | caa | gca | gca | ctc | cga | aaa | cat | agt | tcc | aga | gaa | ttg | ctt | tat | aaa | 816 |
| Arg | Gln | Ala | Ala | Leu | Arg | Lys | His | Ser | Ser | Arg | Glu | Leu | Leu | Tyr | Lys | |
| | | | 260 | | | | | 265 | | | | | 270 | | | |

```
                              -continued agt agg tct tct tcc tct tca ctt tct agt aac aac tta ttg gca aac      864
Ser Arg Ser Ser Ser Ser Ser Leu Ser Ser Asn Asn Leu Leu Ala Asn
        275                 280                 285 aag gac aat tct ata aca tcc aat aat ggt tct caa ccc agg cga aaa      912
Lys Asp Asn Ser Ile Thr Ser Asn Asn Gly Ser Gln Pro Arg Arg Lys
290                 295                 300 gtt tct act gga tca tct tca tct aag tca tcg atc gaa ata aga aga      960
Val Ser Thr Gly Ser Ser Ser Ser Lys Ser Ser Ile Glu Ile Arg Arg
305                 310                 315                 320 gct ctc aag gag aat att gat act agc aat aac agc aat ttc aac agc     1008
Ala Leu Lys Glu Asn Ile Asp Thr Ser Asn Asn Ser Asn Phe Asn Ser
                325                 330                 335 cca att cat aaa att tat aaa gga att tcc aga aat aaa gat tcc gac     1056
Pro Ile His Lys Ile Tyr Lys Gly Ile Ser Arg Asn Lys Asp Ser Asp
            340                 345                 350 tcc gaa aaa aga gaa gta ctg cga aac ata agc ata aat gca aat cac     1104
Ser Glu Lys Arg Glu Val Leu Arg Asn Ile Ser Ile Asn Ala Asn His
355                 360                 365 gct gat aat ctc ctt caa caa gag aat aag aga cta aaa cga tca ttg     1152
Ala Asp Asn Leu Leu Gln Gln Glu Asn Lys Arg Leu Lys Arg Ser Leu
370                 375                 380 gat gat gca ata acg aat gag aat ata aac agt aaa aat cta gaa gta     1200
Asp Asp Ala Ile Thr Asn Glu Asn Ile Asn Ser Lys Asn Leu Glu Val
385                 390                 395                 400 ttt tac cat cga cct gct ccc aaa cct cca gtc acc aag aaa gtt gaa     1248
Phe Tyr His Arg Pro Ala Pro Lys Pro Pro Val Thr Lys Lys Val Glu
                405                 410                 415 att gtt gaa cct gca aag tcc gct tct tta tcg aat aat aga aat ata     1296
Ile Val Glu Pro Ala Lys Ser Ala Ser Leu Ser Asn Asn Arg Asn Ile
            420                 425                 430 att aca gta aat gac tcc cag tac gaa aaa ata gaa ctt ttg ggt aga     1344
Ile Thr Val Asn Asp Ser Gln Tyr Glu Lys Ile Glu Leu Leu Gly Arg
435                 440                 445 ggt gga tcc tcc aga gtt tac aag gtg aaa gga tct ggc aat agg gta     1392
Gly Gly Ser Ser Arg Val Tyr Lys Val Lys Gly Ser Gly Asn Arg Val
450                 455                 460 tac gcg ctc aaa agg gtg tct ttt gac gct ttt gac gat tca agt att     1440
Tyr Ala Leu Lys Arg Val Ser Phe Asp Ala Phe Asp Asp Ser Ser Ile
465                 470                 475                 480 gat gga ttc aaa gga gaa ata gaa ctt ctg gaa aaa ttg aaa gac caa     1488
Asp Gly Phe Lys Gly Glu Ile Glu Leu Leu Glu Lys Leu Lys Asp Gln
                485                 490                 495 aag cgt gta atc caa cta cta gat tat gaa atg ggg gat ggt tta ttg     1536
Lys Arg Val Ile Gln Leu Leu Asp Tyr Glu Met Gly Asp Gly Leu Leu
            500                 505                 510 tat ttg ata atg gaa tgt ggt gat cat gat ttg tca caa atc ctt aac     1584
Tyr Leu Ile Met Glu Cys Gly Asp His Asp Leu Ser Gln Ile Leu Asn
        515                 520                 525 caa aga agc ggc atg cca ctg gat ttt aat ttt gtt aga ttc tat aca     1632
Gln Arg Ser Gly Met Pro Leu Asp Phe Asn Phe Val Arg Phe Tyr Thr
530                 535                 540 aag gaa atg ttg ctg tgc att aaa gta gtt cat gat gcg ggc ata gtt     1680
Lys Glu Met Leu Leu Cys Ile Lys Val Val His Asp Ala Gly Ile Val
545                 550                 555                 560 cat tcg gat tta aaa cct gca aat ttt gtt tta gtg aaa ggt atc tta     1728
His Ser Asp Leu Lys Pro Ala Asn Phe Val Leu Val Lys Gly Ile Leu
                565                 570                 575 aaa atc att gat ttt ggt ata gca aac gcg gta ccg gaa cat acg gtg     1776
Lys Ile Ile Asp Phe Gly Ile Ala Asn Ala Val Pro Glu His Thr Val
```

```
                    580                 585                 590
aat ata tat cgt gaa act caa att ggg act cca aat tat atg gca cca    1824
Asn Ile Tyr Arg Glu Thr Gln Ile Gly Thr Pro Asn Tyr Met Ala Pro
        595                 600                 605 gaa gca cta gtt gct atg aat tac aca caa aat agt gag aac caa cat    1872
Glu Ala Leu Val Ala Met Asn Tyr Thr Gln Asn Ser Glu Asn Gln His
    610                 615                 620 gag gga aac aag tgg aaa gtg ggg aga cca tct gat atg tgg tca tgc    1920
Glu Gly Asn Lys Trp Lys Val Gly Arg Pro Ser Asp Met Trp Ser Cys
625                 630                 635                 640 ggt tgt att ata tat cag atg att tac ggg aaa ccc cca tat ggc agt    1968
Gly Cys Ile Ile Tyr Gln Met Ile Tyr Gly Lys Pro Pro Tyr Gly Ser
                645                 650                 655 ttc caa ggc caa aat agg ctg ttg gct att atg aat cct gat gtg aaa    2016
Phe Gln Gly Gln Asn Arg Leu Leu Ala Ile Met Asn Pro Asp Val Lys
            660                 665                 670 atc cca ttt cct gaa cat act agc aat aat gaa aag att cca aag tct    2064
Ile Pro Phe Pro Glu His Thr Ser Asn Asn Glu Lys Ile Pro Lys Ser
        675                 680                 685 gcc att gaa tta atg aaa gca tgt ctg tac agg aac cca gac aaa aga    2112
Ala Ile Glu Leu Met Lys Ala Cys Leu Tyr Arg Asn Pro Asp Lys Arg
    690                 695                 700 tgg act gtg gat aaa gtc ctg agt agc act ttc ctt caa cct ttt atg    2160
Trp Thr Val Asp Lys Val Leu Ser Ser Thr Phe Leu Gln Pro Phe Met
705                 710                 715                 720 ata tcc gga tcg att atg gaa gac ctt att agg aat gcc gtt aga tat    2208
Ile Ser Gly Ser Ile Met Glu Asp Leu Ile Arg Asn Ala Val Arg Tyr
                725                 730                 735 ggc tct gag aag cct cat ata tca caa gat gat ctc aat gat gtg gta    2256
Gly Ser Glu Lys Pro His Ile Ser Gln Asp Asp Leu Asn Asp Val Val
            740                 745                 750 gac act gtt tta agg aaa ttt gca gat tac aaa att tag                2295
Asp Thr Val Leu Arg Lys Phe Ala Asp Tyr Lys Ile  *
        755                 760

<210> SEQ ID NO 30
<211> LENGTH: 764
<212> TYPE: PRT
<213> ORGANISM: Saccharomyces cerevisiae

<400> SEQUENCE: 30

Met Ser Thr Asn Ser Phe His Asp Tyr Val Asp Leu Lys Ser Arg Thr
1               5                   10                  15

Asn Thr Arg Gln Phe Ser Asp Asp Glu Glu Phe Thr Thr Pro Pro Lys
            20                  25                  30

Leu Ser Asn Phe Gly Ser Ala Leu Leu Ser His Thr Glu Lys Thr Ser
        35                  40                  45

Ala Ser Glu Ile Leu Ser Ser His Asn Asn Asp Lys Ile Ala Asn Arg
    50                  55                  60

Leu Glu Glu Met Asp Arg Ser Ser Ser Arg Ser His Pro Pro Pro Ser
65                  70                  75                  80

Met Gly Asn Leu Thr Ser Gly His Thr Ser Thr Ser Ser His Ser Thr
                85                  90                  95

Leu Phe Gly Arg Tyr Leu Arg Asn Asn His Gln Thr Ser Met Thr Thr
            100                 105                 110

Met Asn Thr Ser Asp Ile Glu Ile Asn Val Gly Asn Ser Leu Asp Lys
        115                 120                 125

Ser Phe Glu Arg Ile Arg Asn Leu Arg Gln Asn Met Lys Glu Asp Ile
```

-continued

```
            130                 135                 140
Thr Ala Lys Tyr Ala Glu Arg Arg Ser Lys Arg Phe Leu Ile Ser Asn
145                 150                 155                 160

Arg Thr Thr Lys Leu Gly Pro Ala Lys Arg Ala Met Thr Leu Thr Asn
                165                 170                 175

Ile Phe Asp Glu Asp Val Pro Asn Ser Pro Asn Gln Pro Ile Asn Ala
                180                 185                 190

Arg Glu Thr Val Glu Leu Pro Leu Glu Asp Ser His Gln Thr Asn Phe
                195                 200                 205

Lys Glu Arg Arg Glu Asn Thr Asp Tyr Asp Ser Ile Asp Phe Gly Asp
210                 215                 220

Leu Asn Pro Ile Gln Tyr Ile Lys Lys His Asn Leu Pro Thr Ser Asp
225                 230                 235                 240

Leu Pro Leu Ile Ser Gln Ile Tyr Phe Asp Lys Gln Arg Glu Glu Asn
                245                 250                 255

Arg Gln Ala Ala Leu Arg Lys His Ser Ser Arg Glu Leu Leu Tyr Lys
                260                 265                 270

Ser Arg Ser Ser Ser Ser Leu Ser Ser Asn Asn Leu Leu Ala Asn
                275                 280                 285

Lys Asp Asn Ser Ile Thr Ser Asn Asn Gly Ser Gln Pro Arg Arg Lys
290                 295                 300

Val Ser Thr Gly Ser Ser Ser Lys Ser Ser Ile Glu Ile Arg Arg
305                 310                 315                 320

Ala Leu Lys Glu Asn Ile Asp Thr Ser Asn Asn Ser Asn Phe Asn Ser
                325                 330                 335

Pro Ile His Lys Ile Tyr Lys Gly Ile Ser Arg Asn Lys Asp Ser Asp
                340                 345                 350

Ser Glu Lys Arg Glu Val Leu Arg Asn Ile Ser Ile Asn Ala Asn His
                355                 360                 365

Ala Asp Asn Leu Leu Gln Gln Glu Asn Lys Arg Leu Lys Arg Ser Leu
                370                 375                 380

Asp Asp Ala Ile Thr Asn Glu Asn Ile Asn Ser Lys Asn Leu Glu Val
385                 390                 395                 400

Phe Tyr His Arg Pro Ala Pro Lys Pro Pro Val Thr Lys Lys Val Glu
                405                 410                 415

Ile Val Glu Pro Ala Lys Ser Ala Ser Leu Ser Asn Asn Arg Asn Ile
                420                 425                 430

Ile Thr Val Asn Asp Ser Gln Tyr Glu Lys Ile Glu Leu Leu Gly Arg
                435                 440                 445

Gly Gly Ser Ser Arg Val Tyr Lys Val Lys Gly Ser Gly Asn Arg Val
450                 455                 460

Tyr Ala Leu Lys Arg Val Ser Phe Asp Ala Phe Asp Ser Ser Ile
465                 470                 475                 480

Asp Gly Phe Lys Gly Glu Ile Glu Leu Leu Glu Lys Leu Lys Asp Gln
                485                 490                 495

Lys Arg Val Ile Gln Leu Leu Asp Tyr Glu Met Gly Asp Gly Leu Leu
                500                 505                 510

Tyr Leu Ile Met Glu Cys Gly Asp His Asp Leu Ser Gln Ile Leu Asn
                515                 520                 525

Gln Arg Ser Gly Met Pro Leu Asp Phe Asn Phe Val Arg Phe Tyr Thr
                530                 535                 540

Lys Glu Met Leu Leu Cys Ile Lys Val Val His Asp Ala Gly Ile Val
545                 550                 555                 560
```

```
His Ser Asp Leu Lys Pro Ala Asn Phe Val Leu Val Lys Gly Ile Leu
            565                 570                 575
Lys Ile Ile Asp Phe Gly Ile Ala Asn Ala Val Pro Glu His Thr Val
            580                 585                 590
Asn Ile Tyr Arg Glu Thr Gln Ile Gly Thr Pro Asn Tyr Met Ala Pro
            595                 600                 605
Glu Ala Leu Val Ala Met Asn Tyr Thr Gln Asn Ser Glu Asn Gln His
            610                 615                 620
Glu Gly Asn Lys Trp Lys Val Gly Arg Pro Ser Asp Met Trp Ser Cys
625                 630                 635                 640
Gly Cys Ile Ile Tyr Gln Met Ile Tyr Gly Lys Pro Pro Tyr Gly Ser
            645                 650                 655
Phe Gln Gly Gln Asn Arg Leu Leu Ala Ile Met Asn Pro Asp Val Lys
            660                 665                 670
Ile Pro Phe Pro Glu His Thr Ser Asn Asn Glu Lys Ile Pro Lys Ser
            675                 680                 685
Ala Ile Glu Leu Met Lys Ala Cys Leu Tyr Arg Asn Pro Asp Lys Arg
            690                 695                 700
Trp Thr Val Asp Lys Val Leu Ser Ser Thr Phe Leu Gln Pro Phe Met
705                 710                 715                 720
Ile Ser Gly Ser Ile Met Glu Asp Leu Ile Arg Asn Ala Val Arg Tyr
            725                 730                 735
Gly Ser Glu Lys Pro His Ile Ser Gln Asp Asp Leu Asn Asp Val Val
            740                 745                 750
Asp Thr Val Leu Arg Lys Phe Ala Asp Tyr Lys Ile
            755                 760

<210> SEQ ID NO 31
<211> LENGTH: 2079
<212> TYPE: DNA
<213> ORGANISM: Schizosaccharomyces pombe
<220> FEATURE:
<221> NAME/KEY: CDS
<222> LOCATION: (30)...(2066)

<400> SEQUENCE: 31
ggaatgctcg ttttttagta actgtgttt atg tct aag cgc aat cct cct gtg      53
                                Met Ser Lys Arg Asn Pro Pro Val
                                  1               5 act aat atc gcg gac ttg gtg tca gat tct tcc tta gat gaa gac tcg     101
Thr Asn Ile Ala Asp Leu Val Ser Asp Ser Ser Leu Asp Glu Asp Ser
         10                  15                  20 ctt tct ttt ctc gaa gag ctt cag gat cca gaa tta tac ttc aaa aac     149
Leu Ser Phe Leu Glu Glu Leu Gln Asp Pro Glu Leu Tyr Phe Lys Asn
 25                  30                  35                  40 gac act ttc tct tcc aag agt agc cat tct gat ggc acc gtt act ggg     197
Asp Thr Phe Ser Ser Lys Ser Ser His Ser Asp Gly Thr Val Thr Gly
                 45                  50                  55 gat acg ttg cgt agg cag tca agc ggt gca act gct tta gag aga ttg     245
Asp Thr Leu Arg Arg Gln Ser Ser Gly Ala Thr Ala Leu Glu Arg Leu
             60                  65                  70 gtc tca cat cct cgt act aaa aat ttt gat ttg caa gga aat gga gga     293
Val Ser His Pro Arg Thr Lys Asn Phe Asp Leu Gln Gly Asn Gly Gly
         75                  80                  85 caa aat tct gct ttg aag gaa gtg aat act cca gca tat cag tca atg     341
Gln Asn Ser Ala Leu Lys Glu Val Asn Thr Pro Ala Tyr Gln Ser Met
 90                  95                 100
```

-continued

| | | |
|---|---|---|
| cac cat ttc gag cat tta ata aca ccc ttg ccc tct act aat gcg tct<br>His His Phe Glu His Leu Ile Thr Pro Leu Pro Ser Thr Asn Ala Ser<br>105                    110                    115                    120 | 389 |
| cac agt gaa gtt tca ctc agt gca gga gtg aat gat ctc aat tct aat<br>His Ser Glu Val Ser Leu Ser Ala Gly Val Asn Asp Leu Asn Ser Asn<br>              125                    130                    135 | 437 |
| tcg gag cat gat ttg tta cct aaa agt gta aac aaa acc ccc ggt tct<br>Ser Glu His Asp Leu Leu Pro Lys Ser Val Asn Lys Thr Pro Gly Ser<br>        140                    145                    150 | 485 |
| tta tca att tca aga cga cga aga atc ggc aga att gga tta ggc cct<br>Leu Ser Ile Ser Arg Arg Arg Arg Ile Gly Arg Ile Gly Leu Gly Pro<br>155                    160                    165 | 533 |
| cca aag cgt gct gag tac acg ttg acg gat ccc tcg aag act tcc gat<br>Pro Lys Arg Ala Glu Tyr Thr Leu Thr Asp Pro Ser Lys Thr Ser Asp<br>    170                    175                    180 | 581 |
| acc aaa aac tct aca gaa gca gat gag gat att gaa atg aaa tct cga<br>Thr Lys Asn Ser Thr Glu Ala Asp Glu Asp Ile Glu Met Lys Ser Arg<br>185                    190                    195                    200 | 629 |
| gaa gta tca cca gct tcc aac tct gtt gct gca aca act tta aaa cct<br>Glu Val Ser Pro Ala Ser Asn Ser Val Ala Ala Thr Thr Leu Lys Pro<br>                    205                    210                    215 | 677 |
| ctg cag ctg cat aac act cct ttg caa aca tcc cag gag cat ccc aaa<br>Leu Gln Leu His Asn Thr Pro Leu Gln Thr Ser Gln Glu His Pro Lys<br>        220                    225                    230 | 725 |
| cct tct ttt cat cct tct cag ttt gag agc tct ttt tct cct agg gtg<br>Pro Ser Phe His Pro Ser Gln Phe Glu Ser Ser Phe Ser Pro Arg Val<br>235                    240                    245 | 773 |
| cag ttt gat cac gat gtt gaa aga aga gct agt gaa ctt cat tct cgt<br>Gln Phe Asp His Asp Val Glu Arg Arg Ala Ser Glu Leu His Ser Arg<br>    250                    255                    260 | 821 |
| cca gtc acc gtt ttc caa gag cct cag cgt tct gct tct caa cca tat<br>Pro Val Thr Val Phe Gln Glu Pro Gln Arg Ser Ala Ser Gln Pro Tyr<br>265                    270                    275                    280 | 869 |
| gaa tct cat gct ctt tct cca aag gtg gct ccg tta ttt gat aac agt<br>Glu Ser His Ala Leu Ser Pro Lys Val Ala Pro Leu Phe Asp Asn Ser<br>                    285                    290                    295 | 917 |
| caa gct act ccc ata ccc aag cgt cag cag gac gtt gtt act gtt gcc<br>Gln Ala Thr Pro Ile Pro Lys Arg Gln Gln Asp Val Val Thr Val Ala<br>        300                    305                    310 | 965 |
| aat cta caa ttt atc aaa tta gga gtt gtt gga aag ggt gga agt agt<br>Asn Leu Gln Phe Ile Lys Leu Gly Val Val Gly Lys Gly Gly Ser Ser<br>315                    320                    325 | 1013 |
| atg gta tat cgc ata ttt tcc ccc gat aac agt cgt tta tac gct ttg<br>Met Val Tyr Arg Ile Phe Ser Pro Asp Asn Ser Arg Leu Tyr Ala Leu<br>    330                    335                    340 | 1061 |
| aaa gag gtg aac ttt att aat gca gac caa act act ata caa gga tac<br>Lys Glu Val Asn Phe Ile Asn Ala Asp Gln Thr Thr Ile Gln Gly Tyr<br>345                    350                    355                    360 | 1109 |
| aag aac gaa att gca tta tta aga aag ctt tca ggc aat gat cgc ata<br>Lys Asn Glu Ile Ala Leu Leu Arg Lys Leu Ser Gly Asn Asp Arg Ile<br>                    365                    370                    375 | 1157 |
| att aaa tta tat gct gcc gaa gtt aat gat act tta ggg caa ctc aat<br>Ile Lys Leu Tyr Ala Ala Glu Val Asn Asp Thr Leu Gly Gln Leu Asn<br>        380                    385                    390 | 1205 |
| atg gtg atg gaa tgc gga gaa acg gat tta gca aac ctt tta atg aaa<br>Met Val Met Glu Cys Gly Glu Thr Asp Leu Ala Asn Leu Leu Met Lys<br>395                    400                    405 | 1253 |
| aac atg aag aaa ccc att aat ctt aat ttc atc aga atg tat tgg gag<br>Asn Met Lys Lys Pro Ile Asn Leu Asn Phe Ile Arg Met Tyr Trp Glu<br>    410                    415                    420 | 1301 |

-continued

| | | |
|---|---|---|
| caa atg cta gag gcg gtc cag gta gtt cat gat caa aat ata gtg cat<br>Gln Met Leu Glu Ala Val Gln Val Val His Asp Gln Asn Ile Val His<br>425                       430                       435                       440 | 1349 |
| tcg gat ttg aag ccg gcc aat ttc ctg ctt gta gaa ggg aat ttg aag<br>Ser Asp Leu Lys Pro Ala Asn Phe Leu Leu Val Glu Gly Asn Leu Lys<br>                     445                       450                       455 | 1397 |
| ctg att gat ttt ggc att gcc aaa gca att ggt aat gac acc act aat<br>Leu Ile Asp Phe Gly Ile Ala Lys Ala Ile Gly Asn Asp Thr Thr Asn<br>               460                       465                       470 | 1445 |
| atc cat cgt gat tcc cac atc ggt act att aat tat atg gca cct gaa<br>Ile His Arg Asp Ser His Ile Gly Thr Ile Asn Tyr Met Ala Pro Glu<br>475                       480                       485 | 1493 |
| gct ttg aca gac atg aat gct cac aca aac tct ggc gtg aaa ctc gta<br>Ala Leu Thr Asp Met Asn Ala His Thr Asn Ser Gly Val Lys Leu Val<br>          490                       495                       500 | 1541 |
| aag ttg ggc agg ccc agc gac gtg tgg agt ttg gga tgt ata tta tat<br>Lys Leu Gly Arg Pro Ser Asp Val Trp Ser Leu Gly Cys Ile Leu Tyr<br>505                       510                       515                       520 | 1589 |
| cag atg gtg tat ggg agg gcc ccg ttt gct cat cta aaa atg atc caa<br>Gln Met Val Tyr Gly Arg Ala Pro Phe Ala His Leu Lys Met Ile Gln<br>               525                       530                       535 | 1637 |
| gct ata gca gct atc cct aat gaa caa tat cac att cat ttc ccc gaa<br>Ala Ile Ala Ala Ile Pro Asn Glu Gln Tyr His Ile His Phe Pro Glu<br>540                       545                       550 | 1685 |
| gtt gcc tta cct gct aat gct gtc cag gag aaa gag gga tcg ttg cca<br>Val Ala Leu Pro Ala Asn Ala Val Gln Glu Lys Glu Gly Ser Leu Pro<br>               555                       560                       565 | 1733 |
| ggt gta act gtc ggg cct gat cta atg gat gtt atg aaa aga tgc ctg<br>Gly Val Thr Val Gly Pro Asp Leu Met Asp Val Met Lys Arg Cys Leu<br>570                       575                       580 | 1781 |
| gaa agg gat caa cgg aag aga ctt aca ata ccg gaa ttg ctg gtt cat<br>Glu Arg Asp Gln Arg Lys Arg Leu Thr Ile Pro Glu Leu Leu Val His<br>585                       590                       595                       600 | 1829 |
| ccc ttt tta aac cct ttg cca tcc tat ttg aca cct ttg gcc aaa aag<br>Pro Phe Leu Asn Pro Leu Pro Ser Tyr Leu Thr Pro Leu Ala Lys Lys<br>                     605                       610                       615 | 1877 |
| ccg tta cct gtt tct ggg cac acc aat aat gct cat cca ctt aga ctc<br>Pro Leu Pro Val Ser Gly His Thr Asn Asn Ala His Pro Leu Arg Leu<br>          620                       625                       630 | 1925 |
| agc aca gaa atc tca gct tct caa tta tca atg att ata gaa agg tcg<br>Ser Thr Glu Ile Ser Ala Ser Gln Leu Ser Met Ile Ile Glu Arg Ser<br>               635                       640                       645 | 1973 |
| gtg gag ttg agt aag cac aag cga tta aat aag gaa ctt att gat agc<br>Val Glu Leu Ser Lys His Lys Arg Leu Asn Lys Glu Leu Ile Asp Ser<br>650                       655                       660 | 2021 |
| atg gct tat gat tgc gtt agc aat tta cga aaa atg cca gaa tag<br>Met Ala Tyr Asp Cys Val Ser Asn Leu Arg Lys Met Pro Glu *<br>665                       670                       675 | 2066 |
| aggcactaaa ttt | 2079 |

```
<210> SEQ ID NO 32
<211> LENGTH: 678
<212> TYPE: PRT
<213> ORGANISM: Schizosaccharomyces pombe

<400> SEQUENCE: 32
```

Met Ser Lys Arg Asn Pro Pro Val Thr Asn Ile Ala Asp Leu Val Ser
1               5                     10                     15

Asp Ser Ser Leu Asp Glu Asp Ser Leu Ser Phe Leu Glu Glu Leu Gln

-continued

```
                    20                  25                  30
Asp Pro Glu Leu Tyr Phe Lys Asn Asp Thr Phe Ser Ser Lys Ser Ser
                35                  40                  45
His Ser Asp Gly Thr Val Thr Gly Asp Thr Leu Arg Arg Gln Ser Ser
        50                  55                  60
Gly Ala Thr Ala Leu Glu Arg Leu Val Ser His Pro Arg Thr Lys Asn
65                  70                  75                  80
Phe Asp Leu Gln Gly Asn Gly Gln Asn Ser Ala Leu Lys Glu Val
                85                  90                  95
Asn Thr Pro Ala Tyr Gln Ser Met His His Phe Glu His Leu Ile Thr
                100                 105                 110
Pro Leu Pro Ser Thr Asn Ala Ser His Ser Glu Val Ser Leu Ser Ala
            115                 120                 125
Gly Val Asn Asp Leu Asn Ser Asn Ser Glu His Asp Leu Leu Pro Lys
        130                 135                 140
Ser Val Asn Lys Thr Pro Gly Ser Leu Ser Ile Ser Arg Arg Arg Arg
145                 150                 155                 160
Ile Gly Arg Ile Gly Leu Gly Pro Pro Lys Arg Ala Glu Tyr Thr Leu
                165                 170                 175
Thr Asp Pro Ser Lys Thr Ser Asp Thr Lys Asn Ser Thr Glu Ala Asp
                180                 185                 190
Glu Asp Ile Glu Met Lys Ser Arg Glu Val Ser Pro Ala Ser Asn Ser
            195                 200                 205
Val Ala Ala Thr Thr Leu Lys Pro Leu Gln Leu His Asn Thr Pro Leu
        210                 215                 220
Gln Thr Ser Gln Glu His Pro Lys Pro Ser Phe His Pro Ser Gln Phe
225                 230                 235                 240
Glu Ser Ser Phe Ser Pro Arg Val Gln Phe Asp His Asp Val Glu Arg
                245                 250                 255
Arg Ala Ser Glu Leu His Ser Arg Pro Val Thr Val Phe Gln Glu Pro
                260                 265                 270
Gln Arg Ser Ala Ser Gln Pro Tyr Glu Ser His Ala Leu Ser Pro Lys
            275                 280                 285
Val Ala Pro Leu Phe Asp Asn Ser Gln Ala Thr Pro Ile Pro Lys Arg
        290                 295                 300
Gln Gln Asp Val Val Thr Val Ala Asn Leu Gln Phe Ile Lys Leu Gly
305                 310                 315                 320
Val Val Gly Lys Gly Ser Ser Met Val Tyr Arg Ile Phe Ser Pro
                325                 330                 335
Asp Asn Ser Arg Leu Tyr Ala Leu Lys Glu Val Asn Phe Ile Asn Ala
                340                 345                 350
Asp Gln Thr Thr Ile Gln Gly Tyr Lys Asn Glu Ile Ala Leu Leu Arg
            355                 360                 365
Lys Leu Ser Gly Asn Asp Arg Ile Ile Lys Leu Tyr Ala Ala Glu Val
        370                 375                 380
Asn Asp Thr Leu Gly Gln Leu Asn Met Val Met Glu Cys Gly Glu Thr
385                 390                 395                 400
Asp Leu Ala Asn Leu Leu Met Lys Asn Met Lys Pro Ile Asn Leu
                405                 410                 415
Asn Phe Ile Arg Met Tyr Trp Glu Gln Met Leu Glu Ala Val Gln Val
                420                 425                 430
Val His Asp Gln Asn Ile Val His Ser Asp Leu Lys Pro Ala Asn Phe
            435                 440                 445
```

```
Leu Leu Val Glu Gly Asn Leu Lys Leu Ile Asp Phe Gly Ile Ala Lys
    450                 455                 460

Ala Ile Gly Asn Asp Thr Thr Asn Ile His Arg Asp Ser His Ile Gly
465                 470                 475                 480

Thr Ile Asn Tyr Met Ala Pro Glu Ala Leu Thr Asp Met Asn Ala His
                485                 490                 495

Thr Asn Ser Gly Val Lys Leu Val Lys Leu Gly Arg Pro Ser Asp Val
            500                 505                 510

Trp Ser Leu Gly Cys Ile Leu Tyr Gln Met Val Tyr Gly Arg Ala Pro
        515                 520                 525

Phe Ala His Leu Lys Met Ile Gln Ala Ile Ala Ala Ile Pro Asn Glu
    530                 535                 540

Gln Tyr His Ile His Phe Pro Glu Val Ala Leu Pro Ala Asn Ala Val
545                 550                 555                 560

Gln Glu Lys Glu Gly Ser Leu Pro Gly Val Thr Val Gly Pro Asp Leu
                565                 570                 575

Met Asp Val Met Lys Arg Cys Leu Glu Arg Asp Gln Arg Lys Arg Leu
            580                 585                 590

Thr Ile Pro Glu Leu Leu Val His Pro Phe Leu Asn Pro Leu Pro Ser
        595                 600                 605

Tyr Leu Thr Pro Leu Ala Lys Lys Pro Leu Pro Val Ser Gly His Thr
    610                 615                 620

Asn Asn Ala His Pro Leu Arg Leu Ser Thr Glu Ile Ser Ala Ser Gln
625                 630                 635                 640

Leu Ser Met Ile Ile Glu Arg Ser Val Glu Leu Ser Lys His Lys Arg
                645                 650                 655

Leu Asn Lys Glu Leu Ile Asp Ser Met Ala Tyr Asp Cys Val Ser Asn
            660                 665                 670

Leu Arg Lys Met Pro Glu
        675

<210> SEQ ID NO 33
<211> LENGTH: 2263
<212> TYPE: DNA
<213> ORGANISM: Homo sapiens
<220> FEATURE:
<221> NAME/KEY: CDS
<222> LOCATION: (379)...(1491)

<400> SEQUENCE: 33
gatatcacag caacattgaa atgctaaaaa gtttttaaac actctcaatt tctaattcac      60
catgtcacag actggtgaaa aaaaaaaaaa aagcggccgc ttcccccggg ccgggccccc     120
gccgccccgc ggtccccaga gcgccaggcc cccggggggga gggagggagg gcgccgggcc    180
ggtgggagcc agcggcgcgc ggtgggaccc acggagcccc gcgacccgcc gagcctggag    240
ccgggccggc tcggggaagc cggctccagc ccggagcgaa cttcgcagcc cgtcgggggg    300
cggcggggag ggggcccgga gccggaggag gggcggccg cgggcacccc cgcctgtgcc    360
ccggcgtccc cgggcacc atg ctg tcc aac tcc cag ggc cag agc ccg ccg     411
                    Met Leu Ser Asn Ser Gln Gly Gln Ser Pro Pro
                    1               5                   10 gtg ccg ttc ccc gcc ccg gcc ccg ccg cag ccc ccc acc cct gcc         459
Val Pro Phe Pro Ala Pro Ala Pro Pro Gln Pro Pro Thr Pro Ala
            15                  20                  25 ctg ccg cac ccc ccg gcg cag ccg ccg ccg ccc ccg cag cag ttc         507
Leu Pro His Pro Pro Ala Gln Pro Pro Pro Pro Pro Gln Gln Phe
```

```
                 30                  35                  40
ccg cag ttc cac gtc aag tcc ggc ctg cag atc aag aag aac gcc atc     555
Pro Gln Phe His Val Lys Ser Gly Leu Gln Ile Lys Lys Asn Ala Ile
    45                  50                  55 atc gat gac tac aag gtc acc agc cag gtc ctg ggg ctg ggc atc aac     603
Ile Asp Asp Tyr Lys Val Thr Ser Gln Val Leu Gly Leu Gly Ile Asn
60                  65                  70                  75 ggc aaa gtt ttg cag atc ttc aac aag agg acc cag gag aaa ttc gcc     651
Gly Lys Val Leu Gln Ile Phe Asn Lys Arg Thr Gln Glu Lys Phe Ala
                80                  85                  90 ctc aaa atg ctt cag gac tgc ccc aag gcc cgc agg gag gtg gag ctg     699
Leu Lys Met Leu Gln Asp Cys Pro Lys Ala Arg Arg Glu Val Glu Leu
            95                 100                 105 cac tgg cgg gcc tcc cag tgc ccg cac atc gta cgg atc gtg gat gtg     747
His Trp Arg Ala Ser Gln Cys Pro His Ile Val Arg Ile Val Asp Val
        110                 115                 120 tac gag aat ctg tac gca ggg agg aag tgc ctg ctg att gtc atg gaa     795
Tyr Glu Asn Leu Tyr Ala Gly Arg Lys Cys Leu Leu Ile Val Met Glu
    125                 130                 135 tgt ttg gac ggt gga gaa ctc ttt agc cga atc cag gat cga gga gac     843
Cys Leu Asp Gly Gly Glu Leu Phe Ser Arg Ile Gln Asp Arg Gly Asp
140                 145                 150                 155 cag gca ttc aca gaa aga gaa gca tcc gaa atc atg aag agc atc ggt     891
Gln Ala Phe Thr Glu Arg Glu Ala Ser Glu Ile Met Lys Ser Ile Gly
                160                 165                 170 gag gcc atc cag tat ctg cat tca atc aac att gcc cat cgg gat gtc     939
Glu Ala Ile Gln Tyr Leu His Ser Ile Asn Ile Ala His Arg Asp Val
            175                 180                 185 aag cct gag aat ctc tta tac acc tcc aaa agg ccc aac gcc atc ctg     987
Lys Pro Glu Asn Leu Leu Tyr Thr Ser Lys Arg Pro Asn Ala Ile Leu
        190                 195                 200 aaa ctc act gac ttt ggc ttt gcc aag gaa acc acc agc cac aac tct    1035
Lys Leu Thr Asp Phe Gly Phe Ala Lys Glu Thr Thr Ser His Asn Ser
    205                 210                 215 ttg acc act cct tgt tat aca ccg tac tat gtg gct cca gaa gtg ctg    1083
Leu Thr Thr Pro Cys Tyr Thr Pro Tyr Tyr Val Ala Pro Glu Val Leu
220                 225                 230                 235 ggt cca gag aag tat gac aag tcc tgt gac atg tgg tcc ctg ggt gtc    1131
Gly Pro Glu Lys Tyr Asp Lys Ser Cys Asp Met Trp Ser Leu Gly Val
                240                 245                 250 atc atg tac atc ctg ctg tgt ggg tat ccc ccc ttc tac tcc aac cac    1179
Ile Met Tyr Ile Leu Leu Cys Gly Tyr Pro Pro Phe Tyr Ser Asn His
            255                 260                 265 ggc ctt gcc atc tct ccg ggc atg aag act cgc atc cga atg ggc cag    1227
Gly Leu Ala Ile Ser Pro Gly Met Lys Thr Arg Ile Arg Met Gly Gln
        270                 275                 280 tat gaa ttt ccc aac cca gaa tgg tca gaa gta tca gag gaa gtg aag    1275
Tyr Glu Phe Pro Asn Pro Glu Trp Ser Glu Val Ser Glu Glu Val Lys
    285                 290                 295 atg ctc att cgg aat ctg ctg aaa aca gag ccc acc cag aga atg acc    1323
Met Leu Ile Arg Asn Leu Leu Lys Thr Glu Pro Thr Gln Arg Met Thr
300                 305                 310                 315 atc acc gag ttt atg aac cac cct tgg atc atg caa tca aca aag gtc    1371
Ile Thr Glu Phe Met Asn His Pro Trp Ile Met Gln Ser Thr Lys Val
                320                 325                 330 cct caa acc cca ctg cac acc agc cgg gtc ctg aag gag gac aag gag    1419
Pro Gln Thr Pro Leu His Thr Ser Arg Val Leu Lys Glu Asp Lys Glu
            335                 340                 345 cgg tgg gag gat gtc aag ggg tgt ctt cat gac aag aac agc gac cag    1467
```

-continued

```
Arg Trp Glu Asp Val Lys Gly Cys Leu His Asp Lys Asn Ser Asp Gln
        350                 355                 360 gcc act tgg ctg acc agg ttg tga gcagaggatt ctgtgttcct gtccaaactc    1521
Ala Thr Trp Leu Thr Arg Leu  *
        365                 370 agtgctgttt cttagaatcc ttttattccc tgggtctcta atgggacctt aaagaccatc    1581
tggtatcatc ttctcatttt gcagaagaga aactgaggcc cagaggcgga gggcagtctg    1641
ctcaaggtca cgcagctggt gactggttgg ggcagaccgg acccaggttt cctgactcct    1701
ggcccaagtc tcttcctcct atcctgcggg atcactgggg ggctctcagg gaacagcagc    1761
agtgccatag ccaggctctc tgctgcccag cgctggggtg aggctgccgt tgtcagcgtg    1821
gaccactaac cagcccgtct tctctctctg ctcccacccc tgccgccctc accctgccct    1881
tgttgtctct gtctctcacg tctctcttct gctgtctctc ctaccgtct tctggctctc    1941 tctgtaccct tcctggtgct gccgtgcccc caggaggaga tgaccagtgc cttggccaca    2001
atgcgcgttg actacgagca gatcaagata aaaaagattg aagatgcatc caaccctctg    2061
ctgctgaaga ggcggaagaa agctcgggcc ctggaggctg cggctctggc ccactgagcc    2121
accgcgccct cctgcccacg ggaggacaag caataactct ctacaggaat atattttta    2181 aacgaagaga cagaactgtc cacatctgcc tcctctcctc ctcagctgca tggagcctgg    2241
aactgcatca gtgactgaat tc                                             2263
```

<210> SEQ ID NO 34
<211> LENGTH: 370
<212> TYPE: PRT
<213> ORGANISM: Homo sapiens

<400> SEQUENCE: 34

```
Met Leu Ser Asn Ser Gln Gly Gln Ser Pro Val Pro Phe Pro Ala
 1               5                  10                  15

Pro Ala Pro Pro Gln Pro Pro Thr Pro Ala Leu Pro His Pro Pro
                20                  25                  30

Ala Gln Pro Pro Pro Pro Pro Gln Gln Phe Pro Gln Phe His Val
                35                  40                  45

Lys Ser Gly Leu Gln Ile Lys Lys Asn Ala Ile Ile Asp Asp Tyr Lys
 50                  55                  60

Val Thr Ser Gln Val Leu Gly Leu Gly Ile Asn Gly Lys Val Leu Gln
 65                  70                  75                  80

Ile Phe Asn Lys Arg Thr Gln Glu Lys Phe Ala Leu Lys Met Leu Gln
                 85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
                115                 120                 125

Ala Gly Arg Lys Cys Leu Leu Ile Val Met Glu Cys Leu Asp Gly Gly
                130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
                180                 185                 190

Leu Tyr Thr Ser Lys Arg Pro Asn Ala Ile Leu Lys Leu Thr Asp Phe
                195                 200                 205
```

```
Gly Phe Ala Lys Glu Thr Thr Ser His Asn Ser Leu Thr Thr Pro Cys
    210                 215                 220
Tyr Thr Pro Tyr Tyr Val Ala Pro Glu Val Leu Gly Pro Glu Lys Tyr
225                 230                 235                 240
Asp Lys Ser Cys Asp Met Trp Ser Leu Gly Val Ile Met Tyr Ile Leu
                245                 250                 255
Leu Cys Gly Tyr Pro Pro Phe Tyr Ser Asn His Gly Leu Ala Ile Ser
            260                 265                 270
Pro Gly Met Lys Thr Arg Ile Arg Met Gly Gln Tyr Glu Phe Pro Asn
        275                 280                 285
Pro Glu Trp Ser Glu Val Ser Glu Glu Val Lys Met Leu Ile Arg Asn
    290                 295                 300
Leu Leu Lys Thr Glu Pro Thr Gln Arg Met Thr Ile Thr Glu Phe Met
305                 310                 315                 320
Asn His Pro Trp Ile Met Gln Ser Thr Lys Val Pro Gln Thr Pro Leu
                325                 330                 335
His Thr Ser Arg Val Leu Lys Glu Asp Lys Glu Arg Trp Glu Asp Val
            340                 345                 350
Lys Gly Cys Leu His Asp Lys Asn Ser Asp Gln Ala Thr Trp Leu Thr
        355                 360                 365
Arg Leu
    370

<210> SEQ ID NO 35
<211> LENGTH: 1074
<212> TYPE: DNA
<213> ORGANISM: Homo sapiens
<220> FEATURE:
<221> NAME/KEY: CDS
<222> LOCATION: (628)...(831)

<400> SEQUENCE: 35
ttttactttt tttaagcaca aaattttgtt ttttttctcc cctccccaca gatcccatct    60
caaatcattc tgttaaccac cattccaaca ggtcgaggag agcttaaaca ccttcttcct   120
ctgccttgtt tctattttt tattttttg catcagtatt aatgttttg catactctcc     180 atctttatcc aaaaatgtaa acttcctttg tcaatctatg gatatgccca tatatgaaag   240
agatgggtgg gtcaaaaagg gatatcaaat gaagtgatag gggtcacaat ggggaaatgg   300
aagtggtaca taacattgcc aaaataatgt gccactagaa atggtgtaaa ggctgtcttt   360
ttttttaaga aagttatta ccatgtattt tgtgaggcag gtttacaaca ctacaagtct    420
tgactaagaa ggaaagagga aaaagaaaa acaccaata cccatattta aaaaaaaaa     480 aatgatcata gtcttaggag ttcatttaaa ccataggaac ttttcactta tctcatgtta   540
ggtgtaccag tcagtgatta agtagaacta caagttatat aggctgtatt gtttattgct   600
ggtttatgac cttaataaag tgtaatt atg tat tac cag cag ggt gtt ttt aac  654
                             Met Tyr Tyr Gln Gln Gly Val Phe Asn
                             1               5 tgt gac tat tgt ata aaa aca aat ctt gat atc cag aag cac atg aag   702
Cys Asp Tyr Cys Ile Lys Thr Asn Leu Asp Ile Gln Lys His Met Lys
10              15                  20                  25 ttt gcg act ttc cac cct gcc cat ttt tgt aaa act gca gtc atc ttg    750
Phe Ala Thr Phe His Pro Ala His Phe Cys Lys Thr Ala Val Ile Leu
            30                  35                  40 gac ctt tta aac aca aat ttt aaa ctc aac caa gct gtg ata agc gga    798
Asp Leu Leu Asn Thr Asn Phe Lys Leu Asn Gln Ala Val Ile Ser Gly
```

```
                45                  50                  55
atg gtt act gtt tat act gtg gta tgt ttt tga ttacagcaga taatgctttc    851
Met Val Thr Val Tyr Thr Val Val Cys Phe  *
                60                  65 ttttccagtc atctttgaga ataaaggaaa aaaaaaatct tcagatgcaa tggttttgtg    911
tagcatcttg tctatcatgt tttgtaaatg ctggagaagc gtcgaccaat ttgacttaga    971
gatggaatgt aactttgctt acaaaaattg ctattaaact cctacttaag gtgttctaat   1031
tttctgtgag cacactaaaa acaaaaatat atgtgaataa aat                    1074

<210> SEQ ID NO 36
<211> LENGTH: 67
<212> TYPE: PRT
<213> ORGANISM: Homo sapiens

<400> SEQUENCE: 36

Met Tyr Tyr Gln Gln Gly Val Phe Asn Cys Asp Tyr Cys Ile Lys Thr
 1               5                  10                  15

Asn Leu Asp Ile Gln Lys His Met Lys Phe Ala Thr Phe His Pro Ala
            20                  25                  30

His Phe Cys Lys Thr Ala Val Ile Leu Asp Leu Leu Asn Thr Asn Phe
        35                  40                  45

Lys Leu Asn Gln Ala Val Ile Ser Gly Met Val Thr Val Tyr Thr Val
    50                  55                  60

Val Cys Phe
65

<210> SEQ ID NO 37
<211> LENGTH: 1356
<212> TYPE: DNA
<213> ORGANISM: Homo sapiens
<220> FEATURE:
<221> NAME/KEY: CDS
<222> LOCATION: (553)...(1095)

<400> SEQUENCE: 37
ttctcccgca accttccctt cgctccctcc cgtccccccc agctcctagc ctccgactcc     60 ctcccccct cacgcccgcc ctctcgcctt cgccgaacca agtggatta attacacgct     120 ttctgtttct ctccgtgctg ttctctcccg ctgtgcgcct gccgcctct cgctgtcctc    180 tctcccctc gccctctctt cggcccccc ctttcacgtt cactctgtct ctcccactat    240
ctctgccccc ctctatcctt gatacaacag ctgacctcat ttcccgatac cttttccccc    300
ccgaaaagta caacatctgg cccgcccag cccgaagaca gcccgtcctc cctggacaat    360
cagacgaatt ctccccccc ccccaaaaaa aaaagccatc ccccgctct gccccgtcgc    420 acattcggcc cccgcgactc ggccagagcg gcgctggcag aggagtgtcc ggcaggaggg    480
ccaacgcccg ctgttcggtt tgcgacacgc agcaggagg tgggcggcag cgtcgccggc    540
ttccagacac ca atg gga atc cca atg ggg aag tcg atg ctg gtg ctt ctc    591
              Met Gly Ile Pro Met Gly Lys Ser Met Leu Val Leu Leu
                1                   5                  10 acc ttc ttg gcc ttc gcc tcg tgc tgc att gct gct tac cgc ccc agt    639
Thr Phe Leu Ala Phe Ala Ser Cys Cys Ile Ala Ala Tyr Arg Pro Ser
        15                  20                  25 gag acc ctg tgc ggc ggg gag ctg gtg gac acc ctc cag ttc gtc tgt    687
Glu Thr Leu Cys Gly Gly Glu Leu Val Asp Thr Leu Gln Phe Val Cys
30                  35                  40                  45 ggg gac cgc ggc ttc tac ttc agc agg ccc gca agc cgt gtg agc cgt    735
```

-continued

```
                Gly Asp Arg Gly Phe Tyr Phe Ser Arg Pro Ala Ser Arg Val Ser Arg
                                50                  55                  60 cgc agc cgt ggc atc gtt gag gag tgc tgt ttc cgc agc tgt gac ctg        783
Arg Ser Arg Gly Ile Val Glu Glu Cys Cys Phe Arg Ser Cys Asp Leu
             65                  70                  75 gcc ctc ctg gag acg tac tgt gct acc ccc gcc aag tcc gag agg gac        831
Ala Leu Leu Glu Thr Tyr Cys Ala Thr Pro Ala Lys Ser Glu Arg Asp
         80                  85                  90 gtg tcg acc cct ccg acc gtg ctt ccg gac aac ttc ccc aga tac ccc        879
Val Ser Thr Pro Pro Thr Val Leu Pro Asp Asn Phe Pro Arg Tyr Pro
     95                 100                 105 gtg ggc aag ttc ttc caa tat gac acc tgg aag cag tcc acc cag cgc        927
Val Gly Lys Phe Phe Gln Tyr Asp Thr Trp Lys Gln Ser Thr Gln Arg
110                 115                 120                 125 ctg cgc agg ggc ctg cct gcc ctc ctg cgt gcc cgc ggt cac gtg            975
Leu Arg Arg Gly Leu Pro Ala Leu Leu Arg Ala Arg Gly His Val
                130                 135                 140 ctc gcc aag gag ctc gag gcg ttc agg gag gcc aaa cgt cac cgt ccc       1023
Leu Ala Lys Glu Leu Glu Ala Phe Arg Glu Ala Lys Arg His Arg Pro
                145                 150                 155 ctg att gct cta ccc acc caa gac ccc gcc cac ggg ggc gcc ccc cca       1071
Leu Ile Ala Leu Pro Thr Gln Asp Pro Ala His Gly Gly Ala Pro Pro
            160                 165                 170 gag atg gcc agc aat cgg aag tga gcaaaactgc cgcaagtctg cagcccggcg      1125
Glu Met Ala Ser Asn Arg Lys *
        175                 180 ccaccatcct gcagcctcct cctgaccacg gacgtttcca tcaggttcca tcccgaaaat    1185
ctctcggttc cacgtccccc tggggcttct cctgacccag tccccgtgcc ccgcctcccc    1245
gaaacaggct actctcctcg gcccctcca tcgggctgag gaagcacagc agcatcttca     1305
aacatgtaca aaatcgattg gctttaaaca cccttcacat accctccccc c             1356

<210> SEQ ID NO 38
<211> LENGTH: 180
<212> TYPE: PRT
<213> ORGANISM: Homo sapiens

<400> SEQUENCE: 38

Met Gly Ile Pro Met Gly Lys Ser Met Leu Val Leu Leu Thr Phe Leu
 1                5                  10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
             35                  40                  45

Gly Phe Tyr Phe Ser Arg Pro Ala Ser Arg Val Ser Arg Arg Ser Arg
         50                  55                  60

Gly Ile Val Glu Glu Cys Cys Phe Arg Ser Cys Asp Leu Ala Leu Leu
 65                  70                  75                  80

Glu Thr Tyr Cys Ala Thr Pro Ala Lys Ser Glu Arg Asp Val Ser Thr
                 85                  90                  95

Pro Pro Thr Val Leu Pro Asp Asn Phe Pro Arg Tyr Pro Val Gly Lys
                100                 105                 110

Phe Phe Gln Tyr Asp Thr Trp Lys Gln Ser Thr Gln Arg Leu Arg Arg
            115                 120                 125

Gly Leu Pro Ala Leu Leu Arg Ala Arg Gly His Val Leu Ala Lys
        130                 135                 140

Glu Leu Glu Ala Phe Arg Glu Ala Lys Arg His Arg Pro Leu Ile Ala
```

```
                145                 150                 155                 160
Leu Pro Thr Gln Asp Pro Ala His Gly Gly Ala Pro Pro Glu Met Ala
                    165                 170                 175

Ser Asn Arg Lys
        180

<210> SEQ ID NO 39
<211> LENGTH: 1894
<212> TYPE: DNA
<213> ORGANISM: Homo sapiens
<220> FEATURE:
<221> NAME/KEY: CDS
<222> LOCATION: (416)...(1423)
<223> OTHER INFORMATION: Human JKETS.

<400> SEQUENCE: 39
gtctgacttc ctcccagcac attcctgcac tctgccgtgt ccacactgcc ccacagaccc      60
agtcctccaa gctgctgcc agctccctgc aagcccctca ggttgggcct tgccacggtg     120
ccagcaggca gccctgggct gggggtaggg gactccctac aggcacgcag ccctgagacc    180
tcagagggcc accccttgag ggtggccagg cccccagtgg ccaacctgag tgctgcctct    240
gccaccagcc ctgctggccc ctggttccgc tggccccca gatgcctggc tgagacacgc     300
cagtggcctc agctgcccac acctcttccc ggccctgaa gttggcactg cagcagacag     360
ctccctgggc accaggcagc taacagacac agccgccagc ccaaacagca gcggc atg    418
                                                                Met
                                                                  1 ggc agc gcc agc ccg ggt ctg agc agc gta tcc ccc agc cac ctc ctg    466
Gly Ser Ala Ser Pro Gly Leu Ser Ser Val Ser Pro Ser His Leu Leu
                5                  10                 15 ctg ccc ccc gac acg gtg tcg cgg aca ggc ttg gag aag gcg gca gcg    514
Leu Pro Pro Asp Thr Val Ser Arg Thr Gly Leu Glu Lys Ala Ala Ala
         20                  25                 30 ggg gca gtg ggt ctc gag aga cgg gac tgg agt ccc agt cca ccc gcc    562
Gly Ala Val Gly Leu Glu Arg Arg Asp Trp Ser Pro Ser Pro Pro Ala
 35                  40                 45 acg ccc gag cag ggc ctg tcc gcc ttc tac ctc tcc tac ttt gac atg    610
Thr Pro Glu Gln Gly Leu Ser Ala Phe Tyr Leu Ser Tyr Phe Asp Met
 50                  55                 60                 65 ctg tac cct gag gac agc agc tgg gca gcc aag gcc cct ggg gcc agc    658
Leu Tyr Pro Glu Asp Ser Ser Trp Ala Ala Lys Ala Pro Gly Ala Ser
                 70                 75                 80 agt cgg gag gag cca cct gag gag cct gag cag tgc ccg gtc att gac    706
Ser Arg Glu Glu Pro Pro Glu Glu Pro Glu Gln Cys Pro Val Ile Asp
             85                 90                 95 agc caa gcc cca gcg ggc agc ctg gac ttg gtg ccc ggc ggg ctg acc    754
Ser Gln Ala Pro Ala Gly Ser Leu Asp Leu Val Pro Gly Gly Leu Thr
        100                 105                110 ttg gag gag cac tcg ctg gag cag gtg cag tcc atg gtg gtg ggc gaa    802
Leu Glu Glu His Ser Leu Glu Gln Val Gln Ser Met Val Val Gly Glu
    115                 120                 125 gtg ctc aag gac atc gag acg gcc tgc aag ctg ctc aac atc acc gca    850
Val Leu Lys Asp Ile Glu Thr Ala Cys Lys Leu Leu Asn Ile Thr Ala
130                 135                 140                 145 gat ccc atg gac tgg agc ccc agc aat gtg cag aag tgg ctc ctg tgg    898
Asp Pro Met Asp Trp Ser Pro Ser Asn Val Gln Lys Trp Leu Leu Trp
                150                 155                 160 aca gag cac caa tac cgg ctg ccc ccc atg ggc aag gcc ttc cag gag    946
Thr Glu His Gln Tyr Arg Leu Pro Pro Met Gly Lys Ala Phe Gln Glu
            165                 170                 175
```

```
ctg gcg ggc aag gag ctg tgc gcc atg tcg gag gag cag ttc cgc cag    994
Leu Ala Gly Lys Glu Leu Cys Ala Met Ser Glu Glu Gln Phe Arg Gln
            180                 185                 190 cgc tcg ccc ctg ggt ggg gat gtg ctg cac gcc cac ctg gac atc tgg   1042
Arg Ser Pro Leu Gly Gly Asp Val Leu His Ala His Leu Asp Ile Trp
        195                 200                 205 aag tca gcg gcc tgg atg aaa gag cgg act tca cct ggg gcg att cac   1090
Lys Ser Ala Ala Trp Met Lys Glu Arg Thr Ser Pro Gly Ala Ile His
210                 215                 220                 225 tac tgt gcc tcg acc agt gag gag agc tgg acc gac agc gag gtg gac   1138
Tyr Cys Ala Ser Thr Ser Glu Glu Ser Trp Thr Asp Ser Glu Val Asp
                230                 235                 240 tca tca tgc tcc ggg cag ccc atc cac ctg tgg cag ttc ctc aag gag   1186
Ser Ser Cys Ser Gly Gln Pro Ile His Leu Trp Gln Phe Leu Lys Glu
            245                 250                 255 ttg cta ctc aag ccc cac agc tat ggc cgc ttc att agg tgg ctc aac   1234
Leu Leu Leu Lys Pro His Ser Tyr Gly Arg Phe Ile Arg Trp Leu Asn
        260                 265                 270 aag gag aag ggc atc ttc aaa att gag gac tca gcc cag gtg gcc cgg   1282
Lys Glu Lys Gly Ile Phe Lys Ile Glu Asp Ser Ala Gln Val Ala Arg
275                 280                 285 ctg tgg ggc atc cgc aag aac cgt ccc gcc atg aac tac gac aag ctg   1330
Leu Trp Gly Ile Arg Lys Asn Arg Pro Ala Met Asn Tyr Asp Lys Leu
290                 295                 300                 305 agc cgc tcc atc cgc cag tat tac aag aag ggc atc atc cgg aag cca   1378
Ser Arg Ser Ile Arg Gln Tyr Tyr Lys Lys Gly Ile Ile Arg Lys Pro
                310                 315                 320 gac atc tcc cag cgc ctc gtc tac cag ttc gtg cac ccc atc tga       1423
Asp Ile Ser Gln Arg Leu Val Tyr Gln Phe Val His Pro Ile *
            325                 330                 335 gtgcctggcc cagggcctga aacccgccct caggggcctc tctcctgcct gccctgcctc    1483
agccaggccc tgagatgggg gaaaacgggc agtctgctct gctgctctga ccttccagag    1543
cccaaggtca gggaggggca accaactgcc caggggggat atgggtcctc tggggccttc    1603
gggaccatgg gcaggggtg cttcctcctc aggcccagct gctcccctgg aggacagagg     1663
gagacagggc tgctccccaa cacctgcctc tgaccccagc atttccagag cagagcctac    1723
agaagggcag tgactcgaca aaggccacag gcagtccagg cctctctctg ctccatcccc    1783
ctgcctccca ttctgcacca cacctggcat ggtgcaggga gacatctgca cccctgagtt    1843
gggcagccag gagtgccccc gggaatggat aataaagata ctagagaact g              1894
```

<210> SEQ ID NO 40
<211> LENGTH: 335
<212> TYPE: PRT
<213> ORGANISM: Homo sapiens

<400> SEQUENCE: 40

```
Met Gly Ser Ala Ser Pro Gly Leu Ser Ser Val Ser Pro Ser His Leu
1               5                   10                  15

Leu Leu Pro Pro Asp Thr Val Ser Arg Thr Gly Leu Glu Lys Ala Ala
            20                  25                  30

Ala Gly Ala Val Gly Leu Glu Arg Arg Asp Trp Ser Pro Ser Pro
        35                  40                  45

Ala Thr Pro Glu Gln Gly Leu Ser Ala Phe Tyr Leu Ser Tyr Phe Asp
    50                  55                  60

Met Leu Tyr Pro Glu Asp Ser Ser Trp Ala Ala Lys Ala Pro Gly Ala
65                  70                  75                  80
```

```
Ser Ser Arg Glu Glu Pro Pro Glu Pro Glu Gln Cys Pro Val Ile
                85                  90                  95

Asp Ser Gln Ala Pro Ala Gly Ser Leu Asp Leu Val Pro Gly Gly Leu
            100                 105                 110

Thr Leu Glu Glu His Ser Leu Glu Gln Val Gln Ser Met Val Val Gly
            115                 120                 125

Glu Val Leu Lys Asp Ile Glu Thr Ala Cys Lys Leu Leu Asn Ile Thr
        130                 135                 140

Ala Asp Pro Met Asp Trp Ser Pro Ser Asn Val Gln Lys Trp Leu Leu
145                 150                 155                 160

Trp Thr Glu His Gln Tyr Arg Leu Pro Pro Met Gly Lys Ala Phe Gln
                165                 170                 175

Glu Leu Ala Gly Lys Glu Leu Cys Ala Met Ser Glu Glu Gln Phe Arg
            180                 185                 190

Gln Arg Ser Pro Leu Gly Gly Asp Val Leu His Ala His Leu Asp Ile
        195                 200                 205

Trp Lys Ser Ala Ala Trp Met Lys Glu Arg Thr Ser Pro Gly Ala Ile
210                 215                 220

His Tyr Cys Ala Ser Thr Ser Glu Glu Ser Trp Thr Asp Ser Glu Val
225                 230                 235                 240

Asp Ser Ser Cys Ser Gly Gln Pro Ile His Leu Trp Gln Phe Leu Lys
                245                 250                 255

Glu Leu Leu Leu Lys Pro His Ser Tyr Gly Arg Phe Ile Arg Trp Leu
            260                 265                 270

Asn Lys Glu Lys Gly Ile Phe Lys Ile Glu Asp Ser Ala Gln Val Ala
        275                 280                 285

Arg Leu Trp Gly Ile Arg Lys Asn Arg Pro Ala Met Asn Tyr Asp Lys
    290                 295                 300

Leu Ser Arg Ser Ile Arg Gln Tyr Tyr Lys Lys Gly Ile Ile Arg Lys
305                 310                 315                 320

Pro Asp Ile Ser Gln Arg Leu Val Tyr Gln Phe Val His Pro Ile
                325                 330                 335

<210> SEQ ID NO 41
<211> LENGTH: 84
<212> TYPE: PRT
<213> ORGANISM: Homo sapiens
<220> FEATURE:
<221> NAME/KEY: DOMAIN
<222> LOCATION: (1)...(84)
<223> OTHER INFORMATION: Ets domain of JKETS.

<400> SEQUENCE: 41

Ile His Leu Trp Gln Phe Leu Lys Glu Leu Leu Lys Pro His Ser
1               5                   10                  15

Tyr Gly Arg Phe Ile Arg Trp Leu Asn Lys Glu Lys Gly Ile Phe Lys
            20                  25                  30

Ile Glu Asp Ser Ala Gln Val Ala Arg Leu Trp Gly Ile Arg Lys Asn
        35                  40                  45

Arg Pro Ala Met Asn Tyr Asp Lys Leu Ser Arg Ser Ile Arg Gln Tyr
    50                  55                  60

Tyr Lys Lys Gly Ile Ile Arg Lys Pro Asp Ile Ser Gln Arg Leu Val
65                  70                  75                  80

Tyr Gln Phe Val
```

```
<210> SEQ ID NO 42
<211> LENGTH: 1907
<212> TYPE: DNA
<213> ORGANISM: Homo sapiens
<220> FEATURE:
<221> NAME/KEY: CDS
<222> LOCATION: (96)...(1211)
<223> OTHER INFORMATION: Human epithelial-restricted with serine box
      (ESX) protein.

<400> SEQUENCE: 42
cggccagata cctcagcgct acctggcgga actggatttc tctcccgcct gccggcctgc        60
ctgccacagc cggactccgc cactccggta gcctc atg gct gca acc tgt gag         113
                                     Met Ala Ala Thr Cys Glu
                                       1               5 att agc aac att ttt agc aac tac ttc agt gcg atg tac agc tcg gag        161
Ile Ser Asn Ile Phe Ser Asn Tyr Phe Ser Ala Met Tyr Ser Ser Glu
             10                  15                  20 gac tcc acc ctg gcc tct gtt ccc cct gct gcc acc ttt ggg gcc gat        209
Asp Ser Thr Leu Ala Ser Val Pro Pro Ala Ala Thr Phe Gly Ala Asp
         25                  30                  35 gac ttg gta ctg acc ctg agc aac ccc cag atg tca ttg gag ggt aca        257
Asp Leu Val Leu Thr Leu Ser Asn Pro Gln Met Ser Leu Glu Gly Thr
     40                  45                  50 gag aag gcc agc tgg ttg ggg gaa cag ccc cag ttc tgg tcg aag acg        305
Glu Lys Ala Ser Trp Leu Gly Glu Gln Pro Gln Phe Trp Ser Lys Thr
 55                  60                  65                  70 cag gtt ctg gac tgg atc agc tac caa gtg gag aag aac aag tac gac        353
Gln Val Leu Asp Trp Ile Ser Tyr Gln Val Glu Lys Asn Lys Tyr Asp
                 75                  80                  85 gca agc gcc att gac ttc tca cga tgt gac atg gat ggc gcc acc ctc        401
Ala Ser Ala Ile Asp Phe Ser Arg Cys Asp Met Asp Gly Ala Thr Leu
             90                  95                 100 tgc aat tgt gcc ctt gag gag ctg cgt ctg gtc ttt ggg cct ctg ggg        449
Cys Asn Cys Ala Leu Glu Glu Leu Arg Leu Val Phe Gly Pro Leu Gly
         105                 110                 115 gac caa ctc cat gcc cag ctg cga gac ctc act tcc agc tct tct gat        497
Asp Gln Leu His Ala Gln Leu Arg Asp Leu Thr Ser Ser Ser Ser Asp
     120                 125                 130 gag ctc agt tgg atc att gag ctg ctg gag aag gat ggc atg gcc ttc        545
Glu Leu Ser Trp Ile Ile Glu Leu Leu Glu Lys Asp Gly Met Ala Phe
135                 140                 145                 150 cag gag gcc cta gac cca ggg ccc ttt gac cag ggc agc ccc ttt gcc        593
Gln Glu Ala Leu Asp Pro Gly Pro Phe Asp Gln Gly Ser Pro Phe Ala
                155                 160                 165 cag gag ctg ctg gac gac ggt cag caa gcc agc ccc tac cac ccc ggc        641
Gln Glu Leu Leu Asp Asp Gly Gln Gln Ala Ser Pro Tyr His Pro Gly
            170                 175                 180 agc tgt ggc gca gga gcc ccc tcc cct ggc agc tct gac gtc tcc acc        689
Ser Cys Gly Ala Gly Ala Pro Ser Pro Gly Ser Ser Asp Val Ser Thr
        185                 190                 195 gca ggg act ggt gct tct cgg agc tcc cac tcc tca gac tcc ggt gga        737
Ala Gly Thr Gly Ala Ser Arg Ser Ser His Ser Ser Asp Ser Gly Gly
    200                 205                 210 agt gac gtg gac ctg gat ccc act gat ggc aag ctc ttc ccc agc gat        785
Ser Asp Val Asp Leu Asp Pro Thr Asp Gly Lys Leu Phe Pro Ser Asp
215                 220                 225                 230 ggt ttt cgt gac tgc aag aag ggg gat ccc aag cac ggg aag cgg aaa        833
Gly Phe Arg Asp Cys Lys Lys Gly Asp Pro Lys His Gly Lys Arg Lys
                235                 240                 245 cga ggc cgg ccc cga aag ctg agc aaa gag tac tgg gac tgt ctc gag        881
```

-continued

```
                Arg Gly Arg Pro Arg Lys Leu Ser Lys Glu Tyr Trp Asp Cys Leu Glu
                            250                 255                 260 ggc aag aag agc aag cac gcg ccc aga ggc acc cac ctg tgg gag ttc              929
Gly Lys Lys Ser Lys His Ala Pro Arg Gly Thr His Leu Trp Glu Phe
            265                 270                 275 atc cgg gac atc ctc atc cac ccg gag ctc aac gag ggc ctc atg aag              977
Ile Arg Asp Ile Leu Ile His Pro Glu Leu Asn Glu Gly Leu Met Lys
        280                 285                 290 tgg gag aat cgg cat gaa ggc gtc ttc aag ttc ctg cgc tcc gag gct             1025
Trp Glu Asn Arg His Glu Gly Val Phe Lys Phe Leu Arg Ser Glu Ala
295                 300                 305                 310 gtg gcc caa cta tgg ggc caa aag aaa aag aac agc aac atg acc tac             1073
Val Ala Gln Leu Trp Gly Gln Lys Lys Lys Asn Ser Asn Met Thr Tyr
                315                 320                 325 gag aag ctg agc cgg gcc atg agg tac tac tac aaa cgg gag atc ctg             1121
Glu Lys Leu Ser Arg Ala Met Arg Tyr Tyr Tyr Lys Arg Glu Ile Leu
            330                 335                 340 gaa cgg gtg gat ggc cgg cga ctc gtc tac aag ttt ggc aaa aac tca             1169
Glu Arg Val Asp Gly Arg Arg Leu Val Tyr Lys Phe Gly Lys Asn Ser
        345                 350                 355 agc ggc tgg aag gag gaa gag gtt ctc cag agt cgg aac tga                     1211
Ser Gly Trp Lys Glu Glu Glu Val Leu Gln Ser Arg Asn *
    360                 365                 370 gggttggaac tatacccggg accaaactca cggaccactc gaggcctgca aaccttcctg           1271
ggaggacagg caggccagat ggcccctcca ctggggaatg ctcccagctg tgctgtggag           1331
agaagctgat gttttggtgt attgtcagcc atcgtccttg gactcggaga ctatggcctc           1391
gcctccccac cctcctcttg gaattacaag ccctggggtt tgaagctgac tttatagctg           1451
caagtgtatc tccttttatc tggtgcctcc tcaaacccag tctcagacac ttaaatgcag           1511
acaacacctt cttcctgcag acacttggac tgagccaagg aggcttggga ggccctaggg           1571
agcaccgtga tggagaggac agagcagggg ctccagcact tctttctgga ctggcgttca           1631
cctccctgct cagtgcttgg gctccacggg caggggtcag agcactccct aatttatgtg           1691
ctatataaat atgtcagatg tacatagaga tctattttt ctaaaacatt ccctccccca           1751
ctcctctccc acagagtgct ggactgttcc aggccctcca gtgggctgat gctgggaccc           1811
ttaggatggg gctcccagct cctttctcct gtgaatggag gcagagacct ccaataaagt           1871
gccttctggg cttttctaa aaaaaaaaaa aaaaaa                                      1907

<210> SEQ ID NO 43
<211> LENGTH: 371
<212> TYPE: PRT
<213> ORGANISM: Homo sapiens

<400> SEQUENCE: 43

Met Ala Ala Thr Cys Glu Ile Ser Asn Ile Phe Ser Asn Tyr Phe Ser
1               5                   10                  15

Ala Met Tyr Ser Ser Glu Asp Ser Thr Leu Ala Ser Val Pro Pro Ala
            20                  25                  30

Ala Thr Phe Gly Ala Asp Asp Leu Val Leu Thr Leu Ser Asn Pro Gln
        35                  40                  45

Met Ser Leu Glu Gly Thr Glu Lys Ala Ser Trp Leu Gly Glu Gln Pro
    50                  55                  60

Gln Phe Trp Ser Lys Thr Gln Val Leu Asp Trp Ile Ser Tyr Gln Val
65                  70                  75                  80

Glu Lys Asn Lys Tyr Asp Ala Ser Ala Ile Asp Phe Ser Arg Cys Asp
```

```
                85                  90                  95
Met Asp Gly Ala Thr Leu Cys Asn Cys Ala Leu Glu Glu Leu Arg Leu
            100                 105                 110

Val Phe Gly Pro Leu Gly Asp Gln Leu His Ala Gln Leu Arg Asp Leu
            115                 120                 125

Thr Ser Ser Ser Asp Glu Leu Ser Trp Ile Ile Glu Leu Leu Glu
            130                 135                 140

Lys Asp Gly Met Ala Phe Gln Glu Ala Leu Asp Pro Gly Pro Phe Asp
145                 150                 155                 160

Gln Gly Ser Pro Phe Ala Gln Glu Leu Leu Asp Asp Gly Gln Gln Ala
                165                 170                 175

Ser Pro Tyr His Pro Gly Ser Cys Gly Ala Gly Ala Pro Ser Pro Gly
            180                 185                 190

Ser Ser Asp Val Ser Thr Ala Gly Thr Gly Ala Ser Arg Ser Ser His
            195                 200                 205

Ser Ser Asp Ser Gly Gly Ser Asp Val Asp Leu Asp Pro Thr Asp Gly
            210                 215                 220

Lys Leu Phe Pro Ser Asp Gly Phe Arg Asp Cys Lys Lys Gly Asp Pro
225                 230                 235                 240

Lys His Gly Lys Arg Lys Arg Gly Arg Pro Arg Lys Leu Ser Lys Glu
                245                 250                 255

Tyr Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
            275                 280                 285

Asn Glu Gly Leu Met Lys Trp Glu Asn Arg His Glu Gly Val Phe Lys
290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
                325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Glu Val Leu Gln
            355                 360                 365

Ser Arg Asn
    370

<210> SEQ ID NO 44
<211> LENGTH: 17
<212> TYPE: PRT
<213> ORGANISM: Artificial Sequence
<220> FEATURE:
<223> OTHER INFORMATION: Synthetic peptide based on JKETS C-terminal
      fragment.

<400> SEQUENCE: 44

Arg Lys Pro Asp Ile Ser Gln Arg Leu Val Tyr Gln Phe Val His Pro
 1               5                  10                  15

Ile

<210> SEQ ID NO 45
<211> LENGTH: 16
<212> TYPE: PRT
<213> ORGANISM: Artificial Sequence
<220> FEATURE:
<223> OTHER INFORMATION: Synthetic peptide based on ESX C-terminal
``` fragment.

<400> SEQUENCE: 45

Gly Lys Asn Ser Ser Gly Trp Lys Glu Glu Glu Val Leu Gln Ser Met
1               5                   10                  15

<210> SEQ ID NO 46
<211> LENGTH: 1751
<212> TYPE: DNA
<213> ORGANISM: Homo sapiens
<220> FEATURE:
<221> NAME/KEY: promoter
<222> LOCATION: (1)...(1381)
<223> OTHER INFORMATION: JKETS promoter
<221> NAME/KEY: TATA_signal
<222> LOCATION: (1356)...(1360)
<223> OTHER INFORMATION: TATA box.

<400> SEQUENCE: 46

```
actatagggc acgcgtggtc gacggcccgg gctagtatta atgcatcaga atgctgtgat      60
ataagccagg cttctgtgag agtggggagg agggaggcgt ggccaccaga gaagcaggca     120
caaaaacgca ctctagggga aggagatcca cctggaaacg cagcgtgtct ttctttattg     180
accctggagg gctggaccat tggggattag gagtggtcga gtgtaccatt tcaggacctt     240
gtgttacctc cccttcctcc gctccatcct ccctcaacct tctctgggga atgactgata     300
actgatcctc aaccaaggtg ccagtgacga taacagccaa gtacagggct ccctggggt     360
gcaaagtgca accttacgtt ggagaatgtg ggtattggtg aaggtgaggg gctagttcta     420
aaggccttgg gatcccctgc agccccagaa tcctcatgct ctcggcagtt acacagttac     480
tcctgaaaca agagaaaaat cagcattatc tagaactttc tcccgtcaga atggaggtag     540
caggtacgtg gagcccttct gagatgattt ggagaaagga aggcccagcc tcagggaca     600
actctcagcc cacctggcag gacatggagg aagccaaaag ctggactgtg tggcccccgc     660
agggctcaag gaggtggagg gtctggggca gcaagtgctt ggtggtgggt atctctgtcc     720
tgcatggcat ccctgccatc accctttggg gctatgggag agcaagttgc tgctgactgg     780
cccccgatta caggcctggg aaagcgagct aggagtcctt cctcaccgcc actgtgtgac     840
aggtctgcat gaggaccctg tggggcacag agaacacagt tcccaccagg tcgcggttgg     900
cccacaagcc tcgggatccc tccccagggt tctctgaagc tctctccatc cctggcctga     960
gtagccagac agcacctcct ccaggaagcc ctcaactgat ttccctagtt ggtgcccacc    1020
ctcagtgccc cctcagtcct ccatctgggc atgggtggtt ctggatctcc actgctgctc    1080
acttgtctgt ctctggccct cagctgatcc atcttagaac cccagccctg gacccactcg    1140
acgtatctct ggcgccttgc acgtaatatg agctgagtgg ctatgcagca accaatgaac    1200
gagtgaatga gcgagtgaat gaatgagtcc cctagctgtc agggcatgga tcccccagca    1260
aggaggggga gacctgcaag ggttaatcag gagcctgcct gtggtctgag gtaagcaagg    1320
agtgtatttg ttcaggtaaa taaggaagga ttacttataa tgggaaatca ggccctgacc    1380
aactcttcat ctcgcggctg tctgacttcc tcccagcaca ttcctgcact ctgccgtgtc    1440
cacactgccc cacagaccca gtcctccaag cctgctgcca gctccctgca agcccctcag    1500
gttgggcctt gccacggtgc cagcaggcag ccctgggctg ggggtagggg actccctaca    1560
ggcacgcagc cctgagacct cagagggcca ccccttgagg gtggccaggc ccccagtgcc    1620
aacctgagtg ctgcctctgc caccagccct gctggcccct ggttccgctg gcccccagga    1680
tgcctggctg agacacgcca gtggcctcag ctgcccacac ctcttcccgg cccctgaagt    1740
```

```
tggcactgca g                                                              1751

<210> SEQ ID NO 47
<211> LENGTH: 1380
<212> TYPE: DNA
<213> ORGANISM: Homo sapiens
<220> FEATURE:
<221> NAME/KEY: promoter
<222> LOCATION: (1)...(1381)
<223> OTHER INFORMATION: JKETS promoter.

<400> SEQUENCE: 47
gatacagtag gtgcctgtta agcagtggtc attagtatta atgcatcaga atgctgtgat          60
ataagccagg cttctgtgag agtggggagg agggaggcgt ggccaccaga gaagcaggca         120
caaaaacgca ctctagggga aggagatcca cctggaaacg cagcgtgtct ttctttattg         180
accctggagg gctggaccat tgggattag  gagtggtcga gtgtaccatt tcaggacctt         240
gtgttacctc cccttcctcc gctccatcct ccctcaacct tctctgggga atgactgata         300
actgatcctc aaccaaggtg ccagtgacga taacagccaa gtacagggct ccctgggggt         360
gcaaagtgca accttacgtt ggagaatgtg ggtattggtg aaggtgaggg gctagttcta         420
aaggccttgg gatccctgc  agccccagaa tcctcatgct ctcggcagtt acacagttac         480
tcctgaaaca agagaaaaat cagcattatc tagaactttc tcccgtcaga atggaggtag         540
caggtacgtg gagcccttct gagatgattt ggagaaagga aggcccagcc tccagggaca         600
actctcagcc cacctggcag gacatggagg aagccaaaag ctggactgtg tggccccgc          660
agggctcaag gaggtggagg gtctgggca  gcaagtgctt ggtggtgggt atctctgtcc         720
tgcatggcat ccctgccatc accctttggg gctatgggga agcaagttgc tgctgactgg         780
cccccgatta caggcctggg aaagcgagct aggagtcctt cctcaccgcc actgtgtgac         840
aggtctgcat gaggaccctg tggggcacag agaacacagt tcccaccagg tcgcggttgg         900
cccacaagcc tcgggatccc tccccagggt tctctgaagc tctctccatc cctggcctga         960
gtagccagac agcacctcct ccaggaagcc ctcaactgat ttccctagtt ggtgcccacc        1020
ctcagtgccc cctcagtcct ccatctgggc atgggtggtt ctggatctcc actgctgctc        1080
acttgtctgt ctctggccct cagctgatcc atcttagaac cccagccctg gacccactcg        1140
acgtatctct ggcgccttgc acgtaatatg agctgagtgg ctatgcagca accaatgaac        1200
gagtgaatga gcgagtgaat gaatgagtcc cctagctgtc agggcatgga tcccccagca        1260
aggaggggga gacctgcaag ggttaatcag gagcctgcct gtggtctgag gtaagcaagg        1320
agtgtatttg ttcaggtaaa taaggaagga ttacttataa tgggaaatca ggccctgacc        1380

<210> SEQ ID NO 48
<211> LENGTH: 31
<212> TYPE: DNA
<213> ORGANISM: Artificial Sequence
<220> FEATURE:
<223> OTHER INFORMATION: GSEF-specific primer

<400> SEQUENCE: 48
cagggagggg caaccaactg ccccaggggg a                                         31

<210> SEQ ID NO 49
<211> LENGTH: 34
<212> TYPE: DNA
<213> ORGANISM: Artificial Sequence
<220> FEATURE:
```

<223> OTHER INFORMATION: GSEF-specific primer

<400> SEQUENCE: 49

```
tatctttatt atccattccc gggggcactc ctgg                               34
```

<210> SEQ ID NO 50
<211> LENGTH: 3317
<212> TYPE: DNA
<213> ORGANISM: Homo sapiens
<220> FEATURE:
<221> NAME/KEY: source
<222> LOCATION: (1)...(3317)
<223> OTHER INFORMATION: GSEF-encoding sequence with promoter (Figs. 2A-2B)
<221> NAME/KEY: promoter
<222> LOCATION: (1)...(1380)
<223> OTHER INFORMATION: Promoter
<221> NAME/KEY: CDS
<222> LOCATION: (1815)...(2819)
<223> OTHER INFORMATION: GSEF coding sequence

<400> SEQUENCE: 50

```
gatacagtag gtgcctgtta agcagtggtc attagtatta atgcatcaga atgctgtgat    60
ataagccagg cttctgtgag agtggggagg agggaggcgt ggccaccaga gaagcaggca   120
caaaaacgca ctctagggga aggagatcca cctggaaacg cagcgtgtct ttctttattg   180
accctggagg gctggaccat tgggattag gagtggtcga gtgtaccatt tcaggacctt   240
gtgttacctc cccttcctcc gctccatcct ccctcaacct tctctgggga atgactgata   300
actgatcctc aaccaaggtg ccagtgacga taacagccaa gtacagggct ccctgggggt   360
gcaaagtgca accttacgtt ggagaatgtg ggtattggtg aaggtgaggg gctagttcta   420
aaggccttgg gatccctgc agccccagaa tcctcatgct ctcggcagtt acacagttac   480
tcctgaaaca agagaaaaat cagcattatc tagaactttc tcccgtcaga atggaggtag   540
caggtacgtg gagcccttct gagatgattt ggagaaagga aggcccagcc tccagggaca   600
actctcagcc cacctggcag gacatggagg aagccaaaag ctggactgtg tggccccgc   660
agggctcaag gaggtggagg gtctgggca gcaagtgctt ggtggtgggt atctctgtcc   720
tgcatggcat ccctgccatc acccttggg gctatgggag agcaagttgc tgctgactgg   780
cccccgatta caggcctggg aaagcgagct aggagtcctt cctcaccgcc actgtgtgac   840
aggtctgcat gaggaccctg tggggcacag agaacacagt tcccaccagg tcgcggttgg   900
cccacaagcc tcgggatccc tccccagggt tctctgaagc tctctccatc cctggcctga   960
gtagccagac agcacctcct ccaggaagcc ctcaactgat ttccctagtt ggtgcccacc  1020
ctcagtgccc cctcagtcct ccatctgggc atgggtggtt ctggatctcc actgctgctc  1080
acttgtctgt ctctggccct cagctgatcc atcttagaac cccagccctg gacccactcg  1140
acgtatctct ggcgccttgc acgtaatatg agctgagtgg ctatgcagca accaatgaac  1200
gagtgaatga gcgagtgaat gaatgagtcc cctagctgtc agggcatgga tcccccagca  1260
aggaggggga gacctgcaag ggttaatcag gagcctgcct gtggtctgag gtaagcaagg  1320
agtgtatttg ttcaggtaaa taaggaagga ttacttataa tgggaaatca ggccctgacc  1380
aactcttcat ctcgcggctg tctgacttcc tcccagcaca ttcctgcact ctgccgtgtc  1440
cacactgccc cacagaccca gtcctccaag cctgctgcca gctccctgca agcccctcag  1500
gttgggcctt gccacggtgc cagcaggcag ccctgggctg ggggtagggg actccctaca  1560
ggcacgcagc cctgagacct cagagggcca cccttgagg gtggccaggc ccccagtggc  1620
```

-continued

```
caacctgagt gctgcctctg ccaccagccc tgctggcccc tggttccgct ggcccccccag    1680 atgcctggct gagacacgcc agtggcctca gctgcccaca cctcttcccg gcccctgaag    1740
ttggcactgc agcagacagc tccctgggca ccaggcagct aacagacaca gccgccagcc    1800
```

| | | | | | | | | | | | | | | | | |
|---|---|---|---|---|---|---|---|---|---|---|---|---|---|---|---|---|
| caaacagcag | cggc | atg | ggc | agc | gcc | agc | ccg | ggt | ctg | agc | agc | gta | tcc | | | 1850 |
| | | Met | Gly | Ser | Ala | Ser | Pro | Gly | Leu | Ser | Ser | Val | Ser | | | |
| | | 1 | | 5 | | | | | | 10 | | | | | | |

```
ccc agc cac ctc ctg ctg ccc ccc gac acg gtg tcg cgg aca ggc ttg    1898
Pro Ser His Leu Leu Leu Pro Pro Asp Thr Val Ser Arg Thr Gly Leu
         15                  20                  25 gag aag gcg gca gcg ggg gca gtg ggt ctc gag aga cgg gac tgg agt    1946
Glu Lys Ala Ala Ala Gly Ala Val Gly Leu Glu Arg Arg Asp Trp Ser
 30                  35                  40 ccc agt cca ccc gcc acg ccc gag cag ggc ctg tcc gcc ttc tac ctc    1994
Pro Ser Pro Pro Ala Thr Pro Glu Gln Gly Leu Ser Ala Phe Tyr Leu
 45                  50                  55                  60 tcc tac ttt gac atg ctg tac cct gag gac agc agc tgg gca gcc aag    2042
Ser Tyr Phe Asp Met Leu Tyr Pro Glu Asp Ser Ser Trp Ala Ala Lys
             65                  70                  75 gcc cct ggg gcc agc agt cgg gag gag cca cct gag gag cct gag cag    2090
Ala Pro Gly Ala Ser Ser Arg Glu Glu Pro Pro Glu Glu Pro Glu Gln
             80                  85                  90 tgc ccg gtc att gac agc caa gcc cca gcg ggc agc ctg gac ttg gtg    2138
Cys Pro Val Ile Asp Ser Gln Ala Pro Ala Gly Ser Leu Asp Leu Val
             95                 100                 105 ccc ggc ggg ctg acc ttg gag gag cac tcg ctg gag cag gtg cag tcc    2186
Pro Gly Gly Leu Thr Leu Glu Glu His Ser Leu Glu Gln Val Gln Ser
110                 115                 120 atg gtg gtg ggc gaa gtg ctc aag gac atc gag acg gcc tgc aag ctg    2234
Met Val Val Gly Glu Val Leu Lys Asp Ile Glu Thr Ala Cys Lys Leu
125                 130                 135                 140 ctc aac atc acc gca gat ccc atg gac tgg agc ccc agc aat gtg cag    2282
Leu Asn Ile Thr Ala Asp Pro Met Asp Trp Ser Pro Ser Asn Val Gln
                145                 150                 155 aag tgg ctc ctg tgg aca gag cac caa tac cgg ctg ccc ccc atg ggc    2330
Lys Trp Leu Leu Trp Thr Glu His Gln Tyr Arg Leu Pro Pro Met Gly
            160                 165                 170 aag gcc ttc cag gag ctg gcg ggc aag gag ctg tgc gcc atg tcg gag    2378
Lys Ala Phe Gln Glu Leu Ala Gly Lys Glu Leu Cys Ala Met Ser Glu
        175                 180                 185 gag cag ttc cgc cag cgc tcg ccc ctg ggt gga gat gtg ctg cac gcc    2426
Glu Gln Phe Arg Gln Arg Ser Pro Leu Gly Gly Asp Val Leu His Ala
    190                 195                 200 cac ctg gac atc tgg aag tca gcg gcc tgg atg aaa gag cgg act tca    2474
His Leu Asp Ile Trp Lys Ser Ala Ala Trp Met Lys Glu Arg Thr Ser
205                 210                 215                 220 cct ggg gcg att cac tac tgt gcc tcg acc agt gag gag agc tgg acc    2522
Pro Gly Ala Ile His Tyr Cys Ala Ser Thr Ser Glu Glu Ser Trp Thr
                225                 230                 235 gac agc gag gtg gac tca tca tgc tcc ggg cag ccc atc cac ctg tgg    2570
Asp Ser Glu Val Asp Ser Ser Cys Ser Gly Gln Pro Ile His Leu Trp
            240                 245                 250 cag ttc ctc aag gag ttg cta ctc aag ccc cac agc tat ggc cgc ttc    2618
Gln Phe Leu Lys Glu Leu Leu Leu Lys Pro His Ser Tyr Gly Arg Phe
        255                 260                 265 att agg tgg ctc aac aag gag aag ggc atc ttc aaa att gag gac tca    2666
Ile Arg Trp Leu Asn Lys Glu Lys Gly Ile Phe Lys Ile Glu Asp Ser
    270                 275                 280 gcc cag gtg gcc cgg ctg tgg ggc atc cgc aag aac cgt ccc gcc atg    2714
Ala Gln Val Ala Arg Leu Trp Gly Ile Arg Lys Asn Arg Pro Ala Met
```

```
Ala Gln Val Ala Arg Leu Trp Gly Ile Arg Lys Asn Arg Pro Ala Met
285                 290                 295                 300 aac tac gac aag ctg agc cgc tcc atc cgc cag tat tac aag aag ggc    2762
Asn Tyr Asp Lys Leu Ser Arg Ser Ile Arg Gln Tyr Tyr Lys Lys Gly
                305                 310                 315 atc atc cgg aag cca gac atc tcc cag cgc ctc gtc tac cag ttc gtg    2810
Ile Ile Arg Lys Pro Asp Ile Ser Gln Arg Leu Val Tyr Gln Phe Val
        320                 325                 330 cac ccc atc tgagtgcctg gcccagggcc tgaaacccgc cctcaggggc            2859
His Pro Ile
        335 ctctctcctg cctgccctgc ctcagccagg ccctgagatg ggggaaaacg ggcagtctgc  2919 tctgctgctc tgaccttcca gagcccaagg tcagggaggg gcaaccaact gccccagggg  2979 gatatgggtc ctctggggcc ttcgggaccc tggggcaggg gtgcttcctc ctcaggccca  3039 gctgctcccc tggaggacag agggagacag ggctgctccc caacacctgc ctctgacccc  3099 agcatttcca gagcagagcc tacagaaggg cagtgactcg acaaaggcca caggcagtcc  3159 aggcctctct ctgctccatc cccctgcctc ccattctgca ccacacctgg catggtgcag  3219 ggagacatct gcaccctga gttgggcagc caggagtgcc cccgggaatg gataatagag   3279 atactagaga actgaaaaaa aaaaaaaaaa aaaaaaa                           3317
```

<210> SEQ ID NO 51
<211> LENGTH: 335
<212> TYPE: PRT
<213> ORGANISM: Homo sapiens

<400> SEQUENCE: 51

```
Met Gly Ser Ala Ser Pro Gly Leu Ser Ser Val Ser Pro Ser His Leu
1               5                   10                  15

Leu Leu Pro Pro Asp Thr Val Ser Arg Thr Gly Leu Glu Lys Ala Ala
                20                  25                  30

Ala Gly Ala Val Gly Leu Glu Arg Arg Asp Trp Ser Pro Ser Pro Pro
            35                  40                  45

Ala Thr Pro Glu Gln Gly Leu Ser Ala Phe Tyr Leu Ser Tyr Phe Asp
        50                  55                  60

Met Leu Tyr Pro Glu Asp Ser Ser Trp Ala Ala Lys Ala Pro Gly Ala
65                  70                  75                  80

Ser Ser Arg Glu Glu Pro Pro Glu Pro Glu Gln Cys Pro Val Ile
                85                  90                  95

Asp Ser Gln Ala Pro Ala Gly Ser Leu Asp Leu Val Pro Gly Gly Leu
                100                 105                 110

Thr Leu Glu Glu His Ser Leu Glu Gln Val Gln Ser Met Val Val Gly
            115                 120                 125

Glu Val Leu Lys Asp Ile Glu Thr Ala Cys Lys Leu Leu Asn Ile Thr
130                 135                 140

Ala Asp Pro Met Asp Trp Ser Pro Ser Asn Val Gln Lys Trp Leu Leu
145                 150                 155                 160

Trp Thr Glu His Gln Tyr Arg Leu Pro Pro Met Gly Lys Ala Phe Gln
                165                 170                 175

Glu Leu Ala Gly Lys Glu Leu Cys Ala Met Ser Glu Glu Gln Phe Arg
            180                 185                 190

Gln Arg Ser Pro Leu Gly Gly Asp Val Leu His Ala His Leu Asp Ile
        195                 200                 205

Trp Lys Ser Ala Ala Trp Met Lys Glu Arg Thr Ser Pro Gly Ala Ile
```

-continued

```
              210                 215                 220
His Tyr Cys Ala Ser Thr Ser Glu Glu Ser Trp Thr Asp Ser Glu Val
225                 230                 235                 240

Asp Ser Ser Cys Ser Gly Gln Pro Ile His Leu Trp Gln Phe Leu Lys
                245                 250                 255

Glu Leu Leu Leu Lys Pro His Ser Tyr Gly Arg Phe Ile Arg Trp Leu
            260                 265                 270

Asn Lys Glu Lys Gly Ile Phe Lys Ile Glu Asp Ser Ala Gln Val Ala
        275                 280                 285

Arg Leu Trp Gly Ile Arg Lys Asn Arg Pro Ala Met Asn Tyr Asp Lys
    290                 295                 300

Leu Ser Arg Ser Ile Arg Gln Tyr Tyr Lys Lys Gly Ile Ile Arg Lys
305                 310                 315                 320

Pro Asp Ile Ser Gln Arg Leu Val Tyr Gln Phe Val His Pro Ile
                325                 330                 335

<210> SEQ ID NO 52
<211> LENGTH: 4612
<212> TYPE: DNA
<213> ORGANISM: Homo Sapiens
<220> FEATURE:
<221> NAME/KEY: CDS
<222> LOCATION: (698)...(3862)

<400> SEQUENCE: 52
atagcacgac tgtgtatgct ctggaggact gaaaggctgt acaagccta tgtatttttt      60 ttcaaatata catatgcatg ggtcttgctg ctgcctcttt tgctgactgt aattggactt    120
tgaagcttcg aagttatatc ataaaaattt gtaaccttg tctgagagag agctcagcta     180
agcaatcact ttccacttct tttcacagga taatataaac gttttcttga agcttgtga    240 acagattgga ttgaaagaag cccagctttt ccatcctgga gatctacagg atttatcaaa   300
tcgagtcact gtcaagcaag aagagactga caggagagtg aaaaatgttt tgataacatt   360
gtactggctg ggaagaaaag cacaaagcaa cccgtactat aatggtcccc atcttaattt   420
gaaagcgttt gagaatcttt taggacaagc actgacgaag gcactcgaag actccagctt   480
cctgaaaaga agtggcaggg acagtggcta cggtgacatc tggtgtcctg aacgtggaga   540
atttcttgct cctccaaggc accataagag agaagattcc tttgaaagct tggactcttt   600
gggctcgagg tcattgacaa gctgctcctc tgatatcacg ttgagagggg ggcgtgaagg   660
ttttgaaagt gacacagatt cggaatttac attcaag atg cag gat tat aat aaa   715
                                           Met Gln Asp Tyr Asn Lys
                                           1               5 gat gat atg tcg tat cga agg att tcg gct gtt gag cca aag act gcg    763
Asp Asp Met Ser Tyr Arg Arg Ile Ser Ala Val Glu Pro Lys Thr Ala
        10                  15                  20 tta ccc ttc aat cgt ttt tta ccc aac aaa agt aga cag cca tcc tat    811
Leu Pro Phe Asn Arg Phe Leu Pro Asn Lys Ser Arg Gln Pro Ser Tyr
            25                  30                  35 gta cca gca cct ctg aga aag aaa aag cca gac aaa cat gag gat aac    859
Val Pro Ala Pro Leu Arg Lys Lys Lys Pro Asp Lys His Glu Asp Asn
        40                  45                  50 aga aga agt tgg gca agc ccg gtt tat aca gaa gca gat gga aca ttt    907
Arg Arg Ser Trp Ala Ser Pro Val Tyr Thr Glu Ala Asp Gly Thr Phe
55                  60                  65                  70 tca agg agt aag tcc atg agt gat gtc agc gca gaa gat gtt caa aac    955
Ser Arg Ser Lys Ser Met Ser Asp Val Ser Ala Glu Asp Val Gln Asn
            75                  80                  85
```

```
ttg cgt cag ctg cgt tac gag gag atg cag aaa ata aaa tca caa tta    1003
Leu Arg Gln Leu Arg Tyr Glu Glu Met Gln Lys Ile Lys Ser Gln Leu
            90                  95                 100 aaa gaa caa gat cag aaa tgg cag gat gac ctt gca aaa tgg aaa gat    1051
Lys Glu Gln Asp Gln Lys Trp Gln Asp Asp Leu Ala Lys Trp Lys Asp
                105                 110                 115 cgt cga aaa agt tac act tca gat ctg cag aag aaa aaa gaa gag aga    1099
Arg Arg Lys Ser Tyr Thr Ser Asp Leu Gln Lys Lys Lys Glu Glu Arg
        120                 125                 130 gaa gaa att gaa aag cag gca ctt gag aag tct aag aga agc tct aag    1147
Glu Glu Ile Glu Lys Gln Ala Leu Glu Lys Ser Lys Arg Ser Ser Lys
135                 140                 145                 150 acg ttt aag gaa atg ctg cag gac agg gaa tcc caa aat caa aag tct    1195
Thr Phe Lys Glu Met Leu Gln Asp Arg Glu Ser Gln Asn Gln Lys Ser
                155                 160                 165 aca gtt ccg tca aga agg aga atg tat tct ttt gat gat gtg ctg gag    1243
Thr Val Pro Ser Arg Arg Arg Met Tyr Ser Phe Asp Asp Val Leu Glu
            170                 175                 180 gaa gga aag cga ccc cct aca atg act gtg tca gaa gca agt tac cag    1291
Glu Gly Lys Arg Pro Pro Thr Met Thr Val Ser Glu Ala Ser Tyr Gln
        185                 190                 195 agt gag aga gta gaa gag aag gga gca act tat cct tca gaa att ccc    1339
Ser Glu Arg Val Glu Glu Lys Gly Ala Thr Tyr Pro Ser Glu Ile Pro
200                 205                 210 aaa gaa gat tct acc act ttt gca aaa aga gag gac cgt gta aca act    1387
Lys Glu Asp Ser Thr Thr Phe Ala Lys Arg Glu Asp Arg Val Thr Thr
215                 220                 225                 230 gaa att cag ctt cct tct caa agt cct gtg gaa gaa caa agc cca gcc    1435
Glu Ile Gln Leu Pro Ser Gln Ser Pro Val Glu Glu Gln Ser Pro Ala
                235                 240                 245 tct ttg tct tct ctg cgt tca cgg agc aca caa atg gaa tca act cgt    1483
Ser Leu Ser Ser Leu Arg Ser Arg Ser Thr Gln Met Glu Ser Thr Arg
            250                 255                 260 gtt tca gct tct ctc ccc aga agt tac cgg aaa act gat aca gtc agg    1531
Val Ser Ala Ser Leu Pro Arg Ser Tyr Arg Lys Thr Asp Thr Val Arg
        265                 270                 275 tta aca tct gtg gtc aca cca aga ccc ttt ggc tct cag aca agg gga    1579
Leu Thr Ser Val Val Thr Pro Arg Pro Phe Gly Ser Gln Thr Arg Gly
280                 285                 290 atc tca tca ctc ccc aga tct tac acg atg gat gat gct tgg aag tat    1627
Ile Ser Ser Leu Pro Arg Ser Tyr Thr Met Asp Asp Ala Trp Lys Tyr
295                 300                 305                 310 aat gga gat gtt gaa gac att aag aga act cca aac aat gtg gtc agc    1675
Asn Gly Asp Val Glu Asp Ile Lys Arg Thr Pro Asn Asn Val Val Ser
                315                 320                 325 acc cct gca cca agc ccg gac gca agc caa ctg gct tca agc tta tct    1723
Thr Pro Ala Pro Ser Pro Asp Ala Ser Gln Leu Ala Ser Ser Leu Ser
            330                 335                 340 agc cag aaa gag gta gca gca aca gaa gaa gat gtg aca agg ctg ccc    1771
Ser Gln Lys Glu Val Ala Ala Thr Glu Glu Asp Val Thr Arg Leu Pro
        345                 350                 355 tct cct aca tcc ccc ttc tca tct ctt tcc caa gac cag gct gcc act    1819
Ser Pro Thr Ser Pro Phe Ser Ser Leu Ser Gln Asp Gln Ala Ala Thr
360                 365                 370 tct aaa gcc aca ttg tct tcc aca tct ggt ctt gat tta atg tct gaa    1867
Ser Lys Ala Thr Leu Ser Ser Thr Ser Gly Leu Asp Leu Met Ser Glu
375                 380                 385                 390 tct gga gaa ggg gaa atc tcc cca caa aga gaa gtc tca aga tcc cag    1915
Ser Gly Glu Gly Glu Ile Ser Pro Gln Arg Glu Val Ser Arg Ser Gln
```

-continued

|     |     | 395 |     |     |     | 400 |     |     |     | 405 |     |     |     |      |
|-----|-----|-----|-----|-----|-----|-----|-----|-----|-----|-----|-----|-----|-----|------|
| gat | cag | ttc | agt | gat | atg | aga | atc | agc | ata | aac | cag | acg | cct | ggg | aag | 1963 |
| Asp | Gln | Phe | Ser | Asp | Met | Arg | Ile | Ser | Ile | Asn | Gln | Thr | Pro | Gly | Lys |     |
|     |     | 410 |     |     |     | 415 |     |     |     | 420 |     |     |     |      | agt ctt gac ttt ggg ttt aca ata aaa tgg gat att cct ggg atc ttc      2011
Ser Leu Asp Phe Gly Phe Thr Ile Lys Trp Asp Ile Pro Gly Ile Phe
            425                 430                 435 gta gca tca gtt gaa gca ggt agc cca gca gaa ttt tct cag cta caa      2059
Val Ala Ser Val Glu Ala Gly Ser Pro Ala Glu Phe Ser Gln Leu Gln
        440                 445                 450 gta gat gat gaa att att gct att aac aac acc aag ttt tca tat aac      2107
Val Asp Asp Glu Ile Ile Ala Ile Asn Asn Thr Lys Phe Ser Tyr Asn
455                 460                 465                 470 gat tca aaa gag tgg gag gaa gcc atg gct aag gct caa gaa act gga      2155
Asp Ser Lys Glu Trp Glu Glu Ala Met Ala Lys Ala Gln Glu Thr Gly
                475                 480                 485 cac cta gtg atg gat gtg agg cgc tat gga aag gct ggt tca cct gaa      2203
His Leu Val Met Asp Val Arg Arg Tyr Gly Lys Ala Gly Ser Pro Glu
            490                 495                 500 aca aag tgg att gat gca act tct gga att tac aac tca gaa aaa tct      2251
Thr Lys Trp Ile Asp Ala Thr Ser Gly Ile Tyr Asn Ser Glu Lys Ser
        505                 510                 515 tca aat cta tct gta aca act gat ttc tcc gaa agc ctt cag agt tct      2299
Ser Asn Leu Ser Val Thr Thr Asp Phe Ser Glu Ser Leu Gln Ser Ser
520                 525                 530 aat att gaa tcc aaa gaa atc aat gga att cat gat gaa agc aat gct      2347
Asn Ile Glu Ser Lys Glu Ile Asn Gly Ile His Asp Glu Ser Asn Ala
                535                 540                 545                 550 ttt gaa tca aaa gca tct gaa tcc att tct ttg aaa aac tta aaa agg      2395
Phe Glu Ser Lys Ala Ser Glu Ser Ile Ser Leu Lys Asn Leu Lys Arg
            555                 560                 565 cga tca caa ttt ttt gaa caa gga agc tct gat tcg gtg gtt cct gat      2443
Arg Ser Gln Phe Phe Glu Gln Gly Ser Ser Asp Ser Val Val Pro Asp
        570                 575                 580 ctt cca gtt cca acc atc agt gcc ccg agt cgc tgg gtg tgg gat caa      2491
Leu Pro Val Pro Thr Ile Ser Ala Pro Ser Arg Trp Val Trp Asp Gln
585                 590                 595 gag gag gag cgg aag cgg cag gag agg tgg cag aag gag cag gac cgc      2539
Glu Glu Glu Arg Lys Arg Gln Glu Arg Trp Gln Lys Glu Gln Asp Arg
                600                 605                 610 cta ctg cag gaa aaa tat caa cgt gag cag gag aaa ctg agg gaa gag      2587
Leu Leu Gln Glu Lys Tyr Gln Arg Glu Gln Glu Lys Leu Arg Glu Glu
615                 620                 625                 630 tgg caa agg gcc aaa cag gag gca gag aga gag aat tcc aag tac ttg      2635
Trp Gln Arg Ala Lys Gln Glu Ala Glu Arg Glu Asn Ser Lys Tyr Leu
            635                 640                 645 gat gag gaa ctg atg gtc cta agc tca aac agc atg tct ctg acc aca      2683
Asp Glu Glu Leu Met Val Leu Ser Ser Asn Ser Met Ser Leu Thr Thr
        650                 655                 660 cgg gag ccc tct ctt gcc acc tgg gaa gct acc tgg agt gaa ggg tcc      2731
Arg Glu Pro Ser Leu Ala Thr Trp Glu Ala Thr Trp Ser Glu Gly Ser
                665                 670                 675 aag tct tca gac aga gaa gga acc cga gca gga gaa gag agg aga          2779
Lys Ser Ser Asp Arg Glu Gly Thr Arg Ala Gly Glu Glu Arg Arg
680                 685                 690 cag cca caa gag gaa gtt gtt cat gag gac caa gga aag aag ccg cag      2827
Gln Pro Gln Glu Glu Val Val His Glu Asp Gln Gly Lys Lys Pro Gln
            695                 700                 705                 710 gat cag ctt gtt att gag aga gag agg aaa tgg gag caa cag ctt cag      2875

```
                Asp Gln Leu Val Ile Glu Arg Glu Arg Lys Trp Glu Gln Gln Leu Gln
                                715                 720                 725 gaa gag caa gag caa aag cgg ctt cag gct gag gct gag gag cag aag            2923
Glu Glu Gln Glu Gln Lys Arg Leu Gln Ala Glu Ala Glu Glu Gln Lys
            730                 735                 740 cgt cct gcg gag gag cag aag cgc cag gca gag ata gag cgg gaa aca            2971
Arg Pro Ala Glu Glu Gln Lys Arg Gln Ala Glu Ile Glu Arg Glu Thr
        745                 750                 755 tca gtc aga ata tac cag tac agg agg cct gtt gat tcc tat gat ata            3019
Ser Val Arg Ile Tyr Gln Tyr Arg Arg Pro Val Asp Ser Tyr Asp Ile
    760                 765                 770 cca aag aca gaa gaa gca tct tca ggt ttt ctt cct ggt gac agg aat            3067
Pro Lys Thr Glu Glu Ala Ser Ser Gly Phe Leu Pro Gly Asp Arg Asn
775                 780                 785                 790 aaa tcc aga tct act act gaa ctg gat gat tac tcc aca aat aaa aat            3115
Lys Ser Arg Ser Thr Thr Glu Leu Asp Asp Tyr Ser Thr Asn Lys Asn
                795                 800                 805 gga aac aat aaa tat tta gac caa att ggg aac acg acc tct tca cag            3163
Gly Asn Asn Lys Tyr Leu Asp Gln Ile Gly Asn Thr Thr Ser Ser Gln
            810                 815                 820 agg aga tcc aag aaa gaa caa gta cca tca gga gca gaa ttg gag agg            3211
Arg Arg Ser Lys Lys Glu Gln Val Pro Ser Gly Ala Glu Leu Glu Arg
        825                 830                 835 caa caa atc ctt cag gaa atg agg aag aga aca ccc ctt cac aat gac            3259
Gln Gln Ile Leu Gln Glu Met Arg Lys Arg Thr Pro Leu His Asn Asp
    840                 845                 850 aac agc tgg atc cga cag cgc agt gcc agt gtc aac aaa gag cct gtt            3307
Asn Ser Trp Ile Arg Gln Arg Ser Ala Ser Val Asn Lys Glu Pro Val
855                 860                 865                 870 agt ctt cct ggg atc atg aga aga ggc gaa tct tta gat aac ctg gac            3355
Ser Leu Pro Gly Ile Met Arg Arg Gly Glu Ser Leu Asp Asn Leu Asp
                875                 880                 885 tcc ccc cga tcc aat tct tgg aga cag cct cct tgg ctc aat cag ccc            3403
Ser Pro Arg Ser Asn Ser Trp Arg Gln Pro Pro Trp Leu Asn Gln Pro
            890                 895                 900 aca gga ttc tat gct tct tcc tct gtg caa gac ttt agt cgc cca cca            3451
Thr Gly Phe Tyr Ala Ser Ser Ser Val Gln Asp Phe Ser Arg Pro Pro
        905                 910                 915 cct cag ctg gtg tcc aca tca aac cgt gcc tac atg cgg aac ccc tcc            3499
Pro Gln Leu Val Ser Thr Ser Asn Arg Ala Tyr Met Arg Asn Pro Ser
    920                 925                 930 tcc agc gtg ccc cca cct tca gct ggc tcc gtg aag acc tcc acc aca            3547
Ser Ser Val Pro Pro Pro Ser Ala Gly Ser Val Lys Thr Ser Thr Thr
935                 940                 945                 950 ggt gtg gcc acc aca cag tcc ccc acc ccg aga agc cat tcc cct tca            3595
Gly Val Ala Thr Thr Gln Ser Pro Thr Pro Arg Ser His Ser Pro Ser
                955                 960                 965 gct tca cag tca ggc tct cag ctg cgt aac agg tca gtc agt ggg aag            3643
Ala Ser Gln Ser Gly Ser Gln Leu Arg Asn Arg Ser Val Ser Gly Lys
            970                 975                 980 cgc ata tgc tcc tac tgc aat aac att ctg ggc aaa gga gcc gcc atg            3691
Arg Ile Cys Ser Tyr Cys Asn Asn Ile Leu Gly Lys Gly Ala Ala Met
        985                 990                 995 atc atc gag tcc ctg ggt ctt tgt tat cat ttg cat tgt ttt aag tgt            3739
Ile Ile Glu Ser Leu Gly Leu Cys Tyr His Leu His Cys Phe Lys Cys
    1000                1005                1010 gtt gcc tgt gag tgt gac ctc gga ggc tct tcc tca gga gct gaa gtc            3787
Val Ala Cys Glu Cys Asp Leu Gly Gly Ser Ser Ser Gly Ala Glu Val
1015                1020                1025                1030
```

```
agg atc aga aac cac caa ctg tac tgc aac gac tgc tat ctc aga ttc    3835
Arg Ile Arg Asn His Gln Leu Tyr Cys Asn Asp Cys Tyr Leu Arg Phe
            1035                1040                1045 aaa tct gga cgg cca acc gcc atg tga tgtaagcctc catacgaaag          3882
Lys Ser Gly Arg Pro Thr Ala Met *
        1050 cactgttgca gatagaagaa gaggtggttg ctgctcatgt agatctataa atatgtgttg  3942
tatgtcttt ttgcttttt tttaaaaaa agaataactt tttttgcctc tttagattac     4002
atagaagcat tgtagtcttg gtagaaccag tattttgtt gtttatttat aaggtaattg   4062
tgtgtgggga aaagtgcagt atttacctgt tgaattcagc atcttgagag cacaagggaa  4122
aaaataagaa cctacgaata ttttgaggc agataatgat ctagtttgac tttctagtta   4182
gtggtgtttt gaagagggta ttttattgtt ttttaaaaaa aggttcttaa acattatttg  4242
aaatagttaa tataaataca taattgcatt tgctctgttt attgtaatgt attctaaatt  4302
aatgcagaac catatggaaa atttcattaa aatctatccc caaatgtgct ttctgtatcc  4362
ttccttctac ctattattct gattttaaa aatgcagtta atgtaccatt tatttgcttg   4422
atgaagggag ctctattttc tttaccagaa atgttgctaa gtaattccca atagaaagct  4482
gcttattttc attaatgaaa ataaccatg gtttgtatac tagaagtctt cttcagaaac   4542
tggtgagcct ttctgttcaa ttgcatttgt aaataaactt gctgatgcat ttaaaaaaaa  4602
aaaaaaaaaa                                                        4612

<210> SEQ ID NO 53
<211> LENGTH: 1054
<212> TYPE: PRT
<213> ORGANISM: Homo Sapiens

<400> SEQUENCE: 53

Met Gln Asp Tyr Asn Lys Asp Asp Met Ser Tyr Arg Arg Ile Ser Ala
1               5                   10                  15

Val Glu Pro Lys Thr Ala Leu Pro Phe Asn Arg Phe Leu Pro Asn Lys
            20                  25                  30

Ser Arg Gln Pro Ser Tyr Val Pro Ala Pro Leu Arg Lys Lys Lys Pro
        35                  40                  45

Asp Lys His Glu Asp Asn Arg Arg Ser Trp Ala Ser Pro Val Tyr Thr
    50                  55                  60

Glu Ala Asp Gly Thr Phe Ser Arg Ser Lys Ser Met Ser Asp Val Ser
65                  70                  75                  80

Ala Glu Asp Val Gln Asn Leu Arg Gln Leu Arg Tyr Glu Glu Met Gln
                85                  90                  95

Lys Ile Lys Ser Gln Leu Lys Glu Gln Asp Gln Lys Trp Gln Asp Asp
            100                 105                 110

Leu Ala Lys Trp Lys Asp Arg Arg Lys Ser Tyr Thr Ser Asp Leu Gln
        115                 120                 125

Lys Lys Lys Glu Glu Arg Glu Glu Ile Glu Lys Gln Ala Leu Glu Lys
    130                 135                 140

Ser Lys Arg Ser Ser Lys Thr Phe Lys Glu Met Leu Gln Asp Arg Glu
145                 150                 155                 160

Ser Gln Asn Gln Lys Ser Thr Val Pro Ser Arg Arg Met Tyr Ser
                165                 170                 175

Phe Asp Asp Val Leu Glu Glu Gly Lys Arg Pro Pro Thr Met Thr Val
            180                 185                 190

Ser Glu Ala Ser Tyr Gln Ser Glu Arg Val Glu Glu Lys Gly Ala Thr
```

-continued

```
              195                 200                 205
Tyr Pro Ser Glu Ile Pro Lys Glu Asp Ser Thr Thr Phe Ala Lys Arg
    210                 215                 220
Glu Asp Arg Val Thr Thr Glu Ile Gln Leu Pro Ser Gln Ser Pro Val
225                 230                 235                 240
Glu Glu Gln Ser Pro Ala Ser Leu Ser Ser Leu Arg Ser Arg Ser Thr
                245                 250                 255
Gln Met Glu Ser Thr Arg Val Ser Ala Ser Leu Pro Arg Ser Tyr Arg
            260                 265                 270
Lys Thr Asp Thr Val Arg Leu Thr Ser Val Val Thr Pro Arg Pro Phe
        275                 280                 285
Gly Ser Gln Thr Arg Gly Ile Ser Ser Leu Pro Arg Ser Tyr Thr Met
    290                 295                 300
Asp Asp Ala Trp Lys Tyr Asn Gly Asp Val Glu Asp Ile Lys Arg Thr
305                 310                 315                 320
Pro Asn Asn Val Val Ser Thr Pro Ala Pro Ser Pro Asp Ala Ser Gln
                325                 330                 335
Leu Ala Ser Ser Leu Ser Ser Gln Lys Glu Val Ala Ala Thr Glu Glu
            340                 345                 350
Asp Val Thr Arg Leu Pro Ser Pro Thr Ser Pro Phe Ser Ser Leu Ser
        355                 360                 365
Gln Asp Gln Ala Ala Thr Ser Lys Ala Thr Leu Ser Ser Thr Ser Gly
    370                 375                 380
Leu Asp Leu Met Ser Glu Ser Gly Glu Gly Glu Ile Ser Pro Gln Arg
385                 390                 395                 400
Glu Val Ser Arg Ser Gln Asp Gln Phe Ser Asp Met Arg Ile Ser Ile
                405                 410                 415
Asn Gln Thr Pro Gly Lys Ser Leu Asp Phe Gly Phe Thr Ile Lys Trp
            420                 425                 430
Asp Ile Pro Gly Ile Phe Val Ala Ser Val Glu Ala Gly Ser Pro Ala
        435                 440                 445
Glu Phe Ser Gln Leu Gln Val Asp Asp Glu Ile Ile Ala Ile Asn Asn
    450                 455                 460
Thr Lys Phe Ser Tyr Asn Asp Ser Lys Glu Trp Glu Ala Met Ala
465                 470                 475                 480
Lys Ala Gln Glu Thr Gly His Leu Val Met Asp Val Arg Arg Tyr Gly
                485                 490                 495
Lys Ala Gly Ser Pro Glu Thr Lys Trp Ile Asp Ala Thr Ser Gly Ile
            500                 505                 510
Tyr Asn Ser Glu Lys Ser Ser Asn Leu Ser Val Thr Thr Asp Phe Ser
        515                 520                 525
Glu Ser Leu Gln Ser Ser Asn Ile Glu Ser Lys Glu Ile Asn Gly Ile
    530                 535                 540
His Asp Glu Ser Asn Ala Phe Glu Ser Lys Ala Ser Glu Ser Ile Ser
545                 550                 555                 560
Leu Lys Asn Leu Lys Arg Arg Ser Gln Phe Phe Glu Gln Gly Ser Ser
                565                 570                 575
Asp Ser Val Val Pro Asp Leu Pro Val Pro Thr Ile Ser Ala Pro Ser
            580                 585                 590
Arg Trp Val Trp Asp Gln Glu Glu Arg Lys Arg Gln Glu Arg Trp
        595                 600                 605
Gln Lys Glu Gln Asp Arg Leu Leu Gln Glu Lys Tyr Gln Arg Glu Gln
    610                 615                 620
```

-continued

```
Glu Lys Leu Arg Glu Glu Trp Gln Arg Ala Lys Gln Glu Ala Glu Arg
625                 630                 635                 640

Glu Asn Ser Lys Tyr Leu Asp Glu Glu Leu Met Val Leu Ser Ser Asn
                645                 650                 655

Ser Met Ser Leu Thr Thr Arg Glu Pro Ser Leu Ala Thr Trp Glu Ala
                660                 665                 670

Thr Trp Ser Glu Gly Ser Lys Ser Ser Asp Arg Glu Gly Thr Arg Ala
                675                 680                 685

Gly Glu Glu Arg Arg Gln Pro Gln Glu Val Val His Glu Asp
690                 695                 700

Gln Gly Lys Lys Pro Gln Asp Gln Leu Val Ile Glu Arg Glu Arg Lys
705                 710                 715                 720

Trp Glu Gln Gln Leu Gln Glu Gln Glu Lys Arg Leu Gln Ala
                725                 730                 735

Glu Ala Glu Glu Gln Lys Arg Pro Ala Glu Glu Gln Lys Arg Gln Ala
                740                 745                 750

Glu Ile Glu Arg Glu Thr Ser Val Arg Ile Tyr Gln Tyr Arg Arg Pro
                755                 760                 765

Val Asp Ser Tyr Asp Ile Pro Lys Thr Glu Ala Ser Ser Gly Phe
770                 775                 780

Leu Pro Gly Asp Arg Asn Lys Ser Arg Ser Thr Thr Glu Leu Asp Asp
785                 790                 795                 800

Tyr Ser Thr Asn Lys Asn Gly Asn Asn Lys Tyr Leu Asp Gln Ile Gly
                805                 810                 815

Asn Thr Thr Ser Ser Gln Arg Arg Ser Lys Lys Glu Gln Val Pro Ser
                820                 825                 830

Gly Ala Glu Leu Glu Arg Gln Gln Ile Leu Gln Glu Met Arg Lys Arg
                835                 840                 845

Thr Pro Leu His Asn Asp Asn Ser Trp Ile Arg Gln Arg Ser Ala Ser
                850                 855                 860

Val Asn Lys Glu Pro Val Ser Leu Pro Gly Ile Met Arg Arg Gly Glu
865                 870                 875                 880

Ser Leu Asp Asn Leu Asp Ser Pro Arg Ser Asn Ser Trp Arg Gln Pro
                885                 890                 895

Pro Trp Leu Asn Gln Pro Thr Gly Phe Tyr Ala Ser Ser Val Gln
                900                 905                 910

Asp Phe Ser Arg Pro Pro Gln Leu Val Ser Thr Ser Asn Arg Ala
                915                 920                 925

Tyr Met Arg Asn Pro Ser Ser Val Pro Pro Ser Ala Gly Ser
930                 935                 940

Val Lys Thr Ser Thr Thr Gly Val Ala Thr Gln Ser Pro Thr Pro
945                 950                 955                 960

Arg Ser His Ser Pro Ser Ala Ser Gln Ser Gly Ser Gln Leu Arg Asn
                965                 970                 975

Arg Ser Val Ser Gly Lys Arg Ile Cys Ser Tyr Cys Asn Asn Ile Leu
                980                 985                 990

Gly Lys Gly Ala Ala Met Ile Ile Glu Ser Leu Gly Leu Cys Tyr His
                995                 1000                1005

Leu His Cys Phe Lys Cys Val Ala Cys Glu Cys Asp Leu Gly Gly Ser
        1010                1015                1020

Ser Ser Gly Ala Glu Val Arg Ile Arg Asn His Gln Leu Tyr Cys Asn
1025                1030                1035                1040
```

```
Asp Cys Tyr Leu Arg Phe Lys Ser Gly Arg Pro Thr Ala Met
            1045                1050

<210> SEQ ID NO 54
<211> LENGTH: 4642
<212> TYPE: DNA
<213> ORGANISM: Homo Sapiens
<220> FEATURE:
<221> NAME/KEY: CDS
<222> LOCATION: (698)...(3892)

<400> SEQUENCE: 54
atagcacgac tgtgtatgct ctggaggact gaaaggctgt acaagcccta tgtatttttt      60
ttcaaatata catatgcatg ggtcttgctg ctgcctcttt tgctgactgt aattggactt     120
tgaagcttcg aagttatatc ataaaaattt gtaacctttg tctgagagag agctcagcta     180
agcaatcact ttccacttct ttttcacagga taatataaac gttttcttga agcttgtga     240 acagattgga ttgaaagaag cccagctttt ccatcctgga gatctacagg atttatcaaa     300
tcgagtcact gtcaagcaag aagagactga caggagagtg aaaaatgttt tgataacatt     360
gtactggctg ggaagaaaag cacaaagcaa cccgtactat aatggtcccc atcttaattt     420
gaaagcgttt gagaatcttt taggacaagc actgacgaag gcactcgaag actccagctt     480
cctgaaaaga gtggcaggg acagtggcta cggtgacatc tggtgtcctg aacgtggaga     540
atttcttgct cctccaaggc accataagag agaagattcc tttgaaagct ggactctttt    600
gggctcgagg tcattgacaa gctgctcctc tgatatcacg ttgagagggg ggcgtgaagg     660
ttttgaaagt gacacagatt cggaatttac attcaag atg cag gat tat aat aaa       715
                                        Met Gln Asp Tyr Asn Lys
                                          1               5 gat gat atg tcg tat cga agg att tcg gct gtt gag cca aag act gcg       763
Asp Asp Met Ser Tyr Arg Arg Ile Ser Ala Val Glu Pro Lys Thr Ala
         10                  15                  20 tta ccc ttc aat cgt ttt tta ccc aac aaa agt aga cag cca tcc tat       811
Leu Pro Phe Asn Arg Phe Leu Pro Asn Lys Ser Arg Gln Pro Ser Tyr
     25                  30                  35 gta cca gca cct ctg aga aag aaa aag cca gac aaa cat gag gat aac       859
Val Pro Ala Pro Leu Arg Lys Lys Lys Pro Asp Lys His Glu Asp Asn
 40                  45                  50 aga aga agt tgg gca agc ccg gtt tat aca gaa gca gat gga aca ttt       907
Arg Arg Ser Trp Ala Ser Pro Val Tyr Thr Glu Ala Asp Gly Thr Phe
 55                  60                  65                  70 tca aga ctc ttt caa aag att tat ggt gag aat ggg agt aag tcc atg       955
Ser Arg Leu Phe Gln Lys Ile Tyr Gly Glu Asn Gly Ser Lys Ser Met
             75                  80                  85 agt gat gtc agc gca gaa gat gtt caa aac ttg cgt cag ctg cgt tac      1003
Ser Asp Val Ser Ala Glu Asp Val Gln Asn Leu Arg Gln Leu Arg Tyr
         90                  95                 100 gag gag atg cag aaa ata aaa tca caa tta aaa gaa caa gat cag aaa      1051
Glu Glu Met Gln Lys Ile Lys Ser Gln Leu Lys Glu Gln Asp Gln Lys
     105                 110                 115 tgg cag gat gac ctt gca aaa tgg aaa gat cgt cga aaa agt tac act      1099
Trp Gln Asp Asp Leu Ala Lys Trp Lys Asp Arg Arg Lys Ser Tyr Thr
120                 125                 130 tca gat ctg cag aag aaa aaa gaa gag aga gaa gaa att gaa aag cag      1147
Ser Asp Leu Gln Lys Lys Lys Glu Glu Arg Glu Glu Ile Glu Lys Gln
135                 140                 145                 150 gca ctt gag aag tct aag aga agc tct aag acg ttt aag gaa atg ctg      1195
Ala Leu Glu Lys Ser Lys Arg Ser Ser Lys Thr Phe Lys Glu Met Leu
             155                 160                 165
```

```
cag gac agg gaa tcc caa aat caa aag tct aca gtt ccg tca aga agg      1243
Gln Asp Arg Glu Ser Gln Asn Gln Lys Ser Thr Val Pro Ser Arg Arg
        170                 175                 180 aga atg tat tct ttt gat gat gtg ctg gag gaa gga aag cga ccc cct      1291
Arg Met Tyr Ser Phe Asp Asp Val Leu Glu Glu Gly Lys Arg Pro Pro
            185                 190                 195 aca atg act gtg tca gaa gca agt tac cag agt gag aga gta gaa gag      1339
Thr Met Thr Val Ser Glu Ala Ser Tyr Gln Ser Glu Arg Val Glu Glu
200                 205                 210 aag gga gca act tat cct tca gaa att ccc aaa gaa gat tct acc act      1387
Lys Gly Ala Thr Tyr Pro Ser Glu Ile Pro Lys Glu Asp Ser Thr Thr
215                 220                 225                 230 ttt gca aaa aga gag gac cgt gta aca act gaa att cag ctt cct tct      1435
Phe Ala Lys Arg Glu Asp Arg Val Thr Thr Glu Ile Gln Leu Pro Ser
                235                 240                 245 caa agt cct gtg gaa gaa caa agc cca gcc tct ttg tct tct ctg cgt      1483
Gln Ser Pro Val Glu Glu Gln Ser Pro Ala Ser Leu Ser Ser Leu Arg
            250                 255                 260 tca cgg agc aca caa atg gaa tca act cgt gtt tca gct tct ctc ccc      1531
Ser Arg Ser Thr Gln Met Glu Ser Thr Arg Val Ser Ala Ser Leu Pro
        265                 270                 275 aga agt tac cgg aaa act gat aca gtc agg tta aca tct gtg gtc aca      1579
Arg Ser Tyr Arg Lys Thr Asp Thr Val Arg Leu Thr Ser Val Val Thr
280                 285                 290 cca aga ccc ttt ggc tct cag aca agg gga atc tca tca ctc ccc aga      1627
Pro Arg Pro Phe Gly Ser Gln Thr Arg Gly Ile Ser Ser Leu Pro Arg
295                 300                 305                 310 tct tac acg atg gat gat gct tgg aag tat aat gga gat gtt gaa gac      1675
Ser Tyr Thr Met Asp Asp Ala Trp Lys Tyr Asn Gly Asp Val Glu Asp
                315                 320                 325 att aag aga act cca aac aat gtg gtc agc acc cct gca cca agc ccg      1723
Ile Lys Arg Thr Pro Asn Asn Val Val Ser Thr Pro Ala Pro Ser Pro
            330                 335                 340 gac gca agc caa ctg gct tca agc tta tct agc cag aaa gag gta gca      1771
Asp Ala Ser Gln Leu Ala Ser Ser Leu Ser Ser Gln Lys Glu Val Ala
        345                 350                 355 gca aca gaa gaa gat gtg aca agg ctg ccc tct cct aca tcc ccc ttc      1819
Ala Thr Glu Glu Asp Val Thr Arg Leu Pro Ser Pro Thr Ser Pro Phe
360                 365                 370 tca tct ctt tcc caa gac cag gct gcc act tct aaa gcc aca ttg tct      1867
Ser Ser Leu Ser Gln Asp Gln Ala Ala Thr Ser Lys Ala Thr Leu Ser
375                 380                 385                 390 tcc aca tct ggt ctt gat tta atg tct gaa tct gga gaa ggg gaa atc      1915
Ser Thr Ser Gly Leu Asp Leu Met Ser Glu Ser Gly Glu Gly Glu Ile
                395                 400                 405 tcc cca caa aga gaa gtc tca aga tcc cag gat cag ttc agt gat atg      1963
Ser Pro Gln Arg Glu Val Ser Arg Ser Gln Asp Gln Phe Ser Asp Met
            410                 415                 420 aga atc agc ata aac cag acg cct ggg aag agt ctt gac ttt ggg ttt      2011
Arg Ile Ser Ile Asn Gln Thr Pro Gly Lys Ser Leu Asp Phe Gly Phe
        425                 430                 435 aca ata aaa tgg gat att cct ggg atc ttc gta gca tca gtt gaa gca      2059
Thr Ile Lys Trp Asp Ile Pro Gly Ile Phe Val Ala Ser Val Glu Ala
440                 445                 450 ggt agc cca gca gaa ttt tct cag cta caa gta gat gat gaa att att      2107
Gly Ser Pro Ala Glu Phe Ser Gln Leu Gln Val Asp Asp Glu Ile Ile
455                 460                 465                 470 gct att aac aac acc aag ttt tca tat aac gat tca aaa gag tgg gag      2155
Ala Ile Asn Asn Thr Lys Phe Ser Tyr Asn Asp Ser Lys Glu Trp Glu
```

-continued

| | | | | |
|---|---|---|---|---|
| | 475 | 480 | 485 | |
| gaa gcc atg gct aag gct caa gaa act gga cac cta gtg atg gat gtg<br>Glu Ala Met Ala Lys Ala Gln Glu Thr Gly His Leu Val Met Asp Val<br>490                       495                     500 | | | | 2203 |
| agg cgc tat gga aag gct ggt tca cct gaa aca aag tgg att gat gca<br>Arg Arg Tyr Gly Lys Ala Gly Ser Pro Glu Thr Lys Trp Ile Asp Ala<br>         505                    510                    515 | | | | 2251 |
| act tct gga att tac aac tca gaa aaa tct tca aat cta tct gta aca<br>Thr Ser Gly Ile Tyr Asn Ser Glu Lys Ser Ser Asn Leu Ser Val Thr<br>520                       525                     530 | | | | 2299 |
| act gat ttc tcc gaa agc ctt cag agt tct aat att gaa tcc aaa gaa<br>Thr Asp Phe Ser Glu Ser Leu Gln Ser Ser Asn Ile Glu Ser Lys Glu<br>535                       540                    545                    550 | | | | 2347 |
| atc aat gga att cat gat gaa agc aat gct ttt gaa tca aaa gca tct<br>Ile Asn Gly Ile His Asp Glu Ser Asn Ala Phe Glu Ser Lys Ala Ser<br>                  555                    560                    565 | | | | 2395 |
| gaa tcc att tct ttg aaa aac tta aaa agg cga tca caa ttt ttt gaa<br>Glu Ser Ile Ser Leu Lys Asn Leu Lys Arg Arg Ser Gln Phe Phe Glu<br>                  570                    575                    580 | | | | 2443 |
| caa gga agc tct gat tcg gtg gtt cct gat ctt cca gtt cca acc atc<br>Gln Gly Ser Ser Asp Ser Val Val Pro Asp Leu Pro Val Pro Thr Ile<br>585                       590                    595 | | | | 2491 |
| agt gcc ccg agt cgc tgg gtg tgg gat caa gag gag gag cgg aag cgg<br>Ser Ala Pro Ser Arg Trp Val Trp Asp Gln Glu Glu Glu Arg Lys Arg<br>600                       605                    610 | | | | 2539 |
| cag gag agg tgg cag aag gag cag gac cgc cta ctg cag gaa aaa tat<br>Gln Glu Arg Trp Gln Lys Glu Gln Asp Arg Leu Leu Gln Glu Lys Tyr<br>615                       620                    625                    630 | | | | 2587 |
| caa cgt gag cag gag aaa ctg agg gaa gag tgg caa agg gcc aaa cag<br>Gln Arg Glu Gln Glu Lys Leu Arg Glu Glu Trp Gln Arg Ala Lys Gln<br>                  635                    640                    645 | | | | 2635 |
| gag gca gag aga gag aat tcc aag tac ttg gat gag gaa ctg atg gtc<br>Glu Ala Glu Arg Glu Asn Ser Lys Tyr Leu Asp Glu Glu Leu Met Val<br>650                       655                    660 | | | | 2683 |
| cta agc tca aac agc atg tct ctg acc aca cgg gag ccc tct ctt gcc<br>Leu Ser Ser Asn Ser Met Ser Leu Thr Thr Arg Glu Pro Ser Leu Ala<br>                  665                    670                    675 | | | | 2731 |
| acc tgg gaa gct acc tgg agt gaa ggg tcc aag tct tca gac aga gaa<br>Thr Trp Glu Ala Thr Trp Ser Glu Gly Ser Lys Ser Ser Asp Arg Glu<br>680                       685                    690 | | | | 2779 |
| gga acc cga gca gga gaa gag gag agg aga cag cca caa gag gaa gtt<br>Gly Thr Arg Ala Gly Glu Glu Glu Arg Arg Gln Pro Gln Glu Glu Val<br>695                       700                    705                    710 | | | | 2827 |
| gtt cat gag gac caa gga aag aag ccg cag gat cag ctt gtt att gag<br>Val His Glu Asp Gln Gly Lys Lys Pro Gln Asp Gln Leu Val Ile Glu<br>                  715                    720                    725 | | | | 2875 |
| aga gag agg aaa tgg gag caa cag ctt cag gaa gag caa gag caa aag<br>Arg Glu Arg Lys Trp Glu Gln Gln Leu Gln Glu Glu Gln Glu Gln Lys<br>730                       735                    740 | | | | 2923 |
| cgg ctt cag gct gag gct gag gag cag aag cgt cct gcg gag gag cag<br>Arg Leu Gln Ala Glu Ala Glu Glu Gln Lys Arg Pro Ala Glu Glu Gln<br>                  745                    750                    755 | | | | 2971 |
| aag cgc cag gca gag ata gag cgg gaa aca tca gtc aga ata tac cag<br>Lys Arg Gln Ala Glu Ile Glu Arg Glu Thr Ser Val Arg Ile Tyr Gln<br>760                       765                    770 | | | | 3019 |
| tac agg agg cct gtt gat tcc tat gat ata cca aag aca gaa gaa gca<br>Tyr Arg Arg Pro Val Asp Ser Tyr Asp Ile Pro Lys Thr Glu Glu Ala<br>775                       780                    785                    790 | | | | 3067 |
| tct tca ggt ttt ctt cct ggt gac agg aat aaa tcc aga tct act act | | | | 3115 |

```
                 Ser Ser Gly Phe Leu Pro Gly Asp Arg Asn Lys Ser Arg Ser Thr Thr
                             795                 800                 805 gaa ctg gat gat tac tcc aca aat aaa aat gga aac aat aaa tat tta        3163
Glu Leu Asp Asp Tyr Ser Thr Asn Lys Asn Gly Asn Asn Lys Tyr Leu
                810                 815                 820 gac caa att ggg aac acg acc tct tca cag agg aga tcc aag aaa gaa        3211
Asp Gln Ile Gly Asn Thr Thr Ser Ser Gln Arg Arg Ser Lys Lys Glu
                825                 830                 835 caa gta cca tca gga gca gaa ttg gag agg caa caa atc ctt cag gaa        3259
Gln Val Pro Ser Gly Ala Glu Leu Glu Arg Gln Gln Ile Leu Gln Glu
                840                 845                 850 atg agg aag aga aca ccc ctt cac aat gac aac agc tgg atc cga cag        3307
Met Arg Lys Arg Thr Pro Leu His Asn Asp Asn Ser Trp Ile Arg Gln
855                 860                 865                 870 cgc agt gcc agt gtc aac aaa gag cct gtt agt ctt cct ggg atc atg        3355
Arg Ser Ala Ser Val Asn Lys Glu Pro Val Ser Leu Pro Gly Ile Met
                875                 880                 885 aga aga ggc gaa tct tta gat aac ctg gac tcc ccc cga tcc aat tct        3403
Arg Arg Gly Glu Ser Leu Asp Asn Leu Asp Ser Pro Arg Ser Asn Ser
                890                 895                 900 tgg aga cag cct cct tgg ctc aat cag ccc aca gga ttc tat gct tct        3451
Trp Arg Gln Pro Pro Trp Leu Asn Gln Pro Thr Gly Phe Tyr Ala Ser
                905                 910                 915 tcc tct gtg caa gac ttt agt cgc cca cca cct cag ctg gtg tcc aca        3499
Ser Ser Val Gln Asp Phe Ser Arg Pro Pro Pro Gln Leu Val Ser Thr
                920                 925                 930 tca aac cgt gcc tac atg cgg aac ccc tcc tcc agc gtg ccc cca cct        3547
Ser Asn Arg Ala Tyr Met Arg Asn Pro Ser Ser Ser Val Pro Pro Pro
935                 940                 945                 950 tca gct ggc tcc gtg aag acc tcc acc aca ggt gtg gcc acc aca cag        3595
Ser Ala Gly Ser Val Lys Thr Ser Thr Thr Gly Val Ala Thr Thr Gln
                955                 960                 965 tcc ccc acc ccg aga agc cat tcc cct tca gct tca cag tca ggc tct        3643
Ser Pro Thr Pro Arg Ser His Ser Pro Ser Ala Ser Gln Ser Gly Ser
                970                 975                 980 cag ctg cgt aac agg tca gtc agt ggg aag cgc ata tgc tcc tac tgc        3691
Gln Leu Arg Asn Arg Ser Val Ser Gly Lys Arg Ile Cys Ser Tyr Cys
                985                 990                 995 aat aac att ctg ggc aaa gga gcc gcc atg atc atc gag tcc ctg ggt        3739
Asn Asn Ile Leu Gly Lys Gly Ala Ala Met Ile Ile Glu Ser Leu Gly
                1000                1005                1010 ctt tgt tat cat ttg cat tgt ttt aag tgt gtt gcc tgt gag tgt gac        3787
Leu Cys Tyr His Leu His Cys Phe Lys Cys Val Ala Cys Glu Cys Asp
1015                1020                1025                1030 ctc gga ggc tct tcc tca gga gct gaa gtc agg atc aga aac cac caa        3835
Leu Gly Gly Ser Ser Ser Gly Ala Glu Val Arg Ile Arg Asn His Gln
                1035                1040                1045 ctg tac tgc aac gac tgc tat ctc aga ttc aaa tct gga cgg cca acc        3883
Leu Tyr Cys Asn Asp Cys Tyr Leu Arg Phe Lys Ser Gly Arg Pro Thr
                1050                1055                1060 gcc atg tga tgtaagcctc catacgaaag cactgttgca gatagaagaa                3932
Ala Met  * gaggtggttg ctgctcatgt agatctataa atatgtgttg tatgtctttt ttgcttttt       3992 tttaaaaaaa agaataactt ttttgcctc tttagattac atagaagcat tgtagtcttg       4052
gtagaaccag tattttgtt gtttattat aaggtaattg tgtgtgggga aaagtgcagt        4112
atttacctgt tgaattcagc atcttgagag cacaagggaa aaaataagaa cctacgaata      4172
tttttgaggc agataatgat ctagtttgac tttctagtta gtggtgtttt gaagagggta      4232
```

```
ttttattgtt ttttaaaaaa aggttcttaa acattatttg aaatagttaa tataaataca    4292
taattgcatt tgctctgttt attgtaatgt attctaaatt aatgcagaac catatggaaa    4352
atttcattaa aatctatccc caaatgtgct ttctgtatcc ttccttctac ctattattct    4412
gattttaaaa aatgcagtta atgtaccatt tatttgcttg atgaagggag ctctatttc     4472 tttaccagaa atgttgctaa gtaattccca atagaaagct gcttattttc attaatgaaa    4532
aataaccatg gtttgtatac tagaagtctt cttcagaaac tggtgagcct ttctgttcaa    4592
ttgcatttgt aaataaactt gctgatgcat ttaaaaaaaa aaaaaaaaa                4642
```

<210> SEQ ID NO 55
<211> LENGTH: 1064
<212> TYPE: PRT
<213> ORGANISM: Homo Sapiens

<400> SEQUENCE: 55

```
Met Gln Asp Tyr Asn Lys Asp Asp Met Ser Tyr Arg Arg Ile Ser Ala
 1               5                  10                  15

Val Glu Pro Lys Thr Ala Leu Pro Phe Asn Arg Phe Leu Pro Asn Lys
            20                  25                  30

Ser Arg Gln Pro Ser Tyr Val Pro Ala Pro Leu Arg Lys Lys Lys Pro
        35                  40                  45

Asp Lys His Glu Asp Asn Arg Arg Ser Trp Ala Ser Pro Val Tyr Thr
    50                  55                  60

Glu Ala Asp Gly Thr Phe Ser Arg Leu Phe Gln Lys Ile Tyr Gly Glu
65                  70                  75                  80

Asn Gly Ser Lys Ser Met Ser Asp Val Ser Ala Glu Asp Val Gln Asn
                85                  90                  95

Leu Arg Gln Leu Arg Tyr Glu Glu Met Gln Lys Ile Lys Ser Gln Leu
            100                 105                 110

Lys Glu Gln Asp Gln Lys Trp Gln Asp Leu Ala Lys Trp Lys Asp
        115                 120                 125

Arg Arg Lys Ser Tyr Thr Ser Asp Leu Gln Lys Lys Lys Glu Glu Arg
    130                 135                 140

Glu Glu Ile Glu Lys Gln Ala Leu Glu Lys Ser Lys Arg Ser Ser Lys
145                 150                 155                 160

Thr Phe Lys Glu Met Leu Gln Asp Arg Glu Ser Gln Asn Gln Lys Ser
                165                 170                 175

Thr Val Pro Ser Arg Arg Arg Met Tyr Ser Phe Asp Asp Val Leu Glu
            180                 185                 190

Glu Gly Lys Arg Pro Pro Thr Met Thr Val Ser Glu Ala Ser Tyr Gln
        195                 200                 205

Ser Glu Arg Val Glu Glu Lys Gly Ala Thr Tyr Pro Ser Glu Ile Pro
    210                 215                 220

Lys Glu Asp Ser Thr Thr Phe Ala Lys Arg Glu Asp Arg Val Thr Thr
225                 230                 235                 240

Glu Ile Gln Leu Pro Ser Gln Ser Pro Val Glu Glu Gln Ser Pro Ala
                245                 250                 255

Ser Leu Ser Ser Leu Arg Ser Arg Ser Thr Gln Met Glu Ser Thr Arg
            260                 265                 270

Val Ser Ala Ser Leu Pro Arg Ser Tyr Arg Lys Thr Asp Thr Val Arg
        275                 280                 285

Leu Thr Ser Val Val Thr Pro Arg Pro Phe Gly Ser Gln Thr Arg Gly
    290                 295                 300
```

```
Ile Ser Ser Leu Pro Arg Ser Tyr Thr Met Asp Asp Ala Trp Lys Tyr
305                 310                 315                 320

Asn Gly Asp Val Glu Asp Ile Lys Arg Thr Pro Asn Asn Val Val Ser
            325                 330                 335

Thr Pro Ala Pro Ser Pro Asp Ala Ser Gln Leu Ala Ser Ser Leu Ser
            340                 345                 350

Ser Gln Lys Glu Val Ala Ala Thr Glu Glu Asp Val Thr Arg Leu Pro
            355                 360                 365

Ser Pro Thr Ser Pro Phe Ser Ser Leu Ser Gln Asp Gln Ala Ala Thr
            370                 375                 380

Ser Lys Ala Thr Leu Ser Ser Thr Ser Gly Leu Asp Leu Met Ser Glu
385                 390                 395                 400

Ser Gly Glu Gly Glu Ile Ser Pro Gln Arg Glu Val Ser Arg Ser Gln
                405                 410                 415

Asp Gln Phe Ser Asp Met Arg Ile Ser Ile Asn Gln Thr Pro Gly Lys
            420                 425                 430

Ser Leu Asp Phe Gly Phe Thr Ile Lys Trp Asp Ile Pro Gly Ile Phe
            435                 440                 445

Val Ala Ser Val Glu Ala Gly Ser Pro Ala Glu Phe Ser Gln Leu Gln
450                 455                 460

Val Asp Asp Glu Ile Ile Ala Ile Asn Asn Thr Lys Phe Ser Tyr Asn
465                 470                 475                 480

Asp Ser Lys Glu Trp Glu Glu Ala Met Ala Lys Ala Gln Glu Thr Gly
            485                 490                 495

His Leu Val Met Asp Val Arg Arg Tyr Gly Lys Ala Gly Ser Pro Glu
            500                 505                 510

Thr Lys Trp Ile Asp Ala Thr Ser Gly Ile Tyr Asn Ser Glu Lys Ser
            515                 520                 525

Ser Asn Leu Ser Val Thr Thr Asp Phe Ser Glu Ser Leu Gln Ser Ser
530                 535                 540

Asn Ile Glu Ser Lys Glu Ile Asn Gly Ile His Asp Glu Ser Asn Ala
545                 550                 555                 560

Phe Glu Ser Lys Ala Ser Glu Ser Ile Ser Leu Lys Asn Leu Lys Arg
            565                 570                 575

Arg Ser Gln Phe Phe Glu Gln Gly Ser Ser Asp Ser Val Val Pro Asp
            580                 585                 590

Leu Pro Val Pro Thr Ile Ser Ala Pro Ser Arg Trp Val Trp Asp Gln
            595                 600                 605

Glu Glu Glu Arg Lys Arg Gln Glu Arg Trp Gln Lys Glu Gln Asp Arg
            610                 615                 620

Leu Leu Gln Glu Lys Tyr Gln Arg Glu Gln Glu Lys Leu Arg Glu Glu
625                 630                 635                 640

Trp Gln Arg Ala Lys Gln Glu Ala Glu Arg Glu Asn Ser Lys Tyr Leu
            645                 650                 655

Asp Glu Glu Leu Met Val Leu Ser Ser Asn Ser Met Ser Leu Thr Thr
            660                 665                 670

Arg Glu Pro Ser Leu Ala Thr Trp Glu Ala Thr Trp Ser Glu Gly Ser
            675                 680                 685

Lys Ser Ser Asp Arg Glu Gly Thr Arg Ala Gly Glu Glu Glu Arg Arg
            690                 695                 700

Gln Pro Gln Glu Glu Val Val His Glu Asp Gln Gly Lys Lys Pro Gln
705                 710                 715                 720
```

| | | | | | | | | | | | |
|---|---|---|---|---|---|---|---|---|---|---|---|
|Asp|Gln|Leu|Val|Ile|Glu|Arg|Glu|Arg|Lys|Trp|Gln|Gln|Leu|Gln|
| | | |725| | | |730| | | |735|

Glu Glu Gln Glu Gln Lys Arg Leu Gln Ala Glu Ala Glu Gln Lys
            740                 745                 750

Arg Pro Ala Glu Glu Gln Lys Arg Gln Ala Glu Ile Glu Arg Glu Thr
            755                 760                 765

Ser Val Arg Ile Tyr Gln Tyr Arg Arg Pro Val Asp Ser Tyr Asp Ile
            770                 775                 780

Pro Lys Thr Glu Glu Ala Ser Ser Gly Phe Leu Pro Gly Asp Arg Asn
785                 790                 795                 800

Lys Ser Arg Ser Thr Thr Glu Leu Asp Asp Tyr Ser Thr Asn Lys Asn
                805                 810                 815

Gly Asn Asn Lys Tyr Leu Asp Gln Ile Gly Asn Thr Thr Ser Ser Gln
                820                 825                 830

Arg Arg Ser Lys Lys Glu Gln Val Pro Ser Gly Ala Glu Leu Glu Arg
                835                 840                 845

Gln Gln Ile Leu Gln Glu Met Arg Lys Arg Thr Pro Leu His Asn Asp
            850                 855                 860

Asn Ser Trp Ile Arg Gln Arg Ser Ala Ser Val Asn Lys Glu Pro Val
865                 870                 875                 880

Ser Leu Pro Gly Ile Met Arg Arg Gly Glu Ser Leu Asp Asn Leu Asp
                885                 890                 895

Ser Pro Arg Ser Asn Ser Trp Arg Gln Pro Pro Trp Leu Asn Gln Pro
                900                 905                 910

Thr Gly Phe Tyr Ala Ser Ser Ser Val Gln Asp Phe Ser Arg Pro Pro
            915                 920                 925

Pro Gln Leu Val Ser Thr Ser Asn Arg Ala Tyr Met Arg Asn Pro Ser
            930                 935                 940

Ser Ser Val Pro Pro Ser Ala Gly Ser Val Lys Thr Ser Thr Thr
945                 950                 955                 960

Gly Val Ala Thr Thr Gln Ser Pro Thr Pro Arg Ser His Ser Pro Ser
                965                 970                 975

Ala Ser Gln Ser Gly Ser Gln Leu Arg Asn Arg Ser Val Ser Gly Lys
            980                 985                 990

Arg Ile Cys Ser Tyr Cys Asn Asn Ile Leu Gly Lys Gly Ala Ala Met
            995                1000                1005

Ile Ile Glu Ser Leu Gly Leu Cys Tyr His Leu His Cys Phe Lys Cys
    1010                1015                1020

Val Ala Cys Glu Cys Asp Leu Gly Gly Ser Ser Ser Gly Ala Glu Val
1025                1030                1035                1040

Arg Ile Arg Asn His Gln Leu Tyr Cys Asn Asp Cys Tyr Leu Arg Phe
                1045                1050                1055

Lys Ser Gly Arg Pro Thr Ala Met
            1060

<210> SEQ ID NO 56
<211> LENGTH: 549
<212> TYPE: DNA
<213> ORGANISM: Homo Sapiens

<400> SEQUENCE: 56
gcaccataag agagaagatt cctttgaaag cttggactct ttgggctcga ggtcattgac      60
aagctgctcc tctgatatca cgttgagagg ggggcgtgaa ggttttgaaa gtgacacaga     120
ttcggaattt acattcaaga tgcaggatta taataaagat gatatgtcgt atcgaaggat     180

-continued

```
ttcggctgtt gagccaaaga ctgcgttacc cttcaatcgt tttttaccca acaaaagtag    240
acagccatcc tatgtaccag cacctctgag aaagaaaaag ccagacaaac atgaggataa    300
cagaagaagt tgggcaagcc cggtttatac agaagcagat ggaacatttt caagactctt    360
tcaaaagatt tatggtgaga atgggagtaa gtccatgagt gatgtcagcg cagaagatgt    420
tcaaaacttg cgtcagctgc gttacgagga gatgcagaaa ataaaatcac aattaaaaga    480
acaagatcag aaatggcagg atgaccttgc aaagtggaaa gatcgtcgaa aaagttacac    540
ttcagatct                                                            549
```

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57 gtaactttt cgacgatctt tccac                                           25

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
tattttctgc atctcctcgt aacgc                                          25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
tgacatcact catggactta ctccc                                          25

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
gttccatctg cttctgtata aaccg                                          25

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
tctgttatcc tcatgtttgt ctggc                                          25

<210> SEQ ID NO 62
<211> LENGTH: 25
<212> TYPE: DNA

```
<213> ORGANISM: Artificial Sequence
<220> FEATURE:
<223> OTHER INFORMATION: Primer

<400> SEQUENCE: 62
tctggctttt tctttctcaa agtgc                                              25

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
aagtgctggt acatagatgg ctgtc                                              25

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
tctacttttg ttggggttga aaacg                                              25

<210> SEQ ID NO 65
<211> LENGTH: 25
<212> TYPE: DNA
<213> ORGANISM: Artificial Sequence
<220> FEATURE:
<223> OTHER INFORMATION: Primer

<400> SEQUENCE: 65
tgtgtcactt tcaaaaactt cacgc                                              25

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
agagcagctt gtctatgaac tccag                                              25

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
cgggaaatcg tgcgtgacat taag                                               24

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
tgatctcctt ctgcatcctg tcgg                                               24
```

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
ttcgtagcat cagttgaagc agg                                          23

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
ggtgaaccag cctttccata gc                                           22

<210> SEQ ID NO 71
<211> LENGTH: 1958
<212> TYPE: DNA
<213> ORGANISM: Homo sapiens

<400> SEQUENCE: 71
aaaagtagct ggagttaggt catttgattt tatactctgt actcaagact gctcctctct    60
gccgactaca acagattgga gccatggctt tggagcagaa ccagtcaaca gattattatt   120
atgaggaaaa tgaaatgaat ggcacttatg actacagtca atatgaactg atctgtatca   180
aagaagatgt cagagaattt gcaaaagttt cctccctgt attcctcaca atagttttcg    240
tcattggact tgcaggcaat tccatggtag tggcaattta tgcctattac aagaaacaga   300
gaaccaaaac agatgtgtac atcctgaatt tggctgtagc agatttactc cttctattca   360
ctctgccttt ttgggctgtt aatgcagttc atgggtgggt tttagggaaa ataatgtgca   420
aaataacttc agccttgtac acactaaact ttgtctctgg aatgcagttt ctggcttgta   480
tcagcataga cagatatgtg gcagtaacta agtccccag ccaatcagga gtgggaaaac    540
catgctggat catctgtttc tgtgtctgga tggctgccat cttgctgagc ataccccagc   600 tggttttta tacagtaaat gacaatgcta ggtgcattcc catttttccc cgctacctag   660
gaacatcaat gaaagcattg attcaaatgc tagagatctg cattggatttt gtagtaccct  720 ttcttattat gggggtgtgc tactttatca cagcaaggac actcatgaag atgccaaaca   780
ttaaaatatc tcgacccta aaagttctgc tcacagtcgt tatagttttc attgtcactc    840 aactgccttta aacattgtc aagttctgcc gagccataga catcatctac tccctgatca   900
ccagctgcaa catgagcaaa cgcatggaca tcgccatcca agtcacagaa agcatcgcac   960
tctttcacag ctgcctcaac ccaatccttt atgtttttat gggagcatct ttcaaaaact  1020
acgttatgaa agtggccaag aaatatgggt cctggagaag acagagacaa agtgtggagg  1080 agtttcctt tgattctgag ggtcctacag agccaaccag tactttagc atttaaaggt    1140 aaaactgctc tgccttttgc ttggatacat atgaatgatg ctttcccctc aaataaaaca  1200
tctgcattat tctgaaactc aaatctcaga cgccgtggtt gcaacttata ataagaatg    1260 ggttggggga aggggagaa ataaaagcca agaagaggaa acaagataat aaatgtacaa    1320
aacatgaaaa ttaaaatgaa caatatagga aaataattgt aacaggcata agtgaataac  1380

```
actctgctgt aacgaagaag agctttgtgg tgataatttt gtatcttggt tgcagtggtg   1440
cttatacaaa tctacacaag tgataaaatg acacagaact atatacacac attgtaccaa   1500
tttcaatttc ctggttttga cattatagta taattatgta agatggaacc attggggaaa   1560
actgggtgaa gggtacccag gaccactctg taccatcttt gtaacttcct gtgaatttat   1620
aataatttca aaataaaaca agttaaaaaa aaacccacta tgctataagt taggccatct   1680
aaaacagatt attaaagagg ttcatgttaa aaggcattta taattatttt taattatcta   1740
agttttaata caagaacgat ttccctgcat aatttagta cttgaataag tatgcagcag   1800
aactccaact atcttttttc ctgtttttt taaatttgta agtaatttta taaaatccac   1860
ctcctccaaa aaagcaataa aaaaaaaaca aactataaaa aaaaaaaaa aaaaaaaaa   1920 aaaaaaaaa aaaaaaaaa aaaaaaaaa aaaaaaa                              1958
```

<210> SEQ ID NO 72
<211> LENGTH: 350
<212> TYPE: PRT
<213> ORGANISM: Homo sapiens

<400> SEQUENCE: 72

```
Met Ala Leu Glu Gln Asn Gln Ser Thr Asp Tyr Tyr Tyr Glu Glu Asn
 1               5                  10                  15

Glu Met Asn Gly Thr Tyr Asp Tyr Ser Gln Tyr Glu Leu Ile Cys Ile
             20                  25                  30

Lys Glu Asp Val Arg Glu Phe Ala Lys Val Phe Leu Pro Val Phe Leu
         35                  40                  45

Thr Ile Val Phe Val Ile Gly Leu Ala Gly Asn Ser Met Val Val Ala
     50                  55                  60

Ile Tyr Ala Tyr Tyr Lys Lys Gln Arg Thr Lys Thr Asp Val Tyr Ile
 65                  70                  75                  80

Leu Asn Leu Ala Val Ala Asp Leu Leu Leu Phe Thr Leu Pro Phe
                 85                  90                  95

Trp Ala Val Asn Ala Val His Gly Trp Val Leu Gly Lys Ile Met Cys
            100                 105                 110

Lys Ile Thr Ser Ala Leu Tyr Thr Leu Asn Phe Val Ser Gly Met Gln
        115                 120                 125

Phe Leu Ala Cys Ile Ser Ile Asp Arg Tyr Val Ala Val Thr Lys Val
    130                 135                 140

Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
        195                 200                 205

Phe Val Val Pro Phe Leu Ile Met Gly Val Cys Tyr Phe Ile Thr Ala
    210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270
```

```
Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
    290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Glu Phe Pro Phe
                325                 330                 335

Asp Ser Glu Gly Pro Thr Glu Pro Thr Ser Thr Phe Ser Ile
                340                 345                 350
```

<210> SEQ ID NO 73
<211> LENGTH: 23
<212> TYPE: DNA
<213> ORGANISM: Homo sapiens

<400> SEQUENCE: 73
actaccaaca ggttggtact tta                                          23

<210> SEQ ID NO 74
<211> LENGTH: 22
<212> TYPE: DNA
<213> ORGANISM: Homo sapiens

<400> SEQUENCE: 74
ctttgccatc tagagtggag cc                                           22

<210> SEQ ID NO 75
<211> LENGTH: 82
<212> TYPE: DNA
<213> ORGANISM: Artificial Sequence
<220> FEATURE:
<223> OTHER INFORMATION: encodes synthetic peptide
<220> FEATURE:
<221> NAME/KEY: misc_feature
<222> LOCATION: (1)...(82)
<223> OTHER INFORMATION: n = A,T,C or G

<400> SEQUENCE: 75
ctttctattc tcactccgct gaannsnnsn nsnnsnnsnn snnsnnsnns nnsnnsnnsn   60
nsnnsccgcc tccacctcca cc                                           82

<210> SEQ ID NO 76
<211> LENGTH: 93
<212> TYPE: DNA
<213> ORGANISM: Artificial Sequence
<220> FEATURE:
<223> OTHER INFORMATION: encodes synthetic peptide
<220> FEATURE:
<221> NAME/KEY: misc_feature
<222> LOCATION: (1)...(93)
<223> OTHER INFORMATION: n = inosine

<400> SEQUENCE: 76
ggccggtgga ggtggaggcg gnnnnnnnnn nnnnnnnnnn nnnnnnnnnn nnnnnnnnnn   60
nnnnnnttca gcggagtgag aatagaaagg tac                               93

<210> SEQ ID NO 77
<211> LENGTH: 36
<212> TYPE: DNA
<213> ORGANISM: Artificial Sequence
<220> FEATURE:
<223> OTHER INFORMATION: primer

```
<400> SEQUENCE: 77
gctgcccgag agatctgtat atatgagtaa acttgg                                36

<210> SEQ ID NO 78
<211> LENGTH: 36
<212> TYPE: DNA
<213> ORGANISM: Artificial Sequence
<220> FEATURE:
<223> OTHER INFORMATION: primer

<400> SEQUENCE: 78
gcaggctcgg gaattcggga aatgtgcgcg gaaccc                                36

<210> SEQ ID NO 79
<211> LENGTH: 21
<212> TYPE: DNA
<213> ORGANISM: Artificial Sequence
<220> FEATURE:
<223> OTHER INFORMATION: mutagenic oligonucleotides

<400> SEQUENCE: 79
aaacttcctc atgaaaaagt c                                                21

<210> SEQ ID NO 80
<211> LENGTH: 25
<212> TYPE: DNA
<213> ORGANISM: Artificial Sequence
<220> FEATURE:
<223> OTHER INFORMATION: mutagenic oligonucleotides

<400> SEQUENCE: 80
agaatagaaa ggtaccacta aagga                                            25

<210> SEQ ID NO 81
<211> LENGTH: 39
<212> TYPE: DNA
<213> ORGANISM: Artificial Sequence
<220> FEATURE:
<223> OTHER INFORMATION: mutagenic oligonucleotides

<400> SEQUENCE: 81
tttagtggta cctttctatt ctcactcggc cgaaactgt                             39

<210> SEQ ID NO 82
<211> LENGTH: 24
<212> TYPE: DNA
<213> ORGANISM: Artificial Sequence
<220> FEATURE:
<223> OTHER INFORMATION: mutagenic oligonucleotides

<400> SEQUENCE: 82
aaagcgcagt ctctgaattt accg                                             24

<210> SEQ ID NO 83
<211> LENGTH: 22
<212> TYPE: DNA
<213> ORGANISM: Artificial Sequence
<220> FEATURE:
<223> OTHER INFORMATION: primers

<400> SEQUENCE: 83
tcgaaagcaa gctgataaac cg                                               22

<210> SEQ ID NO 84
<211> LENGTH: 23
```

```
<212> TYPE: DNA
<213> ORGANISM: Artificial Sequence
<220> FEATURE:
<223> OTHER INFORMATION: primers

<400> SEQUENCE: 84
acagacagcc ctcatagtta gcg                                          23

<210> SEQ ID NO 85
<211> LENGTH: 374
<212> TYPE: PRT
<213> ORGANISM: Homo sapiens

<400> SEQUENCE: 85
```

| | | | | | | | | | | | | | | |
|---|---|---|---|---|---|---|---|---|---|---|---|---|---|---|
| Met | Ser | Gly | Glu | Ser | Met | Asn | Phe | Ser | Asp | Val | Phe | Asp | Ser | Glu |
| 1 | | | | 5 | | | | | 10 | | | | | 15 |
| Asp | Tyr | Phe | Val | Ser | Val | Asn | Thr | Ser | Tyr | Tyr | Ser | Val | Asp | Ser | Glu |
| | | | 20 | | | | | 25 | | | | | 30 | |
| Met | Leu | Leu | Cys | Ser | Leu | Gln | Glu | Val | Arg | Gln | Phe | Ser | Arg | Leu | Phe |
| | | 35 | | | | | 40 | | | | | 45 | | |
| Val | Pro | Ile | Ala | Tyr | Ser | Leu | Ile | Cys | Val | Phe | Gly | Leu | Leu | Gly | Asn |
| | 50 | | | | | 55 | | | | | 60 | | | | |
| Ile | Leu | Val | Val | Ile | Thr | Phe | Ala | Phe | Tyr | Lys | Lys | Ala | Arg | Ser | Met |
| 65 | | | | | 70 | | | | | 75 | | | | | 80 |
| Thr | Asp | Val | Tyr | Leu | Leu | Asn | Met | Ala | Ile | Ala | Asp | Ile | Leu | Phe | Val |
| | | | | 85 | | | | | 90 | | | | | 95 | |
| Leu | Thr | Leu | Pro | Phe | Trp | Ala | Val | Ser | His | Ala | Thr | Gly | Ala | Trp | Val |
| | | | 100 | | | | | 105 | | | | | 110 | | |
| Phe | Ser | Asn | Ala | Thr | Cys | Lys | Leu | Leu | Lys | Gly | Ile | Tyr | Ala | Ile | Asn |
| | | 115 | | | | | 120 | | | | | 125 | | | |
| Phe | Asn | Cys | Gly | Met | Leu | Leu | Leu | Thr | Cys | Ile | Ser | Met | Asp | Arg | Tyr |
| | 130 | | | | | 135 | | | | | 140 | | | | |
| Ile | Ala | Ile | Val | Gln | Ala | Thr | Lys | Ser | Phe | Arg | Leu | Arg | Ser | Arg | Thr |
| 145 | | | | | 150 | | | | | 155 | | | | | 160 |
| Leu | Pro | Arg | Ser | Lys | Ile | Ile | Cys | Leu | Val | Val | Trp | Gly | Leu | Ser | Val |
| | | | | 165 | | | | | 170 | | | | | 175 | |
| Ile | Ile | Ser | Ser | Ser | Thr | Phe | Val | Phe | Asn | Gln | Lys | Tyr | Asn | Thr | Gln |
| | | | 180 | | | | | 185 | | | | | 190 | | |
| Gly | Ser | Asp | Val | Cys | Glu | Pro | Lys | Tyr | Gln | Thr | Val | Ser | Glu | Pro | Ile |
| | | 195 | | | | | 200 | | | | | 205 | | | |
| Arg | Trp | Lys | Leu | Leu | Met | Leu | Gly | Leu | Glu | Leu | Leu | Phe | Gly | Phe | Phe |
| | 210 | | | | | 215 | | | | | 220 | | | | |
| Ile | Pro | Leu | Met | Phe | Met | Ile | Phe | Cys | Tyr | Thr | Phe | Ile | Val | Lys | Thr |
| 225 | | | | | 230 | | | | | 235 | | | | | 240 |
| Leu | Val | Gln | Ala | Gln | Asn | Ser | Lys | Arg | His | Lys | Ala | Ile | Arg | Val | Ile |
| | | | | 245 | | | | | 250 | | | | | 255 | |
| Ile | Ala | Val | Val | Leu | Val | Phe | Leu | Ala | Cys | Gln | Ile | Pro | His | Asn | Met |
| | | | 260 | | | | | 265 | | | | | 270 | | |
| Val | Leu | Leu | Val | Thr | Ala | Ala | Asn | Leu | Gly | Lys | Met | Asn | Arg | Ser | Cys |
| | | 275 | | | | | 280 | | | | | 285 | | | |
| Gln | Ser | Glu | Lys | Leu | Ile | Gly | Tyr | Thr | Lys | Thr | Val | Thr | Glu | Val | Leu |
| | 290 | | | | | 295 | | | | | 300 | | | | |
| Ala | Phe | Leu | His | Cys | Cys | Leu | Asn | Pro | Val | Leu | Tyr | Ala | Phe | Ile | Gly |
| 305 | | | | | 310 | | | | | 315 | | | | | 320 |
| Gln | Lys | Phe | Arg | Asn | Tyr | Phe | Leu | Lys | Ile | Leu | Lys | Asp | Leu | Trp | Cys |
| | | | | 325 | | | | | 330 | | | | | 335 | |

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
            355                 360                 365

Ala Ser Ser Phe Thr Met
        370

<210> SEQ ID NO 86
<211> LENGTH: 378
<212> TYPE: PRT
<213> ORGANISM: Homo sapiens

<400> SEQUENCE: 86

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp

-continued

```
              325                 330                 335
Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
            370                 375

<210> SEQ ID NO 87
<211> LENGTH: 360
<212> TYPE: PRT
<213> ORGANISM: Homo sapiens

<400> SEQUENCE: 87

Met Glu Asp Phe Asn Met Glu Ser Asp Ser Phe Glu Asp Phe Trp Lys
  1               5                  10                  15

Gly Glu Asp Leu Ser Asn Tyr Ser Tyr Ser Ser Thr Leu Pro Pro Phe
             20                  25                  30

Leu Leu Asp Ala Ala Pro Cys Glu Pro Glu Ser Leu Glu Ile Asn Lys
         35                  40                  45

Tyr Phe Val Val Ile Ile Tyr Ala Leu Val Phe Leu Leu Ser Leu Leu
     50                  55                  60

Gly Asn Ser Leu Val Met Leu Val Ile Leu Tyr Ser Arg Val Gly Arg
 65                  70                  75                  80

Ser Val Thr Asp Val Tyr Leu Leu Asn Leu Ala Leu Ala Asp Leu Leu
                 85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320
```

```
Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 88
<211> LENGTH: 5
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 3, 4
<223> OTHER INFORMATION: Xaa = Any Amino Acid

<400> SEQUENCE: 88

Gly Asn Xaa Xaa Val
1               5

<210> SEQ ID NO 89
<211> LENGTH: 10
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 6
<223> OTHER INFORMATION: Xaa = Any Amino Acid

<400> SEQUENCE: 89

Ile Xaa Asn Leu Ala Xaa Ala Ala Asp Leu
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 3, 6
<223> OTHER INFORMATION: Xaa = Any Amino Acid

<400> SEQUENCE: 90

Leu Xaa Xaa Ile Ser Xaa Asp Arg Tyr
1               5

<210> SEQ ID NO 91
<211> LENGTH: 10
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 3, 5, 6, 7, 8, 9
<223> OTHER INFORMATION: Xaa = Any Amino Acid

<400> SEQUENCE: 91

Trp Xaa Xaa Ala Xaa Xaa Xaa Xaa Xaa Pro
1               5                   10

<210> SEQ ID NO 92
```

```
<211> LENGTH: 12
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 3, 5, 6, 7, 9, 10, 11
<223> OTHER INFORMATION: Xaa = Any Amino Acid

<400> SEQUENCE: 92

Phe Xaa Xaa Pro Xaa Xaa Xaa Met Xaa Xaa Xaa Tyr
 1               5                  10

<210> SEQ ID NO 93
<211> LENGTH: 17
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 3, 4, 5, 6, 7, 8, 9, 11, 12, 13, 14, 15
<223> OTHER INFORMATION: Xaa = Any Amino Acid

<400> SEQUENCE: 93

Lys Xaa Xaa Xaa Xaa Xaa Xaa Xaa Xaa Phe Xaa Xaa Xaa Xaa Xaa Pro
 1               5                  10                  15

Tyr

<210> SEQ ID NO 94
<211> LENGTH: 8
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 2, 3, 6, 7
<223> OTHER INFORMATION: Xaa = Any Amino Acid

<400> SEQUENCE: 94

Ser Xaa Xaa Asn Pro Xaa Xaa Tyr
 1               5

<210> SEQ ID NO 95
<211> LENGTH: 62
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (5)...(27)
<223> OTHER INFORMATION: Xaa = Any Amino Acid and up to 7 of them can be
      present or absent
<220> FEATURE:
<221> NAME/KEY: VARIANT
<222> LOCATION: (29)...(30)
<223> OTHER INFORMATION: Xaa = Any Amino Acid
<220> FEATURE:
<221> NAME/KEY: VARIANT
<222> LOCATION: (32)...(33)
<223> OTHER INFORMATION: Xaa = Any Amino Acid
<220> FEATURE:
<221> NAME/KEY: VARIANT
<222> LOCATION: (35)...(36)
<223> OTHER INFORMATION: Xaa = Any Amino Acid
```

```
<220> FEATURE:
<221> NAME/KEY: VARIANT
<222> LOCATION: (37)...(57)
<223> OTHER INFORMATION: Up to 5 of them can be present or absent
<220> FEATURE:
<221> NAME/KEY: VARIANT
<222> LOCATION: (59)...(61)
<223> OTHER INFORMATION: Xaa = Any Amino Acid and up to 1 of them can be
      present or absent
<220> FEATURE:
<221> NAME/KEY: VARIANT
<222> LOCATION: 62
<223> OTHER INFORMATION: Xaa = Cys, His or Asp

<400> SEQUENCE: 95

Cys Xaa Xaa Cys Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa His Xaa Xaa Cys Xaa
            20                  25                  30

Xaa Cys Xaa Xaa Cys Cys Cys Cys Cys Cys Cys Cys Cys Cys
        35                  40                  45

Cys Cys Cys Cys Cys Cys Cys Cys Cys Cys Xaa Xaa Xaa Xaa
    50                  55                  60

<210> SEQ ID NO 96
<211> LENGTH: 23
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: (1)...(23)
<223> OTHER INFORMATION: Xaa = Any Amino Acid

<400> SEQUENCE: 96

Ala Glu Xaa Xaa Xaa Xaa Xaa Xaa Xaa Xaa Xaa Xaa Xaa Xaa Xaa Xaa
 1               5                   10                  15

Xaa Pro Pro Pro Pro Pro Pro
            20
```

HX2004-6 POLYPEPTIDE EXPRESSED IN CANCEROUS CELLS

FIELD OF THE INVENTION

The present invention relates to polynucleotides and polypeptides that are differentially expressed in cancer cells, and uses thereof.

BACKGROUND OF THE INVENTION

Cancer, like many diseases, is not the result of a single, well-defined cause, but rather can be viewed as several diseases, each caused by different aberrations in informational pathways, that ultimately result in apparently similar pathologic phenotypes. Identification of polynucleotides that correspond to genes that are differentially expressed in cancerous, pre-cancerous, or low metastatic potential cells relative to normal cells of the same tissue type, provides the basis for diagnostic tools, facilitates drug discovery by providing for targets for candidate agents, and further serves to identify therapeutic targets for cancer therapies that are more tailored for the type of cancer to be treated.

Identification of differentially expressed gene products also furthers the understanding of the progression and nature of complex diseases such as cancer, and is key to identifying the genetic factors that are responsible for the phenotypes associated with development of, for example, the metastatic phenotype. Identification of gene products that are differentially expressed at various stages, and in various types of cancers, can both provide for early diagnostic tests, and further serve as therapeutic targets. Additionally, the product of a differentially expressed gene can be the basis for screening assays to identify chemotherapeutic agents that modulate its activity (e.g. its expression, biological activity, and the like).

Early disease diagnosis is of central importance to halting disease progression, and reducing morbidity. Analysis of a patient's tumor to identify the gene products that are differentially expressed, and administration of therapeutic agent(s) designed to modulate the activity of those differentially expressed gene products, provides the basis for more specific, rational cancer therapy that may result in diminished adverse side effects relative to conventional therapies. Furthermore, confirmation that a tumor poses less risk to the patient (e.g., that the tumor is benign) can avoid unnecessary therapies. In short, identification of genes and the encoded gene products that are differentially expressed in cancerous cells can provide the basis of therapeutics, diagnostics, prognostics, therametrics, and the like.

For example, breast cancer is a leading cause of death among women. One of the priorities in breast cancer research is the discovery of new biochemical markers that can be used for diagnosis, prognosis and monitoring of breast cancer. The prognostic usefulness of these markers depends on the ability of the marker to distinguish between patients with breast cancer who require aggressive therapeutic treatment and patients who should be monitored.

While the pathogenesis of breast cancer is unclear, transformation of non-tumorigenic breast epithelium to a malignant phenotype may be the result of genetic factors, especially in women under 30 (Miki, et al., Science, 266: 66-71, 1994). However, it is likely that other, non-genetic factors are also significant in the etiology of the disease. Regardless of its origin, breast cancer morbidity increases significantly if a lesion is not detected early in its progression. Thus, considerable effort has focused on the elucidation of early cellular events surrounding transformation in breast tissue. Such effort has led to the identification of several potential breast cancer markers.

Thus, the identification of new markers associated with cancer, for example, breast cancer, and the identification of genes involved in transforming cells into the cancerous phenotype, remains a significant goal in the management of this disease. In exemplary aspects, the invention described herein provides cancer diagnostics, prognostics, therametrics, and therapeutics based upon polynucleotides and/or their encoded gene products.

SUMMARY OF THE INVENTION

The present invention provides methods and compositions useful in detection of cancerous cells, identification of agents that modulate the phenotype of cancerous cells, and identification of therapeutic targets for chemotherapy of cancerous cells. Cancerous, breast, colon and prostate cells are of particular interest in each of these aspects of the invention. More specifically, the invention provides polynucleotides in substantially isolated form, as well as polypeptides encoded thereby, that are differentially expressed in cancer cells. Also provided are antibodies that specifically bind the encoded polypeptides. These polynucleotides, polypeptides and antibodies are thus useful in a variety of diagnostic, therapeutic, and drug discovery methods. In some embodiments, a polynucleotide that is differentially expressed in cancer cells can be used in diagnostic assays to detect cancer cells. In other embodiments, a polynucleotide that is differentially expressed in cancer cells, and/or a polypeptide encoded thereby, is itself a target for therapeutic intervention.

In particular embodiments, the invention relates to four gene products: TTK, GSEF, HX2004-6 and VSHK, and their methods of use. Following below is a summary of the invention for each of these gene products.

TTK

In one aspect, the present invention provides methods for identification of cancerous cells by detection of expression levels of TTK, as well as diagnostic, prognostic and therapeutic methods that take advantage of the differential expression of these genes in mammalian cancer. Such methods can be useful in determining the ability of a subject to respond to a particular therapy, e.g., as the basis of rational therapy. In addition, the invention provides assays for identifying pharmaceuticals that modulate activity of these genes in cancers in which these genes are involved, as well as methods of inhibiting tumor growth by inhibiting activity of TTK.

In a first embodiment, the present invention provides a method for identifying TTK levels in a sample of a subject suspected of having cancer (e.g., a lung, colon, prostate or breast tissue biopsy) comprising quantifying the level of TTK in the sample. The identification of increased levels of TTK in the sample provides an indication of impairment of the cell cycle checkpoint in the sampled cells.

In another embodiment, the invention provides a method for determining the characteristics of a malignant or pre-malignant growth comprising determining (either qualitatively or quantitatively) the level of TTK in the cells of the growth, and comparing levels with known levels in various stages of cancer and/or normal tissue. For example, to determine the characteristics of a particular subject's colon cancer, a sample of the cancer may be removed, the levels of TTK in the cancer determined, and the levels compared to normal tissue and/or levels in various stage colon cancers derived from the same cell type. The levels of TTK identified in the sample can thus be indicative of various characteristics of the malignant or pre-malignant growth, as determined by the characteristics of known tissue and cancers. The TTK levels can be compared directly to the levels in other single samples, or may be compared to a standard that is derived from the data of multiple samples.

In another embodiment, the TTK levels of a sample can be used as one index for determining the appropriate therapeutic intervention for a subject with a malignant or pre-malignant growth. Highly increased levels of TTK, for example, can be indicative of the need for more aggressive therapy, as it is indicative of a later stage cancer. Alternatively, the level of TTK expression may be indicative of the responsiveness of a subject to a particular pharmaceutical, and in particular to a therapeutic intervention that affects the cancer via the mitotic checkpoint.

In another embodiment, the invention features a method for identifying agents for inhibiting growth of a tumor, particular by a breast or colon tumor, by contacting a cell expressing TTK with a candidate agent, and assessing the effect of the agent upon TTK activity.

Accordingly, in one aspect the invention features a method of diagnosing cancer in a subject, the method comprising detection of TTK polynucleotide or polypeptide in a test sample obtained from a subject so as to determine a level of expression of the gene product; and comparing the level of expression of the TTK in the test sample to a level of expression in a normal cell corresponding to the same tissue; wherein detection of an expression level of TTK in the test sample that is significantly increased from the level of expression in a normal cell indicates that the test cell is cancerous. In specific embodiments, the cancer is other than ovarian cancer, with colon cancer and breast cancer being of particular interest.

In another aspect, the invention features a method for determining the prognosis of a cancerous disease in a subject, the method comprising detecting expression of TTK in a test cell from the subject; and comparing a level of expression of TTK in the test cell with a level of TTK expression in a control cell; wherein the level of expression of TTK in the test cell relative to the level of expression in the control cell is indicative of the prognosis of the cancerous disease. For example, where the control cell is a normal cell, an elevated level of TTK expression in the test cell relative to the normal cell is indicative of the continued presence of cancerous cells in the subject and thus a relatively poorer prognosis than where the level of TTK expression in the test cell is at a level comparable to that found in an normal (non-cancer) cell. In specific embodiments, progress of a cancer other than ovarian cancer is of particular interest, especially colon and breast cancer.

In another aspect, the invention features a method for inhibiting growth of a cancerous cell comprising introducing into a cell an antisense polynucleotide for inhibition of TTK expression, wherein inhibition of TTK expression inhibits replication of the cancerous cell.

In still another aspect, the invention features a method for assessing the tumor burden of a subject, the method comprising detecting a level of TTK expression in a test sample from a subject, the test sample suspected of comprising increased TTK expression; wherein detection of the level of TTK expression in the test sample is indicative of the tumor burden in the subject, with an increased level of TTK expression in the test sample relative to a control non-cancer cell indicates the presence of a tumor in the subject.

In yet another aspect, the invention features a method of identifying an agent having anti-TTK activity, the method comprising contacting a cancerous cell displaying elevated expression of TTK with a candidate agent; and determining the effect of the candidate agent on TTK activity; wherein a decrease in TTK activity indicates that the agent has anti-TTK activity. In specific embodiments, TTK activity is detected by detecting TTK expression or by detecting a biological activity of TTK In yet another aspect, the invention features an assay for identifying a candidate agent that inhibits growth of a cancerous cell, comprising contacting a cell expressing TTK polypeptide with a candidate agent; and detecting activity of the TTK polypeptide, comparing the activity of the TTK polypeptide in the cell in the presence of the candidate agent to activity of a TTK polypeptide in a cell in the absence of the candidate agent; wherein reduction of TTK activity in the presence of the candidate agent relative to TTK activity in the absence of the candidate agent indicates that the candidate agent reduces TTK activity and inhibits growth of a cancerous cell.

A primary object of the invention is to exploit TTK as a therapeutic target, e.g. by identifying candidate agents that modulate, usually that decrease, TTK activity in a target cell in order to, for example, inhibit cell growth.

An object of the present invention is to inhibit tumor growth by inhibition of activity of a mitotic checkpoint gene product, particularly though inhibition of TTK activity in the target tumor cell.

Another object of the invention is to facilitate rational cancer therapy. For example, where the cancer in the subject is associated with increased TTK activity levels, a therapeutic agent is selected accordingly so as to facilitate reduction of TTK activity levels.

Another object of the present invention is to design clinical trials based on levels of TTK expression in a cancer, and more particularly to design clinical trials based on TTK expression in combination with other patient attributes.

Yet another object of the invention is to identify the association of TTK expression and intervention attributes that yield efficacious changes in selected disease progression measures.

An advantage of the invention is the ability to project disease progression based on expression of TTK in a malignant or pre-malignant growth.

Another advantage of the present invention is that it allows a more systematic approach for intervention of a cancerous disease based upon objective indicia.

GSEF

In another aspect, the invention features methods for detection of metastatic and potentially metastatic cancerous cells by detection of expression of a gland-specific Ets transcription factor (GSEF) sequence, which encodes an Ets-domain containing protein. The invention also features methods and compositions for modulation of the polypeptide and/or gene activity for prophylactic and therapeutic purposes, such as inhibition of progression of a cell to a metastatic cancerous cell.

It is a primary object of the invention to facilitate identification of cells that are of low metastatic potential (due to expression of GSEF) or high metastatic potential (due to absence of GSEF expression in a cell known to be cancerous).

One advantage of the invention is that detection of GSEF provides for sensitive and accurate detection of cells that are of high metastatic potential, and further provides for distinguishing high metastatic potential cells from low metastatic potential or non metastatic cells.

Additional objects and advantages will be readily apparent to the ordinarily skilled artisan upon reading the instant specification.

Including a human GSEF promoter fragment specific for glandular epithelium of secretory glands (including prostate and breast) useful for gene theapie and the development of cancer mouse models.

HX2004-6

In another aspect, the present invention is based on the discovery of polynucleotides that represent a gene that is differentially expressed in restricted types of cancer cells, specifically, colon, breast, and pancreatic cancer cells, particularly cancerous colon, breast, and pancreatic ductal epithelial cells. The present invention features a human HX2004-6 polypeptide and nucleotide sequences encoding HX2004-6 polypeptides. In a particular aspect, the polynucleotide is the nucleotide sequence of SEQ ID NO:52 and SEQ ID NO:54. In addition, the invention features polynucleotide sequences that hybridize under stringent conditions to SEQ ID NO:52 or SEQ ID NO:54. In related aspects the invention features expression vectors and host cells comprising polynucleotides that encode a human HX2004-6 polypeptide. The present invention also provides antibodies that bind specifically to a human HX2004-6 polypeptide.

The invention further provides methods using the polynucleotides and antibodies of the invention. The methods include methods for producing human HX2004-6 polypeptides; methods for detecting the presence of an HX2004-6 polypeptide or an HX2004-6 polynucleotide in a biological sample; methods for detecting cells expressing HX2004-6; methods for identification of individuals at risk for pancreatic, colon, or breast cancer by detecting alteration in HX2004-6 coding and regulatory sequences and HX2004-6 expression levels.

Another object of the invention is to provide an isolated human HX2004-6 polypeptide-encoding polynucleotide for use in generation of non-human transgenic animal models for HX2004-6 gene function, particularly "knock-in" HX2004-6 non-human transgenic animals characterized by excess or ectopic expression of the HX2004-6 gene.

The invention further provides screening methods to identify agents that modulate expression of human HX2004-, for example, transcription and/or translation of a human HX2004-6 polynucleotide. Of particular interest are those compounds that reduce human HX2004-expression, which compounds can be further evaluated for use in treating adenocarcinomas of breast, colon and pancreatic ductal epithelial cell origin.

VSHK

In a final aspect, the present invention relates to a new seven transmembrane receptor, referred to as VSHK-1 receptor polypeptide. Accordingly, the invention provides isolated VSHK-1 receptor polypeptides. These receptor polypeptides are useful for identifying substances that modulate one or more VSHK-1 functions. Such substances include novel VSHK-1 receptor binding agonists and antagonists. Compositions comprising the isolated VSHK-1 receptor polypeptides are further provided.

The invention further provides isolated VSHK-1 polynucleotides comprising nucleotide sequences encoding native VSHK-1 receptor polypeptides. These polynucleotides are useful for producing VSHK-1 receptor polypeptides. VSHK-1 polynucleotides are further useful for detecting hybridizing polynucleotides, and can therefore be used to detect the presence of and/or measure a level of VSHK-1 mRNA in a biological sample, as well as to detect related polynucleotides. They are further useful in assays to identify substances which modulate a level of VSHK-1 mRNA. Recombinant vectors and host cells comprising the isolated polynucleotides are further provided.

The invention further provides an antibody which specifically binds VSHK-1 receptor polypeptides. Such antibodies are useful in assays to detect the presence of VSHK-1 receptor polypeptides.

Yet another object of the invention is to provide a method for determining (i.e., detecting or measuring) ligand binding to VSHK-1 receptor polypeptides to identify receptor binding agonists or antagonists. The method comprises contacting a VSHK-1 receptor polypeptide with a substance to be tested under conditions that permit formation of a ligand/receptor complex; and detecting the complex formed between a VSHK-1 receptor polypeptide and the substance.

A further object of the invention is to provide methods for determining (i.e., detecting and/or measuring a level of) VSHK-1 receptor polypeptide signal transduction activity to identify receptor binding agonists or antagonists. The methods generally comprise providing a cell expressing a VSHK-1 receptor polypeptide (or cell membrane preparation from such a cell); exposing the expressed VSHK-1 receptor polypeptide to a ligand under conditions that permit formation of a ligand/receptor complex; and measuring VSHK-1 receptor polypeptide signal transduction activity.

Another object of the invention is to provide methods for detecting VSHK-1 polynucleotides in a biological sample. The methods generally comprise hybridizing a sample comprising polynucleotides to a VSHK-1 polynucleotide of the invention under conditions which favor nucleic acid hybridization, and detecting hybridization, if any.

A further object of the invention is to provide methods for detecting VSHK-1 receptor polypeptides in a biological sample. The methods generally comprise contacting a biological sample with a VSHK-1-specific antibody, and detecting antibody binding.

In another embodiment, the present invention provides both compositions and methods for treating or ameliorating VSHK-1 receptor-mediated disorder and/or accompanying biological and physical manifestations. The compositions for treatment or amelioration include: polynucleotides comprising the sequence capable of hybridizing to a VSHK-1 polynucleotide or complement thereof, including antisense, ribozyme and gene therapy nucleic acid constructs; VSHK-1 receptor polypeptides; and antibodies capable of specifically binding VSHK-1 receptor polypeptides.

These and other objects, advantages, and features of the invention will become apparent to those persons skilled in the art upon reading the details of the invention as more fully described below.

BRIEF DESCRIPTION OF THE FIGURES

FIGS. 14A and 14B are schematics showing the nucleotide sequence of GSEF cDNA and 5'promoter region. In FIG. 14A, the promoter region is shown relative to the cDNA. The TATA-box and the putative transcription start (+1) are indicated. Potential ETS transcription factor binding sites are shown in bold letters. In FIG. 14B, the coding and 3' noncoding sequence of human GSEF with deduced amino acid sequence are shown. The C-terminal ETS domain is indicated in bold letters. The full-length cDNA with promoter is provided in the Sequence Listing as SEQ ID NO:40, with the encoded amino acid sequence provided as SEQ ID NO:41.

FIG. 19B is a photograph showing the results of in situ hybridization analysis of GSEF in normal and malignant human breast tissue. H&E staining of the same section is shown in the left panel.

FIG. 23 is a photograph showing the effect of GSEF or E1AF expression upon the morphology of MDA-MB-435 cells.

FIG. 24 is a photograph showing the effect of expression of E1AF or GSEF upon anchorage independent growth of MDA-MB-435 cells.

FIG. 27 depicts the nucleotide sequence of HX2004-6 cDNA clone 1 (SEQ ID NO:52). The initiation codon and stop codons, ATG and TGA, respectively, are shown, in bold and underlined.

FIG. 28 depicts the nucleotide sequence of HX2004-6 cDNA clone 2 (SEQ ID NO:54. The sequence which is the 2004-6 probe (SEQ ID NO:56) is shown as a bold sequence. Within the 2004-6 sequence is the 30-nucleotide insertion (underlined and in lower case letters) relative to SEQ ID NO:52. The initiation codon and stop codons, ATG and TGA, respectively, are shown, in bold and underlined.

FIG. 35 depicts the nucleotide and amino acid sequence of VSHK-1 (SEQ ID NO:71 and NO:72, respectively).

FIG. 37 depicts an amino acid sequence alignment of a VSHK-1 receptor polypeptide amino acid sequence as set forth in SEQ ID NO: 71 with amino acid sequences of human chemokine receptors CCR6 (SEQ ID NO: 85), CCR7 (SEQ ID NO: 86), and CXCR2 (SEQ ID NO: 87), using the ClustalW program with default parameters.

DETAILED DESCRIPTION OF THE INVENTION

Figure 1:
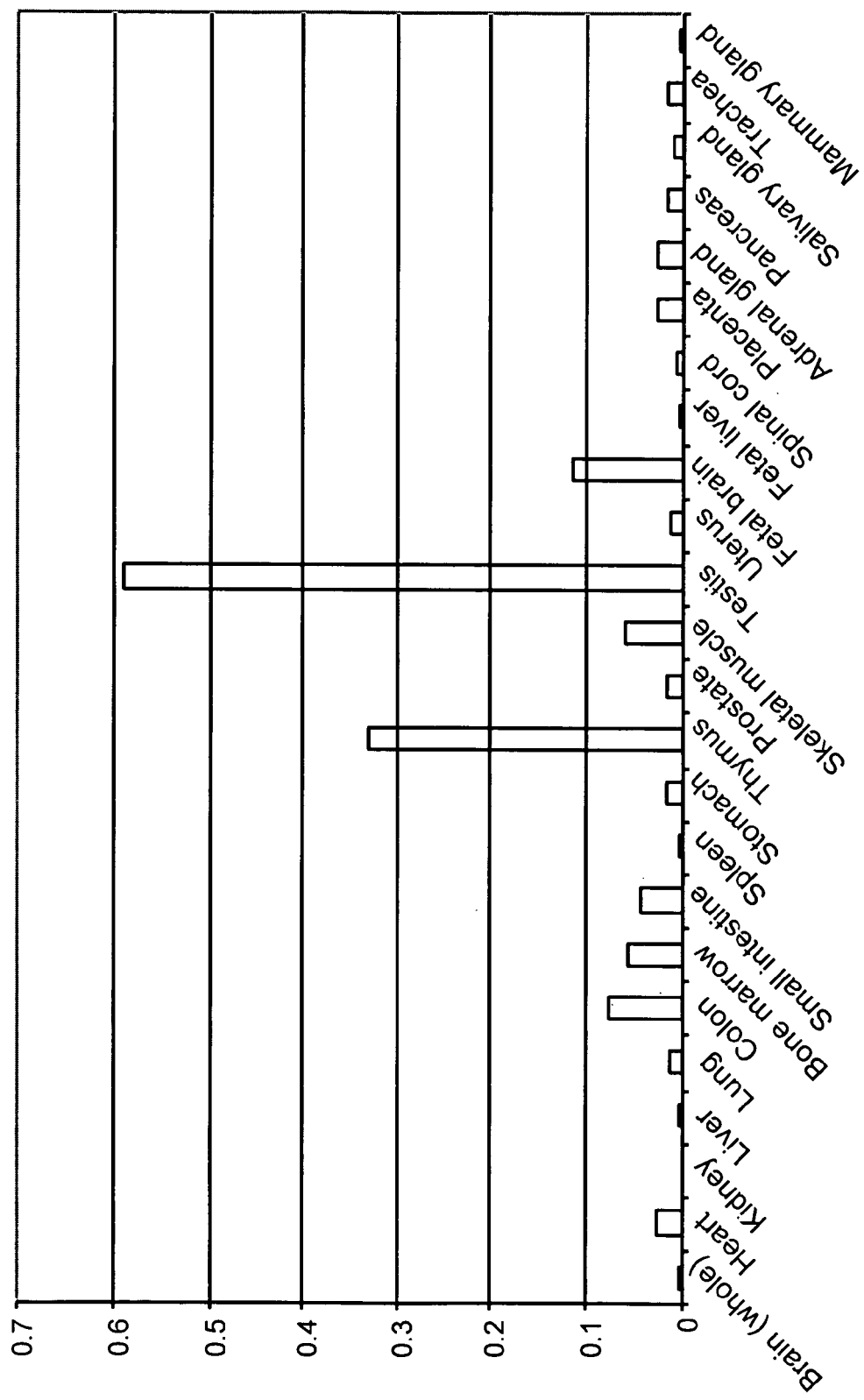
FIG. 1 is a bar graph illustrating expression of TTK in various normal tissue types as detected by PCR.

The present invention provides polynucleotides, as well as polypeptides encoded thereby, that are differentially expressed in cancer cells. Methods are provided in which these polynucleotides and polypeptides are used for detecting and reducing the growth of cancer cells. Also provided are methods in which the polynucleotides and polypeptides of the invention are used in a variety of diagnostic and therapeutic applications for cancer. The invention finds use in the prevention, treatment, detection or research into any cancer, including prostrate, pancreas, colon, brain, lung, breast, bone, skin cancers, etc.

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and patent applications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polynucleotide" includes a plurality of such polynucleotides and reference to "the cancer cell" includes reference to one or more cells and equivalents thereof known to those skilled in the art, and so forth.

The publications and applications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polynucleotide" and "nucleic acid", used interchangeably herein, refer to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptide nucleic acids (Pooga et al Curr Cancer Drug Targets. (2001) 1:231-9).

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term is biopolymeric products that are made using an RNA gene product as a template (i.e. cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

A composition (e.g. a polynucleotide, polypeptide, antibody, or host cell) that is "isolated" or "in substantially isolated form" refers to a composition that is in an environment different from that in which the composition naturally occurs. For example, a polynucleotide that is in substantially isolated form is outside of the host cell in which the polynucleotide naturally occurs, and could be a purified fragment of DNA, could be part of a heterologous vector, or could be contained within a host cell that is not a host cell from which the polynucleotide naturally occurs. The term "isolated" does not refer to a genomic or cDNA library, whole cell total protein or mRNA preparation, genomic DNA preparation, or an isolated human chromosome. A composition which is in substantially isolated form is usually substantially purified.

As used herein, the term "substantially purified" refers to a compound (e.g., a polynucleotide, a polypeptide or an antibody, etc.,) that is removed from its natural environment and is usually at least 60% free, preferably 75% free, and most preferably 90% free from other components with which it is naturally associated. Thus, for example, a composition containing A is "substantially free of" B when at least 85% by weight of the total A+B in the composition is A. Preferably, A comprises at least about 90% by weight of the total of A+B in the composition, more preferably at least about 95% or even 99% by weight. In the case of polynucleotides, "A" and "B" may be two different genes positioned on different chromosomes or adjacently on the same chromosome, or two isolated cDNA species, for example.

The terms "polypeptide" and "protein", interchangeably used herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

"Heterologous" refers to materials that are derived from different sources (e.g., from different genes, different species, etc.).

As used herein, the terms "a gene that is differentially expressed in a cancer cell," and "a polynucleotide that is differentially expressed in a cancer cell" are used interchangeably herein, and generally refer to a polynucleotide that represents or corresponds to a gene that is differentially expressed in a cancerous cell when compared with a cell of the same cell type that is not cancerous, e.g., mRNA is found at levels at least about 25%, at least about 50% to about 75%, at least about 90%, at least about 1.5-fold, at least about 2-fold, at least about 5-fold, at least about 10-fold, or at least about 50-fold or more, different (e.g., higher or lower). The comparison can be made in tissue, for example, if one is using in situ hybridization or another assay method that allows some degree of discrimination among cell types in the tissue. The comparison may also or alternatively be made between cells removed from their tissue source.

"Differentially expressed polynucleotide" as used herein refers to a nucleic acid molecule (RNA or DNA) comprising a sequence that represents a differentially expressed gene, e.g., the differentially expressed polynucleotide comprises a sequence (e.g., an open reading frame encoding a gene product; a non-coding sequence) that uniquely identifies a differentially expressed gene so that detection of the differentially expressed polynucleotide in a sample is correlated with the presence of a differentially expressed gene in a sample. "Differentially expressed polynucleotides" is also meant to encompass fragments of the disclosed polynucleotides, e.g., fragments retaining biological activity, as well as nucleic acids homologous, substantially similar, or substantially identical (e.g., having about 90% sequence identity) to the disclosed polynucleotides.

"Corresponds to" or "represents" when used in the context of, for example, a polynucleotide or sequence that "corresponds to" or "represents" a gene means that at least a portion of a sequence of the polynucleotide is present in the gene or in the nucleic acid gene product (e.g., mRNA or cDNA). A subject nucleic acid may also be "identified" by a polynucleotide if the polynucleotide corresponds to or represents the gene. Genes identified by a polynucleotide may have all or a portion of the identifying sequence wholly present within an exon of a genomic sequence of the gene, or different portions of the sequence of the polynucleotide may be present in different exons (e.g., such that the contiguous polynucleotide sequence is present in an mRNA, either pre- or post-splicing, that is an expression product of the gene). In some embodiments, the polynucleotide may represent or correspond to a gene that is modified in a cancerous cell relative to a normal cell. The gene in the cancerous cell may contain a deletion, insertion, substitution, or translocation relative to the polynucleotide and may have altered regulatory sequences, or may encode a splice variant gene product, for example. The gene in the cancerous cell may be modified by insertion of an endogenous retrovirus, a transposable element, or other naturally occurring or non-naturally occurring nucleic acid. In most cases, a polynucleotide corresponds to or represents a gene if the sequence of the polynucleotide is most identical to the sequence of a gene or its product (e.g. mRNA or cDNA) as compared to other genes or their products. In most embodiments, the most identical gene is determined using a sequence comparison of a polynucleotide to a database of polynucleotides (e.g. GenBank) using the BLAST program at default settings For example, if the most similar gene in the human genome to an exemplary polynucleotide is the protein kinase C gene, the exemplary polynucleotide corresponds to protein kinase C. In most cases, the sequence of a fragment of an exemplary polynucleotide is at least 95%, 96%, 97%, 98%, 99% or up to 100% identical to a sequence of at least 15, 20, 25, 30, 35, 40, 45, or 50 contiguous nucleotides of a corresponding gene or its product (mRNA or cDNA), when nucleotides that are "N" represent G, A, T or C.

An "identifying sequence" is a minimal fragment of a sequence of contiguous nucleotides that uniquely identifies or defines a polynucleotide sequence or its complement. In many embodiments, a fragment of a polynucleotide uniquely identifies or defines a polynucleotide sequence or its complement. In some embodiments, the entire contiguous sequence of a gene, cDNA, EST, or other provided sequence is an identifying sequence.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

As used herein, the term "a polypeptide associated with cancer" refers to a polypeptide encoded by a polynucleotide that is differentially expressed in a cancer cell.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

As used herein "TTK polynucleotide" and "TTK polypeptide" encompass polynucleotides and polypeptides having sequence similarity or sequence identity to the human TTK (having GenBank accession number M86699; SEQ ID NO:13 and 14), or the *S. cerevesiae* kinase mps1 gene and gene products (SEQ ID NO:29 and 30), the *S. pombe* protein mph1 gene and gene products (SEQ ID NO:31 and 32), and other genes and gene products related to TTK, such as SPK1 (SEQ ID NO:15 and 16), Pim1 (SEQ ID NO:17 and 18), PBS2 (SEQ ID NO:19 and 20), CDC2 (SEQ ID NO:21 and 22), and TIK (SEQ ID NO:23 and 24) of at least about 65%, preferably at least about 80%, more preferably at least about 85%, and can be about 90%, 91%, 92%, 93%, 94%, 95%, 96%, 97%, 98%, 99% or more. Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment. Thus, where 10 residues of an 11 residue query sequence matches a test sequence, the percent identity above would be 10 divided by 11, or approximately, 90.9%. Algorithms for computer-based sequence analysis are known in the art, such as BLAST (see, e.g., Altschul et al., *J. Mol. Biol.*, 215:403-10 (1990)), particularly the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1. The human TTK cDNA is represented by the polynucleotide sequence of SEQ ID NO:13 and the human TTK polypeptide is represented by the sequence of SEQ ID NO:14.

"Antisense polynucleotide" or "antisense oligonucleotide" are used interchangeably herein to mean an unmodified or modified nucleic acid having a nucleotide sequence complementary to a given polynucleotide sequence (e.g., a polynucleotide sequence encoding a subject polypeptide) including polynucleotide sequences associated with the transcription or translation of the given polynucleotide sequence (e.g., a promoter of a polynucleotide encoding a subject polypeptide), where the antisense polynucleotide is capable of hybridizing to a subject polypeptide-encoding polynucleotide sequence. Of particular interest are antisense polynucleotides capable of inhibiting transcription and/or translation of a subject polypeptide -encoding polynucleotide either in vitro or in vivo.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing to create a continuous open reading flame encoding a subject polypeptide.

A "variant" as used in the context of a "variant polypeptide" refers to an amino acid sequence that is altered by one or more amino acids relative to a reference amino acid sequence. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted, or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to reference amino acid sequence or nucleotide sequence. Deletions can be of any length, but are preferably approximately 50, 20, 15, 10, 5 or 3 amino acids or nucleotides in length.

An "insertion" or "addition" is that change in an amino acid or nucleotide sequence which has resulted in the addition of one or more amino acid or nucleotide residues, respectively, as compared to a reference amino acid sequence or nucleotide sequence. Insertions or additions can be of any length, but are preferably approximately 50, 20, 15, 10, 5 or 3 amino acids or nucleotides in length.

A "substitution" results from the replacement of one or more amino acids or nucleotides by different amino acids or nucleotides, respectively, as compared to a reference amino acid sequence or nucleotide sequence. Substitutions can be of any length, but are preferably approximately 50, 20, 15, 10, 5 or 3 amino acids or nucleotides in length.

The terms "single nucleotide polymorphism" and "SNP" refer to polymorphisms of a single base change relative to a reference sequence.

The term "biologically active" refers to gene product, usually a polypeptide, having structural, regulatory, or biochemical functions of a naturally occurring gene product, e.g., protein. "Immunologically active" defines the capability of the natural, recombinant, or synthetic polypeptide, or any oligopeptide thereof, to elicit a specific immune response in appropriate animals or cells and to bind with specific antibodies.

The term "derivative" as used herein refers to the chemical modification of a nucleic acid or amino acid sequence relative to a reference nucleic acid or amino acid sequence. Illustrative of such modifications would be replacement of hydrogen by an alkyl, acyl, or amino group. A nucleic acid derivative generally encodes a polypeptide which retains essential biological characteristics of the polypeptide encoded by the reference nucleic acid (e.g., the "parent" molecule).

"Stringency" typically occurs in a range from about Tm −5° C. (5° C. below the Tm of the probe or antibody) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs, Dictionary of Biotechnology, Stockton Press, New York N.Y. (1994)). Amplification as carried out in the polymerase chain reaction technologies is described in Dieffenbach et al., PCR Primer, a Laboratory Manual, Cold Spring Harbor Press, Plainview N.Y. (1995).

The term "transformation" as used herein refers to a permanent or transient genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

The term "construct" as used herein refers to a recombinant nucleic acid, generally recombinant DNA, that has been generated for the purpose of the expression of a specific nucleotide sequence(s), or is to be used in the construction of other recombinant nucleotide sequences.

The terms "correspond to" or "represents" as used in, for example, the phrase "polynucleotide corresponds to a differentially expressed gene" are used to refer to the relationship between a given polynucleotide and the gene from which the polynucleotide sequence is derived (e.g., a polynucleotide that is derived from a coding region of the gene, a splice variant of the gene, an exon, and the like) or to which the polynucleotide hybridizes to under stringer conditions.

The phrase "specific binding pair" as used herein comprises a specific binding member and a binding partner which have a particular specificity for each other and which bind to each other in preference to other molecules under stringent conditions. Examples of specific binding pairs are antigens and antibodies, molecules and receptors and complementary nucleotide sequences. Other examples of binding pairs will be apparent to one skilled in the art upon reading the present disclosure. Further, the term "specific binding pair" is also applicable where either or both of the specific binding member and the binding partner comprise a part of a larger molecule. In embodiments in which the specific binding pair are nucleic acid sequences, they are preferably between 10 to 200 nucleotides long, more preferably greater than 15 to 100 nucleotides long.

By "antibody" is meant an immunoglobulin protein which is capable of binding an antigen. Antibody as used herein is meant to include the entire antibody as well as any antibody fragments (e.g., F(ab')$_2$, Fab', Fab, Fv) capable of binding the epitope, antigen, or antigenic fragment of interest.

Antibodies of the invention are immunoreactive or immunospecific for and therefore specifically and selectively bind to a protein of interest, e.g., human TTK protein. Antibodies which are immunoreactive and immunospecific for human TTK are preferred. Antibodies for human TTK are preferably immunospecific—i.e., not substantially cross-reactive with related materials, although they may recognize TTK homologs across species. The term "antibody" encompasses all types of antibodies (e.g., monoclonal and polyclonal).

By "binds specifically" is meant high avidity and/or high affinity binding of an antibody to a specific polypeptide, e.g., epitope of a TTK protein. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

"TTK activity" as used herein refers to activity of the TTK polypeptide in phosphorylation of a recipient substrate.

"Modulation of TTK activity" as used herein refers to an increase or decrease in TTK activity that can be a result of, for example, interaction of an agent with a TTK polypeptide (e.g., reversible or irreversible binding of an inhibitory agent so as to interfere with TTK polypeptide interaction with a donor molecule or a recipient (acceptor) molecule in the phosphorylation activity of TTK), inhibition of TTK transcription and/or translation (e.g., through antisense interaction with the TTK gene or TTK transcript, through modulation of transcription factors that facilitate TTK expression), and the like. Modulation of TTK activity that results in a decrease of TTK activity is of particular interest in the invention. In this context, TTK activity can be decreased by an inhibitory agent at least 10%, 25%, 50%, 75%, 85%, 90%, up to 100% relative to TTK activity in the absence of an agent. TTK activity can be assessed by assaying enzymatic activity, by assessing TTK polypeptide levels, or by assessing TTK transcription levels. Comparisons of TTK activity can also be accomplished by comparing TTK activity assessed (either qualitatively or quantitatively) in a test sample to a standard TTK activity (e.g., a level of TTK activity in the absence of an inhibitory agent or agonist, that is associated with a normal cell, a level of TTK activity of a cancerous cell of a selected tissue type, and the like).

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al. (1993) *Anticancer Drug Des.* 8:53-63).

As used herein, "HX2004-6 polypeptide" refers to an amino acid sequence of a recombinant or nonrecombinant polypeptide having an amino acid sequence of i) a native HX2004-6 polypeptide, ii) a fragment of an HX2004-6 polypeptide, iii) polypeptide analogs of an HX2004-6 polypeptide, iv) variants of an HX2004-6 polypeptide, and v) an immunologically active fragment of an HX2004-6 polypeptide. HX2004-6 polypeptides of the invention can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human, from any source whether natural, synthetic, semi-synthetic or recombinant. "Human HX2004-6 polypeptide" refers to the amino acid sequences of isolated human HX2004-6 polypeptide obtained from a human, and is meant to include all naturally-occurring allelic variants, and is not meant to limit the amino acid sequence to the complete, native amino acid sequence associated with the recited protein molecule.

The term "immunologically active" defines the capability of the natural, recombinant or synthetic human HX2004-6 polypeptide, or any oligopeptide thereof, to induce a specific immune response in appropriate animals or cells and to bind with specific antibodies.

As used herein, a "HX2004-6 associated disorder" is one that is associated with a neoplasm of pancreatic, colon, or breast cell, particularly an adenocarcinoma of one of these tissues, particularly a neoplasm of a ductal epithelial cell from one of these tissues. A "HX2004-6 associated disorder" is also one that is caused by, directly or indirectly, a neoplasm of one of the aforementioned cells. A "HX2004-6 associated disorder" is also a physiological condition or disease associated with altered HX2004-6 function (e.g., due to aberrant HX2004-6 expression, particularly overexpression of HX2004-6).

"Overexpression" intends that a particular mRNA is found at levels at least about 1.5-fold, usually at least about 2-fold, normally at least about 5-fold, generally at least about 10-fold, and up to at least about 50-fold or higher when compared with a non-cancerous cell of the same cell type. In particular, the comparison is made between a ductal epithelial cell to be tested and a non-cancerous ductal epithelial cell, for example, a non-cancerous normal cell, or a dysplastic non-cancerous cell. The comparison can be made between two tissues, for example, if one is using in situ hybridization or another assay method which allows some degree of discrimination among cell types in the tissue; however, it may be preferable to make the comparison between cells removed from their tissue source. Whether a polynucleotide is over-expressed in a given cell can be readily determined by those skilled in the art using known methods, including, but not limited to, detection of transcripts by hybridization with a polynucleotide that hybridizes to a particular polynucleotide, a polymerase chain reaction using specific oligonucleotide primers, in situ hybridization, by detection of an encoded polypeptide using an immunoassay, and the like.

As used herein, "neoplastic cells" and "neoplasia" (used interchangeably herein with "tumor", "cancer", "cancerous cells", and "carcinoma") refers to cells which exhibit relatively autonomous growth, so that they exhibit an aberrant growth phenotype characterized by a significant loss of control of cell proliferation. Neoplastic cells can be benign or malignant, metastatic or non-metastatic. The term "adenocarcinoma" is one well understood in the art, and denotes a tumor originating in glandular epithelium.

As used herein, "antigenic amino acid sequence" means an amino acid sequence that, either alone or in association with a carrier molecule, can elicit an antibody response in a mammal.

The term "derivative" as used herein refers to the chemical modification of a nucleic acid encoding a subject polypeptide or polypeptide. Illustrative of such modifications would be replacement of hydrogen by an alkyl, acyl, or amino group. A nucleic acid derivative would encode a polypeptide which retains essential biological characteristics of a natural polypeptide.

A "transcriptional control region" (sometimes referred to as a "transcriptional regulatory region") encompasses all the elements necessary for transcription, and may include elements necessary for transcription. Thus, a transcriptional control region includes at least the promoter sequence, and may also include other regulatory sequences such as enhancers, and transcription factor binding sites.

A "transcriptional control region heterologous to a coding region" is one that is not normally associated with the coding region in nature.

"Operably linked" refers to a juxtaposition wherein the components so described are in a relationship permitting them to function in their intended manner. For instance, a promoter is operably linked to a coding sequence if the promoter effects its transcription or expression.

"Regulatory sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

By "operatively inserted" is meant that a nucleotide sequence of interest is positioned adjacent a nucleotide sequence that directs transcription or transcription and translation of the introduced nucleotide sequence of interest (i.e., facilitates the production of, e.g., a polypeptide or a polynucleotide encoded by an subject polynucleotide).

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. A knock-out of an HX2004-6 gene means that function of the HX2004-6 gene has been substantially decreased so that HX2004-6 expression is not detectable or only present at insignificant levels. "Knock-out" transgenics of the invention can be transgenic animals having a heterozygous knock-out of the HX2004-6 gene or a homozygous knock-out of the HX2004-6 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. "Knock-in" transgenics of the invention can be transgenic animals having a heterozygous knock-in of the HX2004-6 gene or a homozygous knock-in of the HX2004-6 gene. "Knock-ins" also encompass conditional knock-ins.

As used herein, the term "native VSHK-1 receptor" refers to the polypeptides found in nature including allelic variants and polymorphisms. An example is a native human VSHK-1 receptor polypeptide.

"Native VSHK-1 receptor activity" refers to the biological and biochemical activities that native polypeptides exhibit, which includes, ligand binding, immunological, signal transduction, and therapeutic activities.

"Signal transduction activity" occurs when a ligand binds to the VSHK-1 receptor and triggers a biological response in a cell or cell extract. The biological response is the result of a cascade of biochemical reactions. Measurement of any one of these reactions can indicate that a biological response was triggered. For example, VSHK-1 receptor is a G-coupled protein which, when proper signal transduction activity occurs, triggers an increase of intracellular $Ca^+$, $IP_3$, and DAG levels. An assay for increased levels of free cytosolic $Ca^{2+}$ is described in Sakurai et al., EP 480 381, and Adachi et al. (1992) *FEBS Lett* 311:179-183. Intracellular $IP_3$ concentrations can be measured according to Sakurai et al., EP 480 381 and Amersham's inositol 1,4,5-trisphosphate assay system (Arlington Heights, Ill., U.S.A.). These assays are effective for determining VSHK-1 receptor signal transduction activity whether the receptor is naturally expressed by the cell or expressed by a heterologous cell type by recombinant techniques. Proper signal transduction activity depends not only on receptor/ligand binding but also depends on the presence of the particular intracellular proteins. Thus, while a number of cells are capable, via recombinant techniques, of expressing VSHK-1 receptor polypeptides, no biological response will be detected despite proper receptor/ligand binding if the host cell does not produce the particular intracellular proteins. Heterologous host cells, COS and Chinese Hamster Ovary (CHO) cells, for instance, can produce a biological response if altered to produce the receptor by recombinant techniques. Signal transduction activity also can be detected in cells that are known to naturally express the VSHK-1 receptor in humans, such as heart cells.

Two elements are "heterologous" if they are not associated together in nature. For example, a mouse promoter inserted into a human cell is heterologous to the cell. As another example, a human endothelin promoter is heterologous to a VSHK-1 coding sequence, since the endothelin promoter is not associated with the VSHK-1 receptor coding sequence in nature.

The term "VSHK-1 receptor-mediated disorder" refers to a disease state or malady which is caused or exacerbated by an activity of VSHK-1 receptor polypeptides. A "VSHK-1 mediated disorder" refers to a disease state or malady which is caused, exacerbated, modulated, or ameliorated by a biological activity of VSHK-1. Examples include glomerulonephritis, asthma, inflammatory bowel disease, allogeneic transplantation rejection, rheumatoid arthritis, inflammation, tissue damage associated with reperfusion injury and chemical pneumonitis, viral infection, angiogenesis, cancer, or hyperproliferation of cells. Another VSHK-1 mediated disorder is the tissue damage associated with reperfusion injury and chemical pneumonitis The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-cancerous (e.g., benign), malignant, pre-metastatic, metastatic, and non-metastatic cells. Detection of cancerous cells is of particular interest.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

A detailed description of the invention for each of TTK, GSEF, HX2004-6 and VSHK is set forth below in the following order: TTK, GSEF, HX2004-6 and VSHK.

EMBODIMENTS RELATING TO TTK

Overview

Human TTK is a mitotic checkpoint gene which encodes an 857 amino acid protein that exhibits activity of a mixed specificity (tyr/thr) kinase. TTK is expressed in rapidly proliferating tissues such as testis and thymus. See, e.g., Mills G B et al., *J Biol Chem.* 267:16000-6 (1992). The present invention is based upon the finding that TTK is differentially expressed in colon tumor cells relative to normal colon cells as detected by microarray analysis. Differential expression was confirmed in cell lines derived from various forms of cancer, indicating that the involvement of TTK in cancer as a more general mechanism. In addition, disruption of TTK function using antisense oligonucleotides to "knock-out" TTK message decreased proliferation, inhibited anchorage independent growth, and induced apoptosis of cancer cell lines, including a metastatic breast cancer cell line (MDA-MB-213) and a colorectal carcinoma cell line (SW620). These data indicate that TTK can be a therapeutic target for chemotherapy in cancers in which TTK is overexpressed.

The identification of the association of TTK with cancer, and the confirmation that inhibition of TTK activity (e.g., by reducing TTK expression) serves as the basis for the materials and methods of the invention, such as are disclosed and discussed herein, for use in, for example, diagnosing cancer of a patient, particularly a cancer that is susceptible to treatment by decreasing activity of TTK. The invention also provides for planning and selection of appropriate therapeutic and/or prophylactic treatment, permitting streamlining of treatment by targeting those most likely to benefit. The invention also provides for treatment of a cancer associated with aberrant TTK levels (e.g., associated with overexpression or overproduction of TTK), e.g. by inhibition of gene product production (e.g., decreasing levels of transcription and/or translation), by decreasing TTK activity (e.g., by decreasing TTK gene product production (e.g., at the level of transcription or translation) and/or by reducing one or more of TTK's kinase activities).

Various aspects of the invention will now be described in more detail.

Diagnostic Methods

In one aspect the invention is based on the discovery that TTK activity is present at higher levels in cancerous cells (particularly in colon cancer and breast cancer) than in normal cells of the same cell type. This discovery serves as the basis for identification of cancerous cells, as well as identification of tumors that are susceptible to therapy by inhibiting activity of TTK, e.g., by inhibiting TTK expression at the level of transcription or translation or both, by inhibiting TTK activity, and the like.

TTK gene products e.g. TTK encoding mRNA or TTK polypeptides are of particular interest as markers (e.g., in bodily fluids (such as blood) or in tissues) to detect the earliest changes along the carcinogenesis pathway (e.g., to differentiate cancerous tissue from non-cancerous tissue) and/or to monitor the efficacy of various therapies and preventive interventions. For example, a relatively increased level of expression of TTK compared to normal cells or tissues of the same type can be indicative of a poorer prognosis, and therefore warrant more aggressive therapy (e.g., chemo- or radiotherapy) for a patient or vice versa. The correlation of surrogate tumor specific features with response to treatment and outcome in patients can define prognostic indicators that allow the design of tailored therapy based on the molecular profile of the tumor. These therapies include antibody targeting, antagonists (e.g., small molecules), and gene therapy. Determining TTK expression and comparison of a patient's profile with known expression in normal tissue and variants of the disease allows a determination of the best possible treatment for a patient, both in terms of specificity of treatment and in terms of comfort level of the patient. Surrogate tumor markers, such as polynucleotide expression, can also be used to better classify, and thus diagnose and treat, different forms and disease states of cancer. Two classifications widely used in oncology that can benefit from identification of TTK expression levels are staging of the cancerous disorder, and grading the nature of the cancerous tissue.

TTK polynucleotides, as well as their encoded gene products, can be useful to monitor patients having or susceptible to cancer to detect potentially malignant events at a molecular level before they are detectable at a gross morphological level. In addition, detection of TTK gene products can be useful as therametrics, e.g., to assess the effectiveness of therapy by using the polynucleotides or their encoded gene products, to assess, for example, tumor burden in the patient before, during, and after therapy.

Furthermore, a polynucleotide identified as corresponding to a gene that is differentially expressed in, and thus is important for, one type of cancer can also have implications for development or risk of development of other types of cancer, e.g., where a polynucleotide represents a gene differentially expressed across various cancer types. Thus, for example, expression of a polynucleotide corresponding to a gene that has clinical implications for metastatic colon cancer can also have clinical implications for stomach cancer or endometrial cancer.

In making a diagnosis, prognosis, risk assessment, or measurement of tumor burden based on the enzymatic activity of TTK or the expression levels of TTK polypeptide or TTK encoding polynucleotides, activity or expression levels may be compared to those of suitable cancerous or non-cancerous control samples. For example, a diagnosis of cancer can be made if TTK activity is increased at by 25%, 50%, 75%, 90%, up to 100%, or, alternatively by 5-fold, 10-fold, 50-fold, or more than 100-fold relative to a normal non-cancerous cell of the same tissue type.

Other gene products that are differentially expressed in cancerous cells relative to, for example, non-cancer cells of between cancer cells of differing malignant potential (e.g., non-malignant tumor cells versus cells of high potential malignancy) can also be assayed in addition to TTK for differential expression in a test cell. Such exemplary gene products include, but are not necessarily limited to MAPKAP kinase 2 (SEQ ID. No. 33 and 34), MARCKS (SEQ ID NO:35 and 36) and/or IGF2 (SEQ ID NO:37 and 38).

Staging. Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage II, the cancer has generally spread to the lymph nodes in near proximity to the site of the primary lesion. Cancers that have spread to a distant part of the body, such as the liver, bone, brain or other site, are Stage IV, the most advanced stage.

The differential expression level of TTK can facilitate fine-tuning of the staging process by identifying markers for the aggressiveness of a cancer, e.g. the metastatic potential, as well as the presence in different areas of the body. Thus, a Stage II cancer with a large differential level of expression of TTK can signify a cancer with a high metastatic potential and can be used to change a borderline Stage II tumor to a Stage III tumor, justifying more aggressive therapy.

Grading of cancers. Grade is a term used to describe how closely a tumor resembles normal tissue of its same type. The microscopic appearance of a tumor is used to identify tumor grade based on parameters such as cell morphology, cellular organization, and other markers of differentiation. As a general rule, the grade of a tumor corresponds to its rate of growth or aggressiveness, with undifferentiated or high-grade tumors generally being more aggressive than well differentiated or low-grade tumors. The following guidelines are generally used for grading tumors: 1) GX Grade cannot be assessed; 2) G1 Well differentiated; G2 Moderately well differentiated; 3) G3 Poorly differentiated; 4) G4 Undifferentiated. TTK activity levels (e.g., expression levels) can be especially valuable in determining the grade of the tumor, as they not only can aid in determining the differentiation status of the cells of a tumor, they can also identify factors other than differentiation that are valuable in determining the aggressiveness of a tumor, such as metastatic potential.

Detection of colon cancer. Polynucleotides and polypeptides corresponding to TTK can be used to detect colon cancer in a subject. Colorectal cancer is one of the most common neoplasms in humans and perhaps the most frequent form of hereditary neoplasia. Prevention and early detection are key factors in controlling and curing colorectal cancer. Colorectal cancer begins as polyps, which are small, benign growths of cells that form on the inner lining of the colon. Over a period of several years, some of these polyps accumulate additional mutations and become cancerous. Multiple familial colorectal cancer disorders have been identified, which are summarized as follows: 1) Familial adenomatous polyposis (FAP); 2) Gardner's syndrome; 3) Hereditary nonpolyposis colon cancer (HNPCC); and 4) Familial colorectal cancer in Ashkenazi Jews. The expression of appropriate polypeptide and polynucleotides can be used in the diagnosis, prognosis and management of colorectal cancer. Detection of colon cancer can be determined using expression levels of TTK alone or in combination with the levels of expression of other genes differentially expressed in colon cancer. Determination of the aggressive nature and/or the metastatic potential of a colon cancer can be determined by comparing levels of TTK with a level associated with a normal cell, and comparing total levels of another sequence known to be differentially expressed, or otherwise be a marker of, cancerous tissue, e.g., expression of p53, DCC, ras, FAP (see, e.g., Fearon E R, et al., *Cell* (1990)

61(5):759; Hamilton S R et al., *Cancer* (1993) 72:957; Bodmer W, et al., *Nat Genet.* (1994) 4(3):217; Fearon E R, *Ann N Y Acad Sci.* (1995) 768:101)or MAPKAP kinase 2 (SEQ ID. No. 33 and 34), MARCKS (SEQ ID NO:35 and 36) and/or IGF2 (SEQ ID NO:37 and 38). For example, development of colon cancer can be detected by examining the level of expression of a gene corresponding to a polynucleotides described herein to the levels of oncogenes (e.g. ras) or tumor suppressor genes (e.g. FAP or p53). Thus expression of specific marker polynucleotides can be used to discriminate between normal and cancerous colon tissue, to discriminate between colon cancers with different cells of origin, to discriminate between colon cancers with different potential metastatic rates, etc. For a review of markers of cancer, see, e.g., Hanahan et al. (2000) *Cell* 100:57-70.

Detection of breast cancer. The majority of breast cancers are adenocarcinomas subtypes, which can be summarized as follows: 1) ductal carcinoma in situ (DCIS), including comedocarcinoma; 2) infiltrating (or invasive) ductal carcinoma (IDC); 3) lobular carcinoma in situ (LCIS); 4) infiltrating (or invasive) lobular carcinoma (ILC); 5) inflammatory breast cancer; 6) medullary carcinoma; 7) mucinous carcinoma; 8) Paget's disease of the nipple; 9) Phyllodes tumor; and 10) tubular carcinoma.

The expression levels of TTK can be used in the diagnosis and management of breast cancer, as well as to distinguish between types of breast cancer. Detection of breast cancer can be determined using expression levels of TTK, either alone or in combination with expression of other gene known to be differentially expressed in breast cancer. Determination of the aggressive nature and/or the metastatic potential of a breast cancer can also be determined by comparing levels of TTK and comparing levels of another sequence known to vary in cancerous tissue, e.g. ER expression. In addition, development of breast cancer can be detected by examining the ratio of expression of TTK to the levels of steroid hormones (e.g., testosterone or estrogen) or to other hormones (e.g., growth hormone, insulin). Thus expression of specific marker polynucleotides and polypeptides can be used to discriminate between normal and cancerous breast tissue, to discriminate between breast cancers with different cells of origin, to discriminate between breast cancers with different potential metastatic rates, etc.

Detection Methods

A number of methods are known in the art for analyzing biological samples from individuals to determine whether the individual has increased expression of a TTK gene product (e.g., RNA or protein) by detecting the TTK gene product in a biological sample from that subject. As discussed above, the purpose of such analysis may be used for diagnosis, to detect the presence of an existing cancer, to help identify the type of cancer, to assist a physician in determining the severity or likely course of the cancer, and/or to optimize treatment of it. In specific non-limiting embodiments, the methods are useful for detecting cancer cells, facilitating diagnosis of cancer and the severity of a cancer (e.g., tumor grade, tumor burden, and the like) in a subject, facilitating a determination of the prognosis of a subject, and assessing the responsiveness of the subject to therapy (e.g., by providing a measure of therapeutic effect through, for example, assessing tumor burden during or following a chemotherapeutic regimen). In additional embodiments, the methods are useful for classification or stratification of cancer cells, e.g., for the purpose of selecting patients to be included in a clinical trial population, for selecting an appropriate therapy (e.g., selecting therapy according to an expression profile of the cancerous cells), and the like.

Kits

The detection methods can be provided as part of a kit. Thus, the invention further provides kits for detecting the presence and/or a level of TTK activity e.g., by detection of a TTK-encoding mRNA and/or a polypeptide encoded thereby or by measuring TTK activity, in a biological sample. Procedures using these kits can be performed by clinical laboratories, experimental laboratories, medical practitioners, or private individuals. The kits of the invention for detecting TTK polypeptide that is differentially expressed in cancer cells comprise a moiety that specifically binds the polypeptide, which may be a specific antibody. The kits of the invention for detecting a TTK-encoding polynucleotide that is differentially expressed in cancer cells comprise a moiety that specifically hybridizes to such a polynucleotide such as a primer. The kits of the invention for detecting TTK activity comprise a recipient substrate capable of being phosphorylated by TTK, and a labeled donor substrate. The kits may optionally provide additional components that are useful in the procedure, including, but not limited to, buffers, developing reagents, labels, reacting surfaces, means for detection, control samples, standards, instructions, and interpretive information.

Screening for TTK Nucleic Acid or Polypeptide

Methods for detection of TTK activity include screening for the presence of TTK nucleic acid sequences representing an expressed TTK gene or alleles or variants thereof, and detecting the TTK polypeptide. The methods make use of biological samples from individuals that are suspected of contain the nucleic acid sequences or polypeptide. Examples of biological samples include blood, plasma, serum, tissue samples, tumor samples, saliva and urine.

Exemplary approaches for detecting TTK nucleic acid or polypeptides include: (a) determining the presence of the polypeptide encoded by the TTK gene; (b) using a specific binding member capable of binding to a TTK nucleic acid sequence (e.g., a known complementary sequence), the specific binding member comprising a nucleic acid that hybridizes with the TTK sequence under stringent conditions (c) using a substance comprising an antibody domain with specificity for a TTK nucleic acid sequence or the polypeptide encoded by it, the specific binding member being labeled to allow detection of the specific binding member to its binding partner is detectable; (d) using PCR involving one or more primers to determine relative levels of TTK in a sample from a patient; and (e) using an assay for TTK activity, e.g., phosphorylation of a TTK substrate.

The determination of TTK levels can include both levels of normal TTK and/or variant forms of TTK. A variant form of the gene may contain one or more insertions, deletions, substitutions and/or additions of one or more nucleotides compared with the wild-type sequence which may or may not alter the gene function. Differences at the nucleic acid level are not necessarily reflected by a difference in the amino acid sequence of the encoded polypeptide due to the degeneracy of the genetic code. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide.

A mutation in a promoter sequence or other regulatory region may alter (e.g., reduce or enhance) expression from the gene or affect the processing or stability of the mRNA transcript.

There are various methods for detecting a particular nucleic acid sequence in a test sample. Tests may be carried out on preparations containing mRNA or cDNA generated from isolated mRNA in a manner that reflects the relative levels of mRNA transcripts in the sample. Levels of RNA can be determined specific amplification reaction such as PCR using one or more pairs of primers may be employed to amplify a region of the nucleic acid, and preferably a region with less homology to other genes. Nucleic acid for testing may be prepared from nucleic acid removed from cells or in a library using a variety of other techniques such as restriction enzyme digest and electrophoresis.

Nucleic acid may be screened using a TTK-specific probe. Such a probe corresponds in sequence to a region of the TTK gene, or its complement. Under stringent conditions, specific hybridization of such a probe to test nucleic acid is indicative of the presence of the TTK nucleic acid in a sample. For efficient screening purposes, more than one probe may be used on the same test sample. The probe may contain as few as 15, 20, 50 or 100 nucleotides of the TTK gene of SEQ ID. No. 13 or may be as long as or 500, 1 kb or as much as 3.8 kb or longer in length.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected. This can be done simultaneous to or sequentially to determining the level of a normal TTK sequence, e.g., to determine the combinatory levels of total TTK.

The presence of absence of a lesion in a promoter or other regulatory sequence may also be assessed by determining the level of mRNA production by transcription or the level of polypeptide production by translation from the mRNA. The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

A test sample of nucleic acid may be provided for example by extracting nucleic acid from cells, e.g., cells from a tumor biopsy.

Detection of TTK Polypeptides

There are various methods for determining the presence or absence in a test sample of a TTK polypeptide. A sample may be tested for the presence of a binding partner for a specific binding member such as an antibody (or mixture of antibodies), specific for wild-type TTK and/or one or more particular variants (e.g., allelic variants) of the TTK polypeptide. In such cases, the sample may be tested by being contacted with a specific binding member such as an antibody under appropriate conditions for specific binding. Where a panel of antibodies is used, different reporting labels may be employed for each antibody so that binding of each can be determined. In addition to detection of TTK polypeptides using anti-TTK antibodies, TTK polypeptide can also be identified using TTK-specific activity assays.

Arrays

Binding agents (such as antibodies or nucleic acid sequences) can also be immobilized in small, discrete locations and/or as arrays on solid supports or on diagnostic chips. These approaches can be particularly valuable as they can provide great sensitivity, particularly through the use of fluorescently labeled reagents, require only very small amounts of biological sample from individuals being tested and allow a variety of separate assays can be carried out simultaneously. This latter advantage can be useful as it provides an assay for different proteins (e.g., an oncogene or tumor suppressor) in tandem with the assay for TTK. Thus, in a further aspect, the present invention provides a support or diagnostic chip having immobilized thereon one or more binding agents capable of specifically binding TTK nucleic acid or polypeptides, optionally in combination with other reagents needed to carrying out an assay.

Methods for Expression of TTK Polypeptide

The full-length or partial polypeptides encoded by TTK may be expressed in any expression system, including, for example, bacterial, yeast, insect, amphibian and mammalian systems. Suitable vectors and host cells for which are described in U.S. Pat. No. 5,654,173. Appropriate polynucleotide constructs are purified using standard recombinant DNA techniques as described in, for example, Sambrook et al., (1989) *Molecular Cloning: A Laboratory Manual*, 2nd ed. (Cold Spring Harbor Press, Cold Spring Harbor, N.Y.), and under current regulations described in United States Dept. of HHS, National Institute of Health (NIH) Guidelines for Recombinant DNA Research.

Bacteria. Expression systems in bacteria include those described in Chang et al., *Nature* (1978) 275:615, Goeddel et al., *Nature* (1979) 281:544, Goeddel et al., *Nucleic Acids Res*. (1980) 8:4057; EP 0 036,776, U.S. Pat. No. 4,551,433, DeBoer et al., *Proc. Natl. Acad. Sci.* (*USA*) (1983) 80:21-25, and Siebenlist et al., *Cell* (1980) 20:269.

Yeast. Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990) 8:135; Kunze et al., *J. Basic Microbial.* (1985) 25:141; Cregg et al., *Mol. Cell. Biol.* (1985) 5:3376, U.S. Pat. Nos. 4,837,148 and 4,929,555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284-289; Tilburn et al., *Gene* (1983) 26:205-221, Yelton et al., *Proc. Natl. Acad. Sci.* (*USA*) (1984) 81:1470-1474, Kelly and Hynes, *EMBO J*. (1985) 4:475479; EP 0 244,234, and WO 91/00357.

Insect Cells. Expression of heterologous genes in insects is accomplished as described in U.S. Pat. No. 4,745,051, Friesen et al. (1986) "The Regulation of Baculovirus Gene Expression" in: The Molecular Biology Of Baculoviruses (W. Doerfler, ed.), EP 0 127,839, EP 0 155,476, and Vlak et al., *J. Gen. Virol.* (1988) 69:765-776, Miller et al., *Ann. Rev. Microbiol.* (1988) 42:177, Carbonell et al., *Gene* (1988) 73:409, Maeda et al., *Nature* (1985) 315:592-594, Lebacq-Verheyden et al., *Mol. Cell. Biol.* (1988) 8:3129; Smith et al., *Proc. Natl. Acad. Sci.* (*USA*) (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., Generic Engineering (Setlow, J. K. et al. eds.), Vol. 8 (Plenum Publishing, 1986), pp. 277-279, and Maeda et al., *Nature*, (1985) 315:592-594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

Screening Assays to Identity Chemotherapeutic Agents

The invention also encompasses screening assays to identify agents that modulate TTK activity, specifically that decrease aberrant TTK activity in an affected cell, e.g., a cancerous or pre-cancerous cell in which TTK is differentially expressed. Such assays may be performed either in vitro or in vivo.

Candidate Agents

The term "agent" as used herein describes any molecule with the capability of altering the expression or physiological function of a gene product of a differentially expressed gene. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, including, but not limited to, organic molecules (e.g., small organic compounds having a molecular weight of more than 50 and less than about 2,500 daltons), peptides, monoclonal antibodies antisense polynucleotides, and ribozymes, and the like. Candidate agents can comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: polynucleotides, peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Candidate agents can be assessed for modulation of TTK activity either singly or in pools.

Screening of Candidate Agents In Vitro

A wide variety of in vitro assays may be used to screen candidate agents for the desired biological activity, including, but not limited to, labeled in vitro protein-protein binding assays, protein-DNA binding assays (e.g., to identify agents that affect expression), electrophoretic mobility shift assays, immunoassays for protein binding, and the like. For example, by providing for the production of large amounts of a differentially expressed polypeptide, one can identify ligands or substrates that bind to, modulate or mimic the action of the polypeptide. Further methods for identifying these ligands and substrates are provided below. The purified polypeptide may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g.,magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g., albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Many mammalian genes have homologs in yeast and lower animals. The study of such homologs physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 *Proc. Natl. Acad. Sci. USA* 88:9578-9582.

Screening of Candidate Agents In Vivo

Candidate agents can be screened in a non-human animal model of cancer (e.g., in animals into which have been injected cancerous cells; in animals that are transgenic for an alteration in expression of a differentially expressed gene as described herein, e.g., a transgenic "knock-out," or a transgenic "knock-in," a polynucleotide encoding all or a portion of a differentially expressed gene product and comprising an operably linked reporter gene, and the like).

In general, the candidate agent is administered to the animal, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing expression of the gene product, growth of the injected tumor cells, and the like.

Identified Candidate Agents

Compounds having the desired pharmacological activity may be administered in a physiologically acceptable carrier to a host for treatment of a condition that is amenable to treatment by modulation of expression of a differentially expressed gene product. The therapeutic agents may be administered in a variety of ways, orally, topically, parenterally e.g., subcutaneously, intraperitoneally, by viral infection, intravascularly, etc. Oral and inhaled treatments are of particular interest. Depending upon the manner of introduction, the compounds may be formulated in a variety of ways. The concentration of therapeutically active compound in the formulation may vary from about 0.1-100 wt. %. The therapeutic agents can be administered in a single dose, or as multiple doses over a course of treatment.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Methods of Screening for Drugs that Modulate TTK Activity

A TTK polypeptide or TTK-encoding nucleic acid according to the present invention may be used in screening for molecules which affect or modulate TTK activity or function. Such molecules may be useful in a therapeutic and/or prophylactic context. Means for screening for substances potentially useful in treating or preventing cancer is provided by the present invention. In general, the methods of the invention are to facilitate identification of modulators of TTK activity (e.g., by modulating activity of TTK polypeptide or other TTK gene product, or by affecting TTK activity by targeting activity of gene products that act either upstream or downstream of TTK in a cascade that leads to TTK activity), with agents that decrease TTK activity generally being of particular interest. Substances identified as modulators of the TTK activity represent an advance in the fight against cancer since they provide basis for design and investigation of pharmaceuticals for in vivo use.

A method of screening for a substance which modulates activity of a polypeptide may include contacting one or more test substances with the polypeptide in a suitable reaction medium, testing the activity of the treated polypeptide (e.g., the ability to phosphorylate its substrate) and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred. Test substances may also be screened for ability to interact with the polypeptide, e.g., in a yeast two-hybrid system. This may be used as a coarse screen prior to testing a substance for actual ability to modulate activity of the polypeptide. Alternatively, the screen could be used to screen test substances for binding to a TTK specific binding partner.

A substance identified using as a modulator of TTK polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

TTK Activity Assays

The activity of the TTK may be measured using any suitable kinase assay known in the art. For example, and not by way of limitation, the methods described in Hogg et al (Oncogene 1994 9:98-96), Mills et al (J. Biol. Chem. 1992 267: 16000-006) and Tomizawa et al 2001 ( FEBS Lett. 2001 492: 221-7), Schmandt et al, (J. Immunol. 1994, 152:96-105) may be used. Further serine, threonine and tyrosine kinase assays are described in Ausubel et al. (Short Protocols in Molecular Biology, 1999, unit 17.6).

TTK assays generally use TTK polypeptide, a labeled donor substrate, and a receptor substrate that is either specific or non-specific for TTK. In such assays TTK transfers a labeled moiety from the donor substrate to the receptor substrate, and kinase activity is measured by the amount of labeled moiety transferred from the donor substrate to the receptor substrate.

TTK polypeptide may be produced using various expression systems as detailed above, may be purified from cells, may be in the form of a cleaved or uncleaved recombinant fusion protein and may have non-TTK polypeptide sequences, for example a His tag or β-galactosidase at its N- or C-terminus. TTK activity may be assayed in cancerous cells lines if the cancerous cell lines are used as a source of the TTK to be assayed. Suitable donor substrates for TTK assays include any molecule that is susceptible to dephosphorylation by TTK include γ-labeled ATP and ATP analogs, wherein the label is $^{33}P$, $^{32}P$, $^{35}S$ or any other radioactive isotope or a suitable fluorescent marker. Suitable recipient substrates for TTK assays include any polypeptide or other molecule that is susceptible to phosphorylation by TTK. Recipient substrates are usually derived from fragments of in vivo targets of TTK. Recipient substrates fragments may be 8 to 50 amino acids in length, usually 10 to 30 amino acids and preferably of about 10, 12, 15, 18, 20 and 25 amino acids in length Further recipient substrates can be determined empirically using a set of different polypeptides or other molecules. Targets of TTK suitable for TTK assays include tau and cdc25. Recipient substrates for TTK are typically capable of being purified from other components of the reaction once the reaction has been performed. This purification is usually done through a molecular interaction, where the recipient substrates is biotinylated and purified through its interaction with streptavidin, or a specific antibody is available that can specifically recognize the recipient substrates. The reaction can be performed in a variety of conditions, such as on a solid support, in a gel, in solution or in living cells.

One exemplary recipient substrate for TTK phosphorylation is the human protein cdc25, SEQ ID NO:26, which is phosphorylated by TTK at the serine residues of amino acid position 214 and 216. Two fragments of cdc25 are used as substrates in the kinase assay described below. These fragments comprise peptides A (SEQ ID NO:27), corresponding to amino acids 209 to 225 of the cdc25 polypeptide sequence or peptide B (SEQ ID NO:28), corresponds to amino acids 210 to 223 of the cdc25 polypeptide. In this assay, two biotinylated polypeptides of comprising either SEQ ID NO:27 (Biotin-SGSGSGLYRSPSMPENLNRPR-NH2) or SEQ ID NO:28 (Biotin-GGGGLYRSPSMPENLNRK-OH) are used.

The choice of detection methods depends on type of label used for the donor molecule and may include, for example, measurement of incorporated radiation or fluorescence by autoradiography, scintillation, scanning or fluorography.

Methods of Inhibiting Tumor Growth and Other Treatment Goals

The invention further provides methods for reducing growth of cancer cells, particular breast or colon cancer cells. In general, the methods comprise contacting a cancer cell that expresses TTK at an aberrant level relative to normal cells with a substance that (1) modulates, generally decreases, expression of TTK (e.g., a antisense polynucleotide corresponding to TTK); or (2) otherwise modulates, generally decreases, TTK polypeptide levels and/or TTK activity in a cancerous cell having aberrant TTK activity.

"Reducing growth of a cancer cell" includes, but is not limited to, reducing proliferation of cancer cells, and reducing the incidence of a normal cell from developing a cancerous phenotype or morphology. Whether a reduction in cancer cell growth has been achieved can be readily determined using any known assay, including, but not limited to, [$^3$H]-thymidine incorporation; counting cell number over a period of time; detecting, measuring a marker associated with colon cancer (e.g., CEA, CA19-9, and LASA), and/or methods well known in the art for assessing tumor burden.

The present invention provides methods for treating cancer (particularly breast and colon cancer or other cancer that is associated with aberrantly high TTK activity) which methods generally comprise administering to an individual an agent that reduces TTK activity in an amount sufficient to reduce cancer cell growth to treat the cancer. Whether a substance, or a specific amount of the substance, is effective in treating cancer can be assessed using any of a variety of known diagnostic assays, e.g. in the case of colon cancer, sigmoidoscopy, proctoscopy, rectal examination, colonoscopy with biopsy, contrast radiographic studies, CAT scans, angiography, and detection of a tumor marker associated with colon cancer in the blood of the individual. The substance can be administered systemically or locally. Thus, in some embodiments, the substance is administered locally, and colon cancer growth is decreased at the site of administration. Local administration may be useful in treating, e.g., a solid tumor.

In one embodiment, the invention features polynucleotides that act as antisense polynucleotides and decrease TTK activity. Antisense TTK polynucleotides generally comprise a polynucleotide of at least about 20 to 3000 nucleotides, usually at least about 20 to 1000 nucleotides and more usually at least about 8 to 50 nucleotides, and preferably about 26, 20, 18, 17, 15, 10 and 8 nucleotides. Exemplary TTK polynucleotides are provided in the Examples and in SEQ ID NO:1-12, although any antisense fragment of SEQ ID NO:13 will suffice.

The therapeutic regimen is selected according to the expression profile. For example, if a patient's tumor indicates that the tumor produces aberrantly high level of TTK relative to normal cells, then a drug having efficacy in the treatment of such TTK-expressing tumors is selected for therapy of that patient.

Pharmaceutical Compositions

Pharmaceutical compositions of the invention can comprise a therapeutically effective amount of a polypeptide, antibody, polynucleotide (including antisense nucleotides and ribozymes), or small molecule or other compound identified as modulating activity of TTK, preferably decreasing TTK activity. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature, and/or in the effect upon tumor load in the subject (e.g., decrease in tumor size or inhibition in tumor growth). The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991). The precise nature of the carrier or other material may depend on the route of administration, e.g., oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is has suitable pH, isotonicity and stability. Suitable solutions, for example, optionally include but are not limited to isotonic vehicles such as sodium chloride, preservatives, stabilizers, buffers, antioxidants and/or other additives as required.

Administration of the pharmaceutical is administered in a prophylactically effective amount or a therapeutically effective amount. The actual amount administered, and rate and time-course of administration, will depend on the nature and severity of what is being treated. Decisions on dosage etc, can be determined by one skilled in the art based upon the disclosed methods, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells. Targeting can be accomplished by, for example, administering a drug-antibody complex to a subject, wherein the antibody is specific for a cancer-associated antigen, and the drug is one that reduces cancer cell growth. Targeting can be accomplished by coupling (e.g., linking, directly or via a linker molecule, either covalently or non-covalently, so as to form a drug-antibody complex) a drug to an antibody specific for a cancer-associated antigen. Methods of coupling a drug to an antibody are well known in the art and need not be elaborated upon herein.

Pharmaceutical agents can also be produced in the target cells by expression from an encoding gene introduced into the cells, e.g., in a viral or liposomal vector. The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. A composition may be administered alone or in combination with other treatments, either simultaneously or sequentially dependent upon the condition to be treated.

Delivery Methods for Therapy

Once formulated, the compositions of the invention or identified using the methods of the invention can be administered directly to the subject (e.g., as polynucleotide or polypeptides). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Once a gene corresponding to a polynucleotide of the invention has been found to correlate with a proliferative disorder, such as neoplasia, dysplasia, and hyperplasia, the disorder can be amenable to treatment by administration of a therapeutic agent based on the provided polynucleotide, corresponding polypeptide or other corresponding molecule (e.g., antisense, ribozyme, etc.).

The dose and the means of administration are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. Preferably, the therapeutic polynucleotide composition contains an expression construct comprising a promoter operably linked to a polynucleotide of at least 12, 15, 17, 18, 22, 25, 30, or 35 contiguous-nucleotides of the polynucleotide disclosed herein. Various methods can be used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (*USA*) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the antisense subgenomic polynucleotides. Where greater expression is desired over a larger area of tissue, larger amounts of antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. For polynucleotide related genes encoding polypeptides or proteins with anti-inflammatory activity, suitable use, doses, and administration are described in U.S. Pat. No. 5,654,173.

The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No.2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581.

Further non-viral delivery suitable for use includes mechanical delivery systems such as the approach described in Woffendin et al., *Proc. Natl. Acad. Sci. USA* (1994) 91(24): 11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer. Gene transfer techniques which selectively target the TTK nucleic acid to the affected cell type are preferred. Examples of this included receptor-mediated gene transfer, in which the nucleic acid is linked to a protein ligand via polylysine, with the ligand being specific for a receptor present on the surface of the target cells.

Screening for Substances Affecting TTK Expression

The present invention also provides the use of all or part of the nucleic acid sequence of the TTK promoter and/or enhancer regions in methods of screening for substances which modulate the activity of the promoter and increase or decrease the level of TTK expression. This assay can be performed to identify anti-cancer agents for therapeutic and/or prophylactic purposes. The level of promoter activity, i.e., the ability to initiate transcription, is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridize with the mRNA and which are labeled or may be used in a specific amplification reaction such as PCR. Use of a reporter gene facilitates determination of promoter activity by reference to protein production.

Generally, a reporter gene under control of the TTK promoter and/or enhancers may be transcribed into mRNA which may be translated into a peptide or polypeptide product which may be detected and preferably quantitated following expression. The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue color on substrate, the assay being by eye or by use of a spectrophotometer to measure absorbance. Fluorescence, for example that produced as a result of luciferase activity, may be quantitated using a spectrophotometer. Radioactive assays may be used, for instance using choloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique.

Those skilled in the art are well aware of a multitude of possible reporter genes and assay techniques which may be used to determine gene activity according to the presently disclosed methods. Any suitable reporter/assay may be used and the present invention is intended to encompass such systems.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug.

Integrated Disease Information System

The levels of TTK in a sample can be used in an integrated disease information system to aid in analysis such as proposed patient interventions, designing clinical trials, performing pharmacoeconomic analysis, and illustrating disease progression for various patients over time. For example, TTK information determined according to the methods of the invention can be used in a system such as that described in U.S. Pat. No. 6,108,635 issued to Herren, et al. on Aug. 22, 2000. Such a system can be for collecting the results of medical treatments given to patients in a plurality of locations. See, e.g., U.S. Pat. No. 5,713,350 issued to Yokota, et al. on Feb. 3, 1998.

EMBODIMENTS RELATING TO GSEF

I. Overview

The present invention is based on the discovery that expression of the gene encoding GSEF (previously referred to as JKETS), an ETS-domain-containing protein is decreased in cells of high metastatic potential relative to cells of either low metastatic potential cells, non-metastatic, cancerous cells, or normal cells. This finding indicates that GSEF is a tumor suppressor gene, and that inhibition of GSEF function (e.g., by inhibition of gene expression, alteration in the GSEF polypeptide biological activity, etc.) leads to development of the metastatic phenotype.

Nucleic acid compositions encoding GSEF polypeptides or fragments thereof are thus useful in, for example, producing or identifying compositions that modulate the expression or function of the encoded proteins; in identifying homologous or related genes; for gene therapy; mapping functional regions of the proteins; and in studying associated physiological pathways.

Characterization of GSEF

The GSEF nucleotide and amino acid sequences are provided herein as SEQ ID NOS:39 and 40, respectively. The GSEF cDNA sequence comprising the GSEF promoter and coding sequence are provided as SEQ ID NO:50, with the encoded GSEF amino acid sequence provided again as SEQ ID NO:51. The functional domains and other features of GSEF, are described in detail below.

GSEF Nucleic Acid Compositions

Nucleic acids encoding the GSEF of the invention may be cDNA, genomic DNA, the corresponding RNA, or a fragment thereof. The term AGSEF gene≅ shall be intended to mean the open reading frame encoding any of the provided GSEF polypeptides (with the GSEF polypeptide of SEQ ID NO:40 being of particular interest), introns, as well as adjacent 5= and 3=non-coding nucleotide sequences involved in the regulation of expression, up to about 20 kb beyond the coding region, but possibly further in either direction. The gene may be introduced into an appropriate vector for extra-chromosomal maintenance or for integration into a host genome. The term "nucleic acid" is meant to encompass, but is not necessarily limited to, DNA, cDNA, genomic DNA, and RNA compositions. Where a specific DNA sequence is referred to, the sequence is understood to encompass both the DNA and its corresponding RNA, unless specifically noted otherwise.

The GSEF-encoding polynucleotides are isolated and obtained in substantial purity, generally as other than an intact chromosome. Usually, the DNA will be obtained substantially free of other nucleic acid sequences that do not include a GSEF sequence or fragment thereof, generally being at least about 50%, usually at least about 90% pure and are typically Arecombinant≅, i.e. flanked by one or more nucleotides with which it is not normally associated on a naturally occurring chromosome. Of particular interest is a DNA encoding a GSEF.

The subject nucleic acids may be DNA, cDNA, genomic DNA, or RNA corresponding to the subject DNA, cDNA, or genomic DNA sequences, as well as fragments of the subject nucleic acids, particularly fragments that encode a biologically active gene product and/or are useful in the methods disclosed herein (e.g., production of antigenic polypeptides for antibody production, antisense, primers, etc.). Double or single stranded fragments of the DNA sequence may be obtained by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The term a as used herein is intended to include all nucleic acids that share the arrangement of sequence elements found in native mature mRNA species, where sequence elements are exons and 3= and 5=non-coding regions. Normally mRNA species have contiguous exons, with the intervening introns, when present, removed by nuclear RNA splicing, to create a continuous open reading frame encoding a GSEF protein.

GSEF genes can also be provided as genomic sequences. An exemplary genomic sequence of interest comprises the nucleic acid present between the initiation codon and the stop codon, as defined in the listed sequences, including all of the introns that are normally present in a native chromosome. It may further include the 3= and 5=untranslated regions found in the mature mRNA. It may further include specific transcriptional and translational regulatory sequences, such as promoters, enhancers, etc., including about 1 kb, but possibly more, of flanking genomic DNA at either the 5= or 3=end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the invention can be used in a variety of ways as will be readily appreciated by the ordinarily skilled artisan upon disclosure of the nucleic acid compositions described herein. For example, the sequence of the 5' flanking region of the genomic sequence may be utilized for promoter elements, including enhancer binding sites, that provide for tissue-specific and/or developmental regulation in tissues where GSEF genes are expressed. The tissue specific expression is useful for determining the pattern of expression, and for providing promoters that mimic the native pattern of expression (e.g., GSEF). In one embodiment, the GSEF promoter is used to direct expression of genes to normal cells or pre-metastatic cells, particularly breast ductal cells.

Naturally occurring polymorphisms in the promoter regions are useful for determining natural variations in expression, particularly those that may be associated with disease. Alternatively, mutations may be introduced into the promoter regions to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1: 194-205; Mortlock et al. (1996) *Genome Res.* 6: 327-33; and Joulin and Richard-Foy (1995) *Eur. J. Biochem.* 232: 620-626.

The regulatory sequences may be used to identify cis acting sequences required for transcriptional or translational regulation of GSEF expression, especially in different tissues or stages of development of cancer (e.g., pre-metastatic or normal cells), and to identify cis acting sequences and trans acting factors that regulate or mediate GSEF expression. Such transcription or translational control regions may be operably linked to a GSEF-encoding gene in order to promote expression of wild type or altered GSEF polypeptides or other proteins of interest in cultured cells, or in embryonic, fetal or adult tissues, and for gene therapy.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of GSEF gene expression in the sample.

Variants, Homologs, and Orthologs

In addition to the specific GSEF sequence provided, GSEF nucleic acid compositions also include nucleic acid sequences having substantial sequence similarity or sequence identity to the specific polynucleotide sequences provided herein. Sequence similarity is calculated based on a reference sequence, which may be a subset of a larger sequence, such as a conserved motif, coding region, flanking region, etc. A reference sequence will usually be at least about 18 contiguous nt long, more usually at least about 30 contiguous nt to about 100 to about 200 contiguous nt long, and may extend to the complete sequence that is being compared. Algorithms for sequence analysis are known in the art, such as BLAST, described in Altschul et al. (1990), *J. Mol. Biol.* 215:403-10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular). Exemplary search parameters for use with the MPSRCH program in order to identify sequences of a desired sequence identity are as follows: gap open penalty: 12; and gap extension penalty: 1.

The GSEF nucleic acid compositions discussed herein also encompass naturally-occurring, synthetic, and recombinant variants of the nucleotide sequences (e.g., degenerate variants, allelic variants, etc.). Allelic variants of the polynucleotides of the invention are identified by hybridization of putative allelic variants with nucleotide sequences disclosed herein under stringent conditions. For example, by using the following wash conditions—2×SSC, 0.1% SDS, room temperature twice, 30 minutes each; then 2×SSC, 0.1% SDS, 50EC once, 30 minutes; then 2×SSC, room temperature twice, 10 minutes each-allelic variants of the polynucleotides of the invention can be identified which contain at most about 25-30% base pair mismatches. In general, allelic variants contain about 15 to 25% base pair mismatches, and may contain as little as about 5-15%, or 2-5%, or 1-2% base pair mismatches, as well as a single base-pair mismatch.

The GSEF nucleic acid compositions also include homologs corresponding to the polynucleotides of the subject invention, where the source of homologous genes may be any mammalian species, e.g., primate species, particularly human; rodents, such as rats, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences.

Modified GSEF-Encoding Nucleic Acid

The nucleic acid compositions of the subject invention also encompass modified GSEF-encoding polynucleotides including, but not necessarily limited to, fragments (e.g., encoding all or a part of the subject polypeptides), polynucleotides encoding genetically modified GSEF polypeptides, etc, with modified GSEF-encoding polynucleotides being of particular interest The sequences of the GSEF-encoding genes, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

When generating the modified GSEF polypeptides and nucleic acids of the invention, the ordinarily skilled artisan will readily appreciate that she can be guided in her selection of amino acid residues to alter or maintain in view of the knowledge surrounding the structure and function of GSEF. For example, modified GSEF can contain a modification within, and/or contain a modification outside of, a conserved region of the GSEF polypeptide-encoding region, e.g., the ETS-domain. The amino acid sequence of the ETS-domain of GSEF is:

IHLWQFLKELLLKPHSYGRFIRWLNKEKGIFKIEDS (SEQ ID NO:41)
AQVARLWGIRKNRPAMNYDKLSRSIRQYYKKGIIRK
PDISQRLVYQFV.

Techniques for in vitro mutagenesis of cloned genes are known. Examples of protocols for site specific mutagenesis may be found in Gustin et al., *Biotechniques* 14:22 (1993); Barany, *Gene* 37:111-23 (1985); Colicelli et al., *Mol Gen Genet* 199:537-9 (1985); and Prentki et al., *Gene* 29:303-13 (1984). Methods for site specific mutagenesis can be found in Sambrook et al., *Molecular Cloning: A Laboratory Manual*, CSH Press 1989, pp. 15.3-15.108; Weiner et al., *Gene* 126: 35-41 (1993); Sayers et al., *Biotechniques* 13:592-6 (1992); Jones and Winistorfer, *Biotechniques* 12:528-30 (1992); Barton et al., *Nucleic Acids Res* 18:7349-55 (1990); Marotti and Tomich, *Gene Anal Tech* 6:67-70 (1989); and Zhu, *Anal Bio*-

*chem* 177:120-4 (1989). Such mutated genes may be used to study structure-function relationships of GSEF genes, particularly to study the differential expression of GSEF in various tissues or to alter properties of these proteins that affect their function or regulation.

GSEF Polypeptides

GSEF nucleic acid sequences may be used to produce all or portions of GSEF polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a GSEF -encoding gene (e.g., native to a GSEF -encoding gene), or may be derived from exogenous sources.

The polypeptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the GSEF gene (e.g., a GSEF gene) in eukaryotic cells, where the recombinant protein will benefit from native folding and post-translational modifications. Small peptides can also be synthesized in the laboratory. Peptides that are subsets of a complete GSEF (e.g, GSEF) sequence may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed GSEF polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of GSEF polypeptides or immunogenic fragments thereof, or may be raised to isolated peptides corresponding to specific domains, or to the native protein. Antibodies that specifically bind a GSEF polypeptide are of particular interest, particularly antibodies that preferentially bind a GSEF polypeptide (e.g., antibodies that preferentially bind human GSEF polypeptides relative to other ETS-domain family proteins).

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage Adisplay≅ libraries, usually in conjunction with in vitro affinity maturation.

Diagnostic Applications

The subject nucleic acid and/or polypeptide compositions may be used in a variety of diagnostic applications. Exemplary embodiments of such diagnostic applications are described below.

Diagnosis and Prognosis of Cancer by Detection of GSEF Expression and/or Expression Levels As noted above, the present invention is based on the discovery that GSEF expression is decreased in cells of high metastatic potential relative to cells of low metastatic potential, cells of non-metastatic potential, and to normal cells. In general, the terms "high metastatic potential" and "low metastatic potential" are used to describe the relative ability of a cell to give rise to metastases in an animal model, with "high metastatic potential" cells giving rise to a larger number of metastases and/or larger metastases than "low metastatic potential" cells. Thus, a cell of high metastatic potential poses a greater risk of metastases to the subject than a cell of low metastatic potential. "Non-metastatic cells" are those cells that are cancerous, but that do not develop detectable metastases following injection in an animal model. Exemplary high metastatic potential cells include MDA-MB435, MDA-MB-231, and ALAB. Exemplary low metastatic potential cells include MDA-MB468, MDA-MB-361, ZR-75-1, and MCF-7.

The invention thus features methods and compositions for diagnosis and prognosis, as well as grading and staging of cancers, by detection of GSEF expression in a biological test sample, e.g, cell sample or tissue sample. The methods of the invention can also be used to monitor patients having a predisposition to develop a particular cancer, e.g., through inheritance of an allele associated with susceptibility to a cancer (e.g., BRCA1, BRCA2, TP53, ATM, or APC for breast cancer). Detection and monitoring of GSEF expression levels can be used to detect potentially malignant events at a molecular level before they are detectable at a gross morphological level.

In general, diagnosis, prognosis, and grading and/or staging of cancers may be performed by a number of methods to determine the relative level of expression of the differentially expressed GSEF gene at the transcriptional level, and/or the absence or presence or altered amounts of a normal or abnormal GSEF polypeptide in patient cells. As used herein, A differentially expressed gene≅ is intended to refer to a gene having an expression level (e.g., which in turn is associated with a level of GSEF polypeptide production and/or GSEF transcription) that is associated with a decrease in expression level of at least about 25%, usually at least about 50% to 75%, more usually at least about 90% or more. In general, such a decrease in differentially expressed GSEF is indicative of the onset or development of the metastatic phenotype.

"Diagnosis" as used herein generally includes determination of a subject's susceptibility to a disease or disorder, determination as to whether a subject is unaffected, susceptible to, or presently affected by a disease or disorder, and/or to identify a tumor as benign, non-cancerous, or cancerous (e.g., non-metastatic or metastatic, e.g., high metastatic potential or low metastatic potential). APrognosis≅ is used herein to generally mean a determination of the severity of disease (e.g., identification or pre-metastatic or metastatic cancerous states, stages of cancer, etc.), which in turn can be correlated with the potential outcome, response to therapy, etc. A complete diagnosis thus can include diagnosis as discussed above, as well as determination of prognosis, cancer staging, and tumor grading. The present invention particularly encompasses diagnosis and prognosis of subjects in the context of cancers of various origins, particularly breast cancer (e.g., carcinoma in situ (e.g., ductal carcinoma in situ), estrogen receptor (ER)-positive breast cancer, ER-negative breast cancer, or other forms and/or stages of breast cancer) and prostate cancer.

As noted above, detection of GSEF expression levels can be used to determine the stage of the tumor and/or to determine the grade of the tumor, e.g., to determine the differentiation status of the cells of a tumor. Staging is a process used by physicians to describe how advanced the cancerous state is in a patient. Staging assists the physician in determining a prognosis, planning treatment and evaluating the results of such treatment. Different staging systems are used for different types of cancer, but each generally involves the following determinations: the type of tumor, indicated by T; whether the cancer has metastasized to nearby lymph nodes, indicated by N; and whether the cancer has metastasized to more distant parts of the body, indicated by M. This system of staging is called the TNM system. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or another site, are called Stage IV, the most advanced stage.

Detection of GSEF expression levels can facilitate fine-tuning of the staging process by serving as identifying marker for the aggressiveness of a cancer, e.g. the metastatic potential, as well as the presence in different areas of the body. Thus, a Stage II cancer with a decreased or undetectable GSEF gene product expression level signifying a high metastatic potential cancer can be used to more accurately classify a Stage II tumor as a Stage III tumor, justifying more aggressive therapy. Conversely, higher or normal GSEF gene product expression levels signifying a lower metastatic potential can facilitate staging of a tumor as less aggressive.

The Agrade≅ of a cancer is used to describe how closely a tumor resembles normal tissue of its same type. Based on the microscopic appearance of a tumor, pathologists identify the grade of a tumor based on parameters such as cell morphology, cellular organization, and other markers of differentiation. As a general rule, the grade of a tumor corresponds to its rate of growth or aggressiveness. That is, undifferentiated or high-grade tumors grow more quickly than well differentiated or low-grade tumors. Information about tumor grade is useful in planning treatment and predicting prognosis.

The American Joint Commission on Cancer has recommended the following guidelines for grading tumors: 1) GX Grade cannot be assessed; 2) G1 Well differentiated; G2 Moderately well differentiated; 3) G3 Poorly differentiated; 4) G4 Undifferentiated. Although grading is used by pathologists to describe most cancers, it plays a more important role in treatment planning for certain types than for others. An example is the Gleason system that is specific for prostate cancer, which uses grade numbers to describe the degree of differentiation. Lower Gleason scores indicate well-differentiated cells. Intermediate scores denote tumors with moderately differentiated cells. Higher scores describe poorly differentiated cells. Grade is also important in some types of brain tumors and soft tissue sarcomas.

AGene product≅ as used in connection with the diagnostic, prognostic, grading, and staging methods of the invention is meant to encompass partial or full-length polypeptides or mRNA. Detection of the mRNA gene product can involve production of cDNA from the mRNA, and detection of the corresponding cDNA so produced.

"Sample" or "biological sample" as used throughout here are generally meant to refer to samples of biological fluids or tissues, particularly samples obtained from tissues, especially from cells of the type associated with the disease for which the diagnostic application is designed (e.g., ductal adenocarcinoma), and the like. "Samples" is also meant to encompass derivatives and fractions of such samples (e.g., cell lysates). Where the sample is solid tissue, the cells of the tissue can be dissociated or tissue sections can be analyzed.

Methods of the subject invention useful in diagnosis or prognosis typically involve comparison of the amount of GSEF gene product in a sample of interest with that of a control to detect relative differences in the expression of the gene product, where the difference can be measured qualitatively and/or quantitatively. Quantitation can be accomplished, for example, by comparing the level of expression product detected in the sample with the amounts of product present in a standard curve. A comparison can be made visually using ELISA to detect relative amounts of GSEF polypeptides in test and control samples; by using a technique such as densitometry, with or without computerized assistance, to detect relative amounts of detectably labeled GSEF polypeptides or GSEF-encoding nucleic acid; by preparing a representative library of cDNA clones of mRNA isolated from a test sample, sequencing the clones in the library to determine that number of cDNA clones corresponding to the same gene product, and analyzing the number of clones corresponding to that same gene product relative to the number of clones of the same gene product in a control sample; or by using an array to detect relative levels of anti-GSEF polypeptide antibody binding, or to detect relative levels of hybridization to a GSEF-encoding nucleic acid sequences, and comparing the pattern of antibody binding or nucleic acid hybridization to that of a control.

In some embodiments of the methods of the invention it may be particularly desirable to detect expression of a GSEF gene product as well as at least one gene product other GSEF. GSEF expression decreases upon development of metastasis, and may be undetectable in metastatic cells, while GSEF is expressed in non-metastatic and in normal cells. It may also be desirable to detect expression of other gene products in addition to GSEF. For example, E1AF is expressed in non-metastatic, low metastatic potential, high metastatic potential, and metastatic cancer cells, but is not expressed at a significant or detectable level in normal cells. Thus detection of an E1AF gene product can serve as a control to distinguish a normal cell from a cancerous cell.

In addition, or alternatively, expression of the ESX gene can serve as an additional marker for detection of cells that exhibit the low metastatic phenotype. Expression of ESX is generally detectable in cells of low metastatic potential, but is generally not detectable in cells of high metastatic potential. Detection of GSEF with E1AF and/or ESX thus can provide a more sensitive assay for the classification of the metastatic potential of a cell. The ESX polynucleotide and amino acid sequences are provided in the Sequence Listing as SEQ ID NOS:42 and 43.

Other gene products that can serve as controls or increase the sensitivity of classification of the metastatic phenotype of a cell, as well as gene products that can serve as controls for identification of normal cells (e.g., gene products that are expressed in normal cells but not in cancerous cells, or expressed in normal cells, but not in metastatic cells, etc.) are known in the art. In addition, the cells can be classified as normal or cancerous based on conventional methodologies such as general morphology as determined by light microscopy. For example, conventional techniques for classifying a cell as cancerous based on morphology can be performed prior to or simultaneously with detection of GSEF expression. Thus, a cell that exhibits abnormal morphology associated with the cancer phenotype, and that expresses a low level of GSEF relative to a normal cells or in which GSEF expression is not detectable is identified as a cell of high metastatic potential.

Methods for qualitative and quantitative detection of polypeptides or nucleic acid in a sample, as well as methods for comparing such to control samples are well known in the art. For example, a variety of different methods for determining the nucleic acid abundance in a sample are known to those of skill in the art, where particular methods of interest include those described in: Pietu et al. *Genome Res.* (1996) 6:492; Zhao et al., *Gene* (1995) 156:207; Soares, *Curr. Opin. Biotechnol.* (1977) 8: 542; Raval, *J. Pharmacol Toxicol Methods* (1994) 32:125; Chalifour et al., *Anal. Biochem* (1994) 216: 299; Stolz et al., *Mol. Biotechnol.* (1996) 6:225; Hong et al., *Biosci. Reports* (1982) 2:907; McGraw, *Anal. Biochem.* (1984) 143:29; and WO 97/27317.

The patient from whom the sample is obtained can be apparently healthy, susceptible to disease (e.g., as determined by family history or exposure to certain environmental factors), or can already be identified as having a condition in which altered expression of a gene product of the invention is implicated.

In the assays of the invention, the diagnosis can be determined based on detected GSEF gene product expression levels, and may also include detection of additional diagnostic markers and/or reference sequences. Where the diagnostic method is designed to detect the presence or susceptibility of a patient to metastatic cancer, the assay preferably involves detection of a GSEF gene product and comparing the detected gene product levels to a level associated with a normal sample, to levels associated with a low metastatic potential sample, and/or to level associated with a high metastatic potential sample. For example, detection of a lower level of GSEF expression relative to a normal level is indicative of the presence in the sample of a cell having high metastatic potential. Given the disclosure provided herein, variations on the diagnostic and prognostic assays described herein will be readily apparent to the ordinarily skilled artisan.

Any of a variety of detectable labels can be used in connection with the various methods of the invention. Suitable detectable levels include fluorochromes, radioactive labels, and the like. Suitable labels include, but are not necessarily limited to, fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The detectable label can involve a two stage system (e.g., biotin-avidin, hapten-anti-hapten antibody, etc.).

Reagents specific for the polynucleotides and polypeptides of the invention, such as detectably labeled antibodies or detectably labeled nucleotide probes, can be supplied in a kit for detecting the presence of an expression product in a biological sample. The kit can also contain buffers or labeling components, as well as instructions for using the reagents to detect and quantify expression products in the biological sample. Exemplary embodiments of the diagnostic methods of the invention are described below in more detail.

Polypeptide Detection in Diagnosis, Prognosis, Cancer Grading and Cancer Staging.

In one embodiment, the test sample is assayed for the level of a GSEF polypeptide. Diagnosis can be accomplished using any of a number of methods to determine the absence or presence of altered amounts of the differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In general, the detected level of GSEF polypeptide in the test sample is compared to a level of the differentially expressed gene product in a reference or control sample, e.g., in a normal cell or in a cell having a known disease state (e.g., cell of high metastatic potential).

mRNA Detection.

The diagnostic, prognostic, grading, and staging methods of the invention can also or alternatively involve detection of mRNA encoded by a GSEF gene. Any suitable qualitative or quantitative methods known in the art for detecting specific mRNAs can be used. mRNA can be detected by, for example, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of mRNA of the invention in a tissue sample suspected of being cancerous, particularly a tissue suspected of being of high metastatic potential, is compared with the expression of the mRNA in a reference sample, e.g., a positive or negative control sample (e.g., normal tissue, cancerous tissue, etc.).

Any suitable method for detecting and comparing mRNA expression levels in a sample can be used in connection with the diagnostic methods of the invention (see, e.g., U.S. Pat. No. 5,804,382). For example, mRNA expression levels in a sample can be determined by generation of a library of expressed sequence tags (ESTs) from the sample, where the EST library is representative of sequences present in the sample (Adams, et al., (1991) *Science* 252:1651). Enumeration of the relative representation of ESTs within the library can be used to approximate the relative representation of the gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Pattern Matching in Diagnosis Using Arrays.

In another embodiment, the diagnostic and/or prognostic methods of the invention involve detection of expression of a selected set of genes in a test sample to produce a test expression pattern (TEP), where the selected set comprises a GSEF gene expression product. The TEP is compared to a reference expression pattern (REP), which is generated by detection of expression of the selected set of genes in a reference sample (e.g., a positive or negative control sample).

"Reference sequences" or "reference polynucleotides" as used herein in the context of differential gene expression analysis and diagnosis/prognosis refers to a selected set of polynucleotides, which selected set includes at least one or more of the differentially expressed polynucleotides described herein. A plurality of reference sequences, preferably comprising positive and negative control sequences, can be included as reference sequences. Additional suitable reference sequences are found in GenBank, Unigene, and other nucleotide sequence databases (including, e.g., expressed sequence tag (EST), partial, and full-length sequences).

"Reference array" means an array having reference sequences for use in hybridization with a sample, where the reference sequences include all, at least one of, or any subset of the differentially expressed polynucleotides described herein. Usually such an array will include at least 1 different reference sequence. Arrays of interest can further comprise sequences, including polymorphisms, of other genetic sequences, particularly other sequences of interest for screening for a disease or disorder (e.g., cancer, dysplasia, or other related or unrelated diseases, disorders, or conditions). The oligonucleotide sequence on the array will usually be at least about 12 nt in length, and can be of about the length of the provided sequences, or can extend into the flanking regions to generate fragments of 100 nt to 200 nt in length or more.

A "reference expression pattern" or "REP" as used herein refers to the relative levels of expression of a selected set of genes, particularly of differentially expressed genes, that is associated with a selected cell type, e.g., a normal cell, a cancerous cell, a cell exposed to an environmental stimulus, and the like. A "test expression pattern" or "TEP" refers to relative levels of expression of a selected set of genes, particularly of differentially expressed genes, in a test sample (e.g., a cell of unknown or suspected disease state, from which mRNA is isolated).

REPs can be generated in a variety of ways according to methods well known in the art. For example, REPs can be generated by hybridizing a control sample to an array having a selected set of polynucleotides, acquiring the hybridization data from the array, and storing the data in a format that allows for ready comparison of the REP with a TEP. Alternatively, all expressed sequences in a control sample can be isolated and sequenced, e.g., by isolating mRNA from a control sample, converting the mRNA into cDNA, and sequencing the cDNA. The resulting sequence information roughly or precisely reflects the identity and relative number of expressed sequences in the sample. The sequence information can then be stored in a format (e.g., a computer-readable format) that allows for ready comparison of the REP with a TEP. The REP can be normalized prior to or after data storage, and/or can be processed to selectively remove sequences of expressed genes that are of less interest or that might complicate analysis (e.g., some or all of the sequences associated with housekeeping genes can be eliminated from REP data).

TEPs can be generated in a manner similar to REPs, e.g., by hybridizing a test sample to an array having a selected set of polynucleotides, particularly a selected set of differentially expressed polynucleotides, acquiring the hybridization data from the array, and storing the data in a format that allows for ready comparison of the TEP with a REP. The REP and TEP to be used in a comparison can be generated simultaneously, or the TEP can be compared to previously generated and stored REPs.

In one embodiment of the invention, comparison of a TEP with a REP involves hybridizing a test sample with a reference array, where the reference array has one or more reference sequences for use in hybridization with a sample. The reference sequences include all, at least one of, or any subset of the differentially expressed polynucleotides described herein. Hybridization data for the test sample is acquired, the data normalized, and the produced TEP compared with a REP generated using an array having the same or similar selected set of differentially expressed polynucleotides. Probes that correspond to sequences differentially expressed between the two samples will show decreased or increased hybridization efficiency for one of the samples relative to the other.

Reference arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with a reference arrays are also well known in the art. For example, the polynucleotides of the reference and test samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample (e.g., a test sample) is compared to the fluorescent signal from another sample (e.g., a reference sample), and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

In general, the test sample is classified as having a gene expression profile corresponding to that associated with a disease or non-disease state by comparing the TEP generated from the test sample to one or more REPs generated from reference samples (e.g., from samples associated with cancer or specific stages of cancer, dysplasia, samples affected by a disease other than cancer, normal samples, etc.). The criteria for a match or a substantial match between a TEP and a REP include expression of the same or substantially the same set of genes, as well as expression of these genes at substantially the same levels (e.g., no significant difference between the samples for a signal associated with a selected reference sequence after normalization of the samples, or at least no greater than about 25% to about 40% difference in signal strength for a given reference sequence). In general for the purposes of the present invention, a pattern match between a TEP and a REP is a match in expression, preferably a match in qualitative or quantitative expression level, of at least a GSEF gene.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Cancers amenable to diagnosis, prognosis, staging and/or grading using the methods of the invention The method of the invention can be used to detect GSEF expression levels in any cell or tissue sample in which GSEF expression levels may be linked to development of the metastatic phenotype. Of particular interest is the detection of GSEF expression levels in samples taken from breast tissue or from prostate tissue. GSEF expression levels may also be linked to development of the metastatic phenotype in cells or tissue of various origins, including, but not limited to, lung, colon, prostate, liver, trachea, epithelia-derived tissues, etc.

GSEF expression levels can indicate the development of the metastatic phenotype in a variety of cancers that may develop within a single tissue. For example, GSEF expression levels can be used to detect the development of the metastatic phenotype in, and to differentiate between, the various types of breast cancer, prostate cancer, lung cancer, or colon cancer. In one embodiment the methods of the invention involve the diagnosis, prognosis, staging, and/or grading of breast tumors or prostate tumors.

Use of the Methods of the Invention in Breast Cancers

Detection of GSEF expression can be used to differentiate between non-cancerous breast tissue, low metastatic potential, and high metastatic potential breast tissue by analyzing differential gene expression between tissues. Similarly, the expression of GSEF can be used in the diagnosis and management of breast cancer. Determination of the aggressive nature and/or the metastatic potential of a breast cancer can be determined by comparing levels of GSEF expression, which can be compared to levels of another sequence known to vary in cancerous tissue, e.g. ER expression. In addition, detection of GSEF expression levels can be performed in conjunction with detection of levels of steroid hormones (e.g., testosterone or estrogen) or to other hormones (e.g., growth hormone, insulin).

Diagnosis of breast cancer can also involve comparing the expression of a polynucleotide of the invention with the expression of other sequences in non-malignant breast tissue samples in comparison to one or more forms of the diseased tissue. A comparison of expression of one or more polynucleotides of the invention between the samples provides information on relative levels of these polynucleotides as well as the ratio of these polynucleotides to the expression of other sequences in the tissue of interest compared to normal. For example, GSEF expression can be examined in a sample of ductal epithelium and compared to a level of GSEF expression in normal ductal epithelium. A decrease of GSEF expression in the ductal epithelium sample relative to GSEF expression in normal ductal epithelium indicates that the sample contains cells of high metastatic potential.

As well as being used for diagnosis and risk assessment, the expression of the polynucleotides of the invention can be of prognostic value for determining the metastatic potential of a malignant breast cancer, as this molecules are differentially expressed between high and low metastatic potential tissues tumors. The levels of these polynucleotides in patients with malignant breast cancer can compared to normal tissue, malignant tissue with a known high potential metastatic level, and malignant tissue with a known lower level of metastatic potential to provide a prognosis for a particular patient. Such a prognosis is predictive of the extent and nature of the cancer. The determined prognosis is useful in determining the prognosis of a patient with breast cancer, both for initial treatment of the disease and for longer-term monitoring of the same patient. If samples are taken from the same individual over a period of time, differences in polynucleotide expression that are specific to that patient can be identified and closely watched.

The specific types of breast cancer that may be of particular interest are described below.

Ductal carcinoma in situ (DCIS): Ductal carcinoma in situ is the most common type of noninvasive breast cancer. In DCIS, the malignant cells have not metastasized through the walls of the ducts into the fatty tissue of the breast. Comedocarcinoma is a type of DCIS that is more likely than other types of DCIS to come back in the same area after lumpectomy, and is more closely linked to eventual development of invasive ductal carcinoma than other forms of DCIS.

Infiltrating (or invasive) ductal carcinoma (IDC): In IDC, cancerous cells have metastasized through the wall of the duct and invaded the fatty tissue of the breast. At this point, it has the potential to use the lymphatic system and bloodstream for metastasis to more distant parts of the body.

Lobular carcinoma in situ (LCIS): While not a true cancer, LCIS (also called lobular neoplasia) is sometimes classified as a type of noninvasive breast cancer. It does not penetrate through the wall of the lobules. Although it does not itself usually become an invasive cancer, women with this condition have a higher risk of developing an invasive breast cancer in the same or opposite breast.

Infiltrating (or invasive) lobular carcinoma (ILC): ILC is similar to IDC, in that it has the potential to metastasize elsewhere in the body. About 10% to 15% of invasive breast cancers are invasive lobular carcinomas, and can be more difficult to detect by mammogram than IDC.

Inflammatory breast cancer: This invasive breast cancer, which accounts for about 1% of all breast cancers, is extremely aggressive. Multiple skin symptoms associated with this cancer are caused by cancer cells blocking lymph vessels or channels in skin over the breast.

Medullary carcinoma: This special type of infiltrating breast cancer, which presently accounts for about 5% of breast cancers, has a relatively well defined, distinct boundary between tumor tissue and normal tissue. The prognosis for medullary carcinoma is better than for other types of invasive breast cancer.

Mucinous carcinoma: Mucinous carcinoma originates from mucus-producing cells. The prognosis for mucinous carcinoma is better than for the more common types of invasive breast cancer.

Paget's disease of the nipple: This type of breast cancer starts in the ducts and spreads to the skin of the nipple and the areola. It is a rare type of breast cancer, occurring in only 1% of all cases. Paget's disease can be associated with in situ carcinoma, or with infiltrating breast carcinoma. If no lump can be felt in the breast tissue, and the biopsy shows DCIS but no invasive cancer, the prognosis is excellent.

Phyllodes tumor: This very rare type of breast tumor forms from the stroma of the breast, in contrast to carcinomas which develop in the ducts or lobules. Phyllodes (also spelled phylloides) tumors are usually benign, but are malignant on rare occasions.

Tubular carcinoma: Accounting for about 2% of all breast cancers, tubular carcinomas are a special type of infiltrating breast carcinoma. They have a better prognosis than usual infiltrating ductal or lobular carcinomas.

Use of the Methods of the Invention in Cancers of Other Origins

In addition to use in diagnosis of breast cancer, detection of GSEF gene product expression levels can be used in the diagnosis, prognosis, grading, and/or stating of cancers of other tissue origins. In general, as noted above, the methods of the invention can be used in conjunction with any tissue in which an alteration in GSEF gene product expression levels is associated with development of a cancer-associated phenotype, e.g., metastasis. Exemplary cancers in which the methods of the invention can find use include, but are not necessarily limited to, prostate cancer, cervical cancers, melanomas, colorectal adenocarcinomas, Wilms= tumor, retinoblastoma, sarcomas, myosarcomas, lung carcinomas, leukemias, such as chronic myelogenous leukemia, promyelocytic leukemia, monocytic leukemia, and myeloid leukemia, and lymphomas, such as histiocytic lymphoma. Of particular interest is the detection of GSEF expression in prostate tissues to facilitate the identification of cancerous prostate cells, as well as the grading and/or staging of such potential prostate tumors.

For example, GSEF gene product expression levels can be used in the diagnosis of prostate cancer, and/or to differentiate between the types or grades of prostate cancer, particularly to distinguish a Stage I or Stage II prostate cancer (non-metastatic or low metastatic potential) from a Stage II (cancer spread outside the prostate capsule) or Stage IV (metastatic) prostate cancer at a early stage (e.g., prior to development of significant metastases). As with breast and other cancers, detection of high metastatic potential cells can also provide information regarding the dangers of recurrence of cancer either before or after therapy (e.g., chemotherapy, surgery, etc.).

GSEF gene product expression levels can also be used in the diagnosis of lung cancers, and/or to differentiate between the types of lung cancers. The two main types of lung cancer are small cell carcinomas and nonsmall cell carcinomas. Small cell carcinoma (also called oat cell carcinoma) usually starts in one of the larger bronchial tubes, grows fairly rapidly, and is likely to be large by the time of conventional diagnosis. Nonsmall cell lung cancer (NSCLC) is made up of three general subtypes: epidermoid carcinoma, adenocarcinoma, and large cell carcinoma. Epidermoid carcinoma (also called squamous cell carcinoma) usually starts in one of the larger bronchial tubes and grows relatively slowly. Adenocarcinoma starts growing near the outside surface of the lung and can vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

GSEF gene product expression levels can also be used to detect, diagnose, and/or differentiate colon cancers. The major types of colon cancer include familial adenomatous polyposis (FAP), Gardner=s syndrome, and hereditary non-polyposis colon cancer (HNPCC. FAP is associated with hundreds or even thousands of polyps in the patient≈ s colon and rectum, which polyps usually first appear during the teenage years. Cancer nearly always develops in one or more of these polyps between the ages of 30 and 50. Like FAP, Gardner's syndrome is associated with polyps and colorectal cancers that develop at a young age, and is also associated with benign tumors of the skin, soft connective tissue, and bones. HNPCC patients tend to develop colorectal cancer at a young age, without first having many polyps. In addition, recent research has found an inherited tendency to developing colorectal cancer among some Jews of Eastern European descent, which population would benefit from prognostic and diagnosis methods for early detection of the development of the metastatic phenotype.

Detection Of Polymorphisms And Rational Therapy

In one embodiment, the nucleic acid and/or polypeptide compositions described herein are used to detect the presence of polymorphisms in the sequence, or variation in the expression of the subject genes, e.g., genotyping. Such analysis may be performed to determine whether a particular polymorphism is associated with a disease state or genetic predisposition to a disease state, particularly conditions, disorders, or diseases associated with GSEF (e.g., metastatic cancers) Analysis of sequence encoding a gene product of interest, e.g., GSEF, or analysis of a sequence of a promoter or other regulatory sequence that provide for expression of such a gene product may also be performed for pharmacogenetic analysis to assess the association between an individual's genotype and that individual's ability to react to a therapeutic agent. Differences in target sensitivity can lead to toxicity or therapeutic failure. Relationships between polymorphisms in expression levels or specificity can be used to optimize therapeutic dose administration.

Genetic polymorphisms can be identified in a GSEF gene (e.g., within a coding region of a GSEF genomic sequence, and/or within a regulatory domain of such a sequence), and the nucleic acids comprising the polymorphic sequences used to screen patients for altered reactivity and adverse side effects in response to drugs that act on GSEF polypeptides. GSEF genotyping can be performed by DNA or RNA sequence and/or hybridization analysis of any convenient sample from a patient, e.g. biopsy material, blood sample, scrapings from cheek, etc. A nucleic acid sample from an individual is analyzed for the presence of polymorphisms in GSEF, particularly those that affect the activity, responsiveness to a therapeutic agent (e.g., inhibitor or enhancer of activity), or expression of GSEF. Specific sequences of interest include any polymorphism that lead to changes in basal expression in one or more tissues, to changes in the modulation of GSEF expression, or alterations in GSEF specificity and/or activity. Of particular interest are those changes that lead to a decrease in GSEF expression or activity, which decrease is associated with development of the metastatic phenotype.

The effect of a polymorphism in a GSEF gene sequence on the response to a particular agent may be determined by in vitro or in vivo assays. Such assays may include monitoring during clinical trials, testing on genetically defined cell lines, etc. The response of an individual to the agent can then be predicted by determining the GSEF genotype with respect to the polymorphism. Where there is a differential distribution of a polymorphism by racial background, guidelines for drug administration can be generally tailored to a particular ethnic group. Such studies can provide an understanding of the individual's nonresponsiveness to a therapy that has proven effective in a large number of patients having a similar syndrome (e.g., to facilitate identification of patients that are or are likely to be nonresponsive to administration of an inhibitor of a gene product that interferes with GSEF activity).

Biochemical studies may be performed to determine whether a sequence polymorphism in a GSEF coding region or control regions is associated with disease, for example the association of a GSEF polymorphisms with specific diseases or conditions, e.g., metastatic cancers, including but not limited to breast cancer, prostate cancer, etc. Disease associated polymorphisms may include deletion or truncation of the gene, mutations that alter expression level, that affect GSEF activity, etc.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of current techniques may be found in Sambrook et al. Molecular Cloning: A Laboratory Manual, CSH Press 1989, pp. 14.2B 14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *Nucl. Acids Res.* 18:2887-2890; and Delahunty et al. (1996) *Am. J. Hum. Genet.* 58:1239-1246. A detectable label may be included in an amplification reaction. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) *Nature Genet.* 14:441-447; Lockhart et al. (1996) *Nature Biotechnol.* 14:1675-1680; and De Risi et al. (1996) *Nature Genet.* 14:457-460.

Screening for polymorphisms in a GSEF amino acid sequence may be based on the functional or antigenic characteristics of the protein. Protein truncation assays are useful in detecting deletions that may affect the biological activity of the protein. Various immunoassays designed to detect polymorphisms in a GSEF proteins may be used in screening. Where many diverse genetic mutations lead to a particular disease phenotype, functional protein assays have proven to be effective screening tools.

Antibodies specific for a GSEF gene product may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Pharmaceutical Compositions and Therapeutic Uses

Pharmaceutical compositions can comprise GSEF polypeptides, antibodies, or GSEF polynucleotides. The pharmaceutical compositions comprise a therapeutically effective amount of either polypeptides, antibodies, or polynucleotides of the claimed invention. In general, the pharmaceutical compositions are based upon molecules that can enhance GSEF biological activity (e.g., by increasing the amount of GSEF present in a cell (e.g., by increasing expression of a GSEF gene product in a cancerous cell, e.g., by introducing a GSEF-encoding sequence into the cell for expression therein)), or by inhibiting a GSEF inhibitor) in order to inhibit, delay, or otherwise interfere with the development of metastasis in a cancerous cell. Similarly, methods for treatment, e.g., inhibition of development of the metastatic phenotype or reversal of the metastatic phenotype, employ such pharmaceutical compositions that enhance GSEF biological activity.

The term Atherapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/ kg to 50 mg/kg or 0.05 mg/kg to about 10 mg/kg of the DNA constructs in the individual to which it is administered.

A pharmaceutical composition can also contain a pharmaceutically acceptable carrier. The term Apharmaceutically acceptable carrier refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington≡ s Pharmaceutical Sciences (Mack Pub. Co., N.J. 1991).

Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier.

Delivery Methods. Once formulated, the compositions of the invention can be (1) administered directly to the subject (e.g., as polynucleotide or polypeptides) or (2) delivered ex vivo, to cells derived from the subject (e.g., as in ex vivo gene therapy, see, e.g., WO 93/14778). In general, the therapy will involve direct delivery of the pharmaceutical composition to the subject. Direct delivery of the compositions will generally be accomplished by injection, either subcutaneously, intraperitoneally, intravenously or intramuscularly, or delivered to the interstitial space of a tissue. The compositions can also be administered directly into a tumor or lesion. Other modes of administration include oral and pulmonary administration, suppositories, and transdermal applications, needles, and gene guns or hyposprays. Dosage treatment can be a single dose schedule or a multiple dose schedule.

Various methods can be used to administer the therapeutic composition directly to a specific site in the body. For example, a small metastatic lesion is located and the therapeutic composition injected several times in several different locations within the body of the tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. X-ray imaging can be used to assist in certain of the above delivery methods.

The therapeutic compositions can also be delivered using receptor-mediated targeted delivery. For examples of such receptor-mediated delivery, see, e.g., Findeis et al., *Trends Biotechnol.* (1993) 11:202; Chiou et al., Gene Therapeutics: Methods And Applications Of Direct Gene Transfer (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (*USA*) (1990) 87:3655; Wu et al., *J. Biol. Chem.* (1991) 266:338.

Where the therapeutic composition comprises a polynucleotide, the polynucleotides can be administered in a range of about 100 ng to about 200 mg of DNA for local administration. Concentration ranges of about 500 ng to about 50 mg, about 1 µg to about 2 mg, about 5 µg to about 500 µg, and about 20 µg to about 100 µg of DNA can also be used. The actual dosage will vary according to a variety of factors that will be readily appreciated by the ordinarily skilled artisan, such as efficiency of transformation and expression. Where greater expression is desired over a larger area of tissue, larger amounts of polynucleotides or the same amounts readministered in a successive protocol of administrations, or several administrations to different adjacent or close tissue portions of, for example, a tumor site, can be performed. In all cases, routine experimentation in clinical trials will determine specific ranges for optimal therapeutic effect.

Various vectors and protocols to accomplish delivery of polynucleotides to, and expression in, a cell in vivo are known in the art. The polynucleotide delivery vehicle can be of viral or non-viral origin (see generally, Jolly, *Cancer Gene Therapy* (1994) 1:51; Kimura, *Human Gene Therapy* (1994)

5:845; Connelly, *Human Gene Therapy* (1995) 1:185; and Kaplitt, *Nature Genetics* (1994) 6:148). Gene therapy vehicles for delivery of constructs including a coding sequence of a GSEF polypeptide can be administered either locally or systemically. Expression of such GSEF coding sequences can be induced using endogenous mammalian or heterologous promoters (i.e., promoters that are derived from a source other than that of the GSEF gene to be expressed), and can be either constitutive or regulated.

Where a viral vector is used, the recombinant viral vector can be based upon, for example, a retroviral vector, alphavirus-based vectors (e.g., vectors based on Sindbis virus, Semliki forest virus, Ross River virus, Venezuelan equine encephalitis virus, etc.), parvoviral-vector (e.g., adeno-associated virus (AAV)), or an adenoviral vector. Retroviral vectors may be less desirable where the target cell is rapidly dividing, e.g., where the target cell is a rapidly dividing cancerous cell.

Non-viral vehicles and methods can be employed. Such vehicles and methods can be based upon, for example, liposomes, lipid:DNA complexes, polycationic condensed DNA (linked or unlinked to killed adenovirus), ligand linked DNA, photopolymerized hydrogel materials; naked DNA; hand-held gene transfer particle guns, ionizing radiation (see, e.g., U.S. Pat. No. 5,206,152), nucleic charge neutralization or fusion with cell membranes. Additional approaches are described in Philip, Mol. Cell Biol. (1994) 14:2411, and in Woffendin, Proc. Natl. Acad. Sci. (1994) 91:1581.

Modulation of Gene Expression

The GSEF genes, gene fragments, or the encoded protein or protein fragments are useful in gene therapy to treat disorders associated with defects in a GSEF gene. GSEF genes, gene fragments, promoter elements, or the encoded protein or protein fragments are of particular interest. Expression vectors may be used to introduce the desired GSEF polypeptide-encoding gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The GSEF polypeptide-encoding gene or may be introduced into tissues or host cells by any number of routes, including, but not necessarily limited to, viral infection, direct injection, microinjection, or fusion of vesicles. Direct injection of DNA for expression is described in, for example, U.S. Pat. No. 5,580,859. Jet injection may also be used for intramuscular administration, as described by Furth et al. (1992) *Anal. Biochem.* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the GSEF DNA, then bombarded into skin cells. Use of liposomes for delivery of DNA into a living cell is also known in the art, see, e.g., U.S. Pat. No. 4,394,448.

Antisense molecules can be used to down-regulate expression of a GSEF in cells, e.g., to study the mechanisms of GSEF in development of the metastatic phenotype, e.g., to identify gene products expressed in the absence of GSEF expression. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be introduced, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3=-O=-5=-S-phosphorothioate, 3=-S-5=-O-phosphorothioate, 3=-CH2-5=-O-phosphonate and 3=-NH-5=-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2=-OH of the ribose sugar may be altered to form 2=-O-methyl or 2=-O-allyl sugars, which provides resistance to degradation without comprising affinity. Modification of the heterocyclic bases must maintain proper base pairing. Some useful substitutions include deoxyuridine for deoxythymidine; 5-methyl-2=-deoxycytidine and 5-bromo-2=-deoxycytidine for deoxycytidine. 5- propynyl-2=-deoxyuridine and 5-propynyl-2=-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl. Biochem. Biotechnol.* 54:43-56.

Genetically Altered Cell or Animal Models for GSEF Function

The subject nucleic acids can be used to generate transgenic animals or site specific gene modifications in cell lines. Transgenic animals may be made through homologous recombination, where the normal GSEF locus is altered. Alternatively, a nucleic acid construct (e.g., encoding a human GSEF cDNA or promoter) is randomly integrated into the genome. Vectors for stable integration include plasmids, retroviruses and other animal viruses, YACs, and the like. Transgenic animals may be homozygous or heterozygous for the gene modification, and may be a "knock-out" transgenic animal (i.e., a transgenic animal in which one allele of the corresponding GSEF -encoding gene is rendered nonfunctional) and/or a "knock-in" transgenic animal (i.e., a transgenic animal having at least one copy of a recombinant GSEF -encoding sequence present in its genome, e.g., in its germ line DNA). Methods for generating transgenic animals are well known in the art.

The modified cells or animals are useful in the study of the function and regulation. of GSEF, particularly with respect to study of the development of the metastatic phenotype, as well as models to develop and test cancer therapies. For example, a series of small deletions and/or substitutions may be made in the GSEF gene to determine the role of GSEF, binding to agents or candidate agents for modulation of GSEF function, etc. Of interest are the use of the nucleic acid compositions of the invention to construct transgenic animal models for conditions or disorders associated with defects in GSEF where expression of GSEF is specifically reduced or absent. Specific constructs of interest include anti-sense GSEF that will inhibit expression of GSEF; expression of dominant negative GSEF mutations; etc. One may also provide for expression of the GSEF gene or variants thereof in cells or tissues where it is not normally expressed or at abnormal times of development.

DNA constructs for homologous recombination can comprise at least a portion of the selected GSEF -encoding gene with the desired genetic modification, and can further comprise regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods Enzymol.* 185:527-537.

Transgenic animals can be generated using any suitable method available in the art. For example, transgenic animals can be generated by using embryonic stem (ES) cells. To this end an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having a heterozygous modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in fictional studies, drug screening, etc., e.g. to determine the effect of a candidate drug on GSEF or related gene activation, oncogenesis, etc.

Screening for Agents that Alter Activity of GSEF and/or Gene Products Regulated by GSEF GSEF expression is associated with suppression of development of the metastatic phenotype. Thus, agents of interest in the present invention for therapy or for study of the role of GSEF and development of cancer therapies are designed to modulate (e.g., inhibit or enhance, preferably enhance in the case of therapy) GSEF activity in suppression of metastasis. Agents that enhance biological activity of GSEF are of particular interest for use in therapy to inhibit metastasis or development of metastasis. In addition, since GSEF acts as a regulator of the expression, gene products that are affected in relative expression levels by GSEF activity are also of interest as therapeutic targets. Thus, candidate agents that modulate the activity of gene products that exhibit enhanced or decreased expression in response to GSEF activity are also of interest in the present invention.

The subject polypeptides may be used in in vitro and in vivo models to test the specificity of novel candidate compounds, and of analogs and derivatives of compounds known to act on GSEF. The subject polypeptides may be used in such assays in their native form (e.g., full-length), or may be modified by sequence deletion, insertion, substitution, etc. Use of modified GSEF in such screening assays can facilitate identification of, for example, regions of the polypeptide that are important in normal biological function of the polypeptide, identification of especially suitable target sites for drug interaction, and/or identification of gene products that have their expression regulated (e.g., upregulated or downregulated) by GSEF activity that may be suitable drug targets. Thus such models facilitate rationale drug design for the development of compounds that specifically inhibit or enhance biological activity of the various GSEF.

In one embodiment, drug screening is performed using an in vitro model, a genetically altered cell or animal, or purified GSEF protein, either as monomers, homomultimers or heteromultimers. One can identify ligands or substrates that bind to, modulate or mimic the action of GSEF, and/or that act on other genes or gene product that facilitate or inhibit GSEF activity, or that exhibit activities that are modulated by GSEF activity. For example, drug screening can identify agents that provide a replacement for GSEF function in abnormal cells having relatively low GSEF activity levels (e.g. cells having high metastatic potential). Of particular interest are screening assays for agents that have a low toxicity for human cells. A wide variety of assays may be used for this purpose, including monitoring GSEF activity levels in the presence of candidate agent, labeled in vitro agent-protein binding assays, electrophoretic mobility shift assays, immunoassays for protein binding, and the like. The purified protein may also be used for determination of three-dimensional crystal structure, which can be used for modeling intermolecular interactions.

In one embodiment of particular interest, the screening method involves the use of a high potential metastatic cell line (e.g., MDA-MB-435) stably transfected with GSEF. Expression of GSEF in the high potential metastatic cell line facilitates reversion of the cell to a low metastatic potential cell. The relative expression levels of genes in the GSEF-reverted cell line can be compared to the expression levels of genes in the parent cell line (i.e., the high metastatic potential cell), as well as to low metastatic potential cells and normal cells, to identify those gene products that are differentially expressed in the presence and absence of GSEF expression or activity. Such differentially expressed genes represent potential therapeutic targets that act downstream of GSEF. In short, GSEF can be used to turn on and to turn off expression of genes that can have a role in development or inhibition of the metastatic phenotype.

The term "agent" as used herein describes any molecule, e.g. protein or pharmaceutical, with the capability of altering or mimicking the physiological function of GSEF or of a gene regulated by GSEF. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as- acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Of particular interest in the present invention is the identification of agents that substantially specifically affect GSEF biological activity. Agents that enhance GSEF activity, e.g., by increasing GSEF expression, by mimicking GSEF activity, and/or by inhibiting an endogenous inhibitor of GSEF activity, thus are useful in the treatment of cancer, particularly metastatic or high potential metastatic cancer, particularly breast cancer.

The compounds having the desired pharmacological activity may be administered in a physiologically acceptable carrier to a host in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-100 wt. %. The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EMBODIMENTS RELATING TO HX2004-6

Overview

The present invention is based upon the identification and isolation of a polynucleotide sequence encoding a human HX2004-6 polypeptide. Accordingly, the present invention encompasses such human HX2004-6 polypeptide-encoding polynucleotides, as well as human HX2004-6 polypeptides encoded by such polynucleotides. Overexpression of HX2004-6 is linked to adenocarcinomas of pancreas, colon, and breast, particularly neoplasms of ductal epithelial cells of pancreas, colon, and breast.

The present invention provides methods of detecting an HX2004-6 polynucleotide or polypeptide in a biological sample for diagnostic purposes. The invention also encompasses the use of the polynucleotides disclosed herein to facilitate identification and isolation of polynucleotide and polypeptide sequences having homology to a human HX2004-6 polynucleotide and polypeptide of the invention. The human HX2004-6 polypeptides and polynucleotides of the invention are also useful in the identification of human HX2004-6 polypeptide-binding compounds, particularly compounds which specifically bind human HX2004-6 polypeptide. Compounds which specifically bind HX2004-6 are useful in diagnostic assays to detect the presence of and/or measure a level of HX2004-6 polypeptide. In addition, the human HX2004-6 polypeptides, polynucleotides, and antibodies of the invention are useful in the diagnosis, prevention and treatment of disease associated with human HX2004-6 overexpression.

The human HX2004-6 polypeptide-encoding polynucleotides of the invention can also be used as a molecular probe with which to determine the structure, location, and expression of the human HX2004-6 polypeptide and related polypeptides in mammals (including humans), and to investigate potential associations between disease states or clinical disorders and defects or alterations in human HX2004-6 polypeptide structure, expression, or function.

The human HX2004-6 polynucleotides and antibodies specific for HX2004-6 polypeptides are also useful in screening assays to identify substances which modulate HX2004-6 expression in a cell.

HX2004-6 Nucleic Acid

The present invention provides isolated HX2004-6 nucleic acids. These nucleic acids are useful in methods to produce HX2004-6 polypeptides, as well as in diagnostic methods, including methods to detect an HX2004-6 mRNA in a biological sample, methods to identify polynucleotides having sequence similarity to HX2004-6 polynucleotides of the invention, methods to detect an alteration in HX2004-6 polynucleotide sequence in a cell, and methods to identify substances which modulate HX2004-6 mRNA and/or polypeptide levels in a cell.

Figures 29, 30:
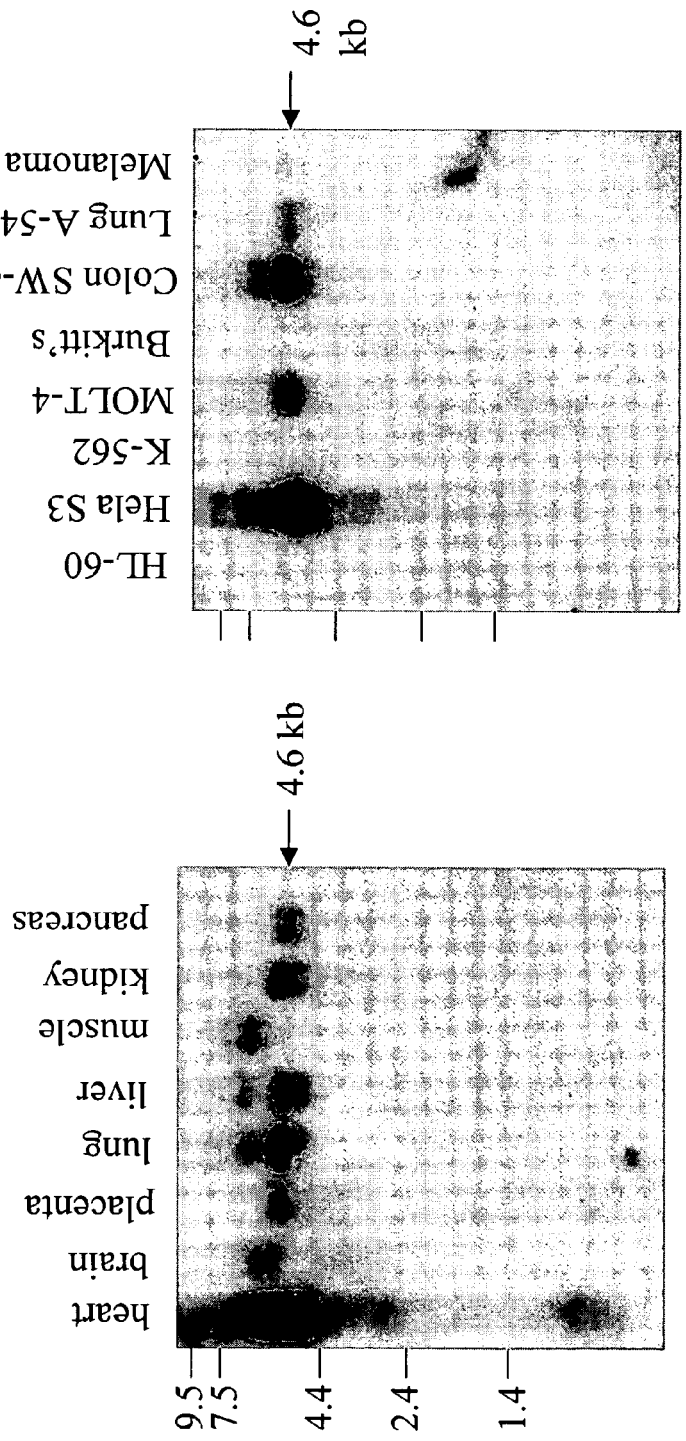
FIG. 29 depicts an autoradiograph of a human multiple tissue Northern blot probed with PCR-2004. RNA was from the following tissues: Lane 1, heart; Lane 2, brain; Lane 3, placenta; Lane 4, lung; Lane 5, liver; Lane 6, skeletal muscle; Lane 7, kidney; Lane 8, pancreas.
FIG. 30 depicts an autoradiograph of a human multiple cancer cell line Northern blot probed with PCR-2004. Cell lines were as follows: Lane 1, HL-60 (promyelocytic leukemia); Lane 2, HeLa cell S3; Lane 3, K-562 (chronic myelogenous leukemia); Lane 4, MOLT-4 (acute lymphoblastic leukemia); Lane 5, Raji (Burkitt's lymphoma); Lane 6, SW480 (colorectal adenocarcinoma); Lane 7, A549 (lung carcinoma); Lane 8, G361 (melanoma).

In some embodiments, an HX2004-6 polynucleotide of the invention has the sequence shown in SEQ ID NO:52 (FIG. 28). In other embodiments, an HX2004-6 polynucleotide has the sequence shown in nucleotides 1-1724 of SEQ ID NO:52. In other embodiments, an HX2004-6 polynucleotide has the sequence shown in nucleotides 698-1724 of SEQ ID NO:52. In other embodiments, an HX2004-6 polynucleotide has the sequence shown in SEQ ID NO:54 (FIG. 29). In other embodiments, an HX2004-6 polynucleotide has the sequence shown in nucleotides 1-1754 of SEQ ID NO:54. In still other embodiments, an HX2004-6 polynucleotide has the sequence shown in nucleotides 728-1754 of SEQ ID NO:54. Also encompassed are the complement of any of the aforementioned sequences. Also encompassed by "HX2004-6 polynucleotide" are fragments of the aforementioned sequences. In one embodiment, a fragment of an HX2004-6 polynucleotide has the sequence of nucleotides 559 to 1107 of the sequence shown in SEQ ID NO:54, and shown in bold in FIG. 29. This sequence, which is given as SEQ ID NO:56 is also the sequence of the polynucleotide probe referred to herein as "the 2004-6 probe". Further encompassed are polynucleotides that hybridize under stringent hybridization conditions with any one of the aforementioned sequences, as described in detail herein. The invention also encompasses polypeptides encoded by any of the polynucleotide sequences described herein.

The term "HX2004-6 gene" is encompassed in the term "HX2004-6 polynucleotide" and is used generically to designate HX2004-6 genes and their alternate forms. "HX2004-6 gene" is also intended to mean the open reading frame encoding specific HX2004-6 polypeptides, introns, and adjacent 5' and 3' non-coding nucleotide sequences involved in the regulation of expression, up to about 1 kb beyond the coding region, but possibly further in either direction. The DNA sequences encoding HX2004-6 may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the HX2004-6 polypeptide.

While other genomic HX2004-6 sequences of other sources may have non-contiguous open reading frames (e.g., where introns interrupt the protein coding regions), the human genomic HX2004-6 sequence has no introns interrupting the coding sequence. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where HX2004-6 is expressed. The sequences of the HX2004-6 promoter elements of the invention can be based on the nucleotide sequences of any species (e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human) and can be isolated or produced from any source whether natural, synthetic, semi-synthetic or recombinant.

As shown in Example 20, overexpression of HX2004-6 is restricted to neoplasms of pancreas, breast, and colon, particularly neoplasms of ductal epithelial cells of these tissues. The tissue-restricted overexpression of HX2004-6 is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. 1995 Mol Med 1:194-205; Mortlock et al. 1996 Genome Res. 6: 327-33; and Joulin and Richard-Foy (1995) Eur J Biochem 232: 620-626.

As shown in Example 23, HX2004-6 is overexpressed in certain cancer cells, namely pancreas, colon, and breast cancers, particularly adenocarcinomas, particularly cancerous ductal epithelial cells of these tissues. Accordingly, in some embodiments, HX2004-6 polynucleotides are over-expressed in exocrine pancreatic, colorectal, and/or breast cancer cells, particularly adenocarcinomas, particularly cancerous ductal epithelial cells of these cancers. "Overexpression" intends that an HX2004-6 mRNA is found at levels at least about 1.5-fold, normally at least about 2-fold, usually at least about 5-fold, generally at least about 10-fold, up to at least about 50-fold or higher when compared with a non-cancerous cell of the same cell type. Those skilled in the art can readily determine whether an HX2004-6 nucleic acid is overexpressed, using any known method, including Northern blot analysis, in situ hybridization, and the like, using an HX2004-6 nucleic acid of the invention or fragment thereof.

HX2004-6 regulatory sequences may be used to identify cis acting sequences required for transcriptional or translational regulation of HX2004-6 expression, especially in different tissues or stages of development, and to identify cis acting sequences and trans acting factors that regulate or mediate HX2004-6 expression. Such transcriptional or translational control regions may be operably linked to an HX2004-6 gene or other genes in order to promote expression of wild type or altered HX2004-6 or other proteins of interest in cultured cells, or in embryonic, fetal or adult tissues, and for gene therapy. HX2004-6 transcriptional or translational control regions can also be used to identify extracellular signal molecules that regulate HX2004-6 promoter activity, and thus regulate HX2004-6 expression.

The nucleic acid compositions used in the subject invention may encode all or a part of the HX2004-6 polypeptides as appropriate. SEQ ID NO:53 gives the amino acid translation of the nucleotide sequence given as SEQ ID NO:52. SEQ ID NO:55 gives the amino acid translation of the nucleotide sequence given as SEQ ID NO:54. In some embodiments, an HX2004-6 polynucleotide encodes a polypeptide having the amino acid sequence shown in SEQ ID NO:53. In other embodiments, an HX2004-6 polynucleotide encodes a polypeptide having the amino acid sequence shown as amino acids 1-342 of SEQ ID NO:53. In other embodiments, an HX2004-6 polynucleotide encodes a polypeptide having the amino acid sequence shown in SEQ ID NO:55. In other embodiments, an HX2004-6 polynucleotide encodes a polypeptide having the amino acid sequence given as amino acids 1-352 of SEQ ID NO:55. Also encompassed are HX2004-6 polynucleotides encoding variants, fragments and fusion proteins of the aforementioned polypeptides. Accordingly, the invention encompasses an HX2004-6 polynucleotide which encodes a polypeptide having an amino acid sequence of at least 5, usually at least about 15, usually at least about 30 or more contiguous amino acids of amino acids 1-342 of SEQ ID NO:53 or amino acids 1-352 of SEQ ID NO:55; variants of an HX200-46 polypeptide, particularly variants having conservative amino acid substitutions of the aforementioned fragments; and fusion proteins comprising any one of the aforementioned fragments and a heterologous polypeptide (i.e., a non-HX2004-6 polypeptide).

HX2004-6 nucleic acids can be obtained by chemical or biochemical synthesis, by recombinant DNA techniques, or by isolating the nucleic acids from a biological source. Fragments may be obtained of the DNA sequence by chemically synthesizing oligonucleotides in accordance with conventional methods, by restriction enzyme digestion, by amplification (e.g., by a polymerase chain reaction), etc. For the most part, DNA fragments will be of at least about ten contiguous nucleotides, usually at least about 15 nucleotides (nt), more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The HX2004-6 gene is isolated and obtained in substantial purity, generally as other than an intact mammalian chromosome. Usually, the DNA will be obtained substantially free of other nucleic acid sequences that do not include an HX2004-6 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They can be used in methods to detect HX2004-6 mRNA in a biological sample, as described in more detail below.

They may also be used as probes for identifying homologs of HX2004-6. Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403-10. For the purposes of this invention, sequence identity is determined by the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequences sharing a high degree of nucleotide sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human;

rodents, such as rats and mice, canines, felines, bovines, ovines, equines, yeast, *Drosophila, Caenhorabditis*, etc.

The HX2004-6-encoding DNA may also be used to identify expression of the gene in a biological specimen. The manner in which one probes cells for the presence of particular nucleotide sequences, as genomic DNA or RNA, is well established in the literature and does not require elaboration here. mRNA may be isolated from a cell sample, or may be detected without being first isolated. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an HX2004-6 sequence is indicative of HX2004-6 gene expression in the sample.

The HX2004-6 nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the HX2004-6 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but generally not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of HX2004-6 polypeptides with other polypeptides, or to alter properties of the proteins that affect their function or regulation. Such modified HX2004-6 sequences can be used, for example, to generate transgenic animals.

Techniques for in vitro mutagenesis of cloned genes are known. Examples of protocols for scanning mutations may be found in Gustin et al., 1993 Biotechniques 14:22; Barany, 1985 Gene 37:111-23; Colicelli et al., 1985 Mol Gen Genet 199:537-9; and Prentki et al., 1984 Gene 29:303-13. Methods for site-specific mutagenesis can be found in Sambrook et al., 1989 Molecular Cloning: A Laboratory Manual, CSH Press, pp. 15.3-15.108; Weiner et al., 1993 Gene 126:35-41; Sayers et al., 1992 Biotechniques 13:592-6; Jones and Winistorfer, 1992 Biotechniques 12:528-30; Barton et al., 1990 Nucleic Acids Res. 18:7349-55; Marotti and Tomich, 1989 Gene Anal. Tech. 6:67-70; and Zhu 1989 Anal. Biochem. 177:120-4.

Recombinant Vectors

The present invention further provides recombinant vectors comprising an HX2004-6 polynucleotide of the invention. Recombinant vectors are useful for propagation of the subject HX2004-6 polynucleotides (cloning vectors). They are also useful for effecting expression of an HX2004-6 polynucleotide in a cell. The choice of appropriate vector is well within the skill of the art. A wide variety of vectors, both cloning vectors and expression vectors, are known to those skilled in the art, have been described in, inter alia, Current Protocols in Molecular Biology, (F. M. Ausubel, et al., Eds. 1987, and updates), and can be used in the present invention. Many such vectors are available commercially.

The subject polynucleotides are generally propagated by placing an HX2004-6 polynucleotide in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence.

Other vectors are suitable for expression in cells in culture ("expression vectors"). These vectors will generally include regulatory sequences ("control sequences" or "control regions") which are necessary to effect the expression of an HX2004-6 polynucleotide to which they are operably linked. Still other vectors are suitable for transfer and expression in cells in a whole organism or person.

Host Cells

The present invention further provides isolated host cells comprising HX2004-6 polynucleotides of the invention. Suitable host cells include prokaryotes such as *E. coli, B. subtilis, S. cerevisiae*; and eukaryotic cells, including insect cells in combination with baculovirus vectors, yeast cells, such as *Saccharomyces cerevisiae*, or cells of a higher organism such as vertebrates, particularly mammals, e.g. COS 7 cells, may be used as the expression host cells. Host cells can be used for the purposes of propagating an HX2004-6 polynucleotide, for production of an HX2004-6 polypeptide, or in a screening method as described below.

HX2004-6 Transgenic Animals

The HX2004-6-encoding nucleic acids can be used to generate genetically modified non-human animals or site specific gene modifications in cell lines. The term "transgenic" is intended to encompass genetically modified animals having a deletion or other knock-out of HX2004-6 gene activity, having an exogenous HX2004-6 gene that is stably transmitted in the host cells, "knock-in" having altered HX2004-6 gene expression, or having an exogenous HX2004-6 promoter operably linked to a reporter gene. Of particular interest are homozygous and heterozygous knock-outs of HX2004-6.

Transgenic animals may be made through homologous recombination, where the HX2004-6 locus is altered. Alternatively, a nucleic acid construct is randomly integrated into the genome. Vectors for stable integration include plasmids, retroviruses and other animal viruses, YACs (yeast artificial chromosomes), and the like. Of interest are transgenic mammals, preferably a mammal from a genus selected from the group consisting of *Mus* (e.g., mice), *Rattus* (e.g., rats), *Oryctologus* (e.g., rabbits) and *Mesocricetus* (e.g., hamsters). More preferably the animal is a mouse which is defective or contains some other alteration in HX2004-6 gene expression or function.

A "knock-out" animal is genetically manipulated to substantially reduce, or eliminate endogenous HX2004-6 function, preferably such that target gene expression is undetectable or insignificant. Different approaches may be used to achieve the "knock-out". A chromosomal deletion of all or part of the native HX2004-6 homolog may be induced. Deletions of the non-coding regions, particularly the promoter region, 3' regulatory sequences, enhancers, or deletions of gene that activate expression of the HX2004-6 genes. A functional knock-out may also be achieved by the introduction of an anti-sense construct that blocks expression of the native HX2004-6 gene (for example, see Li and Cohen (1996) Cell 85:319-329).

Conditional knock-outs of HX2004-6 gene function can also be generated. Conditional knock-outs are transgenic animals that exhibit a defect in HX2004-6 gene function upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of HX2004-6 gene function can be produced using the Cre-loxP recombination system (see, e.g., Kilby et al. 1993 Trends Genet 9:413-421). Cre is an enzyme that excises the DNA between two recognition sequences, termed loxP. This system can be used in a variety of ways to create conditional knock-outs of HX2004-6. For example, two independent transgenic mice can be produced: one transgenic for an HX2004-6. sequence flanked by loxP sites and a second transgenic for Cre. The Cre transgene can be under the control of an inducible or developmentally regulated promoter (Gu et al. 1993 Cell 73:1155-1164; Gu et al. 1994 Science 265:103-106), or under control of a tissue-specific or cell type-specific promoter (e.g., a pancreas-specific promoter or brain tissue-specific promoter). The HX2004-6 transgenic is then crossed with the Cre transgenic to produce progeny deficient for the HX2004-6 gene only in those cells that expressed Cre during development.

Transgenic animals may be made having an exogenous HX2004-6 gene. For example, the transgenic animal may comprise a "knock-in" of an HX2004-6 gene, such that the host cell genome contains an alteration that results in altered expression (e.g., increased (including ectopic) or decreased expression) of an HX2004-6 gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the HX2004-6 gene or a homozygous knock-in of the HX2004-6. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an HX2004-6 polypeptide, or may utilize the HX2004-6 promoter operably linked to a reporter gene. Where the introduced gene is a coding sequence, it is usually operably linked to a promoter, which may be constitutive or inducible, and other regulatory sequences required for expression in the host animal.

Specific constructs of interest include, but are not limited to, anti-sense HX2004-6, or a ribozyme based on an HX2004-6 sequence, which will block HX2004-6 expression, as well as expression of dominant negative HX2004-6 mutations, and over-expression of an HX2004-6 gene. A detectable marker, such as lac Z may be introduced into the HX2004-6 locus, where upregulation of expression of the HX2004-6 gene will result in an easily detected change in phenotype. Constructs utilizing a promoter region of the HX2004-6 genes in combination with a reporter gene or with the coding region of HX2004-6 are also of interest. Constructs having a sequence encoding a truncated or altered (e.g, mutated) HX2004-6 are also of interest.

The modified cells or animals are useful in the study of function and regulation of HX2004-6. Such modified cells or animals are also useful in, for example, the study of the function and regulation of genes whose expression is affected by HX2004. Thus, the transgenic animals of the invention are useful in identifying downstream targets of HX2004-6, as such targets may have a role in the phenotypes associated with overexpression of HX2004-6.

Animals may also be used in functional studies, drug screening, etc., e.g. to determine the effect of a candidate drug on HX2004-6 expression. A series of small deletions and/or substitutions may be made in the HX2004-6 genes to determine the role of different polypeptide-encoding regions in DNA binding, transcriptional regulation, etc. By providing expression of HX2004-6 protein in cells in which it is otherwise not normally produced (e.g., ectopic expression), one can induce changes in cell behavior.

DNA constructs for homologous recombination will comprise at least a portion of the HX2004-6 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185: 527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wild-type animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well characterized, such as *C. elegans, D. melanogaster* and *S. cerevisiae*. For example, transposon (Tc1) insertions in the nematode homolog of an HX2004-6 gene or a promoter region of an HX2004-6 gene may be made. The HX2004-6 gene sequences may be used to knock-out or to complement defined genetic lesions in order to determine the physiological and biochemical pathways involved in development of a neoplasm. It is well known that human genes can complement mutations in lower eukaryotic models.

HX2004-6 Polypeptides

The invention provides isolated HX2004-6 polypeptides and methods for making the polypeptides. HX2004-6 polypeptides include polypeptides having the sequences shown in SEQ ID NO:53 and SEQ ID NO:55, amino acids 1-342 of SEQ ID NO:53, amino acids 1-352 of SEQ ID NO:55; variants thereof, particularly variants comprising conservative amino acid substitutions; fragments thereof, particularly fragments having at least about 5, usually at least about 15, usually at least about 30 or more contiguous amino acids of the aforementioned sequences; and fusion proteins thereof. HX2004-6 polypeptides can be chemically synthesized, produced by recombinant methods, isolated from a biological source, or a combination of the foregoing.

HX2004-6-encoding nucleic acid may be employed to synthesize full-length HX2004-6 polypeptides or fragments thereof, for example, fragments at least about 8 amino acids in length, more usually at least about 15 amino acids in length, to about 25 amino acids, and up to the complete open reading frame of the HX2004-6 cDNA; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, or cells of a higher organism such as vertebrates, particularly mammals, e.g. COS 7 cells, may be used as the expression host cells. In many situations, it may be desirable to express the HX2004-6 genes in mammalian cells, particularly isolated mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

Antibodies Specific for HX2004-6 Polypeptides

The invention further provides isolated antibodies specific for HX2004-6 polypeptides of the invention. The HX2004-6 polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of HX2004-6. Antibodies may be raised to isolated peptides corresponding to these domains, or to the native protein, e.g. by immunization with cells expressing HX2004-6, immunization with liposomes having HX2004-6 polypeptides inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage "display" libraries, usually in conjunction with in vitro affinity maturation.

Isolation of HX2004-6 Allelic Variants and Homologs in Other Species

Other mammalian HX2004-6 genes can be identified and isolated and their function characterized using the HX2004-6 genes used in the present invention. Other HX2004-6 genes of interest include, but are not limited to, mammalian (e.g., human, rodent (e.g, murine, or rat), bovine, feline, canine, and the like) and non-mammalian (e.g., chicken, reptile, and the like). Methods for identifying, isolating, sequencing, and characterizing an unknown gene based upon its homology to a known gene sequence are well known in the art (see, e.g., Sambrook et al., Molecular Cloning: A Laboratory Manual, CSH Press 1989.

Detection Methods Using HX2004-6 Polynucleotides and Antibodies of the Invention The present invention provides detection methods using HX2004-6 polynucleotides, and antibodies specific for HX2004-6 polypeptides of the invention. Detection methods using HX2004-6 polynucleotides include methods of detecting a level of HX2004-6 messenger RNA (mRNA) in a biological sample. These methods can be used to monitor HX2004-6 mRNA levels in response to a treatment, such as chemotherapy or radiation therapy, for treating pancreatic, breast, or colon cancer; to assess the efficacy of a drug in lowering HX2004-6 polynucleotide levels in a cell; to detect the presence of cells in an individual or in a culture which overexpress HX2004-6 mRNA, wherein the presence of a cell or cells which overexpress HX2004-6 mRNA is indicative of the presence of cancerous cells; in screening methods to detect agents which modulate levels of HX2004-6 mRNA; and to monitor progression of a cell from a normal to a neoplastic state. Detection methods to detect the presence of a HX2004-6 polynucleotide can also be used to detect a polymorphism in the HX2004-6 polynucleotide, which polymorphism may be indicative or predictive of a predisposition to develop pancreatic, breast, or colon cancer.

Similarly, the invention provides methods of detecting HX2004-6 polypeptides in a biological sample. These methods can be used to assess the efficacy of a drug in lowering HX2004-6 polypeptide levels in a cell; to detect the presence of cells in an individual or in a culture which overexpress HX2004-6 protein, wherein the presence of a cell or cells which overexpress HX2004-6 protein may be indicative of the presence of cancerous cells; in screening methods to detect agents which modulate levels of HX2004-6 polypeptides; and to monitor progression of a cell from a normal to a neoplastic state. Detection methods to detect the presence of a HX2004-6 polypeptide can also be used to detect the presence an abnormal HX2004-6 polypeptide, such as a truncated polypeptide, or other mutant HX2004-6 protein.

Methods of Detecting HX2004-6 mRNA in a Biological Sample

The present invention provides methods of detecting an HX2004-6 messenger RNA (mRNA) in a biological sample. Such methods are useful diagnostic methods to assess the potential of a cell to become neoplastic (where overexpression of HX2004-6 is an indication that a cell is, or is predisposed to become, neoplastic), to assess the efficacy of a chemotherapeutic regimen, as part of a screening method to identify agents that reduce the expression of HX2004-6 mRNA, and/or to detect the presence of a cell(s) which overexpress HX2004-6 mRNA. The methods generally involve contacting a biological sample with an HX2004-6 polynucleotide capable of hybridizing to an HX2004-6 mRNA, or the complement thereof as appropriate, and detecting hybridization. mRNA can be detected directly, or can first be reverse transcribed into cDNA for analysis. In addition, multiple copies of the mRNA can be made by amplification reactions, if desired.

mRNA may be isolated from a biological sample, or may be detected without being first isolated. Alternatively, the mRNA sample is separated by gel electrophoresis, transferred to a suitable support, e.g. nitrocellulose, nylon, etc., and then probed with all or a fragment of HX2004-6 cDNA as a probe, and detecting hybridization by Northern blotting, liquid hybridization techniques, and the like. Where mRNA is being directly hybridized to an HX2004-6 polynucleotide, the HX2004-6 polynucleotide comprises a sequence complementary to the HX2004-6 mRNA being detected.

Alternatively, mRNA may be amplified by RT-PCR, using reverse transcriptase to form a complementary DNA strand, followed by a polymerase chain reaction amplification using primers specific for the subject DNA sequences.

For example, pancreatic cells may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. 1985 Science 239:487; a review of current techniques may be found in Sambrook, et al. Molecular Cloning: A Laboratory Manual, CSH Press 1989, pp.14.2-14.33.

In some instances, it may be desirable to analyze many samples at the same time for HX2004-6 mRNA expression levels. A variety of arrays have been described, and can be used in these methods. Quantitative monitoring of gene expression patterns with a complementary DNA microarray is described in Schena et al. (1995) *Science* 270:467. DeRisi et al. (1997) *Science* 270:680-686 explore gene expression on a genomic scale. Analysis of gene expression patterns in human cancer using a cDNA microarray is described in DeRisi et al. (1996) *Nat. Genet.* 14:457. Expression analysis using nucleic acid arrays is reviewed by Ramsay (1998) *Nat. Biotech.* 16:40-44. Methods for creating microarrays of biological samples, such as arrays of DNA samples to be used in DNA hybridization assays, are described in PCT publication no. WO 95/35505, published Dec. 28, 1995; U.S. Pat. No. 5,445,934; Drmanac et al., *Science* 260:1649; and Yershov et al. (1996) Genetics 93:4913. Use of differential display to identify differential gene expression is described in, for example, U.S. Pat. Nos. 5,776,683; and 5,807,680.

Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Other techniques, such as oligonucleotide ligation assays, and in situ hybridizations, can also be used. In situ hybridization is described in a variety of textbooks, including, for example, Current Protocols in Molecular Biology, Ausubel et al., eds. For example, a fragment of HX2004-6 cDNA, particularly and oligonucleotide of about 18-30 nucleotides in length, can be labeled, for example, with biotin, and used to probe a tissue section. The tissue section can then be developed using an avidin-coupled enzyme and a substrate for the enzyme which yields a colored product. Counterstaining with, for example, hematoxylin and eosin, according to standard protocols, can be carried out.

In other embodiments, mRNA is detected by amplifing reverse-transcribed cDNA copies of the mRNA, using oligonucleotide primers that are detectably labeled. In these embodiments, a detectable label is included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. Detection of the reverse-transcribed and amplified HX2004-6 mRNA is achieved by standard methods to detect, as appropriate, fluorescence, radioactivity, the product(s) of an enzymatic reaction, etc.

Overexpression of HX2004-6 mRNA is assessed relative to an appropriate control, e.g., a counterpart cell that is known to be normal, and/or a cell line of the same cell type which is known to have normal expression of HX2004-6 mRNA.

Methods of Detecting HX2004-6 Polypeptides in a Biological Sample

The present invention further provides methods of detecting HX2004-6 polypeptides in a biological sample. Antibodies specific for HX2004-6 polypeptides can be used in these detection methods. The methods generally comprise contacting a biological sample with an antibody specific for an HX2004-6 polypeptide, and detecting specific binding.

A sample is taken from a patient suspected of having an HX2004-6-associated disorder. Samples, as used herein, include tissue biopsies, biological fluids, organ or tissue culture derived fluids, and fluids extracted from physiological tissues, as well as derivatives and fractions of such fluids. If the polypeptide to be detected is associated with a cell, the number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence of HX2004-6 polypeptide in the biological sample being tested. For example, detection may utilize staining of cells or histological sections, performed in accordance with conventional methods. Antibodies specific for HX2004-6 polypeptides are added to the cell sample, and incubated for a period of time sufficient to allow binding to the epitope(s), usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and HX2004-6 polypeptides in a cell lysate or other biological fluid. Measuring the concentration of HX2004-6 binding in a sample or fraction thereof may be accomplished by a variety of specific assays. A conventional sandwich type assay may be used. For example, a sandwich assay may first attach HX2004-6-specific antibodies to an insoluble surface or support. The particular manner of binding is not crucial so long as it is compatible with the reagents and overall methods of the invention. They may be bound to the plates covalently or non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Cell lysates (or other biological fluid) are then added to separately assayable supports (for example, separate wells of a microtiter plate) containing antibodies. Preferably, a series of standards, containing known concentrations of normal and/or abnormal HX2004-6 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hours is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind HX2004-6 with sufficient specificity such that it can be distinguished from other components present in the sample. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for HX2004-6 as desired, conveniently using a labeling method as described for the sandwich assay. Antibody arrays may be formed wherein antibody specific for HX2004-6 polypeptide is attached to a solid support and, after allowing binding of a test sample, HX2004-6 polypeptide is detected using a detectably labeled antibody specific for HX2004-6 polypeptide.

Screening Assays

The transgenic animals, recombinant host cells, polynucleotides, and antibodies of the invention can be used to identify candidate agents that affect HX2004-6 expression (e.g., by affecting HX2004-6 promoter function) or that interact with HX2004-6 polypeptides. Agents of interest can include those that enhance, inhibit, regulate, or otherwise affect HX2004-6 expression. Of particular interest are agents that reduce expression of HX2004-6. Agents that reduce HX2004-6 expression can be used to, for example, treat or study disorders associated with overexpression of HX2004-6 (e.g., pancreatic, breast, and/or colon cancer. "Candidate agents" is meant to include synthetic molecules (e.g., small molecule drugs, peptides, or other synthetically produced molecules or compounds, as well as recombinantly produced gene products) as well as naturally occurring compounds (e.g., polypeptides, hormones, plant extracts, and the like). In the screening assays of the invention, results obtained with test substances are compared to results obtained with appropriate controls. An appropriate control is provided by conducting the assay in the absence of the test substance.

Drug Screening Assays

Of particular interest in the present invention is the identification of agents that have activity in affecting HX2004-6 expression and/or function. Such agents are candidates for development of treatments for, for example, cancer or other condition that may be associated with overexpression of HX2004-6. Drug screening identifies agents that provide for down-regulation of HX2004-6 expression or function in affected cells. Of particular interest are screening assays for agents that have a low toxicity for human cells.

The term "agent" as used herein describes any molecule, e.g. protein or pharmaceutical, with the capability of reducing expression of HX2004-6 and/or of reducing HX2004-6 polypeptide function. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents In Vivo

Agents can be screened for their ability to affect HX2004-6 expression or function or to mitigate an undesirable phenotype (e.g., a symptom) associated with an alteration in HX2004-6 expression or function. In some embodiments, screening of candidate agents is performed in vivo in a transgenic animal described herein. Transgenic animals suitable for use in screening assays include any transgenic animal having an alteration in HX2004-6 expression, and can include transgenic animals having, for example, an exogenous and stably transmitted human HX2004-6 gene sequence, a reporter gene composed of an isolated human HX2004-6 promoter sequence operably linked to a reporter gene (e.g., β-galactosidase, CAT, luciferase, or other gene that can be easily assayed for expression), or a homozygous or heterozygous knockout of an HX2004-6 gene. The transgenic animals can be either homozygous or heterozygous for the genetic alteration and, where a sequence is introduced into the animal's genome for expression, may contain multiple copies of the introduced sequence. Where the in vivo screening assay is to identify agents that affect the activity of the HX2004-6 promoter, the HX2004-6 promoter can be operably linked to a reporter gene (e.g., luciferase) and integrated into the non-human host animal's genome.

The candidate agent is administered to a non-human, transgenic animal having altered HX2004-6 expression, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing HX2004-6 function as appropriate (e.g., by examining expression of a reporter or fusion gene), or by assessing a phenotype associated with the HX2004-6 expression. For example, where the transgenic animal used in the screen exhibits overexpression of HX2004-6, the effect of the candidate agent can be assessed by determining levels of HX2004-6 mRNA produced in normal non-transgenic littermates and/or in wildtype mice Levels of HX2004-6 mRNA can be measured using techniques that are well known in the art. Where the in vivo screening assay is to identify agents that affect the activity of the HX2004-6 promoter and the non-human transgenic animal (or cultured mammalian cell line) comprises an HX2004-6 promoter operably linked to a reporter gene, the effects of candidate agents upon HX2004-6 promoter activity can be screened by, for example, monitoring the expression from the HX2004-6 promoter (through detection of the reporter gene) and correlation of altered HX2004-6 promoter activity an aberrant cellular phenotype, such as aberrant mitotic activity, or other indications of neoplastic transformation. Alternatively or in addition, HX2004-6 promoter activity can be assessed by detection (qualitative or quantitative) of HX2004-6 mRNA or protein levels. Where the candidate agent affects HX2004-6 expression, and/or affects an HX2004-6-associated phenotype, in a desired manner, the candidate agent is identified as an agent which may be suitable for use in therapy of an HX2004-6-associated disorder in vivo.

Screening of Candidate Agents Using Cell-Based Assays

In addition to screening of agents in HX2004-6 transgenic animals, a wide variety of cell-based assays may be used for this purpose, using, for example, a mammalian cell transformed with a construct comprising HX2004-6 cDNA such that the cDNA is overexpressed, or, alternatively, a construct comprising an HX2004-6 promoter operably linked to a reporter gene.

Accordingly, the present invention provides a method for identifying an agent, particularly a biologically active agent, that modulates a level of human HX2004-6 expression in a cell, the method comprising: combining a candidate agent to be tested with a cell comprising a nucleic acid which encodes a human HX2004-6 polypeptide; and determining the effect of said agent on HX2004-6 expression. "Modulation" of HX2004-6 expression levels includes increasing the level and decreasing the level of HX2004-6 mRNA and/or HX2004-6 polypeptide encoded by the HX2004-6 polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of HX2004-6 mRNA and/or polypeptide following contacting the cell with a candidate agent being tested, compared to a control to which no agent is added, is an indication that the agent modulates HX2004-6 expression.

An agent being tested for its effect on HX2004-6 expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cultures of ductal epithelial cells, or may be immortalized cell lines.

HX2004-6 mRNA and/or polypeptide whose levels are being measured can be encoded by an endogenous HX2004-6 polynucleotide, or the HX2004-6 polynucleotide can be one that is comprised within a recombinant vector and introduced into the cell, i.e., the HX2004-6 mRNA and/or polypeptide can be encoded by an exogenous HX2004-6 polynucleotide. For example, a recombinant vector may comprise an isolated human HX2004-6 transcriptional regulatory sequence, such as a promoter sequence, operably linked to a reporter gene (e.g,. β-galactosidase, CAT, luciferase, or other gene that can be easily assayed for expression). In these embodiments, the method for identifying an agent that modulates a level of human HX2004-6 expression in a cell, comprises: combining a candidate agent to be tested with a cell comprising a nucleic acid which comprises a human HX2004-6 gene transcriptional regulatory element operably linked to a reporter gene; and determining the effect of said agent on reporter gene expression. A recombinant vector may comprise comprise an isolated human HX2004-6 transcriptional regulatory sequence, such as a promoter sequence, operably linked to sequences coding for an HX2004-6 polypeptide; or the transcriptional control sequences can be operably linked to coding sequences for an HX2004-6 fusion protein comprising HX2004-6 polypeptide fused to a polypeptide which facilitates detection. In these embodiments, the method comprises combining a candidate agent to be tested with a cell comprising a nucleic acid which comprises a human HX2004-6 gene transcriptional regulatory element operably linked to an HX2004-6 polypeptide-coding sequence; and determining the effect of said agent on HX2004 expression, which determination can be carried out by measuring an amount of HX2004-6 mRNA, HX2004-6 polypeptide, or HX2004-6 fusion polypeptide produced by the cell.

Cell-based assays generally comprise the steps of contacting the cell with an agent to be tested, forming a test sample, and, after a suitable time, assessing the effect of the agent on HX2004-6 expression. A control sample comprises the same cell without the candidate agent added. HX2004-6 expression levels are measured in both the test sample and the control sample. A comparison is made between HX2004-6 expression level in the test sample and the control sample. HX2004-6 expression can be assessed using conventional assays. For example, when a mammalian cell line is transformed with a construct that results in expression of HX2004-6, HX2004-6 mRNA levels can be detected and measured, as described above, or HX2004-6 polypeptide levels can be detected and measured, as described above. A suitable period of time for contacting the agent with the cell can be determined empirically, and is generally a time sufficient to allow entry of the agent into the cell and to allow the agent to have a measurable effect on HX2004-6 mRNA and/or polypeptide levels. Generally, a suitable time is between 10 minutes and 24 hours, more typically about 1-8 hours. Methods of measuring HX2004-6 mRNA levels are known in the art, several of which have been described above, and any of these methods can be used in the methods of the present invention to identify an agent which modulates HX2004-6 mRNA level in a cell, including, but not limited to, a PCR, such as a PCR employing detectably labeled oligonucleotide primers, and any of a variety of hybridization assays. Similarly, HX2004-6 polypeptide levels can be measured using any standard method, several of which have been described herein, including, but not limited to, an immunoassay such as ELISA, for example an ELISA employing a detectably labeled antibody specific for an HX2004-6 polypeptide.

The method described above is useful for identifying agents which may be useful in treating certain cancers. An agent which reduces HX2004-6 expression and is not cytotoxic is considered a possible agent for treatment of adenocarcinomas of pancreatic, breast, and colon ductal epithelial cell origin, e.g., to facilitate tumor regression, reduction in tumor mass, etc. Such agents are then further evaluated for safety and efficacy.

Screening of Candidate Agents Using Cell-Free Assays

Cell-free assays, i.e., assays which measure HX2004-6 polypeptide levels or function directly, include, but are not limited to, labeled in vitro protein-protein binding assays, protein-DNA binding assays, electrophoretic mobility shift assays, immunoassays for protein binding, and the like. Using these methods, one can identify substances that bind specifically to HX2004-6 polypeptides. Such substances are useful as diagnostic agents to detect the presence of and/or to measure a level of HX2004-6 polypeptide in a biological.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 Proc. Natl. Acad. Sci. USA 88:9578-9582. Two-hybrid system analysis is of particular interest for exploring transcriptional activation by HX2004-6 proteins and to identify cDNAs encoding polypeptides that interact with HX2004-6.

Identified Candidate Agents

The compounds having the desired activity (i.e., modulation of HX2004-6 expression) may be administered in a physiologically acceptable carrier to a host for treatment of a condition attributable to overexpression of HX2004-6 (e.g., a neoplasm of a pancreatic, breast, or colon cell, particular an adenocarcinoma of one of these tissues). The therapeutic agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

EMBODIMENTS RELATING TO VSHK

Isolated VSHK-1 Receptor Polypeptides

The present invention provides isolated VHSK-1 receptor polypeptides. VSHK-1 receptor polypeptides can be used to generate antibodies which specifically bind to VSHK-1 receptor polypeptides. VSHK-1 receptor polypeptides are also useful in assay methods to identify agents which modulate VSHK-1 receptor signal transduction activity, in assays to identify proteins that interact with VSHK-1 receptor polypeptides, and in assay methods to identify ligands of VSHK-1 receptor polypeptides.

In certain embodiments of interest, a VSHK-1 receptor polypeptide is present in a composition that is substantially free of the constituents that are present in its naturally occurring environment. For example, a VSHK-1 receptor polypeptide comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's constituents will still be present in the composition prepared from the naturally occurring source.

A VSHK-1 receptor polypeptide of the subject invention may also be present as an isolate, by which is meant that the VSHK-1 receptor polypeptide is substantially free of both non-VSHK-1 receptor proteins and other naturally occurring biologic molecules, such as oligosaccharides, polynucleotides and fragments thereof, and the like, where substantially free in this instance means that less than 70%, usually less than 60% and more usually less than 50% of the composition containing the isolated VSHK-1 receptor polypeptide is a non-VSHK-1 receptor naturally occurring biological molecule. In certain embodiments, the VSHK-1 receptor polypeptide is present in substantially pure form, where by substantially pure form is meant at least 95%, usually at least 97% and more usually at least 99% pure.

The term "VSHK-1 receptor polypeptide" encompasses VSHK-1 receptor polypeptides from a variety of eukaryotic species, including, but not limited to, mammalian species, such as rat, mouse, and human; insect species; reptiles; yeast; nematodes; and amphibians.

As used herein, "VSHK-1 receptor polypeptide" refers to an amino acid sequence of a recombinant or non-recombinant polypeptide having an amino acid sequence of i) a native VSHK-1 receptor polypeptide, ii) a fragment of a VSHK-1 receptor polypeptide, iii) polypeptide analogs of a VSHK-1 receptor polypeptide, iv) variants of a VSHK-1 receptor polypeptide; v) an immunologically active fragment of a VSHK-1 receptor polypeptide; vi) isoforms of a VSHK-1 receptor polypeptide; and vii) fusion proteins comprising a VSHK-1 receptor polypeptide. VSHK-1 receptor polypeptides of the invention can be obtained from a biological sample, or from any source whether natural, synthetic, semi-synthetic or recombinant.

"VSHK-1 receptor polypeptides" include mutants, fragments, and fusions as well as native VSHK-1 receptors. Mutants of the native VSHK-1 receptor polypeptides include additions, substitution, or deletions of native VSHK-1 receptor polypeptides. Fragments may possess the same amino acid sequence as native or mutant VSHK-1 receptor polypeptides except fragments lack the amino and/or carboxyl terminal sequences of the native or mutant VSHK-1 receptor polypeptides. Fusions are mutants, fragments, or native VSHK-1 receptor polypeptides that include amino and/or carboxyl terminal amino acid extensions. The number or type of the amino acid substitutions, additions, or deletions is not critical, nor is the length or number of the amino acid deletions, or amino acid extensions that are incorporated in the VSHK-1 receptor polypeptides. However, all of these polypeptides will exhibit at least 20% of at least one of the native VSHK-1 receptor polypeptide activities. More typically, the polypeptides exhibit at least 40%, even more typically the polypeptides exhibit at least 60% of at least one of the native VSHK-1 receptor activities. All these polypeptides will retain at least about 50% amino acid identity with SEQ ID NO:72; more typically, at least 60%; even more typically, at least 80%. Preferably, these polypeptides will retain at least 85% amino acid sequence identity with SEQ ID NO:72; more preferably, at least 90%; even more preferably, at least 91%, 92%, or 93% sequence identity; even more preferably at least 94%, 95%, or 96% sequence identity; even more preferably, at least 97%, 98% or 99% sequence identity. The percent amino acid sequence identity is calculated using the ClustalW program, using default parameters according to software specifications, which include: open gap penalty=10; extended gap penalty=0.1; similarity matrix=BLOSUM. In addition, VSHK-1 receptor polypeptides can include up to 50 amino acid changes as compared to a native VSHK-1 receptor polypeptide sequence; generally, up to 35 amino acids; more generally, up to 30, 25, or 20 amino acid changes; even more generally, up to 18, 15, or 12 amino acid changes; even more generally, up to 10, 9, 8, 7, 6, 5, 4, 3, 2, or 1 amino acid changes.

"VSHK-1 receptor polypeptide" refers to the amino acid sequences of isolated VSHK-1 receptor polypeptide obtained from a prokaryotic or eukaryotic organism, and is meant to include all naturally-occurring allelic variants, and is not meant to limit the amino acid sequence to the complete, native amino acid sequence associated with the recited protein molecule. The term "VSHK-1 receptor polypeptide" encompasses an amino acid sequence encoded by an open reading frame (ORF) of the VSHK-1 polynucleotides described herein, including the full-length native polypeptide and fragments thereof, particularly biologically active fragments and/or fragments corresponding to structural or functional domains, e.g., a transmembrane domain, a signal transduction domain or region, a ligand-binding domain, a G-protein-binding domain, etc.; and including fusions of the subject polypeptides to other proteins or parts thereof.

Those skilled in the art will appreciate that changes can be made to VSHK-1 receptor polypeptide sequences, including the sequences depicted in SEQ ID NO:72 (VSHK-1) without substantially affecting a function of the VSHK-1 receptor polypeptide. Thus, the term "VSHK-1 receptor polypeptide" encompasses polypeptides with conservative amino acid substitutions compared with the sequences depicted in SEQ ID NO:72. Examples of conservative amino acid substitutions include Ser/Thr; Ala/Val; Leu/Ile; Asp/Glu; and Phe/Tyr/Trp. Clearly, other amino acid substitutions, deletions, and insertions can be made to the polypeptide without affecting one or more functions of the polypeptide.

In many preferred embodiments, VSHK-1 receptor polypeptide is present in its naturally glycosylated state, i.e. it will have the same glycosylation pattern as that found in naturally occurring VSHK-1 receptor polypeptide such that it is a glycoprotein. In other embodiments, the proteins are non-naturally glycosylated. By non-naturally glycosylated is meant that the protein has a glycosylation pattern, if present, which is not the same as the glycosylation pattern found in the corresponding naturally occurring protein. Non-naturally glycosylated VSHK-1 receptor polypeptides of this embodiment include non-glycosylated VSHK-1 receptor polypeptide, i.e. proteins having no covalently bound glycosyl groups.

A subset of mutants, or "muteins", is a group of polypeptides with the non-disulfide bond participating cysteines substituted with a neutral amino acid, generally, with serines. These mutants may be stable over a broader temperature range than native VSHK-1 receptor polypeptides. Preferably, cysteines in the N-terminal loop and the third extracellular region are conserved if disulfide bonding is desired between these two regions. These residues include Cys 112 and Cys 184. However, cysteines in other regions can be substituted or deleted. In addition, the third intracellular loop fragment of native VSHK-1 receptor polypeptides is basic due to the number of residues that are positively charged at physiological pH. Changes to the third intracellular loop can include those that permit the loop fragment to remain positively charged at physiological pH. To retain an overall net positive charge at the desired pH, a number of positively charged amino acids, such as histidine, lysine, arginine, asparagine, and glutamine, can be substituted or inserted into the native VSHK-1 receptor amino acid sequence.

Further, the N-terminal loop of native VSHK-1 receptor polypeptides are acidic, containing a number of residues that are negatively charged at physiological pH. Thus, substitutions, additions, or deletions can be made that permit the loop fragment to retain a negative charge at the desired pH. Such naturally occurring residues, including aspartic acid and glutamic acid, retain a negative charge under physiological pH and can be substituted or inserted into mutants of the N-terminal loop to retain acidic characteristics.

The N-terminal loop can be used as a viral inhibitor which binds to infecting virus to prevent entry into a cell. Typically, the N-terminal loop fragment can be mutated, but will retain its acidic nature and will retain its tyrosine residues. Two potential glycosylation sites in the N-terminal loop can be conserved, deleted, or altered, depending on whether glycosylation is desired.

Preferably, the arginine in the seventh transmembrane domain is conserved or substituted with another positively charged amino acid, such as histidine, lysine, asparagine, or glutamine.

Other motifs that can be conserved in VSHK-1 receptor polypeptides are located in transmembrane regions as follows:

TM1: GNXXV (SEQ ID NO: 88)
TM2: IXNLAXAADL (SEQ ID NO: 89)
TM3: LXXISXDRY (SEQ ID NO: 90)
TM4: WXXAXXXXXP (SEQ ID NO: 91)
TM5: FXXPXXXMXXXY (SEQ ID NO: 92)
TM6: KXXXXXXXXFXXXXPY (SEQ ID NO: 93)
TM7: SXXNPXXY (SEQ ID NO: 94).

The one-letter amino acid abbreviations are used to describe the above-listed motifs, with X indicating any amino acid.

Those skilled in the art, given the guidance provided in the instant specification, can readily determine whether a given function of a VSHK-1 receptor polypeptide is preserved. One such function is signal transduction by a VSHK-1 receptor polypeptide of the invention. Yet another function is binding to other protein(s), e.g., one or more G-proteins. Still another function is ligand binding.

Whether a VSHK-1 receptor polypeptide functions in signal transduction and/or ligand binding and/or G-protein binding is readily determined, using any known assay, including the signal transduction assays described herein.

The term "VSHK-1 receptor polypeptide" encompasses a polypeptide comprising 8 or more contiguous amino acids of the sequence depicted in SEQ ID NO:72. Thus, the term "VSHK-1 receptor polypeptide" encompasses a polypeptide comprising at least about 8, 10, 15, 20, 25, 50, 75, 100, 200, 300, or 325 contiguous amino acids of the sequence set forth in SEQ ID NO:72. In some embodiments, a VSHK-1 polypeptide has the entire sequence as shown in SEQ ID NO:72. The term "VSHK-1 receptor polypeptide" also encompasses a polypeptide comprising at least about 8, 10, 15, 20, 25, 50, 75, or 80 contiguous amino acids of amino acids 1-80 of the sequence set forth in SEQ ID NO:72. The term "VSHK-1 receptor polypeptide" also encompasses a polypeptide comprising at least about 8, 10, 15, 20, 25, 50, 75, 100, 125, 150, or 162 contiguous amino acids of amino acids 189-350 of the sequence set forth in SEQ ID NO:72.

Figure 37:
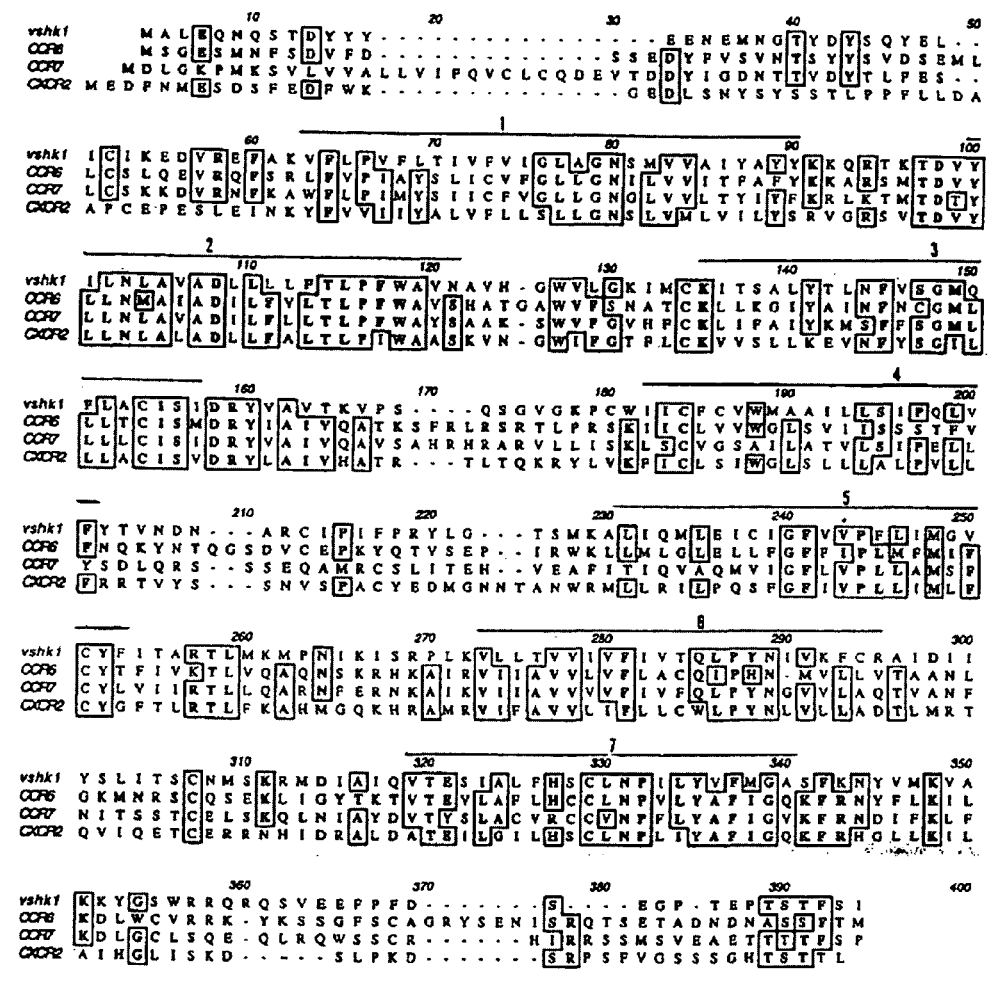

VSHK-1 receptor polypeptide having the sequence set forth in SEQ ID NO:72 has some sequence similarity to chemokine receptors. Chemokine receptors play pivotal roles in leukocyte migration, and in entry of human immunodeficiency virus into cells. See, for example, Pelchen-Matthews et al. (1999) Immunol. Rev. 168:33-49; Wells et al. (1999) Immunol. Lett. 65:35-40; and Berger et al. (1999) Ann. Rev. Immunol. 17:657-700. FIG. 37 shows a VSHK-1 receptor polypeptide having the sequence set forth in SEQ ID NO:72 aligned with chemokine receptors CCR6, CCR7, and CXCR2. CCR6 and CCR7 share 32% and 37% amino acid sequence identity, respectively, with the amino acid sequence set forth in SEQ ID NO:72. The alignment was performed using the ClustalW program, using default parameters provided by the software developer. The ClustalW program is described in Thompson et al. (1994) Nucl. Acids Res. 22:4673-4680.

Accordingly, also encompassed by the term "VSHK-1 receptor polypeptide" is a polypeptide sharing at least about 40%, more preferably at least about 50%, more preferably at least about 60%, more preferably at least about 70%, more preferably at least about 80%, more preferably at least about 85%, even more preferably at least about 90% or more amino acid sequence identity with the sequence depicted in SEQ ID NO:72, as calculated using the ClustalW program with default parameters.

On the basis of similarity with other chemokine receptors, a VSHK-1 receptor polypeptide may exhibit one or more of the following biological activities: (1) Mediation of chemotaxis of neutrophils, lymphocytes, tumor-infiltrating, lymphocytes, hemopoietic progenitors, monocytes, natural killer cells. Assays for chemotaxis relating to neutrophils are described in Walz et al. (1987) *Biochem. Biophys. Res. Commun.* 149:755; Yoshimura et al. (1987) *Proc. Natl. Acad. Sci. USA* 84:9233; and Schroder et al. (1987) *J. Immunol.* 139: 3474; lymphocytes, Larsen et al., *Science* 243: 1464: (1989); Carr et al., *Proc. Natl. Acad. Sci. USA* 91: 3652 (1994); tumor-infiltrating lymphocytes, Liao et al., *J. Exp. Med.* 182: 1301 (1995); hemopoietic progentors, Aiuti et al., *J. Exp. Med.* 185: 111 (1997); monocytes, Valente et al., Biochem. 27: 4162 (1988); natural killer cells, Loetscher et al., *J. Immunol.* 156: 322 (1996), and Allavena et al. (1994) *Eur. J. Immunol.* 24:3233; (2) involvement in angiogenesis or cell proliferation. The assays for such activities is described in Maione et al., *Science* 247: 77 (1990); (3) involvement in glycosaminoglycan production. A method for detecting this activity is described in Castor et al. (1983) *Proc. Natl. Acad. Sci. USA* 80:765; (4) involvement in histamine release from basophils. The assay for release is described in Dahinden et al. (1989) *J. Exp. Med.* 170: 1787; and White et al.(1989) *Immunol. Lett.* 22:151; (5) Heparin binding as described in Luster et al. (1995) *J. Exp. Med.* 182:219; (6) involvement in the inflammatory response of viruses. This activity can be assayed as described in Bleul et al. (1996) *Nature* 382:829; and Oberlin et al. (1996) *Nature* 382:833; (7) promotion of exocytosis of monocytes. The assay for such activity is described in Uguccioni et al. (1995) *Eur. J Immunol.* 25: 64; (8) involvement in hemapoietic stem cell proliferation. The method for testing for such activity is reported in Graham et al. (1990) *Nature* 344: 442.

Also encompassed by the term "VSHK-1 receptor polypeptide" are specific fragments of VSHK-1. Specific fragments of VSHK-1 receptor polypeptides provided by the present invention include (1) fragments of the N-terminal extracellular tail of native VSHK-1 comprising amino acids 1 to 41, amino acids 10 to 41, amino acids 30 to 41 of SEQ ID NO:72; (2) fragments of the second extracellular loop of native VSHK-1 receptor polypeptide, comprising amino acids 100 to 112, amino acids 105 to 112, amino acids 97 to 115 of SEQ ID NO:72; (3) fragments of the third extracellular loop of native VSHK-1 receptor polypeptide, comprising amino acids 178 to 198, amino acids 180 to 190, amino acids 175 to 201 of SEQ ID NO:72; (4) fragments of the fourth extracellular loop of native VSHK-1 receptor polypeptide, comprising amino acids 264 to 282, amino acids 267 to 279, amino acids 257 to 295 of SEQ ID NO:72; (5) the first transmembrane domain of native VSHK-1 receptor polypeptide, comprising amino acids 42 to 67, amino acids 39 to 70, amino acids 58 to 62 of SEQ ID NO:72; (6) the second transmembrane domain of native VSHK-1 receptor polypeptide, comprising amino acids 74 to 99, amino acids 71 to 102, amino acids 80 to 88 of SEQ ID NO:72; (7) the third transmembrane domain of native VSHK-1 receptor polypeptide, comprising 113 to 138, amino acids 110 to 141, amino acids 130 to 138 of SEQ ID NO:72; (8) the fourth transmembrane domain of native VSHK-1 receptor polypeptide, comprising amino acids 152 to 177, amino acids 149 to 180, amino acids 160 to 172 of SEQ ID NO:72; (9) the fifth transmembrane domain of native VSHK-1 receptor polypeptide, comprising amino acids 198 to 224, amino acids 195 to 227, amino acids 209 to 220 of SEQ ID NO:72; (10) the sixth transmembrane domain of native VSHK-1 receptor polypeptide, comprising amino acids 238 to 263, amino acids 235 to 266, amino acids 240 to 256 of SEQ ID NO:72; (11) the seventh transmembrane domain of native VSHK-1 receptor polypeptide, comprising amino acids 283 to 308, amino acids 280 to 311, amino acids 296 to 303 of SEQ ID NO:72; (12) the C-terminal intracellular tail of native VSHK-1 receptor polypeptide, comprising amino acids 309 to 350, amino acids 330 to 350, amino acids 340 to 350 of SEQ ID NO:72; (13) the first intracellular loop of native VSHK-1 receptor polypeptide, comprising amino acids 68 to 73, amino acids 68 to 76, amino acids 65 to 76 of SEQ ID NO:72; (14) the second intracellular loop of native VSHK-1 receptor polypeptide, comprising amino acids 139 to 151, amino acids 139 to 154, amino acids 136 to 154 of SEQ ID NO:72; and (15) the third intracellular loop of native VSHK-1 receptor polypeptide, comprising amino acids 225 to 237, amino acids 222 to 237, amino acids 222 to 240 of SEQ ID NO:72. Also included are polypeptides comprising one or more of the foregoing fragments; fusion proteins including one or more of the foregoing fragments; any of the foregoing fragments comprising conservative amino acid changes, and polypeptides comprising such fragments.

VSHK-1 receptor polypeptides can be used in methods to detect factors, such as proteins, that bind to a VSHK-1 receptor polypeptide. Accordingly, the invention provides methods of identifying proteins that bind to a VSHK-1 receptor polypeptide. The methods generally comprise contacting a test substance with a VSHK-1 receptor polypeptide under conditions that permit formation of a protein-protein complex; and detecting the presence of any complexes formed. Any known method for identifying interacting proteins can be used, including, but not limited to, a yeast two-hybrid screen, also known as protein interactive trapping; and interaction cloning. These methods have been amply described in the literature and need not be described in detail herein. Publications describing these methods include, for example, *Current Protocols in Molecular Biology*, (F. M. Ausubel, et al., Eds. 1987, and updates); *Short Protocols in Molecular Biology* (F. M. Ausubel et al., Eds. 1999), Chapter 19; Blanar and Ruttner (1992) *Science* 256:1014-1018; and McAlister-Henn et al. (1999) *Methods* 19:330-337, and references cited therein describing protein interactive trapping. These methods can be used, for example, to identify a G-protein which binds to a VSHK-1 receptor polypeptide of the invention.

Also included in the term "VSHK-1 receptor polypeptide" are antigenic epitopes of a VSHK-1 receptor polypeptide. Extracellular loops are exposed on the cell surface and would therefore be more likely to contain antigenic epitopes, including the above-described peptide fragments. Those skilled in the art can readily determine which peptide fragments are antigenic epitopes. As a non-limiting example of how one can determine which region(s) of a protein are likely to be exposed on the surface (i.e., hydrophilic domains), and therefore potentially antigenic, one can analyze the amino acid sequence using Kyte-Doolittle hydropathicity analysis and/or Hopp-Woods hydrophilicity analysis. Kyte and Doolittle (1982) *J. Mol. Biol.* 157:105; and Hopp and Woods (1981) *Proc. Natl. Acad. Sci. USA* 78:3824.

Production of VSHK-1 Receptor Polypeptides

VSHK-1 receptor polypeptides can be isolated from a biological source, can be produced synthetically, or can be produced recombinantly, i.e., a VSHK-1 receptor-coding region can be inserted into an expression vector, and the VSHK-1 receptor coding region transcribed and translated.

VSHK-1 receptor polypeptides can be isolated from biological sources, using standard methods of protein purification known in the art. VSHK-1 receptor can also be isolated from a biological source by affinity chromatography, using a VSHK-1 receptor-specific antibody, using standard methods known in the art.

One may employ solid phase peptide synthesis techniques, where such techniques are known to those of skill in the art. See Jones, *The Chemical Synthesis of Peptides* (Clarendon Press, Oxford) (1994). Generally, in such methods a peptide is produced through the sequential additional of activated monomeric units to a solid phase-bound growing peptide chain.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, or 293 cells, may be used as the expression host cells. In some situations, it is desirable to express the gene in eukaryotic cells, where the protein will benefit from native folding and post-translational modifications. Small peptides can also be synthesized in the laboratory. Polypeptides that are subsets of the complete amino acid sequence may be used to identify and investigate parts of the protein important for function, or to raise antibodies directed against these regions.

The purified VSHK-1 receptor polypeptides are useful for signal transduction assays and ligand/receptor binding assays. The purified polypeptides can also be utilized to produce VSHK-1 receptor polypeptide-specific antibodies.

For ligand/receptor binding studies, the crude cell membrane fractions can be utilized. These membrane extracts can be isolated from cells which expressed VSHK-1 receptor polypeptides by lysing the cells and separating the cell membrane fraction from the intracellular fractions by centrifugation. See Adachi et al. (1992) *FEBS Lett.* 311:179-183 for an ligand binding assay procedure using cell membranes.

Once the polypeptide has been dissociated from the cell membrane, the desired VSHK-1 receptor polypeptide can also be affinity purified with specific VSHK-1 receptor antibodies.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

Isolated VSHK-1 Polynucleotides

The present invention provides isolated VSHK-1 polynucleotides encoding a VSHK-1 receptor polypeptide. These polynucleotides can be used, when in a recombinant expression vector, to produce the encoded VSHK-1 receptor polypeptide. They are also useful as hybridization probes in methods of detecting VSHK-1 gene expression, specifically transcription. Accordingly, the invention further provides recombinant vectors and host cells comprising VSHK-1 polynucleotides of the invention.

The VSHK-1 polynucleotides of the subject invention are isolated and obtained in substantial purity, generally as other than an intact chromosome. Usually, the DNA will be obtained substantially free of other nucleic acid sequences that do not include a VSHK-1 polynucleotide sequence or fragment thereof, generally being at least about 50%, usually at least about 90% pure and are typically "recombinant", i.e. flanked by one or more nucleotides with which it is not normally associated on a naturally occurring chromosome.

Novel polynucleotides of the invention comprise a sequence set forth in SEQ ID NO:71 (VSHK-1 nt), or an identifying sequence thereof. An "identifying sequence" is a contiguous sequence of residues at least about 10 nucleotides (nt) to about 20 nt in length, usually at least about 50 nt to about 100 nt in length, that uniquely identifies the provided sequence.

An expressed sequence tag (EST) was made publicly available through GenBank (GenBank Accession No. H67224). The H67224 EST provides the nucleotide sequence of a 328-nucleotide fragment from human olfactory epithelium. This sequence is identical to nucleotides 325 to 651 of SEQ ID NO:71. Hillier et al. (1996) *Genome Res.* 6:807-828.

Encompassed in the term "VSHK-1 polynucleotide" are polynucleotides comprising about 330, 350, 400, 500, 600, 700, 800, 900, 1000, 1500, or 1950 contiguous nucleotides of SEQ ID NO:71, including the entire coding region of SEQ ID NO:71. Also encompassed are polynucleotides comprising nucleotides 1-324 of SEQ ID NO:71, encoding amino acids 1-80 of VSHK-1 having the amino acid sequence set forth in SEQ ID NO:72. Further included are polynucleotides comprising at least about 18, 20, 30, 40, 50, 100, 150, 200, 250, and/or 300 contiguous nucleotides of nucleotides 1-324 of SEQ ID NO:71. Also encompassed are polynucleotides comprising nucleotides 652-1890 of SEQ ID NO:71. Further encompassed are polynucleotides comprising at least about 18, 30, 50, 100, 150, 200, 500, 750, 1000, and/or 1239 contiguous nucleotides of nucleotides 652-1890 of SEQ ID NO:71. Polynucleotides comprising sequences which encode the region of the VSHK-1 receptor protein that interacts with a G-protein are also of interest. Such fragments are often contained within the coding region, and may be about 250 to 500 nucleotides in length, up to the complete coding sequence.

Polynucleotides of the invention also include nucleic acids having sequence similarity or sequence identity to the sequence provided in SEQ ID NO:71. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate). Hybridization methods and conditions are well known in the art, see, e.g., U.S. Pat. No. 5,707,829. Nucleic acids that are substantially identical to the provided nucleic acid sequences, e.g. allelic variants, genetically altered versions of the gene, etc., bind to the provided nucleic acid sequence (SEQ ID NO:71) under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, yeast, nematodes, etc.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., Molecular Cloning: A Laboratory Manual, 2nd Ed. (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., supra, at page 9.50.

Variables to consider when performing, for example, a Southern blot are (1) the complexity of the DNA being blotted and (2) the homology between the target and the sequences being detected. The total amount of the polynucleotides to be studied can vary a magnitude of 10, from 0.1 to 1 µg for a plasmid or phage digest to $10^{-9}$ to $10^{-8}$ µg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 µg of yeast DNA, blotting for two hours, and hybridizing for 4-8 hours with a target polynucleotide radiolabeled with $10^8$ cpm/µg. For a single-copy mammalian gene a conservative approach would start with 10 µg of DNA, blot overnight, and hybridize overnight in the presence of 10% dextran sulfate using a target polynucleotide radiolabeled with greater than 108 cpm/µg, resulting in an exposure time of ~24 hours.

Several factors can affect the melting temperature ($T_m$) of a DNA-DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a single equation:

$$T_m = 81 + 16.6(\log 10Ci) + 0.4[\% \, G+C)] - 0.6(\% \text{ formamide}) - 600/n - 1.5(\% \text{ mismatch}),$$

where Ci is the salt concentration (monovalent ions) and n is the length of the hybrid in base pairs (slightly modified from Meinkoth and Wahl (1984) *Anal. Biochem.* 138:267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of about 5×SSC at 65° C., or at least about 4×SSC at 42° C.; see, for example, U.S. Pat. No. 5,707,829, the disclosure of which is herein incorporated by reference.

Generally, hybridization is performed using at least 18 contiguous nucleotides of SEQ ID NO:71. That is, when at least 18 contiguous nucleotides of the disclosed SEQ ID NO:71 is used as a probe, the probe will preferentially hybridize with a nucleic acid or mRNA comprising the complementary sequence, allowing the identification and retrieval of the nucleic acids of the biological material that uniquely hybridize to the selected probe. Probes of more than 18 nucleotides can be used, e.g. probes of from about 25 nucleotides to about 100 nucleotides, from about 100 nucleotides to about 500 nucleotides, up to the entire coding region can be used, but 18 nucleotides generally represents sufficient sequence for unique identification.

The nucleic acids of the invention also include naturally occurring variants of the nucleotide sequences, e.g. degenerate variants, allelic variants, etc. Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair mismatches relative to the selected nucleic acid probe. In general, allelic variants contain 15-25% base pair mismatches, and can contain as few as even 5-15%, or 2-5%, or 1-2% base pair mismatches, as well as a single base-pair mismatch.

Homologs of the VSHK-1 are also provided in the present invention. Such homologs can be identified by any of a number of methods known to those skilled in the art. A fragment of the provided cDNA may be used as a hybridization probe against a cDNA library from the target organism of interest, where low stringency conditions are used. The probe may be a large fragment, or one or more short degenerate primers.

The invention also encompasses homologs corresponding to the nucleic acids of SEQ ID NO:71, where the source of homologous genes can be any related species within the same genus or group. Within a group, homologs have substantial sequence similarity, e.g. at least 75% sequence identity, usually at least 90%, more usually at least 95% between nucleotide sequences, as determined using the BLAST alignment program. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared.

The term "VSHK-1 polynucleotide" encompasses polynucleotides which encode a VSHK-1 polypeptide, a fragment thereof, or a fusion protein thereof, as described above. Thus, in some embodiments, a VSHK-1 polynucleotide comprises a nucleotide sequence encoding a polypeptide comprising at least about 8, 10, 15, 20, 25, 50, 75, 100, 200, 300, or 325 contiguous amino acids of the sequence set forth in SEQ ID NO:72. In other embodiments, a VSHK-1 polynucleotide comprises a nucleotide sequence encoding the entire polypeptide having the amino acid sequence set forth in SEQ ID NO:72. In other embodiments a VSHK-1 polynucleotide comprises a polynucleotide sequence encoding a polypeptide comprising at least about 8, 10, 15, 20, 25, 50, 75, 100, 125, 150, or 162 contiguous amino acids of amino acids 189-350 of the sequence set forth in SEQ ID NO:72. In still other embodiments, a VSHK-1 polynucleotide comprises a nucleotide sequence which encodes a polypeptide comprising an amino acid sequence sharing at least about 70%, more preferably at least about 80%, even more preferably at least about 90% or more amino acid sequence identity, as determined using the ClustalW program with default parameters, with the sequence depicted in SEQ ID NO:72.

Also encompassed by the term "VSHK-1 polynucleotide" are polynucleotides complementary to a VSHK-1 polynucleotide, as defined above. Further encompassed are VSHK-1 antisense polynucleotides and ribozymes. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense and/or ribozyme sequences may be used to inhibit spermatogenesis. Antisense polynucleotides, and methods of using such, are described in numerous publications, including, e.g., "Antisense Technology: A Practical Approach" Lichtenstein and Nellen, eds. (1997) IRL Press.

Antisense molecules can be used to down-regulate expression of VSHK-1 genes in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43-56.

A VSHK-1 polynucleotide may be a VSHK-1 cDNA. The term "cDNA" as used herein is intended to include all nucleic acids that share the arrangement of sequence elements found in native mature mRNA species, where sequence elements are exons and 3" and 5" non-coding regions. Normally mRNA species have contiguous exons, with the intervening introns, when present, removed by nuclear RNA splicing, to create a continuous open reading frame encoding the protein protein Also encompassed by the term "VSHK-1 polynucleotide" are VSHK-1 genomic sequences. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, up to about 6 kb, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where VSHK-1 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1:194-205; Mortlock et al. (1996) *Genome Res.* 6:327-33; and Joulin and Richard-Foy (1995) *Eur. J. Biochem.* 232:620-626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to one of the subject genes in order to promote expression of wild type or altered VSHK-1 protein, or other proteins of interest in cultured cells, or in embryonic, fetal or adult tissues, and for gene therapy.

The nucleic acid compositions of the subject invention may encode all or a part of the VSHK-1 receptor polypeptides of the invention. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 18 nt, usually at least 25 nt or 50 nt, and may be at least about 100 nt. Such small DNA fragments are useful as primers for PCR, hybridization screening probes, etc. Larger DNA fragments, i.e. greater than 500 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The polynucleotides of the invention are isolated and obtained in substantial purity, generally as other than an intact chromosome. Usually, the DNA will be obtained substantially free of nucleic acid sequences other than a VSHK-1 polynucleotide, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by reverse transcriptase-polymerase chain reaction (RT-PCR), using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of VSHK-1 gene expression (i.e., at least transcription) in the sample.

The sequence of genes encoding VSHK-1 receptor, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. One of skill in the art will recognize that, in general, such mutations will occur outside of regions that affect VSHK-1 signal transduction activity. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993) *Biotechniques* 14:22; Barany (1985) *Gene* 37:111-23; Colicelli et al. (1985) *Mol. Gen. Genet.* 199:537-9; Prentki et al. (1984) *Gene* 29:303-13; and Shyamala and Ames (1991) *Gene* 97:1-6. Methods for site specific mutagenesis can be found in Sambrook et al. *Molecular Cloning: A Laboratory Manual*, CSH Press 1989, pp. 15.3-15.108; Weiner, et al., (1993) *Gene* 126:35-41; Sayers et al., (1992) *Biotechniques* 13:592-6; Jones, et al. (1992) *Biotechniques* 12:528-30; Barton et al., (1990) *Nucleic Acids Res.* 18:7349-55; Marotti,et al. (1989) *Gene Anal. Tech.* 6:67-70; and Zhu (1989) *Anal Biochem* 177:120-4. Such mutated genes maybe used to study structure-function relationships of VSHK-1 polypeptides, or to alter properties of the protein that affect its function or regulation.

VSHK-1 polynucleotides can be prepared in a number of different ways. For example, the nucleic acid may be synthesized using solid phase synthesis techniques, as are known in the art. Oligonucleotide synthesis is also described in Edge et al. (1981) *Nature* 292:756; Duckworth et al. (1981) *Nucleic Acids Res* 9:1691 and Beaucage et al. (1981) *Tet. Letts* 22: 1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject polypeptide products under suitable conditions.

Recombinant Vectors of the Invention

The present invention further provides recombinant vectors ("constructs") comprising VSHK-1 polynucleotides of the invention. Recombinant vectors are useful for propagation of the subject VSHK-1 polynucleotides (cloning vectors). They are also useful for effecting expression of a VSHK-1 polynucleotide in a cell (expression vectors). Some vectors accomplish both cloning and expression functions. The choice of appropriate vector is well within the skill of the art. Many such vectors are available commercially.

A variety of host-vector systems may be utilized to propagate and/or express the VSHK-1 polynucleotides of the invention. Such host-vector systems represent vehicles by which coding sequences of interest may be produced and subsequently purified, and also represent cells that may, when transformed or transfected with the appropriate nucleotide coding sequences, produce VSHK-1 receptor polypeptides of the invention. These include, but are not limited to, microorganisms (e.g., *E. coli, B. subtilis*) transformed with recombinant bacteriophage vectors, plasmid DNA, or cosmid DNA vectors comprising VSHK-1 polynucleotides; yeast (e.g., Saccharomyces, Pichia) transformed with recombinant yeast vectors comprising VSHK-1 polynucleotides); insect cell systems (e.g., *Spodoptera frugiperda*) infected with recombinant virus expression vectors (e.g., baculovirus vectors, many of which are commercially available, including, for example, pBacPAK8, and BacPAK6) comprising VSHK-1 polynucleotides; plant cell systems; or mammalian cell systems (e.g., COS, CHO, BHK, 293, 3T3) harboring recombinant vectors comprising mammalian promoters (e.g., metallothionein promoter) or promoters from viruses which replicate in mammalian cells (e.g., adenovirus late promoter; vaccinia virus promoter, and the like). Examples of prokaryotic cloning vectors which find use in propagating VSHK-1 polynucleotides of the invention are pBR322, M13 vectors, pUC 18, pcDNA, and pUC 19. Prokaryotic expression vectors which find use in expressing VSHK-1 -polypeptides in prokaryotic cells include pTrc99A, pK223-3, pEZZ18, pRIT2T, and pMC1871. Eukaryotic expression vectors which find use in expressing VSHK-1 polynucleotides and VSHK-1 polypeptides in eukaryotic cells include commercially available vectors such as pSVK3, pSVL, pMSG, pCH110, pMAMneo, pMAMneo-LUC, pPUR, and the like.

Generally, a bacterial host will be transformed to contain the expression system using a vector. A variety of vectors may be employed so long as they introduce the expression system into the host in a manner whereby the product encoded by the expression system can be expressed. Thus, the vector could be one that is capable homologously recombining with a region of the host chromosome such that the expression system becomes integrated into the host chromosome such that expression of the protein encoded thereby can occur. See Thomas and Capecchi (1987) *Cell* 51:503-512; as well as U.S. Pat. Nos. 5,631,153; 5,627,059; 5,487,992 and 5,464,764, the disclosure of which is herein incorporated by reference.

Generally, the expression cassette will be a plasmid that provides for expression of the encoded VSHK-1 receptor polypeptide under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and ColE1. Expression vectors generally have convenient restriction sites located near the promoter sequence to provide for the insertion of nucleic acid sequences encoding heterologous proteins. In addition, the expression vector will also typically comprise a marker which provides for detection of the clones that have been transformed with the vector. A variety of markers are known and may be present on the vector, where such markers include those that confer antibiotic resistance, e.g. resistance to ampicillin, tetracycline, chloramphenicol, kanamycin (neomycin), markers that provide for histochemical detection, etc. Specific vectors that may find use in the subject methods include: pBR322, pUC18, pUC19, pcDNA, and the like. Introduction of the nucleic acid encoding the subject peptide product into the expression vector is accomplished by cutting the expression vector and inserting the polynucleotide encoding the desired product.

Following preparation of the expression vector comprising the nucleic acid, the expression vector will be introduced into an appropriate host cell for production of the VSHK-1 polypeptide, i.e. a host cell will be transformed with the expression vector. Transformation of host cells may be accomplished in any convenient manner, where two representative means of transformation are treatment with divalent cation transformation compositions and electrotransformation. In transformation through divalent cation treatment, the host cells are typically incubated with the one or more divalent cations, e.g. $CaCl_2$, which serves to make the host cell permeable to the vector DNA. See Cohen et al. (1972) *Proc. Nat'l. Acad. Sci. USA* 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al. (1988) *Nucleic Acids Research* 16:6127.

A variety of host cells are suitable and may be used in the production of the VSHK-1 receptor polypeptides, where such host cells may be bacterial cells, yeast cells, or other cells, such as plant cells (see Depicker (1982) *J. Mol. Appl. Gen.* 1:561, where the host cell will generally be bacterial, e.g. *E. coli, B. subtilis*, where an *E. coli* strain is often the host cell of choice; or mammalian, e.g., COS, CHO, 3T3, and the like. *E. coli* strains that may be used include DH1, DH5, MM294, LE392, MC1061 and JM109.

Following transformation, bacterial host cells are screened for incorporation of the expression vector. Transformed colonies, e.g. host cells harboring the expression vector with the nucleic acid encoding the VSHK-1 receptor polypeptide are identified, and then grown up in large quantity. Where appropriate, agents that induce expression of the VSHK-1 receptor polypeptide are contacted with the host cell, e.g. isopropylthiogalactoside (IPTG).

Following colony growth, the expressed product will be harvested and purified for subsequent use. Typically, purification of the product involves disruption of the host cell, inactivation and removal of the native host proteins and precipitation of the nucleic acids. The product is separated from the other host cell constituents using one or more of a number of separation techniques known to those of skill in the art, e.g. centrifugation, dialysis, gel filtration chromatography, ion exchange chromatography, and the like. See Guide to Protein Purification (Murray P. Deutscher ed., Harcourt Brace & Co.) (1990). Using these protein purification techniques, isolated product may be prepared, where by isolated is meant a composition that is at least about 95% by weight peptidic product, usually at least about 98% by weight peptidic product and more usually at least about 99% by weight product, when the composition is dehydrated, e.g. lyophilized.

The subject nucleic acid molecules are generally propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence.

Other vectors are suitable for expression in cells in culture. These vectors will generally include regulatory sequences ("control sequences" or "control regions") which are necessary to effect the expression of a VSHK-1 polynucleotide to which they are operably linked. Still other vectors are suitable for transfer and expression in cells in a whole organism or person.

The VSHK-1 polynucleotides and receptor polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly (1994) Cancer Gene Therapy 1:51-64; Kimura (1994) Human Gene Therapy 5:845-852; Connelly (1995) Human Gene Therapy 1:185-193; and Kaplitt (1994) Nature Genetics 6:148-153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5, 219,740; WO 93/11230; WO 93/10218; Vile and Hart, Cancer Res. (1993) 53:3860-3864; Vile and Hart, Cancer Res. (1993) 53:962-967; Ram et al., Cancer Res. (1993) 53:83-88; Takamiya et al., J. Neurosci. Res. (1992) 33:493-503; Baba et al., J. Neurosurg. (1993) 79:729-735; U.S. Pat. No. 4,777,127; GB Patent No. 2,200,651; and EP 345 242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822-3828; Mendelson et al., Virol. (1988) 166:154-165; and Flotte et al., PNAS (1993) 90:10613-10617.

Also of interest are adenoviral vectors, e.g., those described by Berkner, Biotechniques (1988) 6:616-627; Rosenfeld et al.(1991) Science 252:431-434; WO 93/19191; Kolls et al. (1994) Proc. Natl. Acad. Sci. USA 91:215-219; Kass-Eisler et al. (1993) Proc. Natl. Acad. Sci. USA 90:11498-11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) Hum. Gene Ther. 3:147-154; ligand linked DNA, for example see Wu (1989) J. Biol. Chem. 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell Biol. 14:2411-2418, and in Woffendin (1994) Proc. Natl Acad. Sci. 91:1581-1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Further non-viral delivery suitable for use includes mechanical delivery systems such as the approach described in Woffendin et al.(1994) Proc. Natl. Acad. Sci. USA 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Host Cells of the Invention

The present invention further provides host cells, which may be isolated host cells, comprising VSHK-1 polynucleotides of the invention. Suitable host cells include prokaryotes such as E. coli, B. subtilis, eukaryotes, including insect cells in combination with baculovirus vectors, yeast cells, such as Saccharomyces cerevisiae, or cells of a higher organism such as vertebrates, including amphibians (e.g., Xenopus laevis oocytes), and mammals, particularly mammals, e.g. COS cells, CHO cells, 293 cells, 3T3 cells, and the like, may be used as the expression host cells. Host cells can be used for the purposes of propagating a VSHK-1 polynucleotide, for production of a VSHK-1 receptor polypeptide, or in cell-based methods for identifying agents which modulate a level of VSHK-1 mRNA and/or protein and/or enzyme activity in a cell.

The subject nucleic acids can be used to generate transgenic animals or site specific gene modifications in cell lines. The modified cells or animals are useful in the study of VSHK-1 function and regulation. For example, a series of small deletions or substitutions may be made in the VSHK-1 gene to determine the role of different coding regions in signal transduction, etc.

DNA constructs for homologous recombination will comprise at least a portion of the VSHK-1 gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the VSHK-1 gene and males and females having the modification are mated to produce homozygous progeny. The transgenic animals may be any non-human mammal, such as laboratory animals, domestic animals, etc. The transgenic animals may be used to determine the effect of a candidate drug on controlling unwanted cell proliferation, e.g., a reduction in cancer cell growth, in an in vivo environment.

Antibodies

Antibodies against VSHK-1 receptor polypeptides are useful for affinity chromatography, immunofluorescent assays, and detecting VSHK-1 receptor polypeptides. Further, antibodies can be useful to treat a VSHK-1 receptor mediated disorder. Antibodies which recognize the extracellular portions of native VSHK-1 receptors are of particular interest.

As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a VSHK-1 receptor polypeptide.

Antibodies to the proteins of the invention, both polyclonal and monoclonal, may be prepared by conventional methods. Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetra-methylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Compositions of the Invention

The present invention further provides compositions comprising the polypeptides, polynucleotides, recombinant vectors, host cells, and antibodies of the invention. These compositions may include a buffer, which is selected according to the desired use of the polypeptide, polynucleotide, recombinant vector, host cell, or antibody, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, *Remington: The Science and Practice of Pharmacy*, 19th Ed. (1995) Mack Publishing Co.

Methods Using the Polypeptides and Polynucleotides of the Invention

The present invention provides a variety of detection methods, which methods are useful in diagnostic assays. Also provided are assays for detecting VSHK-1 receptor ligands. Also provided are a variety of screening assays, which assays are useful for identifying agents which affect VSHK-1 receptor signal transduction or other activity, and/or VSHK-1 mRNA and/or VSHK-1 receptor polypeptide levels.

Detection Methods

Detection methods of the present invention include methods for detecting VSHK-1 receptor polypeptide in a biological sample, methods for detecting VSHK-1 mRNA in a biological sample, and methods for detecting VSHK-1 receptor signal transduction activity in a biological sample.

The detection methods can be provided as part of a kit. Thus, the invention further provides kits for detecting the presence and/or a level of VSHK-1 receptor polypeptide or VSHK-1 polynucleotides in a biological sample. Procedures using these kits can be performed by clinical laboratories, experimental laboratories, medical practioners, or private individuals. The kits of the invention for detecting a VSHK-1 receptor polypeptide comprise a moiety that specifically binds VSHK-1 receptor, including, but not limited to, a VSHK-1-specific antibody, and a VSHK-1 receptor ligand. The kits of the invention for detecting a VSHK-1 polynucleotide comprise a moiety that specifically hybridizes to a VSHK-1 polynucleotide. The kit may optionally provide additional components that are useful in the procedure, including, but not limited to, buffers, developing reagents, labels, reacting surfaces, means for detections, control samples, standards, instructions, and interpretive information.

Methods of Detecting a VSHK-1 Receptor Polypeptide in a Biological Sample

Immunoassays and ligand binding assays can be utilized to determine if a host cell is expressing the desired VSHK-1 receptor polypeptide.

For example, an immunofluorescence assay can be easily performed on host cells without separating the VSHK-1 receptor polypeptides from the cell membrane. The host cells are first fixed onto a solid support, such as a microscope slide or microtiter well. This fixing step can permeabilize the cell membrane. The permeablization of the cell membrane permits the antibodies to bind to the intracellular portions of native receptors, such as the second cytoplasmic loop of the VSHK-1 receptor polypeptides.

Next, the fixed host cells are exposed to an anti-VSHK-1 receptor polypeptide antibody. Preferably, to increase the sensitivity of the assay, the fixed cells are exposed to a second antibody, which is labeled and binds to the anti-VSHK-1 receptor polypeptide antibody. Typically, the secondary antibody is labeled with a fluorescent marker. The host cells which express the VSHK-1 receptor polypeptides will be fluorescently labelled and easily visualized under the microscope. See, for example, Hashido et al. (1992) *Biochem. Biophys. Res. Comm.* 187:1241-1248.

Also, the VSHK-1 receptor polypeptides do not need to be separated from the cell membrane for ligand binding assay. The host cells may be fixed to a solid support, such as a microtiter plate. Alternatively, a crude membrane fraction can be separated from lysed host cells by centrifugation (See Adachi et al. (1992) *FEBS Lett.* 311:179-183). The fixed host cells or the crude membrane fraction is exposed to labeled ligand, endogenous or non-natural. Typically, the ligand is labeled with radioactive atoms. The host cells which express the desired VSHK-1 receptor polypeptide can bind with the labeled ligand which can be easily detected.

Alternatively, whole cells, expressing VSHK-1 receptor polypeptides, can be cultured in a microtiter plate, for example, and used for ligand binding assay. See Sakamoto et al. (1991) *Biochem. Biophys. Res. Comm.* 178:656-663 for a description of such an assay.

Other assays can be used to determine if a host cell is expressing a VSHK-1 receptor polypeptide, such as signal transduction assays and immunoassays. These assays are described below.

The present invention further provides methods for detecting the presence of and/or measuring a level of a VSHK-1 receptor polypeptide in a biological sample, using a VSHK-1 receptor-specific antibody. The methods generally comprise:

a) contacting the sample with an antibody specific for a VSHK-1 receptor polypeptide; and b) detecting binding between the antibody and molecules of the sample.

Detection of specific binding of the VSHK-1 receptor -specific antibody, when compared to a suitable control, is an indication that VSHK-1 receptor polypeptides are present in the sample. Suitable controls include a sample known not to contain a VSHK-1 receptor polypeptide; and a sample contacted with an antibody not specific for VSHK-1 receptor, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the VSHK-1 receptor-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for VSHK-1 receptor-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled VSHK-1 receptor-specific antibody. Detection methods are known in the art and will be chosen as appropriate to the signal emitted by the detectable label. Detection is generally accomplished in comparison to suitable controls, and to appropriate standards.

Methods of Detecting a VSHK-1 mRNA in a Biological Sample The present invention further provides methods for detecting the presence of VSHK-1 mRNA in a biological sample. The methods can be used, for example, to assess whether a test compound affects VSHK-1 gene expression, directly or indirectly.

The methods generally comprise:

a) contacting the sample with a VSHK-1 polynucleotide of the invention under conditions which allow hybridization; and b) detecting hybridization, if any.

Detection of hybridization, when compared to a suitable control, is an indication of the presence in the sample of a VSHK-1 polynucleotide. Appropriate controls include, for example, a sample which is known not to contain VSHK-1 mRNA, and use of a labelled polynucleotide of the same "sense" as a VSHK-1 mRNA. Conditions which allow hybridization are known in the art, and have been described in more detail above. Detection can be accomplished by any known method, including, but not limited to, in situ hybridization, PCR, RT-PCR, and "Northern" or RNA blotting, or combinations of such techniques, using a suitably labelled VSHK-1 polynucleotide. A variety of labels and labelling methods for polynucleotides are known in the art and can be used in the assay methods of the invention. Specific hybridization can be determined by comparison to appropriate controls.

Methods using PCR amplification can be performed on the DNA from a single cell, although it is convenient to use at least about $10^5$ cells. The use of the polymerase chain reaction is described in Saiki et al. (1985) *Science* 239:487, and a review of current techniques may be found in Sambrook, et al. *Molecular Cloning: A Laboratory Manual*, CSH Press 1989, pp.14.2-14.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Screening Assays

The present invention provides screening methods for identifying agents which modulate VSHK-1 receptor signal transduction activity, methods for identifying agents which are VSHK-1 receptor ligands, methods for identifying agents which modulate a level of VSHK-1 receptor polypeptide in a cell, and methods for identifying agents which modulate a level of VSHK-1 mRNA in a cell.

The terms "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may be peptides, or peptoids. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Methods of Detecting VSHK-1 Receptor Ligands, Agonists, and Antagonists

VSHK-1 receptor polypeptides can also be used to screen libraries of compounds, such as peptide libraries, to identify receptor binding moieties. Receptor binding moieties includes ligands, which may be receptor agonists or antagonists. Accordingly, the screening methods of the invention include methods for identifying VSHK-1 receptor polypeptide ligands, and methods for identifying agents that effect or modulate a VSHK-1 receptor signal transduction activity. As used herein, the term "modulate" encompasses "increase"and "decrease". Assays are conducted in vitro, and can be cell-based or cell-free.

Methods to identify VSHK-1 receptor ligands generally comprise a) contacting a substance to be tested with a sample containing a VSHK-1 receptor polypeptide; and b) assaying a signal transduction activity of the VSHK-1 receptor polypeptide in the presence of the substance. Signal transduction in the presence of the substance is an indication that the substance is a VSHK-1 receptor ligand.

Methods to identify substances which modulate a signal transduction activity of a VSHK-1 receptor polypeptide generally comprise: a) contacting a substance to be tested with a sample containing a VSHK-1 receptor polypeptide; and b) assaying a signal transduction activity of the VSHK-1 receptor polypeptide in the presence of the substance. An increase or a decrease in signal transduction activity in comparison to VSHK-1 receptor signal transduction activity in a suitable control (e.g., a sample comprising a VSHK-1 receptor polypeptide in the absence of the substance being tested) is an indication that the substance modulates a signal transduction activity of the VSHK-1 receptor polypeptide. An increase in signal transduction activity indicates that the substance is a VSHK-1 receptor agonist. An agonist generally promotes signal transduction nearly as well, as well, or better, than a known ligand. A decrease in signal transduction activity indicates that the substance is a VSHK-1 receptor antagonist. To identify a receptor antagonist, the assay results are generally compared to a signal transduction level mediated by a known ligand.

Signal transduction activity can be assayed by measuring a level of one or more of: intracellular $Ca^{2+}$, intracellular IP3, and intracellular DAG, as described in detail below. Signal transduction activity may be measured in vitro in intact eukaryotic cells, or, alternatively, in cell-free membrane preparations. The cells used may be cells which express endogenous VSHK-1 receptor polypeptide in the cell membrane. Alternatively, the cell may be transduced with a recombinant construct comprising a nucleotide sequence encoding a VSHK-1 receptor polypeptide, as long as other components necessary for signal transduction activity of VSHK-1 receptor are present in the cell. In these situations, the VSHK-1 receptor polypeptide-encoding nucleotide sequence may be operably linked to a heterologous promoter, e.g., an inducible promoter, a constitutive promoter, and the like, depending on the assay.

In some embodiments, the candidate agent is a peptide. Various methods have been described for identifying a receptor-binding peptide, any of which may be suitable for use herein. Following are two non-limiting examples of suitable methods.

A "library" of peptides may be synthesized following the methods disclosed in U.S. Pat. No. 5,010,175. Briefly, one prepares a mixture of peptides, which is then screened to determine the peptides exhibiting the desired signal transduction and receptor binding activity. In the method disclosed in U.S. Pat. No. 5,010,175, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected VSHK-1 receptor polypeptide. The peptides are then tested for their ability to inhibit or enhance VSHK-1 receptor signal transduction activity. Peptides exhibiting the desired activity are then isolated and sequenced.

Another method for identifying receptor-binding peptides is provided in PCT WO91/17823. This method is similar to the method described in U.S. Pat. No. 5,010,175. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1-2,000 candidates each are exposed to the desired VSHK-1 receptor polypeptide. Each subpool that produces a positive result is then resynthesized as a group of smaller subpools (sub-subpools) containing, e.g., 20-100 candidates, and reassayed. Positive sub-subpools may be resynthesized as individual compounds, and assayed finally to determine the peptides, which exhibit a high binding constant. Then, these peptides can be tested for their ability to inhibit or enhance the VSHK-1 receptor signal transduction activity. The methods described in '17823 and U.S. Pat. No. 5,194,392 (herein incorporated by reference) enable the preparation of such pools and subpools by automated techniques in parallel, such that all synthesis and resynthesis may be performed in a matter of days.

Compounds which act as VSHK-1 receptor binding ligands, agonists, and antagonists are screened using any known method. The methods described herein are presently preferred. The assay conditions ideally should resemble the conditions under which the VSHK-1 receptor signal transduction is exhibited in vivo, i.e., under physiologic pH, temperature, ionic strength, etc. Suitable agonists or antagonists will exhibit strong inhibition or enhancement of the VSHK-1 receptor signal transduction activity at concentrations which do not raise toxic side effects on the cell or in the subject. Agonists or antagonists which compete for binding to the VSHK-1 receptor ligand binding site may require concentrations equal to or greater than the VSHK-1 receptor concentration, while inhibitors capable of binding irreversibly to the VSHK-1 receptor may be added in concentrations on the order of the VSHK-1 receptor concentration.

Signal Transduction Assays

Signal transduction assays and other biological assays are useful for identifying agonists and antagonists, including mutants, fragments and fusions of the native VSHK-1. Signal transduction can be measured by Ca+ release, inositol triphosphate concentration, and/or cAMP concentration. Signal transduction protocols are known to those skilled in the art, and have been amply described in various publications, including, for example, *Signal Transduction Protocols: Methods in Molecular Biology*, Vol. 41, Kendall and Hill, Eds, Humana Press, 1995; and *Signalling by Inositides: A Practical Approach*, Shears, Ed., IRL Press, 1997.

Most cellular $Ca^{2+}$ ions are sequestered in the mitochondria, endoplasmic reticulum, and other cytoplasmic vesicles, but binding of ligand to VSHK-1 will trigger the increase of free $Ca^{2+}$ ions in the cytoplasm. With fluorescent dyes, such as fura-2, the concentration of free $Ca^{2+}$ can be monitored. The ester of fura-2 is added to the media of the host cells expressing VSHK-1 receptor polypeptides. The ester of fura-2 is lipophilic and diffuses across the membrane. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to the free $Ca^{2+}$ ions, which are released after binding of a ligand to a VSHK-1 receptor polypeptide. The fluorescence can be measured without lysing the cells at an excitation spectrum of 340 nm or 380 nm and at fluorescence spectrum of 500 nm. See Sakurai et al., EP 480 381 and Adachi et al., *FEBS Lett* 311(2): 179-183 (1992) for examples of assays measuring free intracellular $Ca^{2+}$ concentrations.

The rise of free cytosolic $Ca^{2+}$ concentrations is preceded by the hydrolysis of phosphatidylinositol 4,5-bisphosphate. Hydrolysis of this phospholipid by the plasma-membrane enzyme phospholipase C yields 1,2-diacylglycerol (DAG), which remains in the membrane, and the water-soluble inositol 1,4,5-trisphosphate ($IP_3$). Binding of endogenous ligand or agonists will increase the concentration of DAG and $IP_3$. Thus, signal transduction activity can be measured by monitoring the concentration of these hydrolysis products.

To measure the $IP_3$ concentrations, radioactively labelled $^3$H-inositol is added to the media of host cells expressing VSHK-1 receptor polypeptides. The $^3$H-inositol taken up by the cells and after stimulation of the cells with endogenous ligand or agonist, the resulting inositol triphosphate is separated from the mono and di-phosphate forms and measured. See Sakurai et al., EP 480 381. Alternatively, Amersham provides an inosital 1,4,5-trisphosphate assay system. With this system Amersham provides tritylated inosital 1,4,5-trisphosphate and a receptor capable of distinguishing the radioactive inositol from other inositol phosphates. With these reagents an effective and accurate competition assay can be performed to determine the inositol triphosphate levels.

Methods of Detecting Agents which Modulate a Level of VSHK-1 mRNA and/or VSHK-1 Receptor Polypeptide A wide variety of cell-based assays may be used for identifying agents which modulate levels of VSHK-1 mRNA, using, for example, a mammalian cell transformed with a construct comprising a VSHK-1 receptor-encoding cDNA such that the cDNA is overexpressed, or, alternatively, a construct comprising a VSHK-1 promoter operably linked to a reporter gene.

Accordingly, the present invention provides a method for identifying an agent, particularly a biologically active agent, that modulates a level of VSHK-1 expression in a cell, the method comprising: combining a candidate agent to be tested with a cell comprising a nucleic acid which encodes a VSHK-1 receptor polypeptide; and determining the effect of said agent on VSHK-1 expression. "Modulation" of VSHK-1 expression levels includes increasing the level and decreasing the level of VSHK-1 mRNA and/or VSHK-1 receptor polypeptide encoded by the VSHK-1 polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of VSHK-1 mRNA and/or polypeptide following contacting the cell with a candidate agent being tested, compared to a control to which no agent is added, is an indication that the agent modulates VSHK-1 expression.

An agent being tested for its effect on VSHK-1 expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures or may be immortalized cell lines.

VSHK-1 mRNA and/or polypeptide whose levels are being measured can be encoded by an endogenous VSHK-1 polynucleotide, or the VSHK-1 polynucleotide can be one that is comprised within a recombinant vector and introduced into the cell, i.e., the VSHK-1 mRNA and/or polypeptide can be encoded by an exogenous VSHK-1 polynucleotide. For example, a recombinant vector may comprise an isolated VSHK-1 transcriptional regulatory sequence, such as a promoter sequence, operably linked to a reporter gene (e.g., β-galactosidase, CAT, luciferase, or other gene that can be easily assayed for expression). In these embodiments, the method for identifying an agent that modulates a level of VSHK-1 expression in a cell, comprises: combining a candidate agent to be tested with a cell comprising a nucleic acid which comprises a VSHK-1 gene transcriptional regulatory element operably linked to a reporter gene; and determining the effect of said agent on reporter gene expression. A recombinant vector may comprise an isolated VSHK-1 transcriptional regulatory sequence, such as a promoter sequence, operably linked to sequences coding for a VSHK-1 receptor polypeptide; or the transcriptional control sequences can be operably linked to coding sequences for a VSHK-1 fusion protein comprising VSHK-1 receptor polypeptide fused to a polypeptide which facilitates detection. In these embodiments, the method comprises combining a candidate agent to be tested with a cell comprising a nucleic acid which comprises a VSHK-1 gene transcriptional regulatory element operably linked to a VSHK-1 receptor polypeptide-coding sequence; and determining the effect of said agent on VSHK-1 expression, which determination can be carried out by measuring an amount of VSHK-1 mRNA, VSHK-1 receptor polypeptide, or VSHK-1 fusion polypeptide produced by the cell.

Cell-based assays generally comprise the steps of contacting the cell with an agent to be tested, forming a test sample, and, after a suitable time, assessing the effect of the agent on VSHK-1 expression. A control sample comprises the same cell without the candidate agent added. VSHK-1 expression levels are measured in both the test sample and the control sample. A comparison is made between VSHK-1 expression level in the test sample and the control sample. VSHK-1 expression can be assessed using conventional assays. For example, when a mammalian cell line is transformed with a construct that results in expression of VSHK-1, VSHK-1 mRNA levels can be detected and measured, as described above, or VSHK-1 receptor polypeptide levels can be detected and measured, as described above. A suitable period of time for contacting the agent with the cell can be determined empirically, and is generally a time sufficient to allow entry of the agent into the cell and to allow the agent to have a measurable effect on VSHK-1 mRNA and/or polypeptide levels. Generally, a suitable time is between 10 minutes and 24 hours, more typically about 1-8 hours. Methods of measuring VSHK-1 mRNA levels are known in the art, several of which have been described above, and any of these methods can be used in the methods of the present invention to identify an agent which modulates VSHK-1 mRNA level in a cell, including, but not limited to, a PCR, such as a PCR employing detectably labeled oligonucleotide primers, and any of a variety of hybridization assays. Similarly, VSHK-1 receptor polypeptide levels can be measured using any standard method, several of which have been described herein, including, but not limited to, an immunoassay such as ELISA, for example an ELISA employing a detectably labeled antibody specific for a VSHK-1 receptor polypeptide.

Compositions Comprising Identified Substances

The present invention further provides substances identified by any of the above-described screening methods. The substances may be provided in a composition comprising the substance(s). These compositions may include a buffer, which is selected according to the desired use of the substance, appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995) Mack Publishing Co.

Treatment Methods

Treatment of VSHK-1 Receptor Mediated Disorders

Methods of treatment or amelioration include administering compositions of polynucleotides, polypeptides, antibodies, or combinations thereof and can be used
  to inhibit translation and/or transcription;
  to inhibit biological activity;
  as a vaccine antigen; and
  as an immune system inducer.

Such compositions can be administered systemically or locally to the desired site. For example, modulation of genes or gene expression products that are mis-regulated can be used to treat VSHK-1 receptor mediated disorders and/or the accompanying physical and biological manifestations.

Therapeutic compositions may comprise one or more of the following: (1) ribozymes and/or antisense molecules that reduce the level of VSHK-1 mRNA in a cell; (2) a construct comprising nucleotide sequences encoding a VSHK-1 receptor polypeptide; (3) an antibody of the invention; (4) a VSHK-1 receptor polypeptide of the invention; (5) a VSHK-1 ligand; (6) a VSHK-1 receptor agonist; (7) a VSHK-1 antagonist.

The methods generally comprise contacting a eukaryotic cell with a substance which, after entering the cell, inhibits and/or modulates a signal transduction activity of a VSHK-1 receptor polypeptide, and/or which modulates a level of VSHK-1 mRNA and/or VSHK-1 receptor polypeptide in the eukaryotic cell. Generally, the cell is contacted with a composition comprising an effective amount of the substance.

An effective amount of a substance which modulates a signal transduction activity of a VSHK-1 receptor polypeptide is an amount that increases or decreases signal transduction activity of a VSHK-1 receptor polypeptide by at least about 10%, more preferably at least about 15%, more preferably at least about 25%, more preferably at least about 50% or more, when compared to the signal transduction activity of the VSHK-1 receptor polypeptide in the absence of the substance. An effective amount of a substance which modulates a level of VSHK-1 mRNA in a cell is an amount that increases or reduces VSHK-1 mRNA level by at least about 10%, more preferably at least about 15%, more preferably at least about 25%, more preferably at least about 50% or more, when compared to the level of VSHK-1 mRNA in the absence of the substance. An effective amount of a substance which modulates a level of VSHK-1 receptor polypeptide in a cell is an amount that increases or reduces a VSHK-1 receptor polypeptide level by at least about 10%, more preferably at least about 15%, more preferably at least about 25%, more preferably at least about 50% or more, when compared to the level of VSHK-1 receptor polypeptide in the absence of the substance.

Cells which are targets for the methods of the present invention are those which (1) express VSHK-1 mRNA and/or polypeptide at lower than normal levels; (2) express a VSHK-1 receptor polypeptide with abnormal function; or (3) normally express VSHK-1 receptor polypeptide, such as heart cells.

Pharmaceutical Compositions and Therapeutic Uses

Pharmaceutical compositions can comprise polypeptides; antibodies; VSHK-1 ligands, antagonists, or agonists; and/or polynucleotides of the invention. The pharmaceutical compositions will comprise a therapeutically effective amount of either polypeptides, antibodies, or polynucleotides of the invention.

The term "therapeutically effective amount" as used herein refers to an amount of a therapeutic agent to treat, ameliorate, or prevent a desired disease or condition, or to exhibit a detectable therapeutic or preventive effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polynucleotide, polypeptide or antibody compositions in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

The therapeutic agents may be administered in a variety of ways, orally, topically, parenterally e.g. subcutaneously, intraperitoneally, by viral infection, intravascularly, etc. Inhalation treatments may also be of interest. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Once formulated, the polynucleotide compositions of the invention can be (1) administered directly to the subject; (2) delivered ex vivo, to cells derived from the subject; or (3) delivered in vitro for expression of recombinant proteins.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

The sequences disclosed in this patent application were disclosed in several earlier patent applications. The relationship between the SEQ ID NOS in those earlier application and the SEQ ID NOS disclosed herein is shown in Table 3.

TABLE 3 relationship between SEQ ID NOs. this patent application and SEQ ID NOs of parent patent applications

| parent case | parent application no. | filing date | SEQ IDs in parent case | corresponding SEQ IDs in this patent application |
|---|---|---|---|---|
| 16932 | 10/081,119 | Feb. 21, 2002 | 1-38 | 1-38 |
| 1556 | 10/360,848 | Feb. 6, 2003 | 1-13 | 39-51 |
| 1575 | 10/763,692 | Jan. 22, 2004 | 1-19 | 51-70 |
| 1544 | 10/698,959 | Oct. 30, 2003 | 1-14 | 71-84 |

The disclosures of all prior U.S. applications to which the present application claims priority, which includes those U.S. applications referenced in the table above as well as their respective priority applications, are each incorporated herein by referenced in their entireties for all purposes, including the disclosures found in the Sequence Listings, tables, figures and Examples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Source of Patient Tissue Samples

Normal and cancerous tissues were collected from patients using laser capture microdissection (LCM) techniques, which techniques are well known in the art (see, e.g., Ohyama et al. (2000) *Biotechniques* 29:530-6; Curran et al. (2000) *Mol. Pathol.* 53:64-8; Suarez-Quian et al. (1999) *Biotechniques* 26:328-35; Simone et al. (1998) *Trends Genet* 14:272-6; Conia et al. (1997) *J. Clin. Lab. Anal.* 11:28-38; Emmert-Buck et al. (1996) *Science* 274:998-1001). Table 1 provides information about each patient from which the samples were isolated, including: the Patient ID and Path ReportID, numbers assigned to the patient and the pathology reports for identification purposes; the anatomical location of the tumor (AnatomicaLoc); The Primary Tumor Size; the Primary Tumor Grade; the Histopathologic Grade; a description of local sites to which the tumor had invaded (Local Invasion); the presence of lymph node metastases (Lymph Node Metastasis); incidence of lymph node metastases (provided as number of lymph nodes positive for metastasis over the number of lymph nodes examined) (Incidence Lymphnode Metastasis); the Regional Lymphnode Grade; the identification or detection of metastases to sites distant to the tumor and their location (Distant Met & Loc);a description of the distant metastases (Description Distant Met); the grade of distant metastasis (Distant Met Grade); and general comments about the patient or the tumor (Comments). Adenoma was not described in any of the patients; adenoma dysplasia (described as hyperplasia by the pathologist) was described in Patient ID No. 695. Extranodal extensions were described in two patients, Patient ID Nos. 784 and 791. Lymphovascular invasion was described in seven patients, Patient ID Nos. 128, 278, 517, 534, 784, 786, and 791. Crohn's-like infiltrates were described in seven patients, Patient ID Nos. 52, 264, 268, 392, 393, 784, and 791.

TABLE 1

| Pat. ID | Path Report ID | Grp | Anatl. Loc | Prim. Tumor Size | Prim. Tumor Grade | Hist Grade | Local Invasion | Lymph-node Met | Incidence Lymph-node Met | Regional Lymp-node Grade | Distant Met & Loc | Descrip Distant Met | Dist Met Grade | Comment |
|---|---|---|---|---|---|---|---|---|---|---|---|---|---|---|
| 15 | 21 | III | Ascending colon | 4.0 | T3 | G2 | extending into subserosal adipose tissue | positive | 3/8 | N1 | neg | | MX | invasive adenocarcinoma, moderately differentiated; focal perineural invasion is seen |
| 52 | 71 | II | Ascending colon | 9.0 | T3 | G3 | Invasion through muscularis propria, subserosal involvement; ileocec. valve involvement | negative | 0/12 | N0 | neg | | M0 | Hyperplastic polyp in appendix. |
| 121 | 140 | II | Sigmoid | 6 | T4 | G2 | Invasion of muscularis propria into serosa, involving submucosa of urinary bladder | negative | 0/34 | N0 | neg | | M0 | Perineural invasion; donut anastomosis negative. One tubulovillous and one tubular adenoma with no high grade dysplasia. |
| 125 | 144 | II | Cecum | 6 | T3 | G2 | Invasion through the muscularis propria into suserosal adipose tissue. Ileocecal junction. | negative | 0/19 | N0 | neg | | M0 | patient history of metastatic melanoma |
| 128 | 147 | III | Transverse colon | 5.0 | T3 | G2 | Invasion of muscularis propria into percolonic fat | positive | 1/5 | N1 | neg | | M0 | |
| 130 | 149 | | Splenic flexure | 5.5 | T3 | G2 | through wall and into surrounding adipose tissue | positive | 10/24 | N2 | neg | | M1 | |
| 133 | 152 | II | Rectum | 5.0 | T3 | G2 | Invasion through muscularis propria into non-peritonealized pericolic tissue; gross configuration is annular. | negative | 0/9 | N0 | neg | | M0 | Small separate tubular adenoma (0.4 cm) |
| 141 | 160 | IV | Cecum | 5.5 | T3 | G2 | Invasion of muscularis | positive | 7/21 | N2 | Pos Liver | adenocarcinoma consistant | M1 | Perineural invasion |

TABLE 1-continued

| Pat. ID | Path Report ID | Grp | Anatl. Loc | Prim. Tumor Size | Prim. Tumor Grade | Hist Grade | Local Invasion | Lymph-node Met | Incidence Lymph-node Met | Regional Lymph-node Grade | Distant Met & Loc | Descrip Distant Met | Dist Met Grade | Comment |
|---|---|---|---|---|---|---|---|---|---|---|---|---|---|---|
| | | | | | | | propria into pericolonic adipose tissue, but not through serosa. Arising from tubular adenoma. | | | | | with primary | | identified adjacent to metastatic adenocarcinoma. |
| 156 | 175 | III | Hepatic flexure | 3.8 | T3 | G2 | Invasion through muscularis propria into subserosa/ pericolic adipose, no serosal involvement. Gross configuration annular. | positive | 2/13 | N1 | neg | | M0 | Separate tubulovillous and tubular adenomas |
| 228 | 247 | III | Rectum | 5.8 | T3 | G2 to G3 | Invasion through muscularis propria to involve subserosal, perirectoal adipose, and serosa | positive | 1/8 | N1 | neg | | MX | Hyperplastic polyps |
| 264 | 283 | II | Ascending colon | 5.5 | T3 | G2 | Invasion through muscularis propria into subserosal adipose tissue. | negative | 0/10 | N0 | neg | | M0 | Tubulovillous adenoma with high grade dysplasia |
| 266 | 285 | III | Transverse colon | 9 | T3 | G2 | Invades through muscularis propria to involve pericolonic adipose, extends to serosa. | negative | 0/15 | N1 | pos (Mesenteric deposit) | 0.4 cm, may represent lymph node completely replaced by tumor | MX | |
| 268 | 287 | I | Cecum | 6.5 | T2 | G2 | Invades full thickness of muscularis propria, but mesenteric adipose free of malignancy | negative | 0/12 | N0 | neg | | M0 | |
| 278 | 297 | III | Rectum | 4 | T3 | G2 | Invasion into perirectal | positive | 7/10 | N2 | neg | | M0 | Descending colon polyps, |

TABLE 1-continued

| Pat. ID | Path Report ID | Grp | Anatl. Loc | Prim. Tumor Size | Prim. Tumor Grade | Hist Grade | Local Invasion | Lymph-node Met | Incidence Lymph-node Met | Regional Lymph-node Grade | Distant Met & Loc | Descrip Distant Met | Dist Met Grade | Comment |
|---|---|---|---|---|---|---|---|---|---|---|---|---|---|---|
| 295 | | | | | | | adipose tissue. | | | | | | | no HGD or carcinoma identified. |
| | 314 | II | Ascending colon | 5.0 | T3 | G2 | Invasion through muscularis propria into percolic adipose tissue. | negative | 0/12 | N0 | neg | | M0 | Melanosis coli and diverticular disease. |
| 339 | 358 | II | Recto-sigmoid | 6 | T3 | G2 | Extends into perirectal fat but does not reach serosa | negative | 0/6 | N0 | neg | | M0 | 1 hyperplastic polyp identified |
| 341 | 360 | II | Ascending colon | 2 cm invasive | T3 | G2 | Invasion through muscularis propria to involve pericolonic fat. Arising from villous adenoma. | negative | 0/4 | N0 | neg | | MX | |
| 356 | 375 | II | Sigmoid | 6.5 | T3 | G2 | Through colon wall into subserosal adipose tissue. No serosal spread seen. | negative | 0/4 | N0 | neg | | M0 | |
| 360 | 412 | III | Ascending colon | 4.3 | T3 | G2 | Invasion thru muscularis propria to pericolonic fat | positive | 1/5 | N1 | neg | | M0 | Two mucosal polyps |
| 392 | 444 | IV | Ascending colon | 2 | T3 | G2 | Invasion through muscularis propria into subserosal adipose tissue, not serosa. | positive | 1/6 | N1 | Pos Liver | Macrovesicular and microvesicular steatosis | M1 | Tumor arising at prior ileocolic surgical anastomosis. |
| 393 | 445 | II | Cecum | 6.0 | T3 | G2 | Cecum, invades through muscularis propria to involve subserosal adipose tissue but not serosa. | negative | 0/21 | N0 | neg | | M0 | |

TABLE 1-continued

| Pat. ID | Path Report ID | Grp | Anatl. Loc | Prim. Tumor Size | Prim. Tumor Grade | Hist Grade | Local Invasion | Lymph-node Met | Incidence Lymph-node Met | Regional Lymp-node Grade | Distant Met & Loc | Descrip Distant Met | Dist Met Grade | Comment |
|---|---|---|---|---|---|---|---|---|---|---|---|---|---|---|
| 413 | 465 | IV | Ascending colon | 4.8 | T3 | G2 | Invasive through muscularis to involve periserosal fat; abutting ileocecal junction. | negative | 0/7 | N0 | Pos Liver | adenocarcinoma in multiple slides | M1 | rediagnosis of oophorectomy path to metastatic colon cancer. |
| 505 | 383 | IV | | 7.5 cm max dim | T3 | G2 | Invasion through muscularis propria involving pericolic adipose, serosal surface uninvolved | positive | 2/17 | N1 | Pos Liver | moderately differentiated adenocarcinoma, consistant with primary | M1 | Anatomical location of primary not notated in report. Evidence of chronic colitis. |
| 517 | 395 | IV | Sigmoid | 3 | T3 | G2 | penetrates muscularis propria, involves pericolonic fat. | positive | 6/6 | N2 | Neg | | M0 | No mention of distant met in report |
| 534 | 553 | II | Ascending colon | 12 | T3 | G3 | Invasion through the muscularis propria involving pericolic fat. Serosa free of tumor. | negative | 0/8 | N0 | Neg | | M0 | Omentum with fibrosis and fat necrosis. Small bowel with acute and chronic serositis, focal abscess and adhesions. |
| 546 | 565 | IV | Ascending colon | 5.5 | T3 | G2 | Invasion through muscularis propria extensively through submucosal and extending to serosa. | positive | 6/12 | N2 | Pos Liver | Metastatic adenocarcinoma | M1 | |
| 577 | 596 | II | Cecum | 11.5 | T3 | G2 | Invasion through the bowel wall, into suberosal adipose. Serosal surface free of tumor. | negative | 0/58 | N0 | neg | | M0 | Appendix dilated and fibrotic, but not involved by tumor |
| 695 | 714 | II | Cecum | 14 | T3 | G2 | extending through bowel wall into | negative | 0/22 | N0 | neg | | MX | tubular adenoma and hyperplstic polyps present, |

TABLE 1-continued

| Pat. ID | Path Report ID | Grp | Anatl. Loc | Prim. Tumor Size | Prim. Tumor Grade | Hist Grade | Local Invasion | Lymph-node Met | Incidence Lymph-node Met | Regional Lymp-node Grade | Distant Met & Loc | Descrip Distant Met | Dist Met Grade | Comment |
|---|---|---|---|---|---|---|---|---|---|---|---|---|---|---|
| | | | | | | | serosal fat | | | | | | | moderately differentiated adenoma with mucinous diferentiation (% not stated) |
| 784 | 803 | IV | Ascending colon | 3.5 | T3 | G3 | through muscularis propria into pericolic soft tissues | positive | 5/17 | N2 | Pos Liver | | M1 | invasive poorly differentiated adenosquamous carcinoma |
| 786 | 805 | IV | Descending colon | 9.5 | T3 | G2 | through muscularis propria into pericolic fat, but not at serosal surface | negative | 0/12 | N0 | Pos Liver | | M1 | moderately differentiated invasive adenocarcinoma |
| 791 | 810 | IV | Ascending colon | 5.8 | T3 | G3 | through the muscularis propria into pericolic fat | positive | 13/25 | N2 | Pos Liver | | M1 | Poorly differentiated invasive colonic adenocarcinoma |
| 888 | 908 | IV | Ascending colon | 2.0 | T2 | G1 | into muscularis propria | positive | 3/21 | N0 | Pos Liver | | M1 | well- to moderately-differentiated adenocarcinoma; this patient has tumors of the ascending colon and the sigmoid colon |
| 889 | 909 | IV | Cecum | 4.8 | T3 | G2 | through muscularis propria int subserosal tissue | positive | 1/4 | N1 | Pos Liver | | M1 | Moderately differentiated adenocarcinoma |

Example 2

Differential Expression of TTK cDNA probes were prepared from total RNA isolated from the patient cells described in Example 1. Since LCM provides for the isolation of specific cell types to provide a substantially homogenous cell sample, this provided for a similarly pure RNA sample.

Total RNA was first reverse transcribed into cDNA using a primer containing a T7 RNA polymerase promoter, followed by second strand DNA synthesis. cDNA was then transcribed in vitro to produce antisense RNA using the T7 promoter-mediated expression (see, e.g., Luo et al. (1999) *Nature Med* 5:117-122), and the antisense RNA was then converted into cDNA. The second set of cDNAs were again transcribed in vitro, using the T7 promoter, to provide antisense RNA. Optionally, the RNA was again converted into cDNA, allowing for up to a third round of T7-mediated amplification to produce more antisense RNA. Thus the procedure provided for two or three rounds of in vitro transcription to produce the final RNA used for fluorescent labeling. Fluorescent probes were generated by first adding control RNA to the antisense RNA mix, and producing fluorescently labeled cDNA from the RNA starting material. Fluorescently labeled cDNAs prepared from the tumor RNA sample were compared to fluorescently labeled cDNAs prepared from normal cell RNA sample. For example, the cDNA probes from the normal cells were labeled with Cy3 fluorescent dye (green) and the cDNA probes prepared from the tumor cells were labeled with Cy5 fluorescent dye (red).

Each array used had an identical spatial layout and control spot set. Each microarray was divided into two areas, each area having an array with, on each half, twelve groupings of 32×12 spots for a total of about 9,216 spots on each array. The two areas are spotted identically which provide for at least two duplicates of each clone per array. Spotting was accomplished using PCR amplified products from 0.5 kb to 2.0 kb and spotted using a Molecular Dynamics Gen III spotter according to the manufacturer's recommendations. The first row of each of the 24 regions on the array had about 32 control spots, including 4 negative control spots and 8 test polynucleotides. The test polynucleotides were spiked into each sample before the labeling reaction with a range of concentrations from 2-600 pg/slide and ratios of 1:1. For each array design, two slides were hybridized with the test samples reverse-labeled in the labeling reaction. This provided for about 4 duplicate measurements for each clone, two of one color and two of the other, for each sample.

The differential expression assay was performed by mixing equal amounts of probes from tumor cells and normal cells of the same patient. The arrays were prehybridized by incubation for about 2 hrs at 60° C. in 5×SSC/0.2% SDS/1 mM EDTA, and then washed three times in water and twice in isopropanol. Following prehybridization of the array, the probe mixture was then hybridized to the array under conditions of high stringency (overnight at 42° C. in 50% formamide, 5×SSC, and 0.2% SDS. After hybridization, the array was washed at 55° C. three times as follows: 1) first wash in 1×SSC/0.2% SDS; 2) second wash in 0.1×SSC/0.2% SDS; and 3) third wash in 0.1×SSC.

The arrays were then scanned for green and red fluorescence using a Molecular Dynamics Generation III dual color laser-scanner/detector. The images were processed using BioDiscovery Autogene software, and the data from each scan set normalized to provide for a ratio of expression relative to normal. Data from the microarray experiments was analyzed according to the algorithms described in U.S. application Ser. No. 60/252,358, filed Nov. 20, 2000, by E. J. Moler, M. A. Boyle, and F. M. Randazzo, and entitled "Precision and accuracy in cDNA microarray data," which application is specifically incorporated herein by reference.

The experiment was repeated, this time labeling the two probes with the opposite color in order to perform the assay in both "color directions." Each experiment was sometimes repeated with two more slides (one in each color direction). The level fluorescence for each sequence on the array expressed as a ratio of the geometric mean of 8 replicate spots/genes from the four arrays or 4 replicate spots/gene from 2 arrays or some other permutation. The data were normalized using the spiked positive controls present in each duplicated area, and the precision of this normalization was included in the final determination of the significance of each differential. The fluorescent intensity of each spot was also compared to the negative controls in each duplicated area to determine which spots have detected significant expression levels in each sample.

A statistical analysis of the fluorescent intensities was applied to each set of duplicate spots to assess the precision and significance of each differential measurement, resulting in a p-value testing the null hypothesis that there is no differential in the expression level between the tumor and normal samples of each patient. During initial analysis of the microarrays, the hypothesis was accepted if $p>10^{-3}$, and the differential ratio was set to 1.000 for those spots. All other spots have a significant difference in expression between the tumor and normal sample. If the tumor sample has detectable expression and the normal does not, the ratio is truncated at 1000 since the value for expression in the normal sample would be zero, and the ratio would not be a mathematically useful value (e.g., infinity). If the normal sample has detectable expression and the tumor does not, the ratio is truncated to 0.001, since the value for expression in the tumor sample would be zero and the ratio would not be a mathematically useful value. These latter two situations are referred to herein as "on/off." Database tables were populated using a 95% confidence level ($p>0.05$).

The difference in the expression level of TTK in the colon tumor cells relative to the matched normal colon cells was greater than or equal to 2 fold (">=2x") in 39% of the patients, greater than or equal to 2.5 fold in 36% of the patients, and greater than or equal to 5 fold in 27% of the patients examined.

Figure 2:
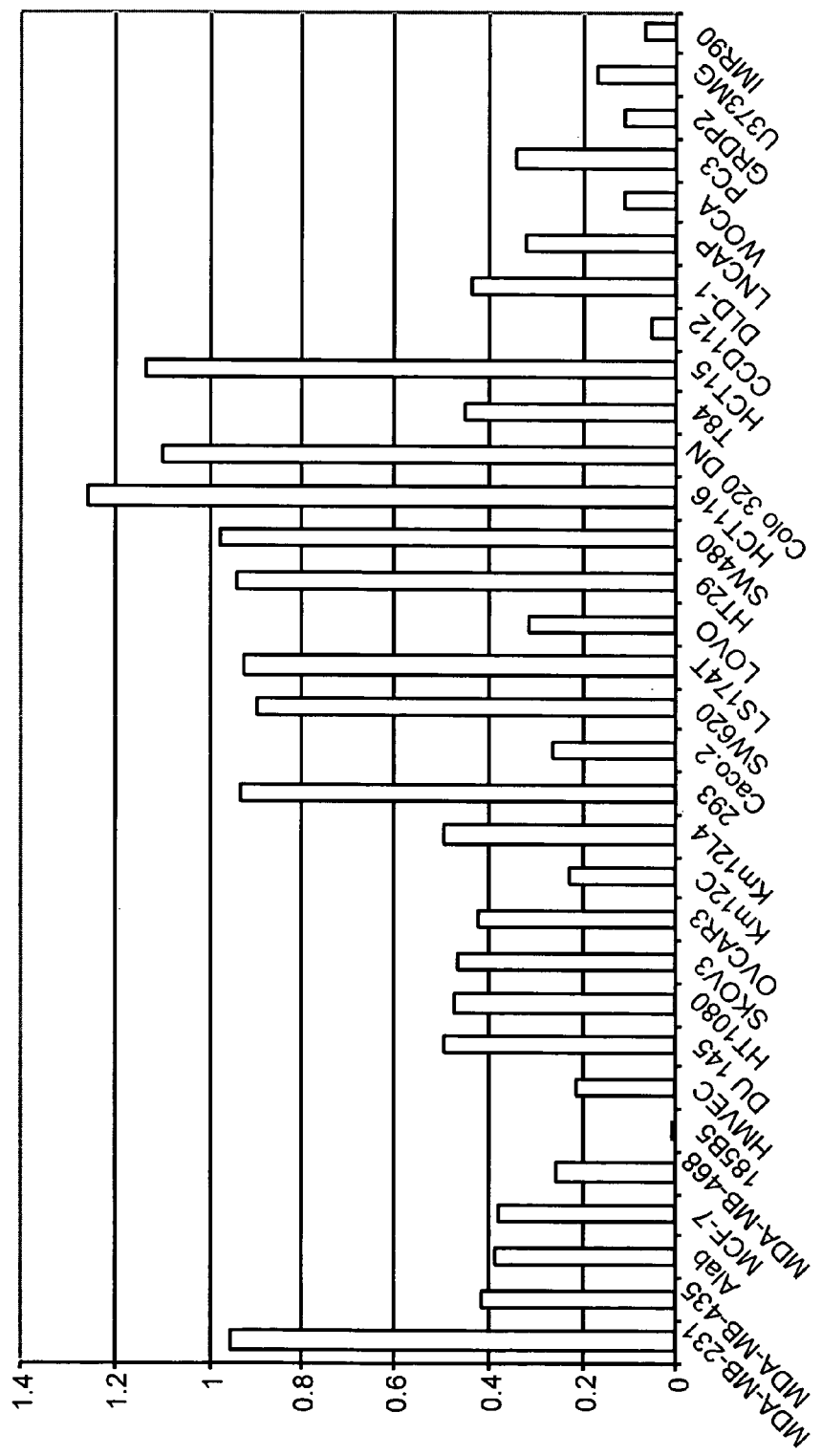
FIG. 2 is a bar graph illustrating expression of TTK in various tumor cell lines as detected by PCR.
Figure 3:
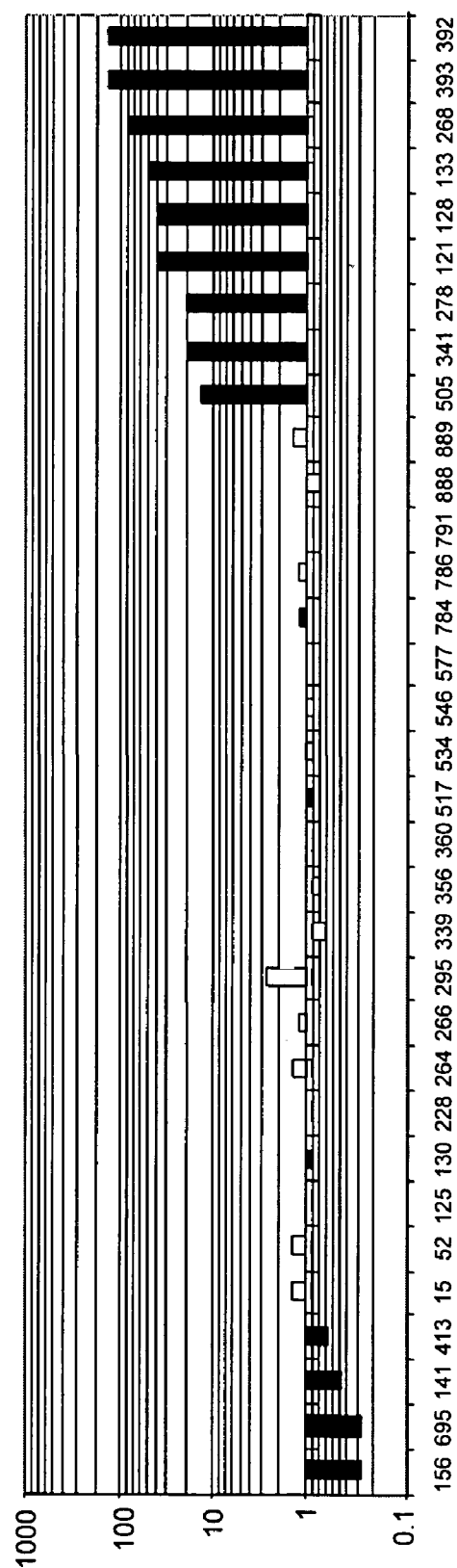
FIGS. 3-6 are graphs illustrating expression profiles for IGF2, MAPKAPPK2, TTK, and MARCKS in patients with colorectal carcinoma.
Figure 4:
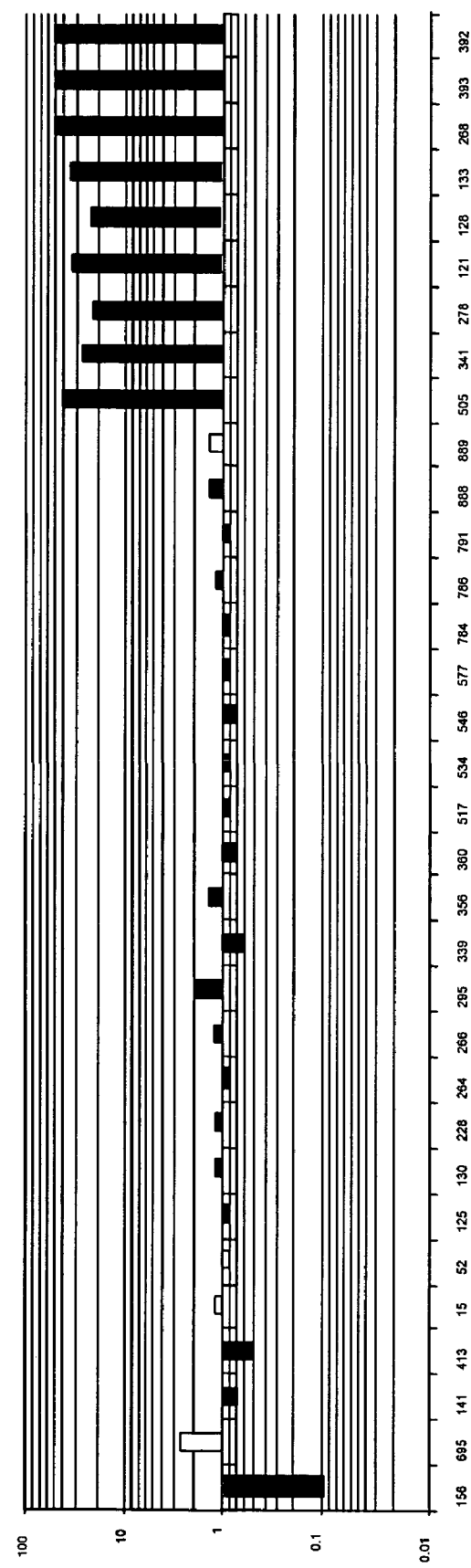
Figure 5:
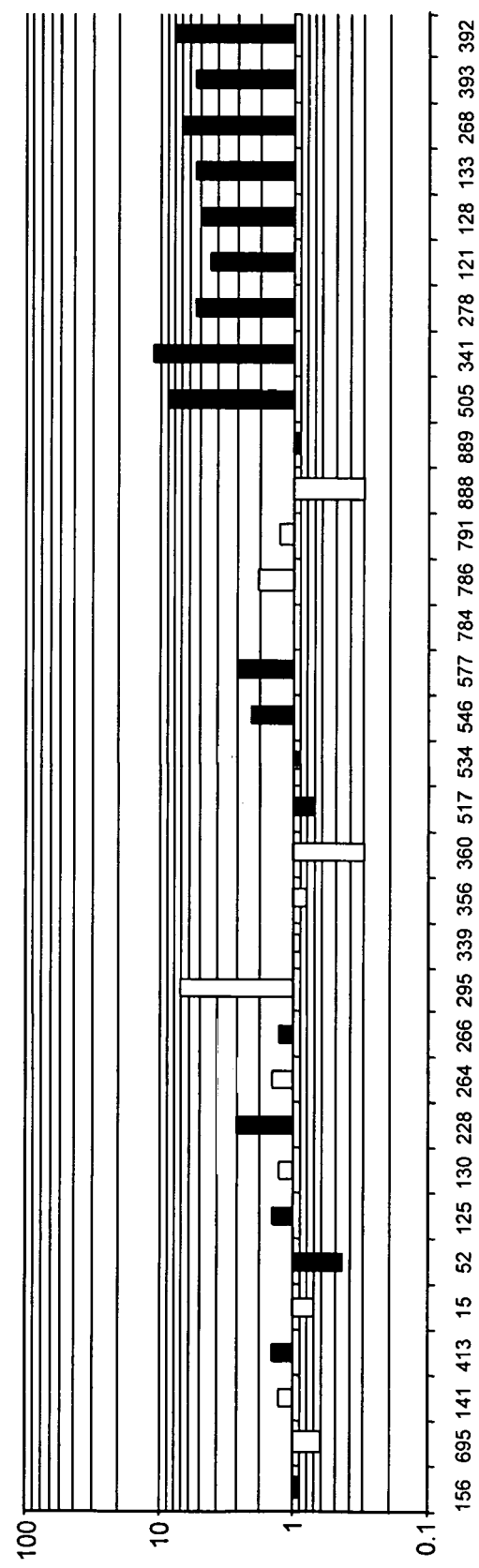
Figure 6:
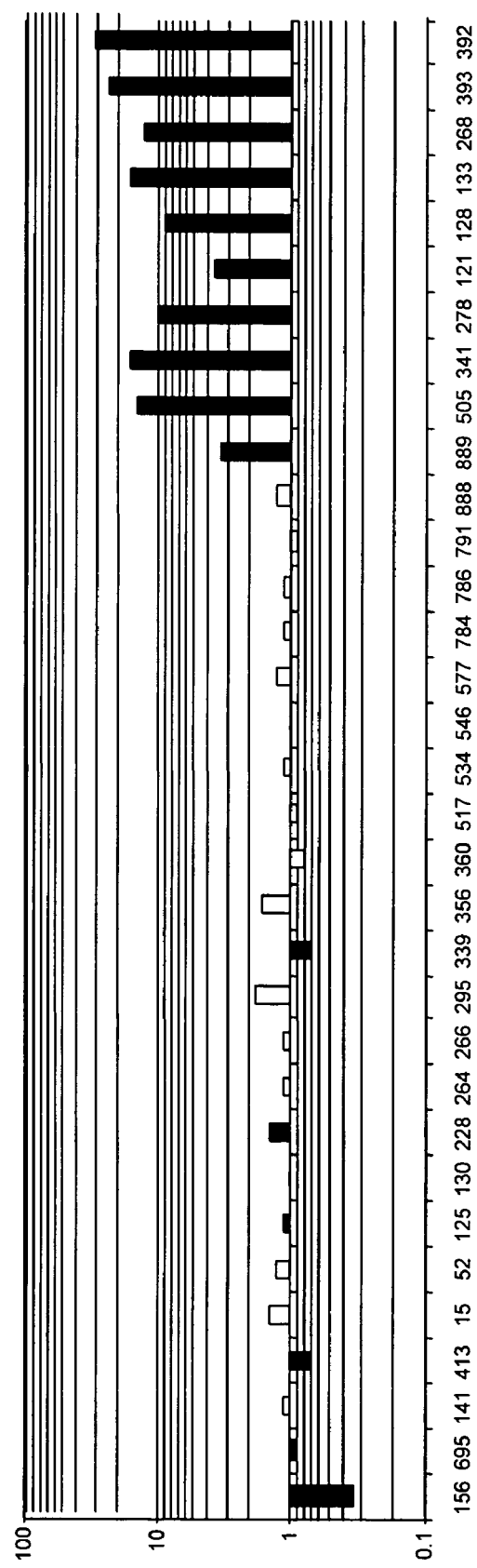

Quantitative PCR of a number of normal tissues and tumor cell lines, particularly colorectal carcinoma cell lines was used to analyze expression of TTK. Quantitative real-time PCR was performed by first isolating RNA from cells using a Roche RNA Isolation kit according to manufacturer's directions. One microgram of RNA was used to synthesize a first-strand cDNA using MMLV reverse transcriptase (Ambion) using the manufacturers buffer and recommended concentrations of oligo dT, nucleotides, and Rnasin. This first-strand cDNA served as a template for quantitative real-time PCR using the Roche light-cycler as recommended in the machine manual. TTK was amplified with the forward primer CGGAATCAAGTCTTCTAGCT (SEQ ID NO:1) and reverse primer GGTTGCTCAAAAGTTGGTATG (SEQ ID NO:2) PCR product was quantified based on the cycle at which the amplification entered the linear phase of amplification in comparison to an internal standard and using the software supplied by the manufacturer. Small differences in amounts or total template in the first-strand cDNA reaction were eliminated by normalizing to amount of actin amplified in a separate quantitative PCR reaction using the forward primer 5'-CGGGAAATCGTGCGTGACATTAAG-3' (SEQ ID NO:3) and the reverse primer: 5'-TGATCTCCTTCTG-CATCCTGTCGG-3' (SEQ ID NO:4). The results for TTK mRNA levels in normal tissues are shown in FIG. 1; the results for TTK mRNA levels in tumor cell lines are shown in FIG. 2. A brief description of the cell lines analyzed is provided in the table below.

| Cell Line | Tissue Source | Cell Line | Tissue Source |
|---|---|---|---|
| MDA-MB-231 | Human breast; high metastatic potential (micromets in lung; adenocarcinoma; pleural effusion | Caco-2 | Human colorectal adenocarcinoma |
| MDA-MB-435 | Human breast, high metastatic potential (macrometastases in lung) | SW620 | Human colorectal adenocarcinoma; from metastatic site (lymph node) |
| MCF-7 | Human breast; non-metastatic | LS174T | High metastatic potential human colorectal adenocarcinoma |
| MDA-MB-468 | Human breast; adenocarcinoma | LOVO | Human colorectal adenocarcinoma; colon; from metastatic site (colon) |
| Alab | Human breast, metastatic | HT29 | Human colorectal adenocarcinoma; colon |
| SKOV3 | Human ovarian adenocarcinoma | SW480 | Human colorectal adenocarcinoma; colon |
| OVCAR3 | Human ovarian adenocarcinoma | HCT116 | Human colorectal carcinoma; colon |
| KM12C | Human colon; low metastatic potential | Colo 320DN | Human colorectal adenocarcinoma; colon |
| KM12L4 | Human colon; high metastatic potential (derived from Km12C) | T84 | Human colorectal carcinoma; colon; from metastatic site (lung) |
| DU 145 | Human prostate; carcinoma; from metastatic site: brain | HCT15 | Human colorectal adenocarcinoma; colon |
| HT1080 | Human sarcoma cell line; | CCD112 | Human colorectal adenocarcinoma, low metastatic potential |
| HMVEC | Primary human microvascular endothelial cells | DLD1 | Human colon; colorectal adenocarcinoma |
| 184B5 | normal breast epithelial cells; chemically transformed | 293 | kidney epithelial cells |
| LNCAP | prostate carcinoma; metastasis to left supraclavicular lymph | GRDP2 | primary prostate epithelium |
| U373MG | glioblastoma cell | IMR90 | primary lung fibroblast |
| WOCA | primary prostate epithelium | PC3 | prostate cancer; androgen receptor negative |

TTK was expressed in normal cells (FIG. 1), with thymus and testis identified as the normal tissues that most highly express the gene for TTK. Numerous cancer cells, however, displayed a significantly elevated level of TTK expression (FIG. 2) as compared to most wild-type tissues.

Example 3

Hierarchical Clustering and Stratification of Colon Cancers Using Differential Expression Data Differential expression patterns from Example 2 were analyzed by applying hierarchical clustering methods to the data sets (see Eisen et al. (1998) *PNAS* 95:14863-14868). In short, hierarchical clustering algorithms are based on the average-linkage method of Sokal and Michener (Sokal, R R & Michener, C D (1958) Univ. Kans. Sci. Bull. 38, 1409-1438), which was developed for clustering correlation matrixes. The object of this algorithm is to compute a dendrogram that assembles all elements into a single tree. For any set of n genes, an upper-diagonal similarity matrix is computed which contains similarity scores for all pairs of genes. The matrix is scanned to identify the highest value (representing a similar pair of genes). Using this technique, four groups of differential expression patterns were identified and assigned to clusters.

Application of hierarchical clustering to the data from Example 2 revealed that IGF2 (insulin-like growth factor 2), TTK (serine, threonine, tyrosine kinase implicated in the cell cycle), MAPKAPK2 (mitogen-activated protein (MAP) kinase-activated protein kinase), and MARCKS (myristoylated alanine-rich C kinase substrate, which is a substrate of protein kinase C) are concurrently upregulated as detected in 9 out of the 33 colon cancer patient samples examined. The data for these experiments is presented in graphical form in FIGS. 3-6. The concurrent upregulation suggests that these genes are co-regulated and that patients with an elevated serum level of IGF2 may be candidates for treatment with inhibitors to TTK, MAPKAP kinase 2, MARCKS and/or IGF2.

Example 4

Antisense Regulation of TTK Expression

Additional functional information on TTK was generated using antisense knockout technology. TTK expression in cancerous cells was further analyzed to confirm the role and function of the gene product in tumorgenesis, e.g., in promoting a metastatic phenotype.

A number of different oligonucleotides complementary to TTK mRNA were designed as potential antisense oligonucleotides, and tested for their ability to suppress expression of TTK. The ability of each designed antisense oligonucleotide to inhibit gene expression was tested through transfection into SW620 colon colorectal carcinoma cells. For each transfection mixture, a carrier molecule, preferably a lipitoid or cholesteroid, was prepared to a working concentration of 0.5 mM in water, sonicated to yield a uniform solution, and filtered through a 0.45 μm PVDF membrane. The antisense or control oligonucleotide was then prepared to a working concentration of 100 μM in sterile Millipore water. The oligonucleotide was further diluted in OptiME™ (Gibco/BRL), in a microfuge tube, to 2 μM, or approximately 20 μg oligo/ml of OptiMEM™. In a separate microfuge tube, lipitoid or cholesteroid, typically in the amount of about 1.5-2 nmol lipitoid/μg antisense oligonucleotide, was diluted into the same volume of OptiMEM™ used to dilute the oligonucleotide. The diluted antisense oligonucleotide was immediately added to the diluted lipitoid and mixed by pipetting up and down. Oligonucleotide was added to the cells to a final concentration of 30 nM.

The level of target mRNA (TTK) in the transfected cells was quantitated in the cancer cell lines using the Roche Light-Cycler™ real-time PCR machine. Values for the target mRNA were normalized versus an internal control (e.g., beta-actin). For each 20 μl reaction, extracted RNA (generally 0.2-1 μg total) was placed into a sterile 0.5 or 1.5 ml microcentrifuige tube, and water was added to a total volume of 12.5 μl. To each tube was added 7.5 μl of a buffer/enzyme mixture, prepared by mixing (in the order listed) 2.5 μl $H_2O$, 2.0 μl 10×reaction buffer, 10 μl oligo dT (20 pmol), 1.0 μl dNTP mix (10 mM each), 0.5 μl RNAsin® (20 u) (Ambion, Inc., Hialeah, Fla.), and 0.5 μl MMLV reverse transcriptase (50 u) (Ambion, Inc.). The contents were mixed by pipetting up and down, and the reaction mixture was incubated at 42° C. for 1 hour. The contents of each tube were centrifuged prior to amplification.

An amplification mixture was prepared by mixing in the following order: 1×PCR buffer II, 3 mM $MgCl_2$, 140 μM each dNTP, 0.175 pmol each oligo, 1:50,000 dil of SYBR® Green, 0.25 mg/ml BSA, 1 unit Taq polymerase, and $H_2O$ to 20 μl. (PCR buffer II is available in 10×concentration from Perkin-Elmer, Norwalk, Conn.). In 1×concentration it contains 10 mM Tris pH 8.3 and 50 mM KCl. SYBR® Green (Molecular Probes, Eugene, Oreg.) is a dye which fluoresces when bound to double stranded DNA. As double stranded PCR product is produced during amplification, the fluorescence from SYBR®) Green increases. To each 20 μl aliquot of amplification mixture, 2 μl of template RT was added, and amplification was carried out according to standard protocols.

The following antisense oligonucleotides were shown to effectively deplete TTK RNA in the transfection assays:
Oligo 79-5AS: GGGACTCTTCCAAATGGGCATGACT (SEQ ID NO:5)
Oligo 79-9AS: TCCAGTAACTCTTGCGTTCCCATGG (SEQ ID NO:6)

The reverse control of each of these antisense oligonucleotides were synthesized, as were oligonucleotides with the identical sequence of the antisense oligonucleotides in reverse orientation (Reverse Control):

```
Oligo 79-5RC:
TCAGTACGGGTAAACCTTCTCAGGG        (SEQ ID NO:7)

Oligo 79-9RC:
GGTACCCTTGCGTTCTCAATGACCT        (SEQ ID NO:8)
```

The antisense oligonucleotides were introduced into a test cell and the effect upon TTK expression of the corresponding gene, as well as the effect induction of the cancerous phenotype, was examined as described below.

Example 5

Effect of TTK Expression on Proliferation

The effect of TTK on proliferation was assessed in metastatic breast cancer cell lines (MDA-MB-231 ("231")), SW620 colon colorectal carcinoma cells, or 847 human immortal fibroblast cells. Transfection was carried out as described above in Example 4.

Cells were plated to approximately 60-80% confluency in 96-well dishes. Antisense or reverse control oligonucleotide was diluted to 2 μM in OptiMEM™ and added to OptiMEM™ into which the delivery vehicle, lipitoid 116-6 in the case of SW620 cells or 1:1 lipitoid 1:cholesteroid 1 in the case of MDA-MB-231 cells, had been diluted. The oligo/delivery vehicle mixture was then further diluted into medium with serum on the cells. The fmal concentration of oligonucleotide for all experiments was 300 nM, and the fmal ratio of oligo to delivery vehicle for all experiments was 1.5 nmol lipitoid/μg oligonucleotide. Cells were transfected overnight at 37° C. and the transfection mixture was replaced with fresh medium the next morning.

Figure 7:
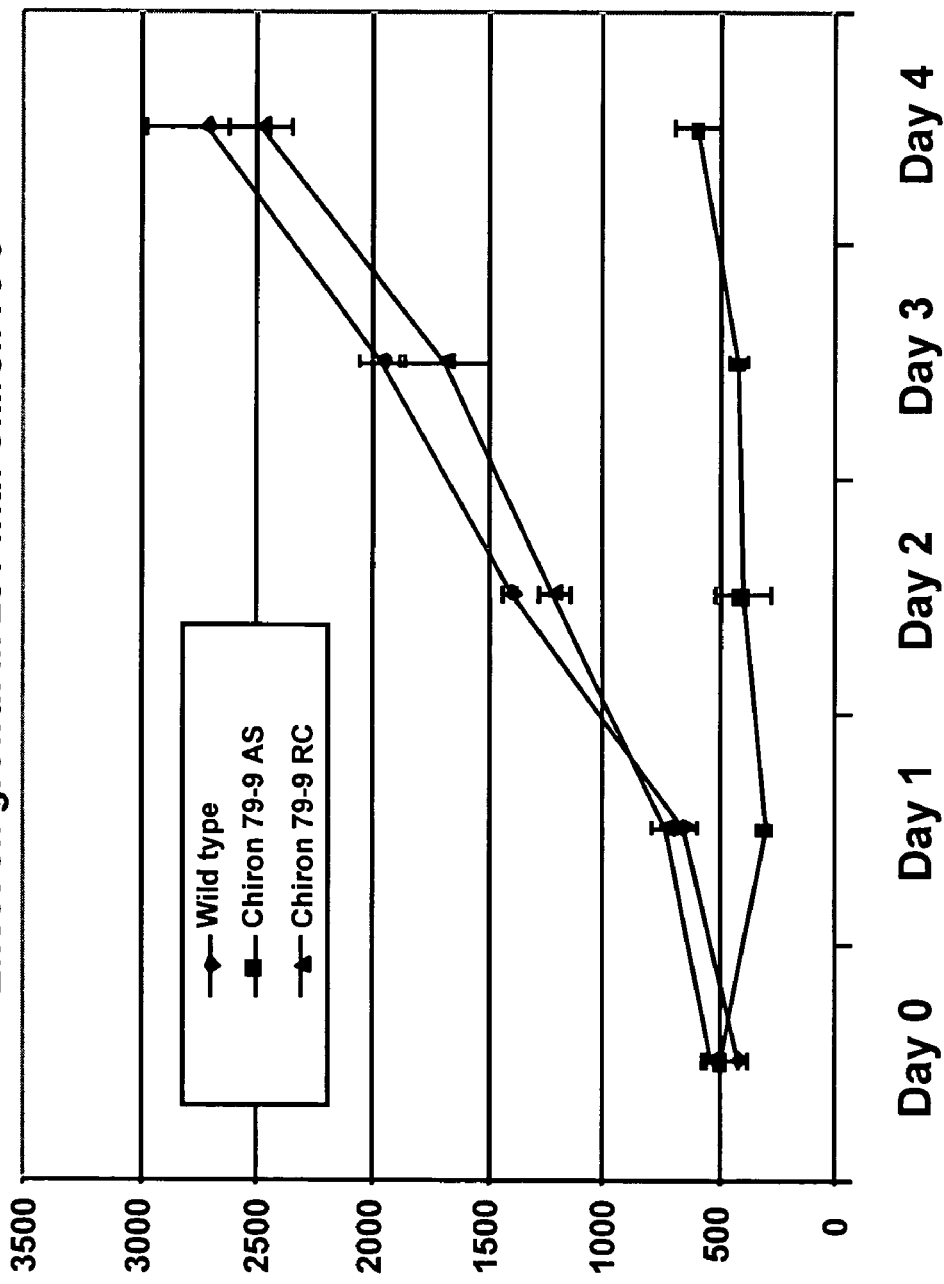
FIGS. 7 and 8 are graphs illustrating growth suppression of MDA-MB-231 cells following antisense suppression of TTK expression.
Figure 8:
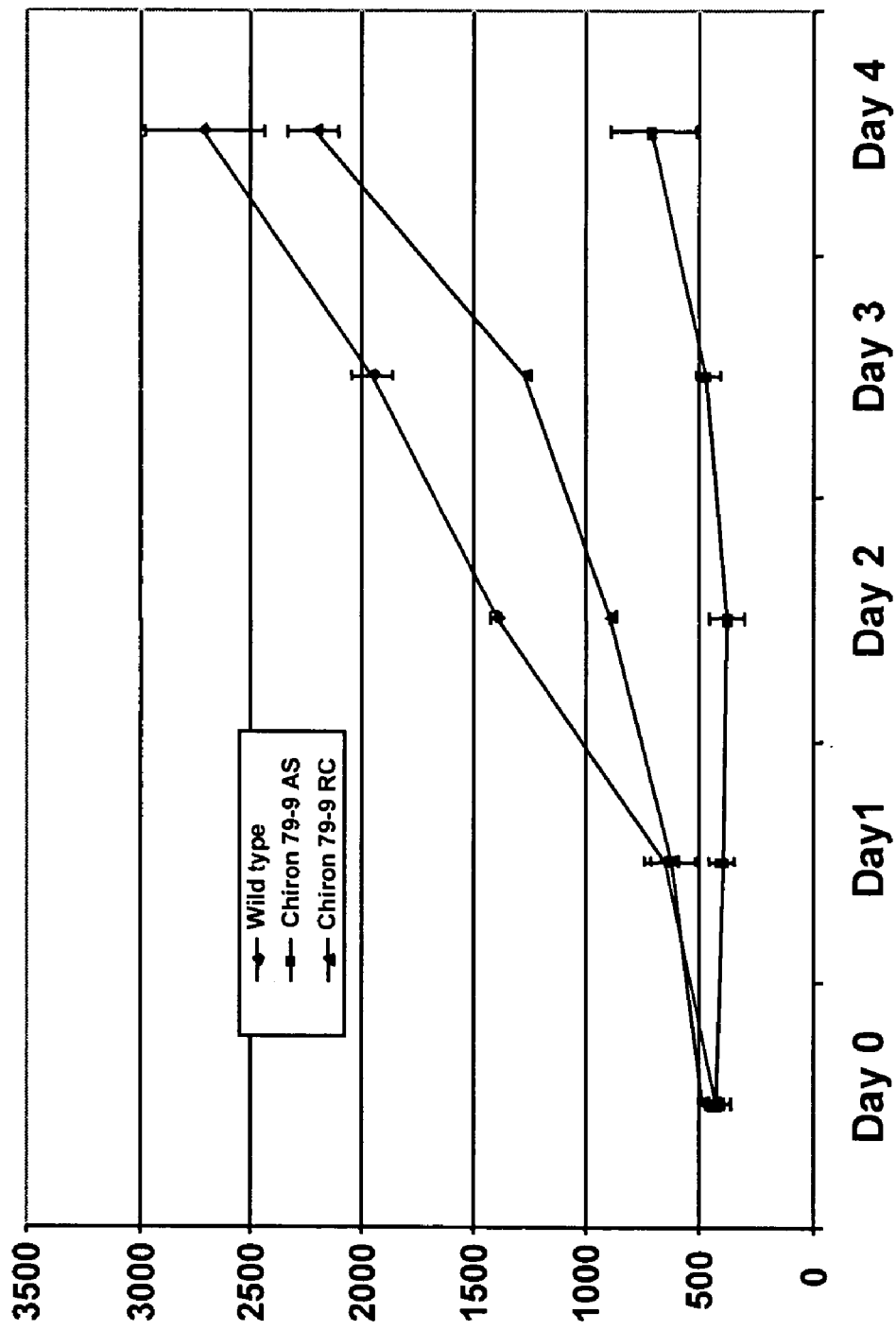
Figure 11:
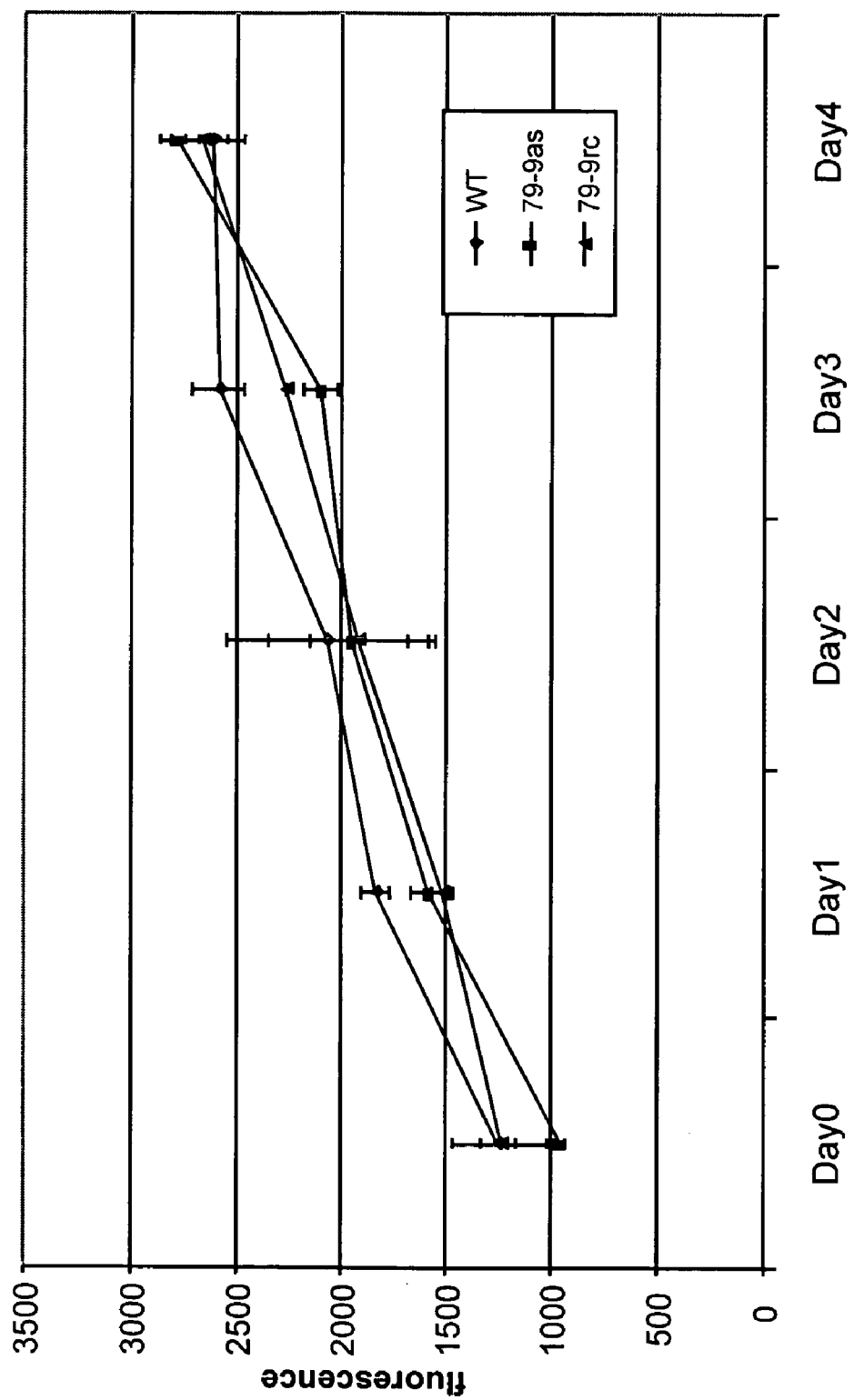
FIG. 11 is a graph illustrating that antisense suppression of TTK has no detectable effect on normal immortal fibroblasts.

Transfection of the antisense oligonucleotides into both SW620 colorectal carcinoma cells (FIG. 7) and 231 cells (FIG. 8) resulted in a decreased rate of proliferation compared to matched reverse control (RC) and oligonucleotides, but no inhibition of growth of 847 human immortal fibroblast cells (FIG. 11), suggesting possible tissue or transformation specificity in the functional role for the TTK protein.

Example 6

Effect of TTK Expression on Colony Formation

The effect of TTK expression upon colony formation was tested in a soft agar assay. Soft agar assays were conducted by first establishing a bottom layer of 2 ml of 0.6% agar in media plated fresh within a few hours of layering on the cells. The cell layer was formed on the bottom layer by removing cells transfected as described above from plates using 0.05% trypsin and washing twice in media. The cells were counted in a Coulter counter, and resuspended to $10^6$ per ml in media. 10 μl aliquots are placed with media in 96-well plates (to check counting with WST1), or diluted further for soft agar assay. 2000 cells are plated in 800 μl 0.4% agar in duplicate wells above 0.6% agar bottom layer. After the cell layer agar solidifies, 2 ml of media is dribbled on top and antisense or reverse control oligo is added without delivery vehicles. Fresh media and oligos are added every 3-4 days. Colonies are formed in 10 days to 3 weeks. Fields of colonies were counted by eye. Wst-1 metabolism values can be used to compensate for small differences in starting cell number. Larger fields can be scanned for visual record of differences.

Figure 9:
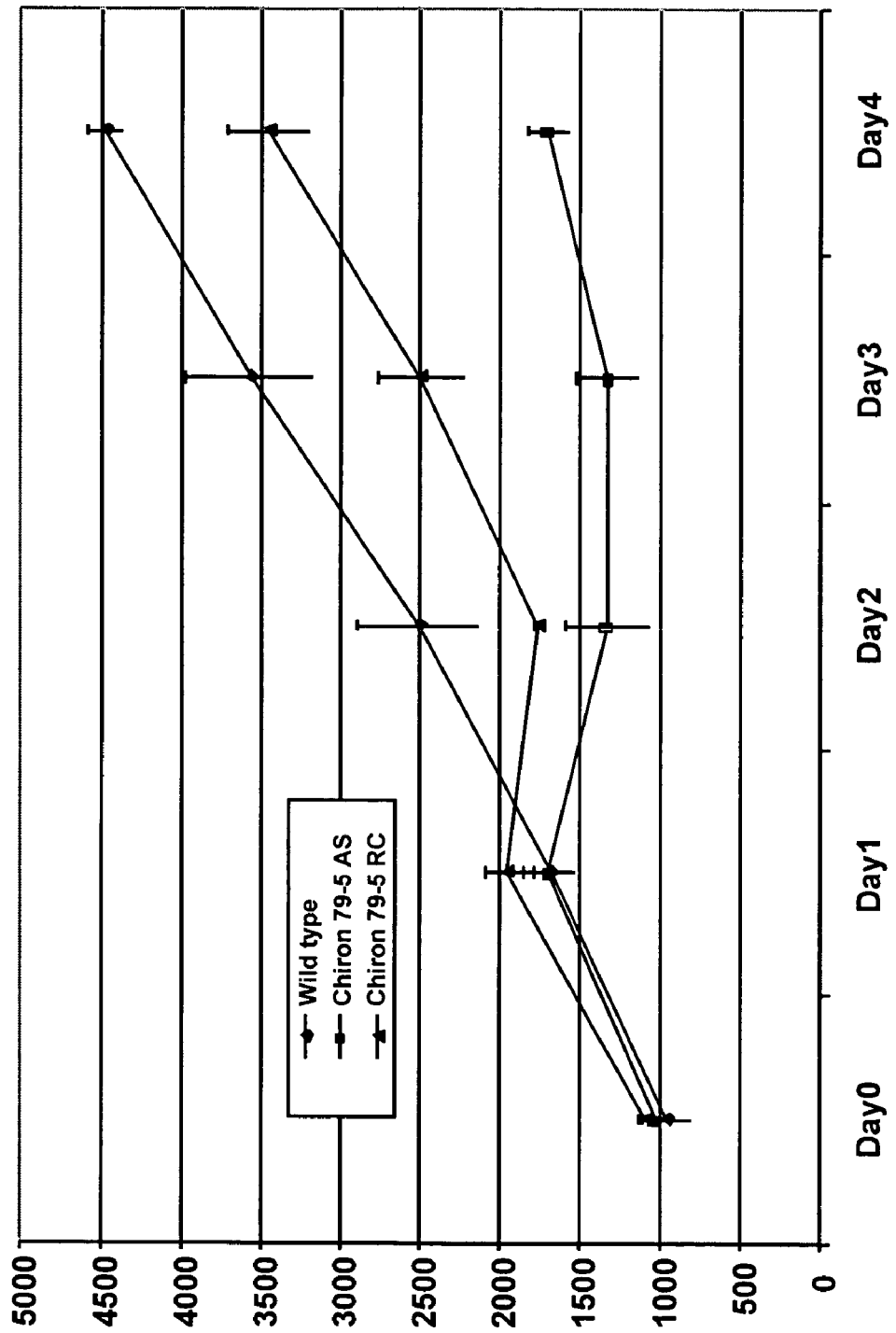
FIG. 9 is a graph illustrating growth suppression of SW620 cells following antisense suppression of TTK expression.
Figure 10:
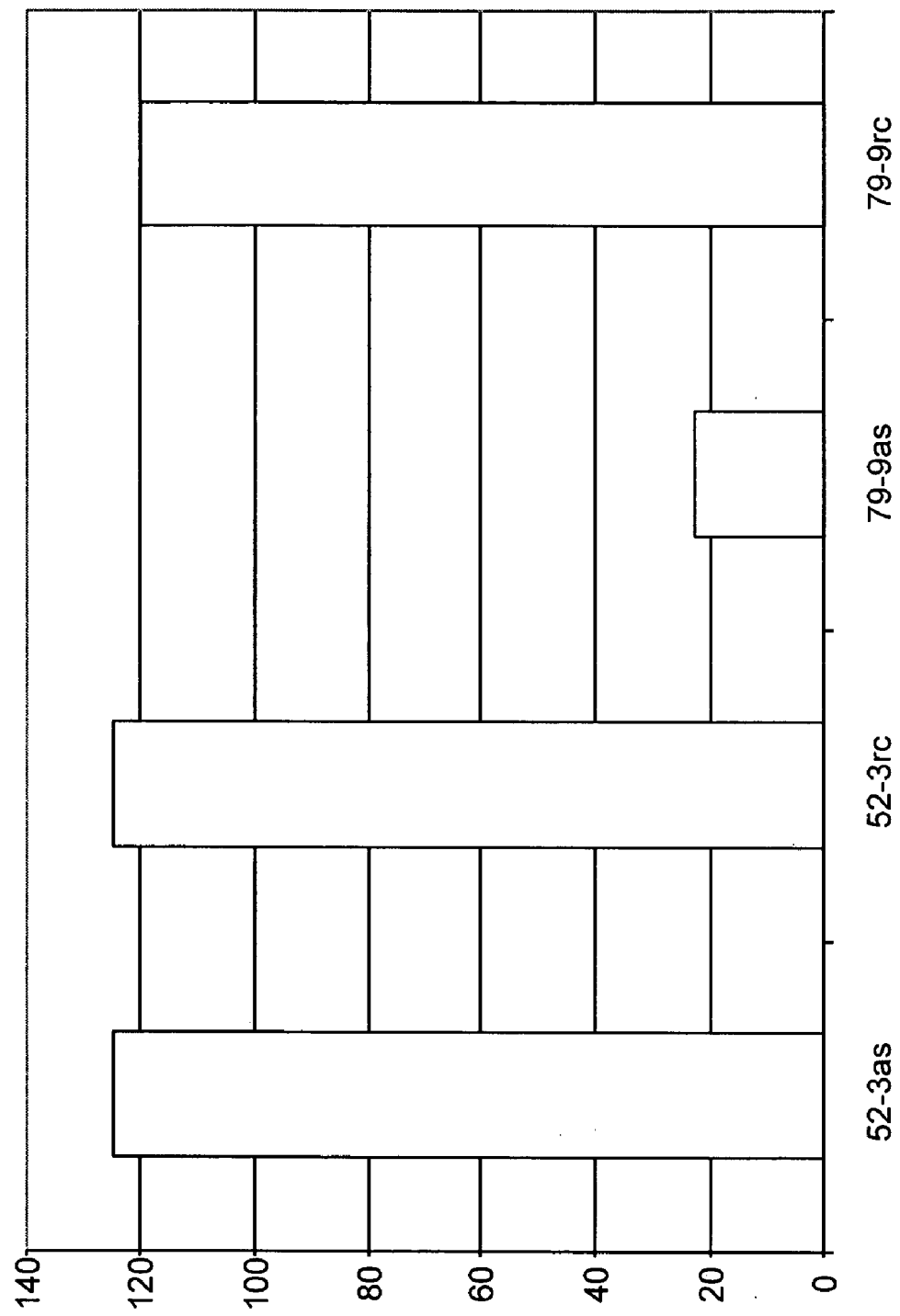
FIG. 10 is a graph illustrating suppression of colony formation of SW620 cells in soft agar following antisense suppression of TTK expression.

As shown in FIG. 9, antisense oligonucleotides to TTK (79-9AS) led to decreased colony size and number compared to control reverse control oligonucleotides (79-9RC) or to control oligonucleotides (52-3AS: TAGGTCTTTGGCCG-GTGATGGGTCG (SEQ ID NO:9) and 52-3RC: GCTGGG-TAGTGGCCGGTTTCTGGAT (SEQ ID NO:10)). The 52-3 antisense oligonucleotide is directed to the hD53 mRNA, and serves as a negative control in the experiment.

Example 7

Induction of Cell Death upon Depletion of TTK ("Antisense Knockout")

SW620 cells were transfected as described for proliferation assays. For cytotoxic effect in the presence of cisplatin (cis), the same protocol was followed but cells were left in the presence of 2 μM drug. Each day, cytotoxicity was monitored by measuring the amount of LDH enzyme released in the medium due to membrane damage. The activity of LDH was measured using the Cytotoxicity Detection Kit from Roche Molecular Biochemicals. The data is provided as a ratio of LDH released in the medium vs. the total LDH present in the well at the same time point and treatment (rLDH/tLDH). A positive control using antisense and reverse control oligonucleotides for BCL2 (a known anti-apoptotic gene) shows that loss of message for BCL2 leads to an increase in cell death compared with treatment with the control oligonucleotide (background cytotoxicity due to transfection).

The following antisense oligonucleotides were tested for the ability to deplete the message levels of the gene corresponding to the indicated cluster. Oligo Name: AS or RC provides the name of the target gene or name of the oligo, and whether the oligo is antisense (AS) or a reverse control (RC).

| Oligo Name: Antisense (AS) or Reverse Control (RC) | Oligo Sequence | SEQ ID NO: |
|---|---|---|
| Chir39-5:AS | ACTCATCTGGCTGGGCTATGGTGGT | SEQ ID NO:11 |
| Chir39-5:RC | TGGTGGTATCGGGTCGGTCTACTCA | SEQ ID NO:12 |
| Chir79-9:AS | TCCAGTAACTCTTGCGTTCCCATGG | SEQ ID NO:6 |
| Chir79-9:RC | GGTACCCTTGCGTTCTCAATGACCT | SEQ ID NO:8 |

Figure 12:
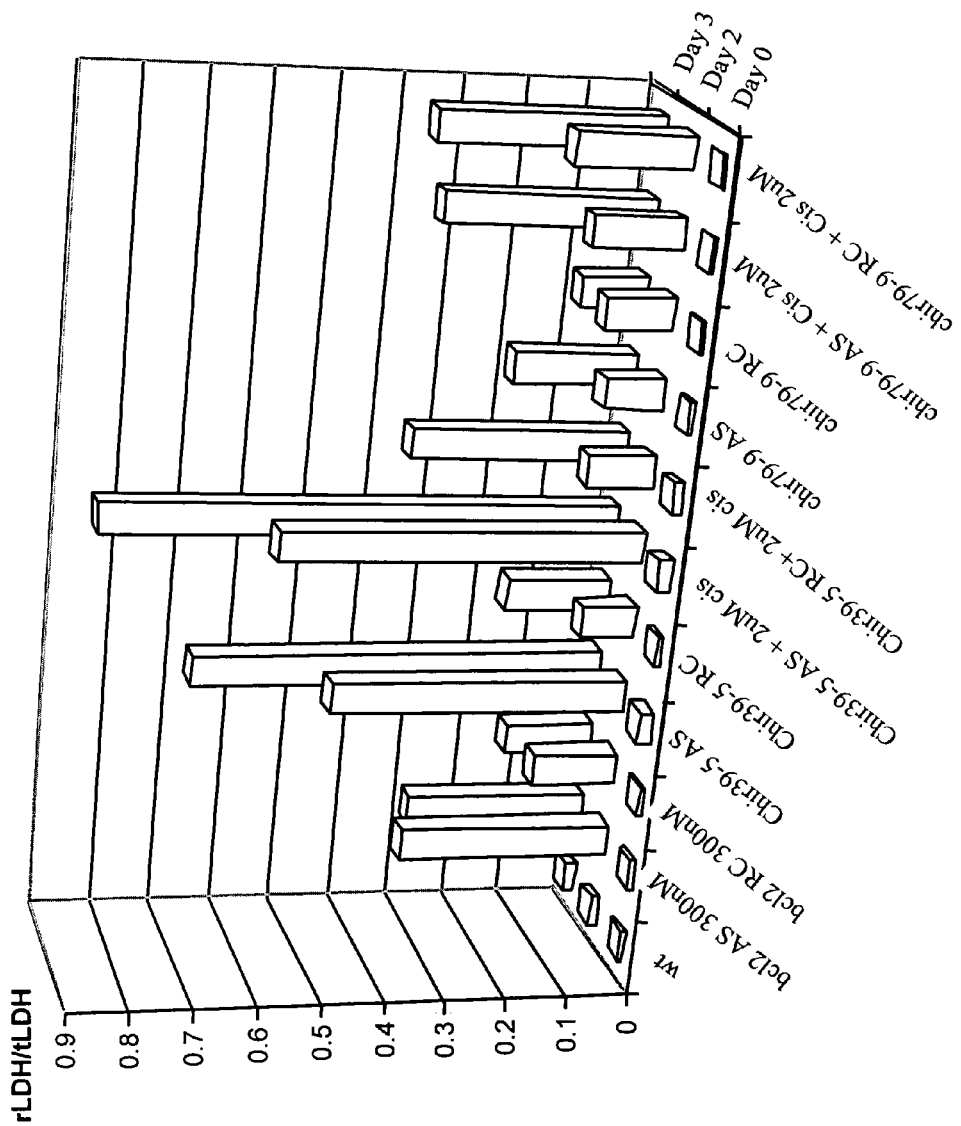
FIG. 12 is a bar graph illustrating induction of cell death upon depletion of TTK from SW620 cells.

As shown in FIG. 12, Chiron 79-9 (TTK) antisense does not sensitize the cells to treatment by cisplatin at a detectable level, but leads to increased death compared to control oligo at day 3.

Example 8

Sample Assay for Agents that Modulate TTK Activity

This assay may be performed in microtitre plates. TTK was purified as a 6×His tagged fusion protein using a baculovirus expression system. Essentially 20 ul of 20 nM TTK (100 kDa) in TTK kinase buffer comprising 50 mM Hepes pH 7.4, 2 mM $MgCl_2$, 10 mM $MnCl_2$, 1 mM NaF, 50 mM NaCl, 1 mM DTT and 1 mg/ml BSA was added to 5 ul of a candidate agent diluted in 20% DMSO, 10 ul of a 2.8 uM solution of a biotinylated substrate peptide derived from cdc25, such as Biotin-SGSGSGLYRSPSMPENLNRPR-NH2 (SEQ ID NO:27) or Biotin-GGGGLYRSPSMPENLNRK-OH (SEQ ID NO:28) and 5 ul of 80 nM $^{33}$p-γATP in a well of a microtitre plate. Samples were mixed, incubated for 2 hours and each reaction is terminated using 20 ul of 0.5 M EDTA pH 8.0. 50 ul of the sample is transferred to a 96 well flat bottom Streptavidin coated flash plate, and the sample is incubated with the plate for 1 hr at room temperature. The wells of the plate are washed four times with 250 ul of calcium and magnesium-free phosphate buffered saline, and scintillation fluid is added to the sample. Activity of TTK was measured by calculating the emission of $^{33}$P, transferred by TTK from $^{33}$P-γATP to a substrate peptide, by scintillation.

Agents modulating TTK activity can be identified by comparing the activity of TTK in the presence of a candidate agent to the activity of TTK in the absence of a candidate agent.

Example 9

Characterization of Human Breast Carcinoma (HBC) Cell Lines Before and After the Mesenchymal Transition The expression of the mesenchymal filament vimentin (VIM) is a prognostic marker for ductal breast carcinoma and has been associated significantly with poor 5-year survival (Domagala (1996) *Clin. Cancer Res.* 2:147-154). Positive VIM staining is only observed in the myoepithelium of normal breast, with clustered staining detected in the primary tumor. More advance infiltrating carcinomas exhibit the strongest vimentin staining, indicating a transition of gene expression to a more mesenchymal pattern.

To establish an in vitro model system for metastasis we used a panel of human breast carcinoma (HBC) cell lines, which have been previously characterized for their tumor formation as well as metastasis formation potential in nude mice. The characteristics of these cell lines are briefly described in the table below.

| Cell Line | Characteristics |
|---|---|
| MDA-MB-435 | High metastatic potential (macrometastases) Metastatic ductal carcinoma; isolated from pleural effusion |
| MDA-MB-231 | High metastatic potential (micrometastases) Adenocarcinoma; isolated from pleural effusions (ATCC HTB 26) |
| ALAB | High metastatic potential (micrometastases) Metastatic ductal carcinoma |
| MDA-MB-468 | Low metastatic potential Adenocarcinoma; isolated from metastasis to brain |
| MDA-MD-361 | Low metastatic potential; Estrogen receptor positive Adenocarcinoma; isolated from metastasis to brain (ATCC HTB 27). |
| ZR-75-1 | Low metastatic potential; Estrogen receptor positive |
| MCF-7 | Low metastatic potential; Estrogen receptor positive Derived from a pleural effusion of a breast adenocarcinoma (ATCC HTB 22) |
| MDA-MD-453 | Non-metastatic (does not form primary tumors) |
| SK-BR-3 | Non-metastatic (does not form primary tumors) Adenocarcinoma; isolated from pleural effusion (ATCC HTB 30) |
| HS578Bst | Primary cell line isolated from human breast; fibroblast-like cell (ATCC HTB-124; 6228) |

Cells were categorized as "high metastatic potential" or "low metastatic potential according to the development of primary tumors and metastases in a scid mouse model. In short, five week old scid CB-17 mice were anesthetized and a small incision made to expose the mammary fat pad. Approximately $2.5 \times 10^6$ cells were injection. Mice injected with MCF-7 cells received a subcutaneous pellet releasing 12-β-estradiol (0.36 mg over a period of 60 days). Other estrogen receptor (ER)-positive cell lines such as ZR-75-1 and MDA-MB-361 did not require exogenous estradiol for tumor growth. Tumor growth was monitored by weekly examination and caliper measurement. To examine the potential of specific human breast cancer cell lines to form distant metastases, primary tumors were surgically removed after 32 to 40 days (for ER-negative cell lines MDA-MB-231, MDA-MB-435, and ALAB; tumor volume 600 to 1,000 $mm^3$) or 60 days (for ER-positive cell lines MCF-7, ZR-75-1, and MDA-MB-361; tumor volumes 60 to 100 $mm^3$). 42 days after removal of primary tumors, mice were sacrificed and inspected for the presence of lung metastasis by haematoxylin and eosin staining after embedding into OCT gel (Sakura Finetek).

Cells identified as high metastatic potential were those cells that produced metastases in lung (MDA-MB-435, MDA-MB-231, and ALAB). MDA-MB-435 rapidly form primary tumors and macrometastases in the lung after resection of the primary tumor whereas MDA-MB-231 and ALAB form micrometastases. Cells that formed primary tumors but did not form detectable metastases in the lung were classified as low metastatic potential (MDA-MB-468, MDA-MB-361, ZR-75-1, MCF-7, and MDA-MB-453). Cells that did not form primary tumors, such as SK-BR-3 were classified as non-metastatic.

Figure 13:
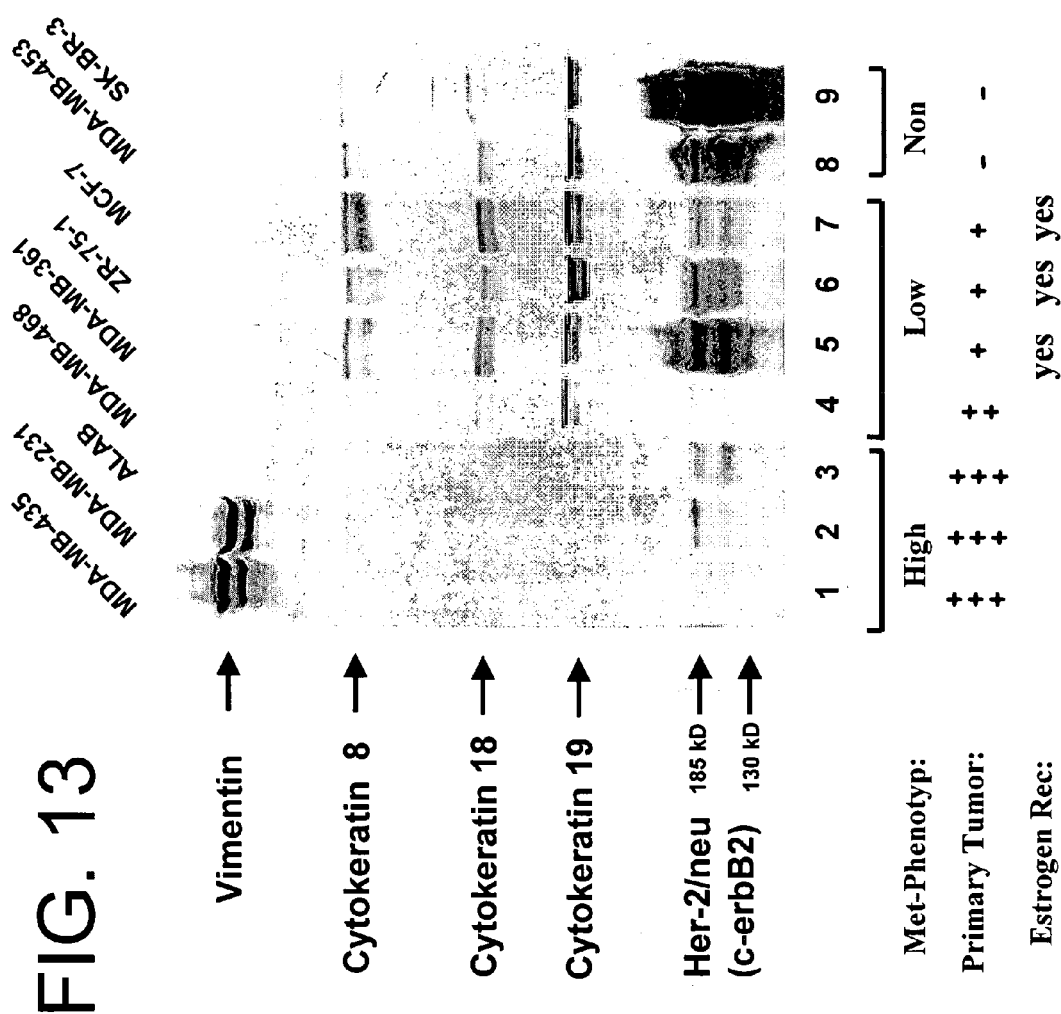
FIG. 13 is a photograph of a Western blot analysis of nine human breast carcinoma (HBC) cell lines with high metastatic potential (MDA-MB-435, MDA-MB-231, and ALAB), low metastatic potential or that are nonmetastatic (MDA-MB-468, MDA-MB-361, ZR-75-1, MCF-7, MDA-MB-453, SK-BR-3) as determined by xenographic injection in nude mice. The metastatic phenotype (Met-Phenotyp), the ability to form primary tumors following injection in an animal model (Primary Tumor), and expression of the estrogen receptor (Estrogen Rec) are indicated beneath the photograph.

In order to analyze the expression phenotype of these cell lines in the context of epithelial to mesenchymal transition (EMT), immunoblot analysis was performed in order to determine the expression status of a series of breast cancer markers including the mesenchymal filament vimentin (FIG. 13). Interestingly two of the three high metastatic cell lines revealed strong vimentin expression whereas all low metastatic cell lines were vimentin negative, indicating that these cell lines shifted to a more mesenchymal phenotype. Cytokeratin 8, 18, and 19 were used as markers for simple epithelium and showed a decreased expression in the more aggressive high metastatic cell lines. All nine cell lines were negative for the myoepithelial marker Cytokeratin 17 (data not shown). Surprisingly Her-2/neu expression was inversely correlated with the ability to form tumors after injection in the mammary pad of nude mice, and showed strongest expression in the non tumor forming cell line SK-BR-3.

Taken together, the data demonstrate that the mesenchymal transition is at least partially conserved in these HBC cell lines and correlates with a more invasive phenotype. Furthermore, this panel of HBC cell lines can serve as a model system to identify gene expression changes associated with the EMT and the metastatic potential.

Example 10

Identification and Cloning of GSEF, an ETS Transcription Factor

To advance our understanding of the molecular regulation of invasiveness in EMT-associated breast carcinoma progression, an extensive gene expression profiling study was performed using the above-characterized HBC cell lines. Since ETS transcription factors have been implicated mechanistically in the progression of breast carcinoma, and have been associated with cell differentiation, carcinogenesis and cell proliferation, the study focused on the ETS transcription factor family. During the course of this study, an EST (GenBank Accession No. AA662164). A PCR approach was used to obtain the full-length cDNA using a breast cDNA library. Since later studies showed a specific expression profile in tissue derived from simple epithelium of human exocrine glands, the gene identified was termed gland-specific Ets transcription factor (GSEF).

The sequence of the full length cDNA as well as the 5' promoter region obtained by 5' RACE are shown in FIGS. 14A-14B. The predicted transcriptional start site, determined by sequence analysis of 5' RACE clones lies 434 bases upstream of the initiation codon. Consistent with the 5' RACE analysis, a TATA box was identified 24 bases 5' of the predicted RNA start site. In addition a consensus initiator sequence overlapping the start site was found, suggesting again that the obtained sequence contains the core promoter. A series of putative ETS binding sites were identified in this promoter fragment (FIG. 14A bold letters). Sequence analysis of the GSEF cDNA revealed an open reading frame of 335 amino acids with an ETS domain localized at the C-terminus (FIG. 14B).

Example 11

Differential Expression of GSEF in High Metastatic Potential and Low Metastatic Potential Cells as Determined by cDNA Library Comparisons The relative expression levels of the GSEF gene was assessed in several cDNA libraries prepared from low metastatic potential breast cells and from high metastatic potential breast cell lines. The table below provides a description of these libraries, including the shortened library name (used hereafter), the mRNA source used to prepared the cDNA library, the "nickname" of the library that is used in the tables below (in quotes), and the approximate number of clones in the library.

Description of cDNA Libraries

| Library | Description | Number of Clones in this Clustering |
| --- | --- | --- |
| 3 | MDA-MB-231 Human Breast Cancer Cell Line, High Metastatic Potential; micro-metastasis in lung "High Met Breast" | 319306 |
| 4 | MCF7 Human Breast Cancer Cell, Non Metastatic "Low Met Breast" | 328941 |

The MDA-MB-231 cell line was originally isolated from pleural effusions (Cailleau, *J. Natl. Cancer. Inst.* (1974) 53:661), is of high metastatic potential, and forms poorly differentiated adenocarcinoma grade II in nude mice consistent with breast carcinoma. The MCF7 cell line was derived from a pleural effusion of a breast adenocarcinoma and is non-metastatic (e.g., is of low metastatic potential). These cell lines are well-recognized in the art as models for the study of human breast cancer (see, e.g., Chandrasekaran et al., *Cancer Res.* (1979) 39:870; Gastpar et al., *J Med Chem* (1998) 41:4965; Ranson et al., *Br J Cancer* (1998) 77:1586; Kuang et al., *Nucleic Acids Res* (1998) 26:1116.

Each of the libraries is composed of a collection of cDNA clones that in turn are representative of the mRNAs expressed in the indicated mRNA source. Methods for generating cDNA libraries from isolated mRNA are well known in the art. In order to facilitate the analysis of the millions of sequences in each library, the sequences were assigned to clusters. The concept of Acluster of clones" is derived from a sorting/grouping of cDNA clones based on their hybridization pattern to a panel of roughly 300 7 bp oligonucleotide probes (see Drmanac et al., *Genomics* (1996) 37(1):29). Random cDNA clones from a tissue library are hybridized at moderate stringency to 300 7 bp oligonucleotides. Each oligonucleotide has some measure of specific hybridization to that specific clone. The combination of 300 of these measures of hybridization for 300 probes equals the Ahybridization signature" for a specific clone. Clones with similar sequence will have similar hybridization signatures. By developing a sorting/grouping algorithm to analyze these signatures, groups of clones in a library can be identified and brought together computationally. These groups of clones are termed Aclusters". Depending on the stringency of the selection in the algorithm (similar to the stringency of hybridization in a classic library cDNA screening protocol), the Apurity" of each cluster can be controlled. For example, artifacts of clustering may occur in computational clustering just as artifacts can occur in Awet-lab" screening of a cDNA library with 400 bp cDNA fragments, at even the highest stringency. The stringency used in the implementation of cluster herein provides groups of clones that are in general from the same cDNA or closely related cDNAs. Closely related clones can be a result of different length clones of the same cDNA, closely related clones from highly related gene families, or splice variants of the same cDNA.

Differential expression for a selected cluster was assessed by first determining the number of cDNA clones corresponding to the selected cluster in the first library (e.g., "high met breast"), and the determining the number of cDNA clones corresponding to the selected cluster in the second library (e.g., "low met breast"). Differential expression of the selected cluster in the first library relative to the second library is expressed as a "ratio" of percent expression between the two libraries. In general, the "ratio" is calculated by: 1) calculating the percent expression of the selected cluster in the first library by dividing the number of clones corresponding to a selected cluster in the first library by the total number of clones analyzed from the first library; 2) calculating the percent expression of the selected cluster in the second library by dividing the number of clones corresponding to a selected cluster in a second library by the total number of clones analyzed from the second library; 3) dividing the calculated percent expression from the first library by the calculated percent expression from the second library. If the "number of clones" corresponding to a selected cluster in a library is zero, the value is set at 1 to aid in calculation. The formula used in calculating the ratio takes into account the "depth" of each of the libraries being compared, i.e., the total number of clones analyzed in each library.

In general, a polynucleotide is said to be significantly differentially expressed between two samples when the ratio value is greater than at least about 2, preferably greater than at least about 3, more preferably greater than at least about 5, where the ratio value is calculated using the method described above. The significance of differential expression is determined using a z score test (Zar, *Biostatistical Analysis*, Prentice Hall, Inc., USA, ADifferences between Proportions," pp 296-298 (1974).

The GSEF gene was analyzed in this manner to determine if GSEF is differentially expressed between cells derived from high metastatic potential breast cancer tissue and low metastatic breast cancer cells. The GSEF specifc cluster was 185412 and Forty-one clones corresponding to the GSEF gene were identified in the MCF7 library ("low met breast"), while the MDA-MB-231 library ("high met breast) contained no clones corresponding to GSEF. These findings indicate that GSEF is differentially expressed between high metastatic potential breast cells and low metastatic potential breast cells. As illustrated in the table below, the ratio of expression is about 40.

| Cell Line | Clones Corresponding to GSEF ClusterNo.: 185412 | Ratio of "Low Met Breast" Expression to "High Met Breast" Expression |
|---|---|---|
| MDA-MB-231 "High Met Breast" (Clones in lib319306) | 0 | |
| MCF7 "Low Met Breast" (Clones in lib: 328941) | 41 | 40.19 |

These data indicate the GSEF is expressed at a higher level in breast cells of low metastatic potential than in breast cells of high metastatic potential.

Example 12

GSEF is Normally Expressed as a Prostate-Specific and Breast-Specific Factor

GSEF expression was analyzed using both an RNA Master Blot (Clontech) and an RNA tissue blot (In Vitrogen). The RNA tissue blot was prepared from various tissues according to methods well known in the art. In short, Northern blot analysis was performed using 20-30 µg total RNA isolated by guanidinium thiocyanate/phenol chloroform extraction from cell lines, from primary tumors, or from metastases in liver. Primary tumors and liver metastases were developed from cell lines injected into scid mice according to methods well known in the art. Plasmids containing either the full-length cDNA clone of GSEF (1-1894 bp cloned into pCR2.0-TA Vector (In Vitrogen)) or the full-length cDNA of E1AF (2 kb coding region) were radiolabeled and hybridized at 65EC in Express-hyb (Clontech).

Figure 16:
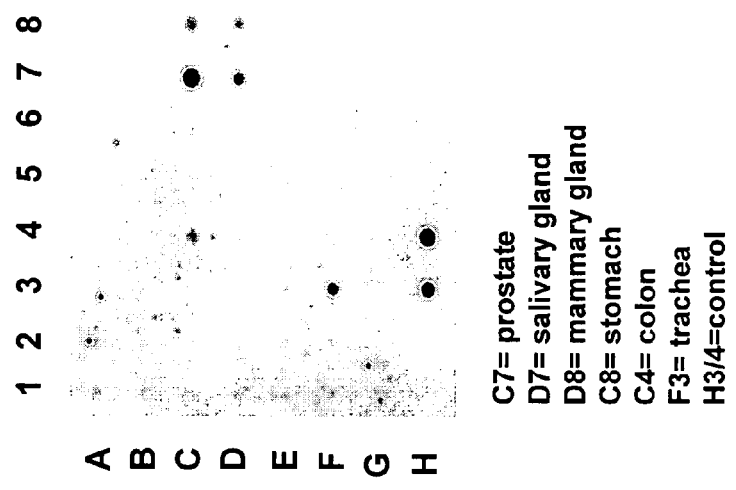
FIG. 16 is a photograph of an RNA tissue blot showing GSEF expression in human heart, brain, placenta, lung, liver, skeletal muscle, kidney, pancreas, spleen, thymus, prostate, testes, ovary, small intestine, colon, and peripheral blood.
Figure 15:
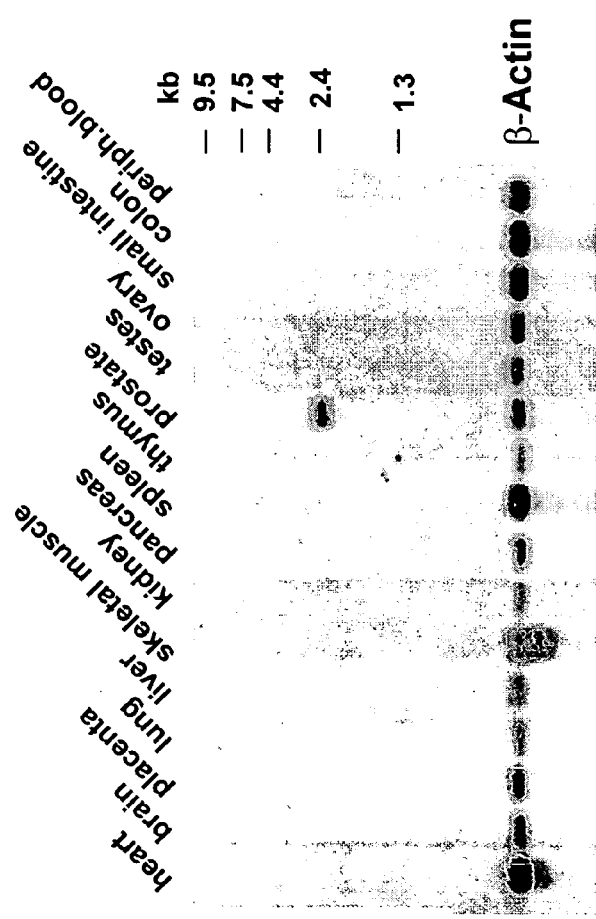
FIG. 15 is a photograph of an RNA blot showing expression of GSEF in a variety of tissues. C7=prostate; D7=salivary gland; D8=mammary gland; C8=stomach; C4=colon; F3=trachea; H3 and H4=positive controls.

The results are shown in FIGS. 15 and 16. In FIG. 16, C7 is prostate; D7 is salivary gland; D8 is mammary gland; C8 is stomach; C4 is colon; F3 is trachea; and H3 and H4 are positive controls. GSEF expression is detected as a band of approximately 2.4 kb.

According to the RNA Master blot and RNA tissue blot, GSEF is expressed primarily in prostate tissue. A relatively low level of GSEF expression was detected in stomach, salivary gland, mammary gland, and trachea. One common feature of these tissues is that they are all associated with secretory functions, suggesting that GSEF is specific for secretory epithelium. To test this hypothesis, in situ hybridization experiments were performed using normal breast tissue and tumor tissue. GSEF expression was detected in luminal or simple epithelial cells of normal breast glands. These cells are also characterized by expression of cytokeratin 8, 18 and 19 (for review see R. Moll, (1998) Subcell. Biochem. 31:205-262). GSEF expression as detected by immunoblot analysis was perfectly correlated with GSEF expression of these simple epithelia-specific cytokerantis.

Taken together these data indicate that GSEF is a ETS homolog specific for simple epithelium of hormone responsive secretory glands (e.g., prostate and mammary glands), a cell type most commonly associated with common adenocarcinomas Example 13

Differential Expression of GSEF in Breast Cancer Cell Lines Detected by Northern Blot To further investigate the differential expression of GSEF, ESX, and E1AF, in breast cancer, expression of these genes was investigated using both Northern and Western blots prepared from a panel of human breast cancer cell lines with defined metastatic phenotypes.

In order to assess expression at the RNA level, expression of these genes was detected in RNA isolated from each of the cell lines, and from cells of primary tumors or metastases according to methods well known in the art, and expression of GSEF, ESX, E1AF, and β-actin (control) detected. As discussed above, E1AF is implicated as an activator of the metastatic phenotype. Expression of the ESX gene was also detected in parallel samples using a probe based on the sequence in GenBank Accession No. U66894. ESX is a Ets domain-containing gene that is overexpressed early during human breast tumorigenesis (Chang et al. (1997) *Oncogene* 14:1617-1622). Plasmids containing either the full-length cDNA clone of GSEF (1 -1894 bp cloned into pCR2.0-TA Vector (In Vitrogen)) or the full-length cDNA of E1AF (2 kb coding region) were radiolabeled and hybridized at 65EC in Express-hyb (Clontech). expression of the ESX gene was also detected in parallel samples using a probe based on the sequence in GenBank Accession No. U66894. ESX is a Ets domain-containing gene that is overexpressed early during human breast tumorigenesis (Chang et al. (1997) *Oncogene* 14:1617-1622). Plasmids containing full length cDNA of β-actin and ESX were labeled as described for the GSEF probe.

Figure 17:
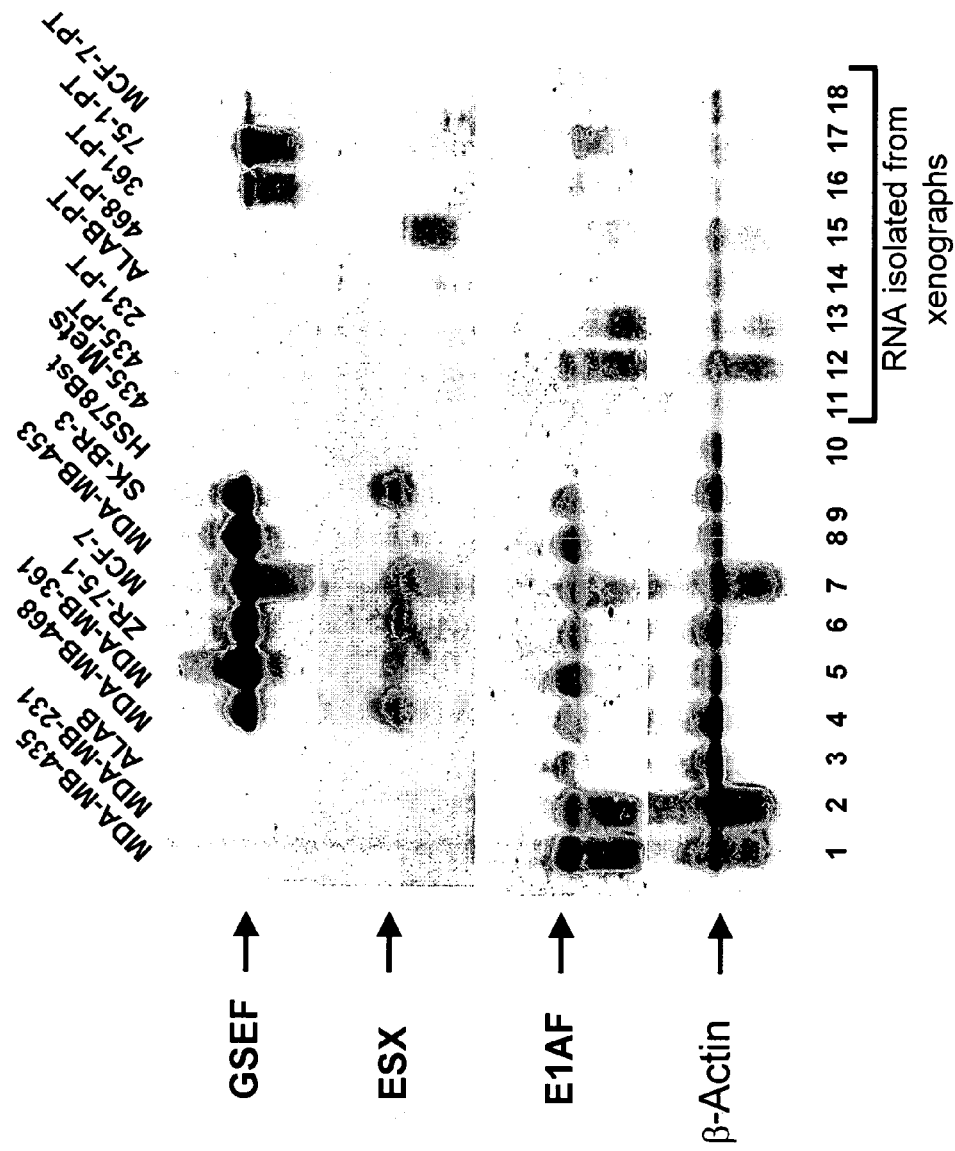
FIG. 17 is a photograph of a Northern blot showing expression of GSEF, ESX, E1AF, and β-actin in using total RNA derived from HBC cell lines or from tumor or metastasis tissue derived from xenographs. Specific signals are indicated by arrows.

The results are shown in FIG. 17, where the upper panel indicates GSEF expression, the second uppermost panel indicates ESX expression, the third panel from the top indicates E1AF expression, and the bottom panel indicates β-actin expression (control). While GSEF expression was detected in both low metastatic potential breast cell lines and in non-metastatic breast cell lines, GSEF expression was substantially undetectable in high metastatic potential breast cell lines in this assay (435, 231, ALAB), indicating a specific loss of function in cell lines with high metastatic potential. The cell line HS578Bst is a cell line derived from breast tissue but has been characterized to be fibroblast-like and did not show any expression whereas the six low metastatic epithelial derived cell lines showed strong expression of GSEF. The same northern blot was probed with an E1AF (PEA3)-specific probe as well as a probe for ESX. E1AF and ESX are both ETS transcription factor implicated in metastasis. Interestingly ESX, an epithelial-specific ETS transcription factor, exhibited an expression profile similar to GSEF, whereas E1AF expression was strongest in the two high metastatic cell lines 435 and 231. It should be noted that some ESX and GSEF mRNA was detected by RT PCR in the high metastatic cell lines, suggesting that the absence of expression is not due chromosomal deletions (data not shown). Thus, GSEF expression correlates inversely with the metastatic potential of breast cancer cells. These data further support the role of GSEF in suppression of the metastatic phenotype.

To exclude the possibility that the expression profiles are influenced by in vitro culture conditions, RNA derived from mouse xenograhs was analyzed (FIG. 17, lanes 11 to 18; PT primary tumors, Mets 435 derived lung metastasis). The cell line specific expression of all three ETS transcription factors was maintained in vivo, thus ruling out culture conditions as a cause for the differential expression.

In order to confirm differential gene expression results on the protein level, specific polyclonal antibodies for GSEF, ESX and E1AF were generated and used in an immunoblot analysis. Equal amounts of nuclear extracts derived from each of the breast cell lines described above were loaded on an SDS-PAGE gel and transferred to a PVDF membrane according to methods well known in the art. Polyclonal antibodies raised against a synthetic C-terminal peptide of GSEF (RKPDISQRLVYQFVHPI (SEQ ID NO:44)) and ESX (GKNSSGWKEEEVLQSM (SEQ ID NO:45)) were used to detect the proteins. Ets1 and E1AF were detected using commercially available antibodies.

Figure 18:
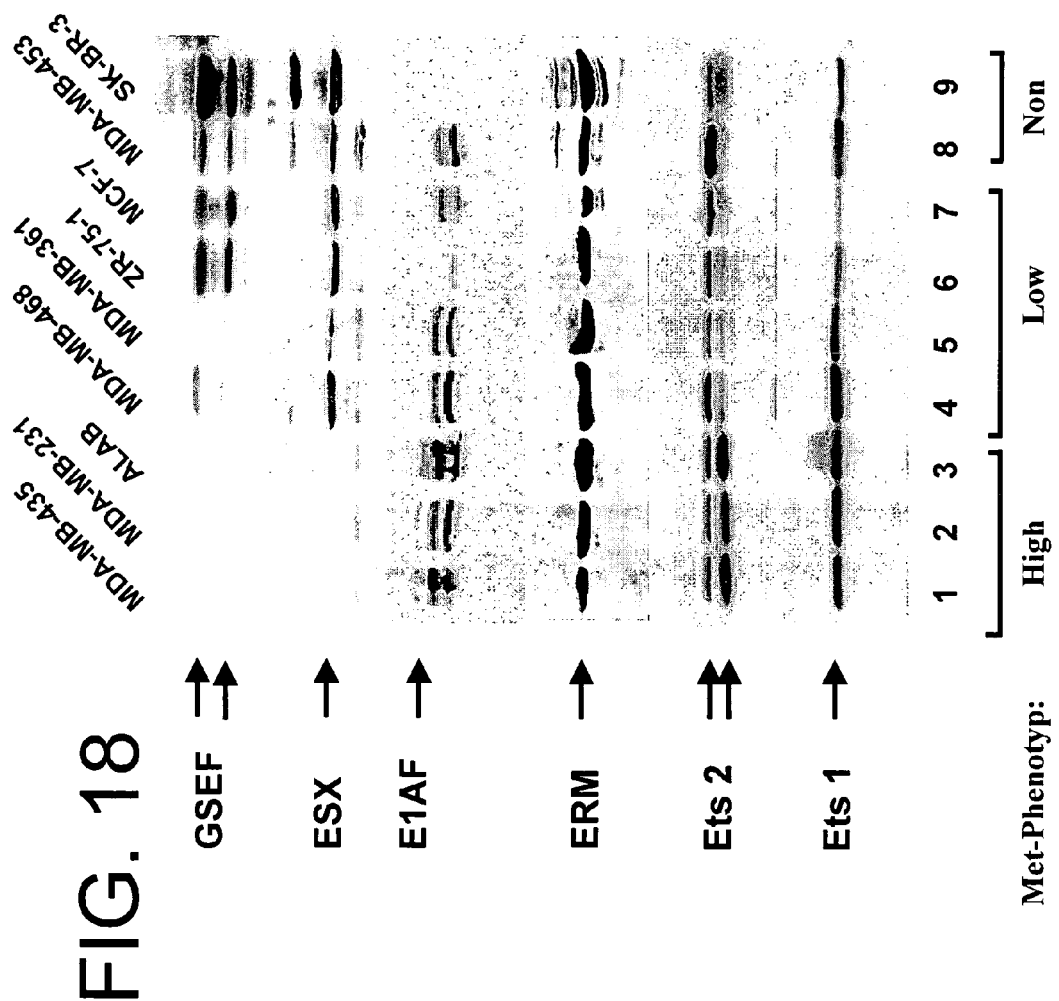
FIG. 18 is a photograph of a Western blot using specific antisera for the indicated ETS transcription factors. Specific signals are indicated by arrows.

As shown in FIG. 18, protein expression confirmed the northern data. GSEF protein expression was highly abundant in four of the six low metastatic cell lines but was not detectable in the high metastatic HBC cell lines (FIG. 16). The ESX protein was also restricted to the low metastatic cell lines suggesting a shift into a more nonepithelial like phenotype in the high metastatic cell lines. The immunoblot for E1AF did show a slight upregulation of E1AF protein in the high metastatic cell lines, but was also detectable in some of the low metastatic cell lines. Immunoblots for three additional ETS factors (ERM, Ets2, Ets1) were performed, but did not reveal a significant correlation with the phenotype of these cell lines. Using the Ets2 specific antibody we observed an additional smaller polypeptide specifically in the high metastatic cell lines(second arrow FIG. 16). This shorter Ets2 specific signal was due to a proteolytic activity in the cell extracts derived from the high metastatic cell lines (data not shown).

Taken together, these data illustrate the identification of two Ets transcription factors, GSEF and ESX, which have their expression specifically downregulated during the EMT.

Example 14

GSEF Expression in Human Tumor Tissue

Figure 19A:
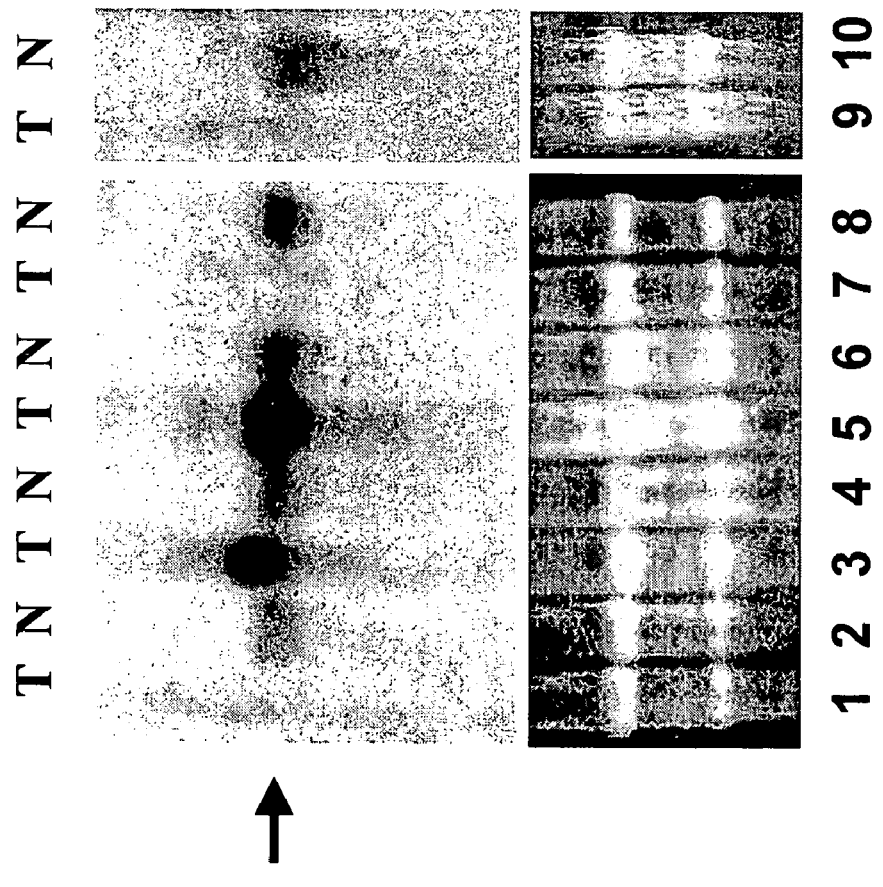
FIG. 19A is a photograph of a Northern blot illustrating that GSEF mRNA is differentially expressed in primary tumor (T) and normal (N) breast tissue. Total RNA from matched normal (even-numbered lanes) and primary tumor (odd-numbered lanes) tissue were used: lane 1: invasive ductal carcinoma; lane 3: invasive ductal carcinoma; lane 5: moderately differentiated invasive ductal carcinoma; lane 7: invasive ductal carcinoma; lane 9: invasive ductal carcinoma.

In view of the results described above, the expression of GSEF in human breast tumor tissue was investigated in matched total RNA derived from normal and tumor breast tissue. As shown in FIG. 19A, all five patients exhibited comparable expression of GSEF in normal tissue (FIG. 19A, even numbered lanes). Two patients exhibited upregulation of GSEF message in tumor tissue when compared to normal, whereas GSEF expression was undetectable in tumors of three patients. These results illustrate the changes in gene expression of GSEF during the progression of breast cancer.

Expression of GSEF was also examined in human breast tissue in situ. Briefly, in situ hybridization was performed on human tissues frozen immediately after surgical removal and cryosectioned at 10 nm, following the protocol of Pfaff et al. (1996) *Cell* 84: 309-320. Digoxigenin-UTP labeled riboprobes were generated with a template containing GSEF cDNA. For the generation of the antisense probe, the DNA was linerarized at the 5'-end and transcribed with T3 polymerase to generate a transcript of approximately 1 kb length. Hybridized probes were detected with alkaline phosphatase-coupled anti-digoxigenin antibodies using BM purple as the substrate (Roch Molecular Biochemicals, Indianapolis, Ind.).

As illustrated in the exemplary results provided in FIG. 19B, GSEF is specifically expressed in normal ductal epithelial cells, with expression decreased or undetectable in metastatic breast cancer cells. Thus, GSEF expression was maintained in the in situ carcinoma of the same patient, again correlating with the in vitro gene expression of GSEF in tumorgenic low metastatic HBC cell lines.

Example 15

Chromosomal Mapping of GSEF

The chromosomal location of GSEF was determined by radiation hybrid mapping. The GSEF-specific primers 5'cagggaggggcaaccaactgccccagggggа3' (SEQ ID NO:48) and 5'tatctttattatccattcccgggggcactcctgg 3' (SEQ ID NO:49) for PCR reactions on genomic DNA derived from human/hamster hybrid cells (Research Genetics™). The result was analysed by an outside laboratory for the nearest marker (SHGC-15970).

GSEF was mapped to chromosome 6, specifically at 6p21.1-6p21.3. Normal human Chromosome 6 has been implicated in the suppression of the metastatic phenotype of C8161 melanoma after microcell transfer (Welch et al., (1994) Oncogene 9:255-262; Barsky et al., (1997) Oncogene 15:2077-2091). Interestingly, cyclin-dependent kinase inhibitor 1A (p21/WAF/CDKN1A), which is considered to be a putative tumor suppressor gene, also mapps to 6p21.2 (Knuutila et al., (1999) *Am. J. Pathol.* 155:683-694). Furthermore, it has been suggested that loss of heterozygosity on chromosome 6p21.2 is a potential marker for recurrence after radiotherapie of cervical cancer (Harima et al., (2000) *Clin. Cancer Res.*6: 1079-1085).

Example 16

Promoter of GSEF

The promoter of GSEF was obtained using the Human Genome Walker Kit™ (Clontech) in combination with PCR primers specific for the GSEF cDNA designed according to methods well known in the art. The resulting PCR products were cloned into TA-cloning vectors (InVitrogen) and double-stand sequenced. The GSEF promoter, as well as the beginning of the cDNA encoding GSEF is provided in SEQ ID NO:46). The sequence of the putative minimal GSEF promoter (e.g., without the GSEF-encoding cDNA sequence) is provided as SEQ ID NO:47 (nucleotides 1-1381 of SEQ ID NO:46). The classic TATA box begins at residue 1356 (TATAA), and a transcriptional start site is positioned at residue 1381.

Example 17

GSEF Promoter and GSEF Protein are Functional in Transient Transfection Assays

In order to characterize the transcriptional regulation of GSEF, a 1380 bp promoter fragment was cloned upstream of a luciferase reporter construct containing either a promoter of c-Fos, a CMV promoter (CMV 10), a promoter of pGL3, or the GSEF promoter, and transfected into the high metastatic cell line MDA-MB-435 and into two low metastatic cell lines (MDA-MB-468, SK-BR-3) using techniques well known in the art. Cotransfection of luciferase promoters is described in, for example, Martin et al., (1999) Mol.Cell. Biol. : 5548-5556 (c-Fos; CMV promoter).

Figure 20:
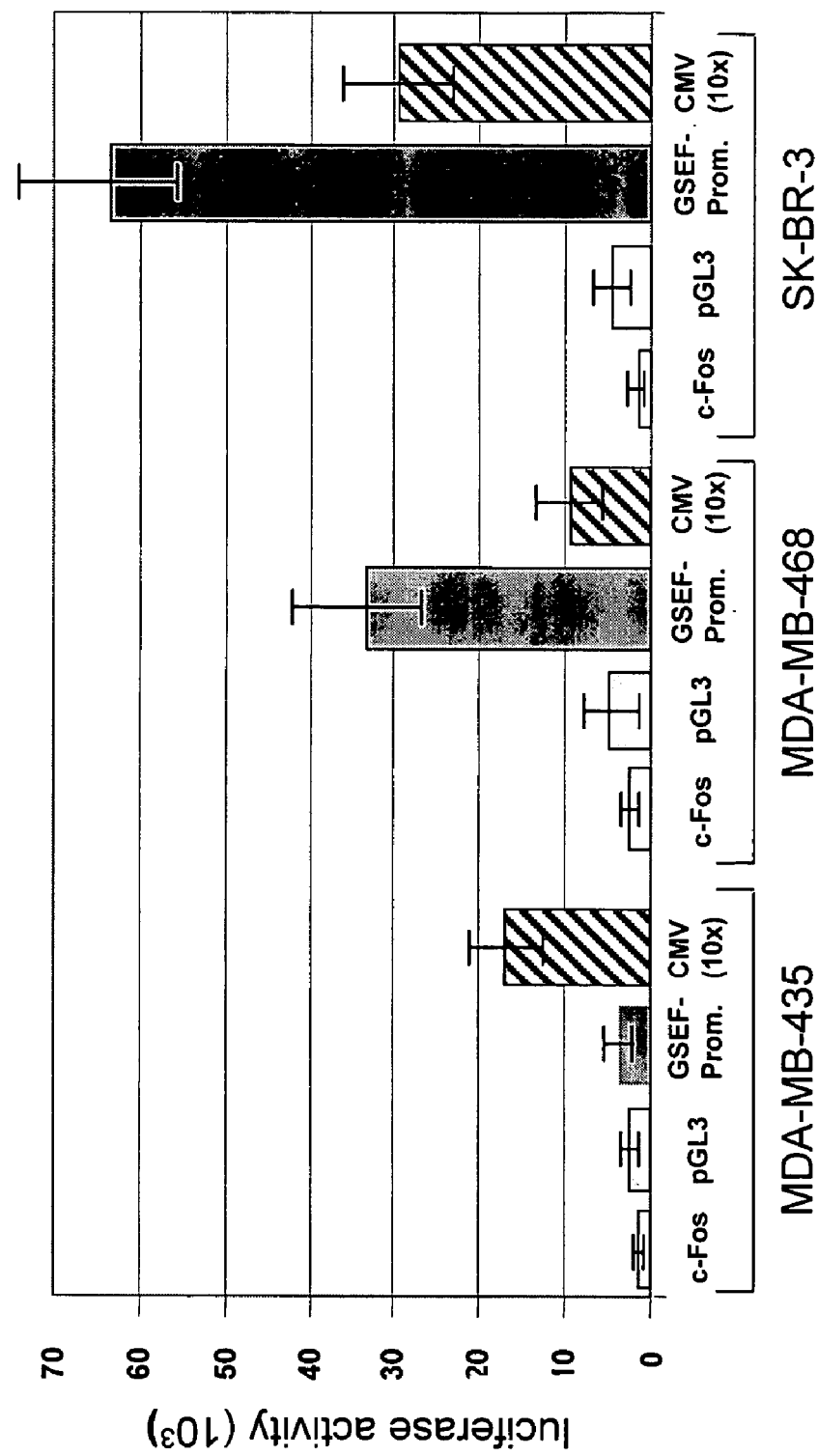
FIG. 20 is a graph illustrating that the activity of the GSEF promoter is greater in low metastatic than in high metastatic HBC cell lines. All promoters are cloned into pGL3 basic luciferase expression plasmid (Promega): pGL-3 promoterless, c-Fos promoter, GSEF-promoter, CMV-promoter (1/10 of the absolute numbers are shown). c-Fos: construct with c-Fos promoter; pGL3; GSEF-Prom: construct with GSEF promoter; CMV (10X): construct with CMV promoter.

The GSEF promoter did not exhibit significant activity in the high metastatic breast cancer cell line MDA-MB-435 (FIG. 20, left panel; compare promoter less pGL3 control with GSEF-promoter construct). However GSEF reporter activity in the low metastatic cell lines increased relative to the CMV, c-FOS and the pGL-3-basic promoter constructs (FIG. 20, absolute luciferase units are shown). This result indicate that the cloned GSEF promoter fragment is sufficient to mediate the low metastatic specific transcriptional regulation and reflects the differential expression of endogenous GSEF.

Example 18

GSEF Acts as a Transcriptional Activator of the GSEF Promoter

The ability of ectopically expressed GSEF protein to act as a transcriptional activator of the GSEF promoter in the high metastatic cell line MDA-MB-435 was investigated. Cotransfection using the indicated reporter constructs in combination with the expression plasmids (pcDNA 3.1) were performed using the EFFECTENE™ transfection reagent (Quiagen) accoding to the manufacturer's protocol (Martin et al., (1999) *Mol. Cell. Biol.:* 5548-5556). GSEF, E1AF, and ESX were expressed in the transfected cells at similar levels as confirmed by Western blot (data not shown).

Figure 21:
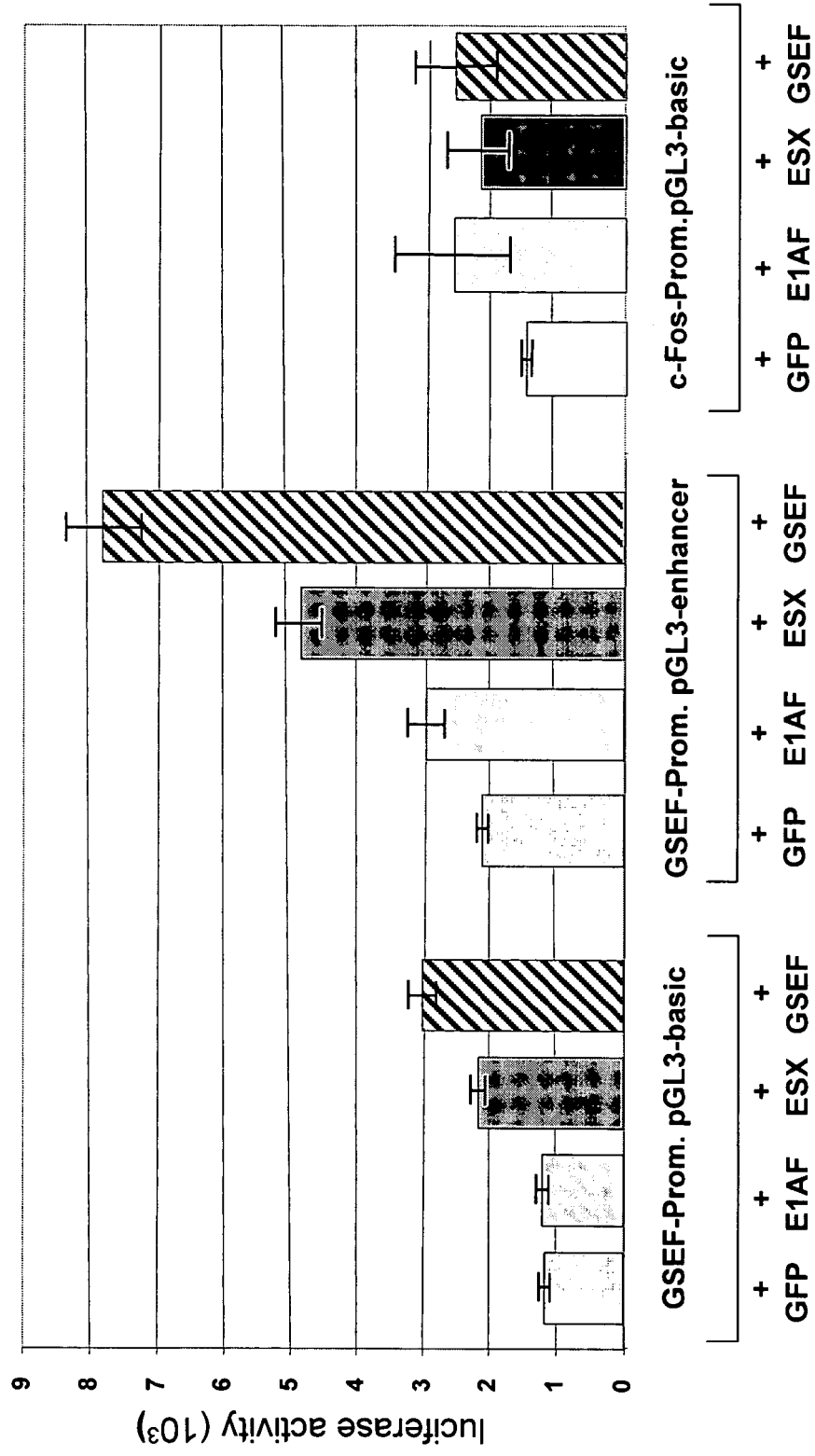
FIG. 21 is a graph illustrating that the GSEF promoter of the GSEF-pGL3-luc construct in the high metastatic breast cell line MDA-MB-435 can be transactivated by GSEF protein. +GFP: GFP expression construct; +E1AF: expression construct; +ESX: ESX expression construct; and GSEF: GSEF expression construct.

Cotransfection of expression plasmids of GSEF, E1AF, ESX and a GFP control revealed that GSEF was the strongest transcriptional transactivator of the GSEF promoter construct (FIG. 21). Both ESX and E1AF also showed some transactivation in these transient transfection assays, which is not surprising given that the GSEF promoter fragment contains a series of ETS binding sites (FIG. 14A, indicated in bold). However the minimal c-Fos promoter was not stimulated by either of these ETS factors.

The activity of GSEF as a transcription factor was confirmed by nuclear localization using immunohistochemistry protocols in combination with DAPI counterstaining (data not shown).

These data indicate that GSEF protein is localized in the nucleus and can function as a transcriptional activator in the high metastatic cell line MDA-MB-435.

Example 19

Ectopic Expression of GSEF does not Affect Vimentin or Cytokeratin 19 Expression, but Changes the Morphology of MDA-MB-435 Cells Having established that the GSEF protein can be expressed in a functional manner in high metastatic potential cells, MDA-MB-435 cell lines that stably express GSEF were produced to address whether GSEF expression can interfere with the metastatic phenotype of MDA-MB-435 cells. The expression plasmids(pcDNA.3, Promega) were transfected into MDA-MB-435 cells (EFFECeNE™ (Quiagen)) and the cells were incubated for 1 week under G418 selection (200 μg/ml). Individual clones were picked and analysed.

Figure 22:
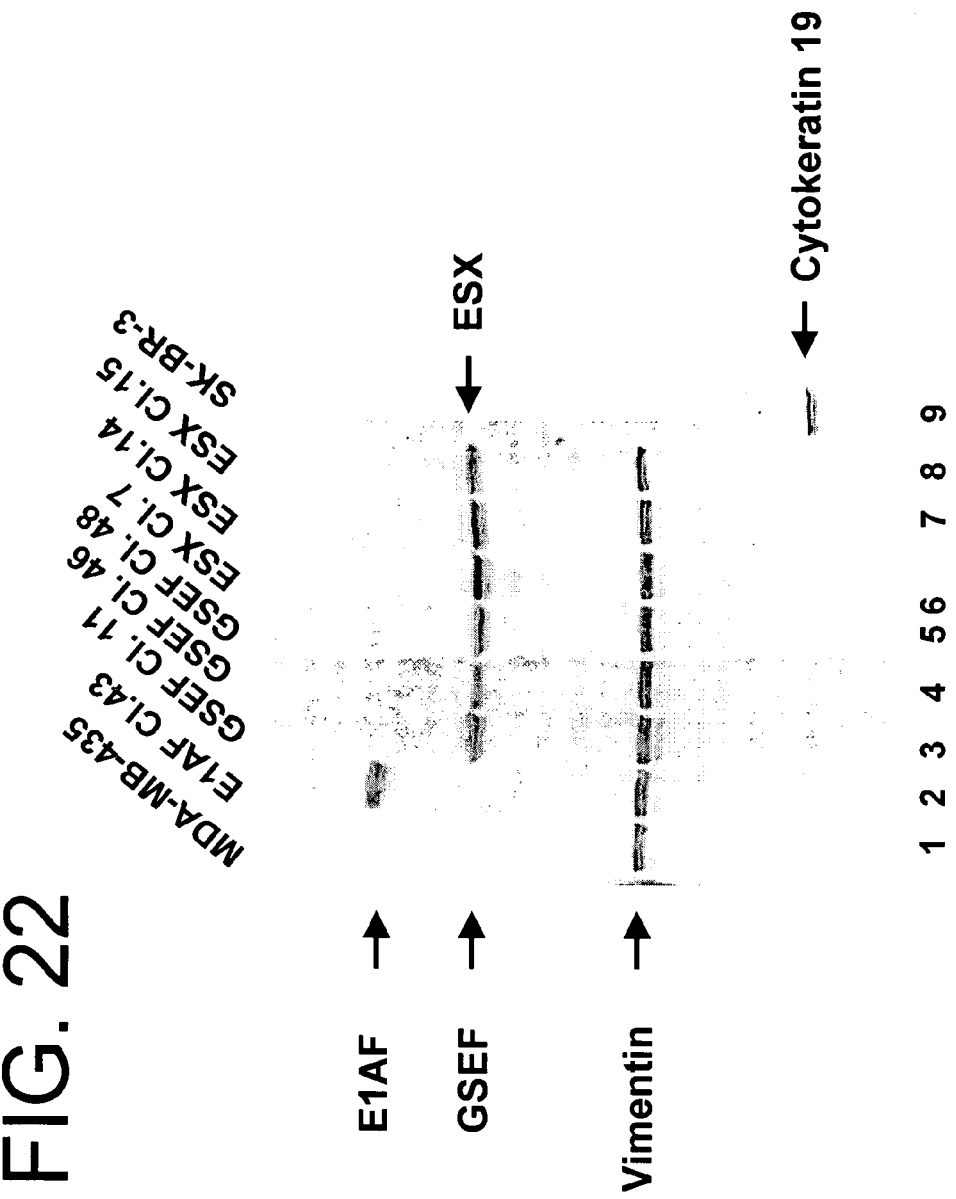
FIG. 22 is a photograph of a Western blot showing the effect of expression of E1AF, GSEF, or ESX upon Vimentin and cytokeratin 19 production in MDA-MB-435 cells.

Expression of GSEF, E1AF, ESX, Vimentin, and Cytokeratin 19 was examined by Western blot of whole cell lysates of MDA-MB-435 cells containing an E1AF expression construct (E1AF C1.43), MDA-MB-435 cells containing a GSEF expression construct (GSEF C1.11, GSEF CL.46, and GSEF C1.48), and MDA-MB-435 cells containing an ESX expression construct (ESX C1.7, ESX C1.15, and ESX C1.15). Whole cell lysates of MDA-MB-435 and SK-BR-3 cells served as controls. Expression of E1AF was used as a negative control since parental MDA-MB-435 cells express endogenous E1AF. As shown in FIG. 22, none of the three ETS transcription factors had an effect on the level of endogenous vimentin and cytokeratin 19 expression.

The effect of GSEF expression upon morphology, anchorage-independent growth (soft agar assay as described previously (Hamburger and Salmon, (1977) *Science*, 197:461-463), and invasiveness of MDA-MB-435 cells (matrigel assay: 3-dimensional reconstituted basemembrane culture were generated as described previously (Peterson et al., (1992) *Proc. Natl. Acad. Sci. USA* 89:9064-9068) using a commercially prepared reconstituted basement membrane (Matrigel; Collaborative Research, Waltham, Mass.) was examined using methods well known in the art.

As shown in FIG. 23, expression of GSEF in MDA-MB-435 cells (MDA-MB-GSEF (C1.46) and MDA-MB-435-GSEF (C1.48)) had significant effects on cell morphology compared to untransfected cells, and further had even more dramatic effects than stable expression of E1AF (MDA-MB-435-E1AF (C1.43))

Having established that the GSEF protein can be expressed in a functional manner, stable MDA-MB-435 cell lines were created. These experiments were designed to address the question of whether GSEF expression can interfere with the metastatic phenotype of MDA-MB-435 cells or might have an effect on the differentiation status of these cells. In short, immunoblot analysis was performed according to methods well known in the art to determine the effect of GSEF, E1AF, and ESX on expression of vimentin and cytokeratin 19. As shown in FIG. 22, the MDA-MB-435 cells expressed approximately equal levels of GSEF, E1AF and ESX. An E1AF expression plasmid was used as a negative control since parental MDA-MB-435 cells express endogenous E1AF (see FIG. 17). However, none of the three ETS transcription factor had an effect on the protein expression level of these EMT indicator genes (FIG. 22).

Studies of the morphology of transfected cells revealed that the cell morphology was noticabley different in the GSEF stable transfectant compared to the parental MDA-MB-435 or the EIAF control transfectant (FIG. 23). The characteristic elongated, needle like morphology of the MDA-MB-435 cells was altered into a more spherical shaped form, lacking the needle like extrusions. Interestingly the morphology of the GSEF stable transfectan more resembled the phenotype of the nontumorigenic SK-BR-3 cells (FIG. 23, uper right panel). The EIAF expressing clones and cells stably transfected with a GFP expression plasmid (data not shown) maintained the needle like structure of MDA-MB-435.

FIG. 24 provides exemplary results of the experiments to test the anchorage-independent growth of GSEF-expressing MDA-MB-435 cells. The stable MDA-MB-435 transfectant was then tested for anchorage-independent cell growth in the presence of serum according to methods well known in the art. Neither of the ectopically expressed Ets transcription factors EIAF or GSEF caused a significant change in the colony formation soft agar assay when compared to the parental MDA-MB-435 cells (FIG. 24). The nontumorigenic SK-BR3 cells serves as a negative control in this assay. These data indicate that ectopically expressed GSEF does not affect nchorage-independent cell growth. However this result was not surprising since two of the low metastatic, tumorigenic HBC cell lines (MCF-7, ZR-75-1) express significant amounts of endogenous GSEF (see FIG. 17). Preliminary data using the mammary fat pad mouse model revealed that all stable transfectants retained the capacity to form primary tumors (data not shown).

Figure 25:
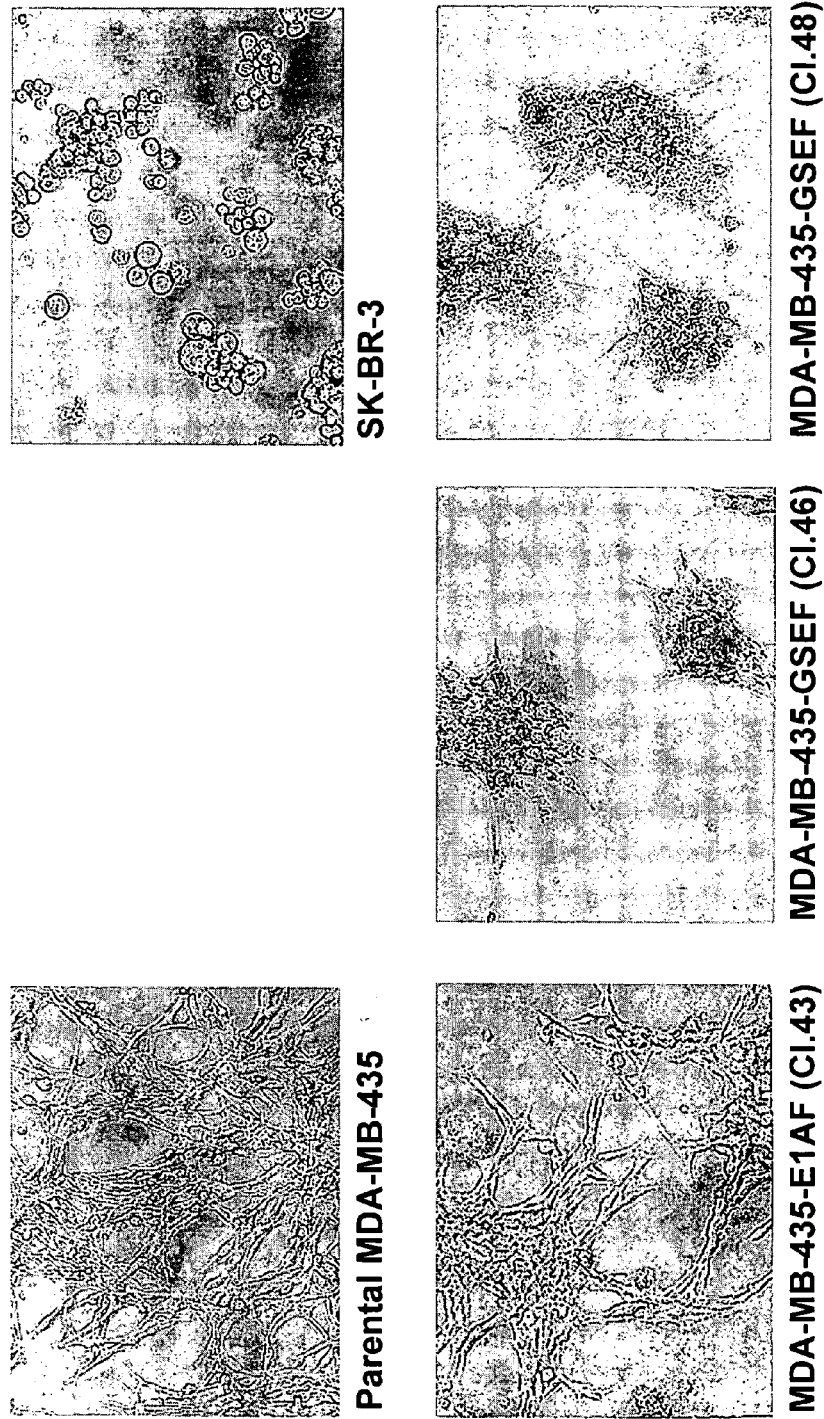
FIG. 25 is a photograph showing the effect of expression of E1AF or GSEF upon invasiveness of MDA-MB-435 cells in a MATRIGEL™ assay.

FIG. 25 provides exemplary results of the Matrigel invasion/motility assay to test the invasiveness of GSEF-expressing MDA-MB-435 cells. Again the SK-BR-3 cell line was used as a negative control and did not exhibit any three-dimensional growth as expected. The parental MDA-MB-435 as well as the E1AF transfectant exhibited characteristic three dimensional growth pattern indicative of metastatic cells (FIG. 25). Both GSEF transfectants analyzed in this assay proliferated in the Matrigel assay, but clearly lacked the three dimensional growth phenotype. These results indicate that the presence of ectopically expressed GSEF protein suppresses migration and or motility of these cells but has no detectable effect on anchorage independent growth as measured in the above-described assay. In general, these data show that expression of GSEF reduces the invasiveness of MDA-MB-435 cells.

Example 20

Identification of a Message Differentially Expressed in Pancreatic Cancer Cells

A family was identified that had several members who had been diagnosed with pancreatic cancer. The family members also have a form of diabetes. The pathological features of disease in the family included progression from normal to metaplasia to dysplasia to cancer. Tissues were obtained from a member of the family diagnosed with pancreatic cancer and from a member of the family diagnosed with dysplasia of pancreatic cells, and primary cultures of ductal cells prepared according to methods well known in the art. Tissue was also obtained from an unrelated person who was diagnosed with pancreatitis, and from an unrelated person who had a normal pancreas, and primary cultures of ductal cells prepared according to methods well known in the art.

The Genomyx HIEROGLYPH™ mRNA profile kit for differential display analysis was used according to the manufacturer's instructions to identify genes that are differentially expressed in the various samples relative to one another. Briefly, RNA was extracted from primary cultures of ductal epithelial cells obtained from patients with normal pancreas, nonspecific pancreatitis, pancreatic dysplasia and pancreatic carcinoma. Two µg of total RNA prepared by the guanidinium method was reverse-transcribed with anchored oligo-dT primer in a 10 µl reaction volume. Two µl of each reaction was subjected to PCR using 200 primer pairs to profile gene expression. [α-32P]dCTP (Amersham Pharmacia Biotech Inc., Piscataway, N.J.) was included in the PCR reaction. The PCR products were then separated on 6% sequencing gels using a GenomyxLR sequencer. The dried gels were subjected to autoradiography on Kodak BioMax films (33×61 cm).

Figure 26:
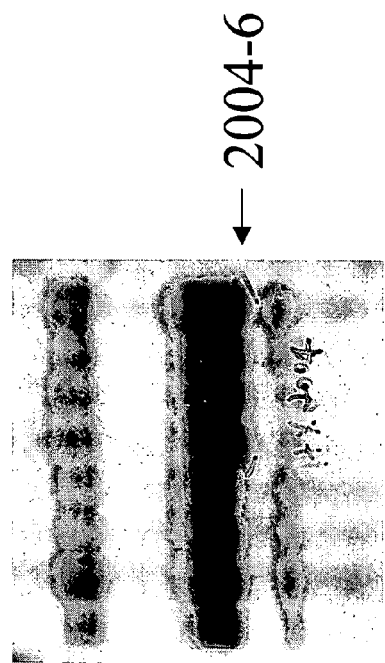
FIG. 26 depicts a sequencing gel autoradiograph of samples from a differential display assay. The arrow indicates the message differentially expressed in primary cultures of ductal epithelial cells from normal pancreas, and pancreas from individuals diagnosed with dysplasia of pancreatic cells, pancreatitis, and pancreatic cancer.

The cDNA fragment pattern in each sample was manually compared to the cDNA fragment pattern in every other sample on the gel. The results, depicted in FIG. 26, show that cDNA 2004-6 (HX2004-6) is expressed in ductal epithelial cells of pancreatic tissue from individuals with pancreatic dysplasia and individuals with pancreatic cancer. In contrast, the transcript was not detectable in normal and pancreatitis samples. Thus, an alternative name assigned to the gene is PCD1 (pancreatic cancer-derived).

Example 21

Isolation and Sequencing of a Human HX2004-6 Polypeptide-Encoding Polynucleotide A band representing a differentially expressed gene product (i.e., a band associated with relatively more or less cDNA in one sample relative to another) was cut from the gel, amplified, cloned, and sequenced. The polynucleotide sequence of cDNA fragments isolated from one such differentially displayed cDNA fragment was identified as being differentially regulated in pancreatic disease and potentially other cancers. A cDNA library prepared from the human colon cell line HT29 was screened to isolate a full-length cDNA. This 4,612-nucleotide sequence ("clone 1") is given as SEQ ID NO:52 in the sequence listing, and depicted in FIG. 27. The predicted translation product of this polynucleotide is a 1054-amino acid polypeptide (provided as SEQ ID NO:53). Another clone ("clone 2") was sequenced, and was found to differ from the sequence shown in SEQ ID NO:52 by an insertion of 30 nucleotides (bold, underlined, lower-case lettering in FIG. 28). Its sequence is provided as SEQ ID NO:54 in the sequence listing. Translation of this polynucleotide predicts a translation product of 1064 amino acids (provided as SEQ ID NO:55). The deduced amino acid sequence contains a PDZ domain in the middle (amino acid residues 427-504) and a highly conserved LIM domain at the C-terminus (amino acid residues 995-1053) (FIG. 28).

PDZ domains (also called DHR or GLGF domains) are found in diverse membrane-proteins including members of the MAGUK family of guanylate kinase homologues, several protein phosphatases and kinases, neuronal nitric oxide synthase, and several dystrophin-associated proteins, collectively known as syntrophins. Many PDZ domain-containing proteins appear to be localized to highly specialized submembranous sites. LIM domains are cysteine-rich domains that bind zinc ions, and which act as the interface for interface for protein-protein interaction. The LIM domain of HX2004-6 matched well with the LIM consensus motif $CX_2CX_{16-23}HX_2CX_2CX_2C_{16-21}CX_{2-3}(C/H/D)$ (SEQ ID NO: 95).

Example 22

Comparison of SEQ ID NO:52 with Sequences in Database

The sequence given as SEQ ID NO:52 was used as a query sequence to search for similar sequences in GenBank, using the BLASTN (2.0.8) program with default parameters. Altschul et al. (1997) *Nucl. Acids. Res.* 25:3389-3402. A 2224-nucleotide sequence having 100% nucleotide identity with nucleotides 1725-3863 of SEQ ID NO:52 was identified. This sequence (GenBank Accession No. AB020665) is a human cDNA clone, from brain tissue, which encodes a polypeptide termed KIAA0858. Nagase et al. (1998) *DNA Res.* 5:355-364. Comparison of the predicted translation product of SEQ ID NO:52 with the translation product of the sequence found in GenBank revealed 100% amino acid sequence identity between amino acids 343-1054 of HX 2004-6 clone 1 polypeptide sequence and the KIAA0858 protein sequence.

Another sequence was found which shares 100% nucleotide sequence identity with nucleotides 2837-3863 of SEQ ID NO:52. This sequence (GenBank Accession No. U90654) is a partial cDNA sequence, from mRNA isolated from human pancreas, encoding a putative human zinc-finger domain. Comparison of the amino acid sequence revealed 100% amino acid sequence identity between amino acids 714-1054 of the predicted translation product of SEQ ID NO:52 and amino acids of the predicted translation product of U90654.

Example 23

Analysis of Tissue and Cell Type Distribution of 2004 Expression

To determine the tissue and cell type distribution of HX2004 expression, the HX2004 cDNA clone was used as a template for PCR to generate a radiolabeled probe corresponding to a portion of the cDNA clone. This radiolabeled fragment ("the PCR-2004 probe" or "the 2004-6 probe") was used to probe various RNA blots. This probe corresponds to nucleotides 559 to 1107 of SEQ ID NO:54, is denoted by bold lettering in FIG. 28, and is given here as SEQ ID NO:56.

When the 2004-6 probe was used as a hybridization probe with multiple tissue RNA blots (Clontech), a 4.6-kb band was observed in heart, placenta, lung, liver, kidney, and pancreas, as shown in FIG. 29. A band corresponding to an approximately 6-kb mRNA species was seen in heart, brain, lung, liver, and skeletal muscle. Thus, mRNA hybridizing with the 2004-6 probe is found in a variety of normal tissues. In addition, tissue-specific splicing event(s) may lead to messages of different lengths.

A multiple tissue RNA blot containing RNA from various cancer cell lines was hybridized with the 2004-6 probe (upper panels) and, to control for amount of RNA loaded per lane, a β-actin probe (lower panels). The results, depicted in FIG. 30, show that the 4.6-kb band was observed in HeLa, MOLT-4 (lymphoblastic leukemia), SW480 (colorectal adenocarcinoma), and faintly in A549 (lung carcinoma) cells.

Figure 31:
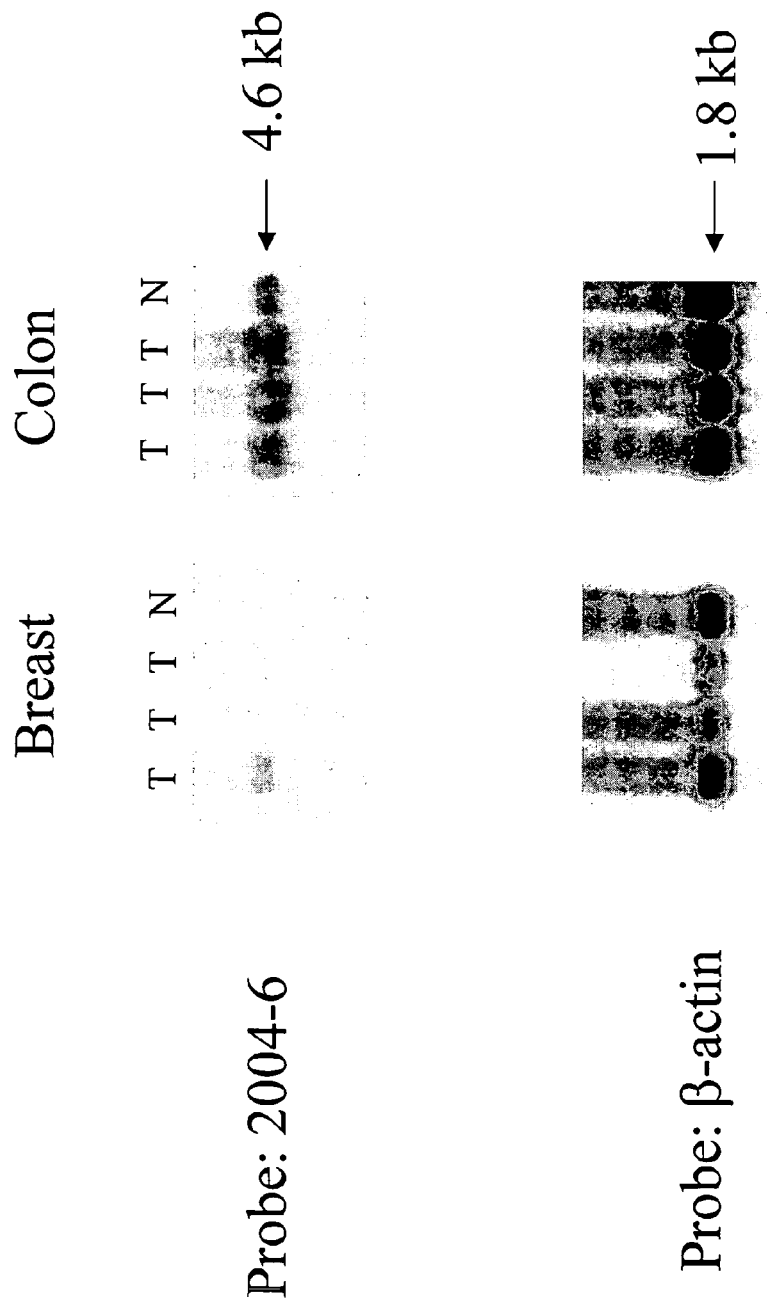
FIG. 31 depicts an autoradiograph of a tumor mRNA Northern blot probed with the 2004-6 probe (upper panels) and, as a control, β-actin (lower panels). mRNA samples were from breast tumor (Left-hand panels; Lanes marked "T") and normal breast (Left-hand panels; Lane "N") tissues, and colon tumor (Right-hand panels; Lanes marked "T") and normal colon tissue (Right-hand panels; Lane "N"), as described above.

To assess whether expression of HX2004 mRNA is associated with a particular cancerous state, a human tumor mRNA Northern blot (Invitrogen) was probed with the PCR-2004 probe. The data, presented in FIG. 31, show that the HX2004-6 message is detected in breast and colon tumors. Lanes marked "T" in the left-hand panels are breast tumor tissue samples. The first and third lanes marked "T" are invasive ductal carcinomas, while second lane marked "T" is a poorly differentiated invasive ductal carcinoma. Lane N in the left-hand panels is normal breast tissue. Lanes marked "T" in the right-hand panels are colon adenocarcinomas, and Lane N in the right-hand panels is normal colon tissue. HX2004-6 transcripts were also detected in normal tissues. This likely reflects the fact that the tissues used to prepare the human tumor material comprise many different cell types, including ductal epithelial cells.

Figure 32:
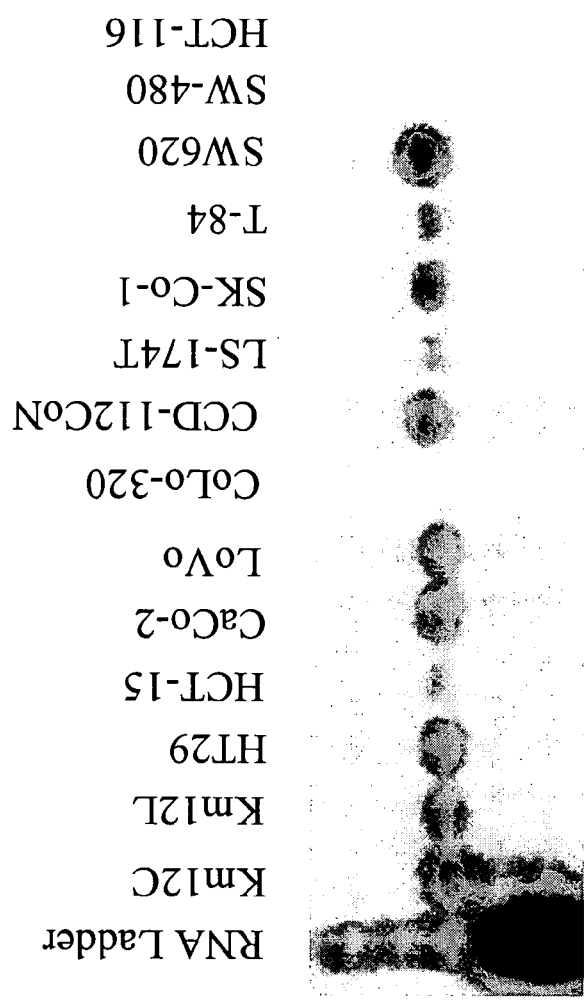
FIG. 32 depicts and autoradiograph of a colon cancer cell line RNA blot probed with the 2004-6 probe.

A variety of colon cancer cell lines were analyzed by Northern blot using the 2004-6 probe. The results, shown in FIG. 32, show that eight cell lines strongly express mRNA hybridizing with the 2004-6 probe; three cell lines show moderate levels of mRNA hybridizing with the 2004-6 probe; and three cell lines show low or undetectable expression of mRNA hybridizing with the 2004-6 probe.

Example 24

In situ Hybridization Analysis of HX2004-6 Expression in Breast, Pancreas, and Colon Cancer Tissue Sections In view of the fact that the tissue samples analyzed in the Northern analysis described in Example 23 comprise many different cell types, and thus would not assess differential expression in any one cell type, in situ hybridization analyses were conducted. Since these analyses use tissue sections, HX2004-6 expression levels in individual cell types can be evaluated.

Normal and cancerous tissue sections were obtained from colon, breast, liver, lung, pancreas, stomach, and prostate tissues using standard methods. The sections were fixed with 4% paraformaldehyde fixative, then overlaid with a mixture of oligonucleotide probes corresponding to HX2004-6, as follows:

Oligo #2
5'-GTAACTTTTTCGACGATCTTTCCAC-3'  (SEQ ID NO:57)

Oligo #4
5'-TATTTTCTGCATCTCCTCGTAACGC-3'  (SEQ ID NO:58)

Oligo #6
5'-TGACATCACTCATGGACTTACTCCC-3'  (SEQ ID NO:59)

Oligo #8
5'-GTTCCATCTGCTTCTGTATAAACCG-3'  (SEQ ID NO:60)

Oligo #13
5'-TCTGTTATCCTCATGTTTGTCTGGC-3'  (SEQ ID NO:61)

Oligo #14
5'-TCTGGCTTTTTCTTTCTCAAAGTGC-3'  (SEQ ID NO:62)

Oligo #16
5'-AAGTGCTGGTACATAGATGGCTGTC-3'  (SEQ ID NO:63)

Oligo #18
5'-TCTACTTTTGTTGGGGTTGAAAACG-3'  (SEQ ID NO:64)

Oligo #19
5'-TGTGTCACTTTCAAAAACTTCACGC-3'  (SEQ ID NO:65)

Oligo #21
5'-AGAGCAGCTTGTCTATGAACTCCAG-3'  (SEQ ID NO:66)

The oligonucleotides were labeled with fluorescein isothiocyanate (FITC) according to standard procedures. Normal and cancerous tissue was stained with hematoxylin-eosin. Hybridization was detected using the Super Sensitive ISH Detection System kit from Biogenex Laboratories, Inc., San Ramon, Calif. All procedures were carried out as instructed in the protocol provided by the manufacturer.

Figure 33:
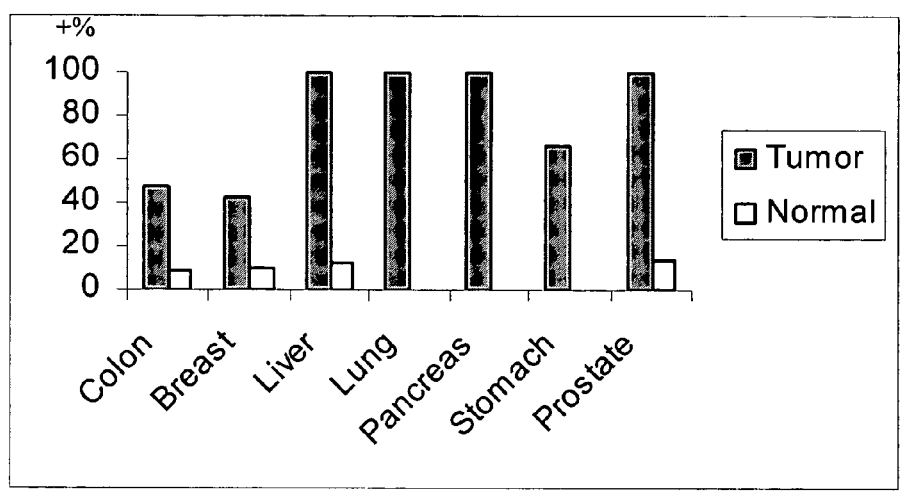
FIG. 33 is a graph showing the percentages of tumor and normal tissue samples expressing PCD1 by in situ hybridization analysis.
Figures 34A, 34B, 34C, 34D:
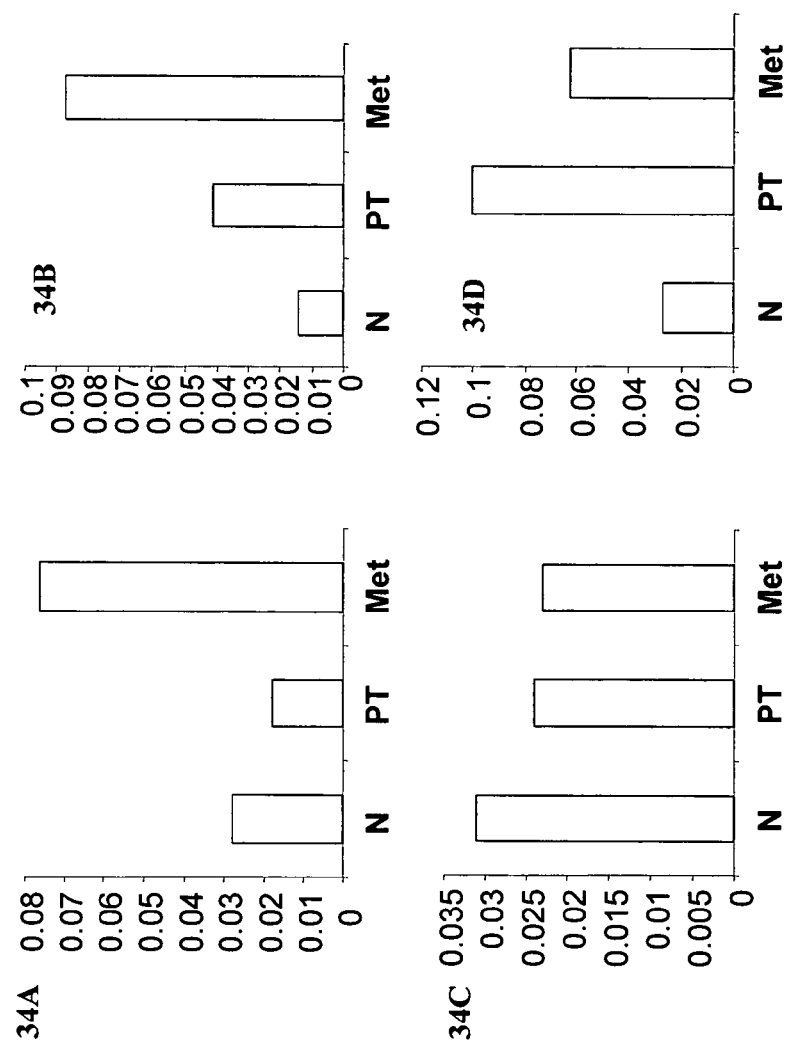
FIGS. 34A-34H (collectively referred to herein as FIG. 9) are a series of graphs showing HX2004-6 expression levels in tissues from eight colon cancer patients. N: normal colon tissue; PT: primary tumor colon tissue; MET: metastatic liver tissue. The expression data (on the Y axis) are adjusted by β-actin expression level and are thus relative values. All PCR reactions were performed in duplicate.
Figures 34E, 34F, 34G, 34H:
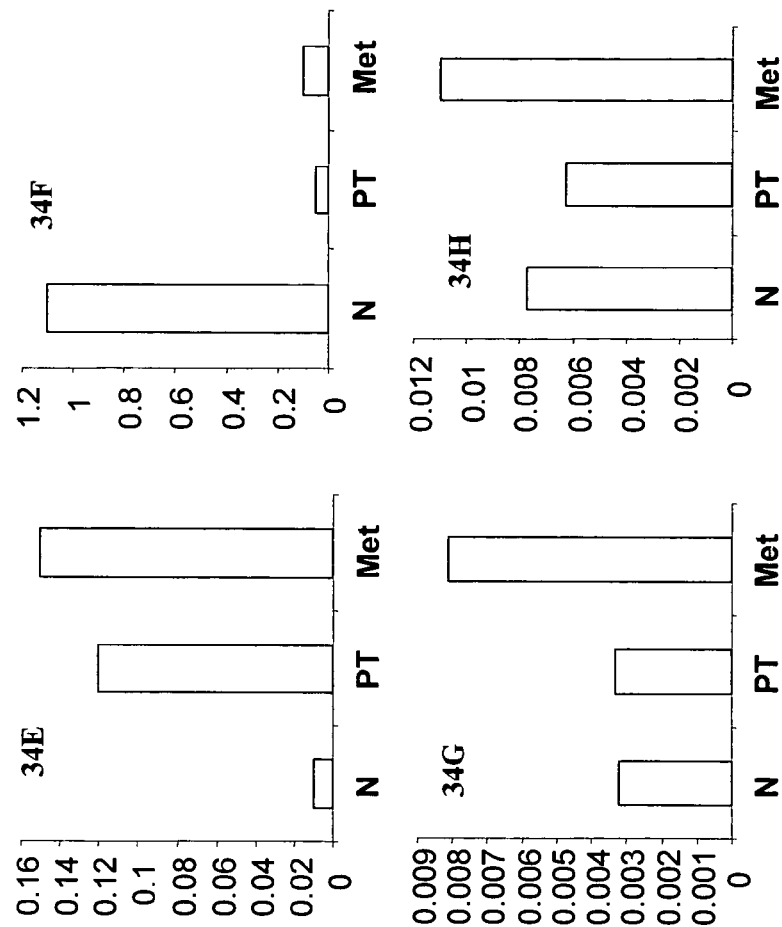

Table 2 summarizes the mRNA expression of HX2004-6 in 7 different tissues which we examined and FIG. 33 shows percentages of tissues which are positive for HX2004-6.

TABLE 2

Summary of HX2004-6 expression in tumor and normal tissues detected by in situ hybridization.

| Tissue | Tumor | | | Normal | | |
|---|---|---|---|---|---|---|
| | + | − | Total | + | − | Total |
| Colon | 65 | 73 | 138 | 4 | 44 | 48 |
| Breast | 76 | 103 | 179 | 3 | 26 | 29 |
| Liver | 51 | 0 | 51 | 1 | 7 | 8 |
| Lung | 20 | 0 | 20 | 0 | 8 | 8 |
| Pancreas | 7 | 0 | 7 | 0 | 4 | 4 |
| Stomach | 2 | 1 | 3 | 0 | 8 | 8 |
| Prostate | 4 | 0 | 4 | 2 | 12 | 14 |

=: srong expression;
−: weak or no detectable expression

For all seven tumor tissues, HX2004-6 expression is highly expressed in a significant portion of the samples tested; in contrast, few or none showed positive HX2004-6 expression in normal samples for each tissue. Therefore, HX2004-6 expression is elevated in a significant portion of tumor tissue samples from colon, breast, liver, lung, pancreas, stomach and prostate cancer patients.

Example 25

Expression Analysis by Real-Time Quantitative RT-PCR

Real-time quantitative PCR was performed using a Lightcycler instrument to investigate expression levels of HX2004-6 message in tumor tissues from eight colon cancer patients.

One μg human placenta total RNA (Clontech, Palo Alto, Calif.) was reverse-transcribed with oligo-dT$_{18}$ primer at 42° C. for 1 hour then heated at 94° C. for 5 minutes in a total reaction volume of 20 μl (1st-Strand™ cDNA Systhesis Kit, Clontech). The reaction mix was used as the 1× template standard for PCR in the Lightcycler. Serial dilutions from the 1× template standard were then prepared: $10^{-1}$×, $10^{-2}$×, $10^{-3}$×, $10^{-4}$×, $10^{-5}$×, template standards.

Patient colon tissue was obtained at surgery and stored frozen in liquid nitrogen. The patient tissue samples were homogenized in TRIZOL reagent. Chloroform was then added to isolate RNA, followed by RNA precipitation with isopropanol. The RNA precipitates were washed with 75% ethanol, dried in air, then dissolved in RNase-free distilled water. The total RNA samples were treated with DNase I (RNase-free) (2 U/μl, Ambion, Austin, Tex.) and cleaned up using RNeasy Mini Kit (Qiagen, Santa Clarita, Calif.) then reverse-transcribed with oligo-dT$_{18}$ primer (1st-StrandTM cDNA Systhesis Kit, Clontech). PCR was performed in the Lightcycler using the following gene-specific primers:

β-actin:
forward primer 5'-CGGGAAATCGTGCGTGACATTAAG-3'  (SEQ ID NO:67)

reverse primer 5'-TGATCTCCTTCTGCATCCTGTCGG-3'  (SEQ ID NO:68)

PCD1:
forward primer 5'-TTCGTAGCATCAGTTGAAGCAGG-3'  (SEQ ID NO:69)

reverse primer 5'-GGTGAACCAGCCTTTCCATAGC-3'  (SEQ ID NO:70)

The 20-μl PCR reaction mix in each Lightcycler capillary contained 2 μl of 10×PCR buffer II, 3 mM MgCl$_2$ (Perkin-Elmer, Foster City, Calif.), 140 μM dNTP, 1:50000 of SYBR Green I, 0.25 mg/ml BSA, 1 unit of Taq polymerase (Boehringer Mannheim, Indianapolis, Ind.), 0.175 μM each primer, 2 μl of RT reaction mix. The PCR amplification began with 20-second denaturation at 95° C., followed by 45 cycles of denaturation at 95° C. for 5 seconds, annealing at 60° C. for 1 second and extension at 72° C. for 30 seconds. At the end of final cycle, PCR products were annealed at 60° C. for 5 seconds, then slowly heated to 95° C. at 0.2° C./second, to measure melting curves of specific PCR products. All experiments were performed in duplicate. Data analysis was performed using Lightcycler Software (Roche Diagnosis) with quantification and melting curve options.

The quantification assay was based on determination of the cycle crossing point, which represents the cycle when the PCR product begins to double with each cycle, i.e., when the log-linear phase begins. A template dilution test was performed and demonstrated that the gene-specific primers for β-actin and HX2004-6 are capable of accurate, sensitive and specific detection of expression levels for β-actin and HX2004-6, respectively (Data not shown).

For each colon cancer patient, RNA was extracted from a trio of surgical specimens: normal colon tissue, primary colon tumor tissue and metastatic liver tissue from patients with colon cancer. The sample trio from each patient was always tested simultaneously in the same run of the Lightcycler. Each run of the Lightcycler included a standard curve established on β-actin expression in the template standards. β-actin expression in patient tissue samples was used as the internal adjustment control.

The results are quantified and shown in FIGS. 34A-34H. HX2004-6 is overexpressed (>2 fold) in primary tumor colon tissue and/or metastatic liver tissue relative to normal colon tissue in 5/8 patients. Specifically, HX2004-6 was overexpressed in metastatic liver tissue relative to normal tissue in 5/8 patients; HX2004-6 was overexpressed in primary tumor tissue relative to normal tissue in 3/8 patients; and HX2004-6 was overexpressed in either primary tumor and/or metastatic liver tissue relative to normal tissue (i.e., in cancerous tissue relative to normal tissue) in 6/8 patients. These results are consistent with the previous results from in situ hybridization and Northern hybridization described above. It is noteworthy that in one patient, HX2004-6 expression levels in primary tumor colon and metastatic liver tissue are dramatically decreased, not increased, relative to normal colon tissue.

Example 26

Chromosomal Localization of HX2004-6

To determine the chromosomal localization of HX2004-6, the 2004-6 probe was labeled and used as a probe on human metaphase chromosomes using fluorescence in situ hybridization according to standard procedures. The results indicated that HX2004-6 localizes to 13q21.33.

Example 27

Fabricating a DNA Array Using Polynucleotides Differentially Expressed in Ductal Epithelial Cells A DNA array is made by spotting DNA fragments onto glass microscope slides that are pretreated with poly-L-lysine. Spotting onto the array is accomplished by a robotic arrayer. The DNA is cross-linked to the glass by ultraviolet irradiation, and the free poly-L-lysine groups are blocked by treatment with 0.05% succinic anhydride, 50% 1-methyl-2-pyrrolidinone and 50% borate buffer.

The spots on the array are oligonucleotides synthesized on an ABI automated synthesizer. Each spot is one of the polynucleotides of SEQ ID NO:52 or SEQ ID NO: 54, a fragment thereof, a complement thereof, or a complement of a fragment thereof, which correspond to a gene that is differentially expressed in pancreatic, breast, or colon epithelial cells according to varying disease states (e.g., overexpressed in cancerous, pancreatic cancer, breast cancer, colorectal cancer cells). The polynucleotides may be present on the array in any of a variety of combinations or subsets. Some internal standards and negative control spots including non-differentially expressed sequences and/or bacterial controls are included.

mRNA from patient samples is isolated, the mRNA used to produce cDNA, amplified and subsequently labeled with fluorescent nucleotides as follows: isolated mRNA is added to a standard PCR reaction containing primers (100 pmoles each), 250 μM nucleotides, and 5 Units of Taq polymerase (Perkin Elmer). In addition, fluorescent nucleotides (Cy3-dUTP (green fluorescence) or Cy5-dUTP (red fluorescence), sold by Amersham) are added to a final concentration of 60:M. The reaction is carried out in a Perkin Elmer thermocycler (PE9600) for 30 cycles using the following cycle profile: 92° C. for 30 seconds, 58° C. for 30 seconds, and 72° C. for 2 minutes. Unincorporated fluorescent nucleotides are removed by size exclusion chromatography (Microcon-30 concentration devices, sold by Amicon).

Buffer replacement, removal of small nucleotides and primers and sample concentration is accomplished by ultrafiltration over an Amicon microconcentrator-30 (mw cut-off=30,000 Da) with three changes of 0.45 ml TE. The sample is reduced to 5 μl and supplemented with 1.4 μl 20×SSC and 5 μg yeast tRNA. Particles are removed from this mixture by filtration through a pre-wetted 0.45μ microspin filter (Ultrafree-MC, Millipore, Bedford, Mass.). SDS is added to a 0.28% final concentration. The fluorescently-labeled cDNA mixture is then heated to 98° C. for 2 min., quickly cooled and applied to the DNA array on a microscope slide. Hybridization proceeds under a coverslip, and the slide assembly is kept in a humidified chamber at 65° C. for 15 hours.

The slide is washed briefly in 1×SSC and 0.03% SDS, followed by a wash in 0.06% SSC. The slide is kept in a humidified chamber until fluorescence scanning was done. Fluorescence scanning and data acquisition are then accomplished using any of a variety of suitable methods well known in the art. For example, fluorescence scanning is set for 20 microns/pixel and two readings are taken per pixel. Data for channel 1 is set to collect fluorescence from Cy3 with excitation at 520 nm and emission at 550-600 nm. Channel 2 collects signals excited at 647 nm and emitted at 660-705 nm, appropriate for Cy5. No neutral density filters are applied to the signal from either channel, and the photomultiplier tube gain is set to 5. Fine adjustments are then made to the photomultiplier gain so that signals collected from the two spots are equivalent.

The data acquired from the scan of the array is then converted to any suitable form for analysis. For example, the data may be analyzed using a computer system, and the data may be displayed in a pictoral format on a computer screen, where the display shows the array as a collection of spots, each spot corresponding to a location of a different polynucleotide on the array. The spots vary in brightness according to the amount of fluorescent probe associated with the spot, which in turn is correlated with an amount of hybridized cDNA in the sample. The relative brightness of the spots on the array can be compared with one another to determine their relative intensities, either qualitatively or quantitatively.

The display of spots on the array, along with their relative brightness, provides a test sample pattern. The test sample pattern can be then compared with reference array patterns associated with positive and negative control samples on the same array, e.g., an array having polynucleotides in substantially the same locations as the array used with the test sample. The reference array patterns used in the comparison can be array patterns generated using samples from normal pancreas cells, cancerous pancreatic cells, pancreatitis-associated pancreas cells, normal breast and breast cancer cells, normal colon and colorectal cancer cells, and the like. A substantial or significant match between the test array pattern and a reference array pattern is indicative of a disease state of the patient from whom the test sample was obtained.

Example 28 cDNA Cloning and Characterization of VSHK-1

Figure 35:
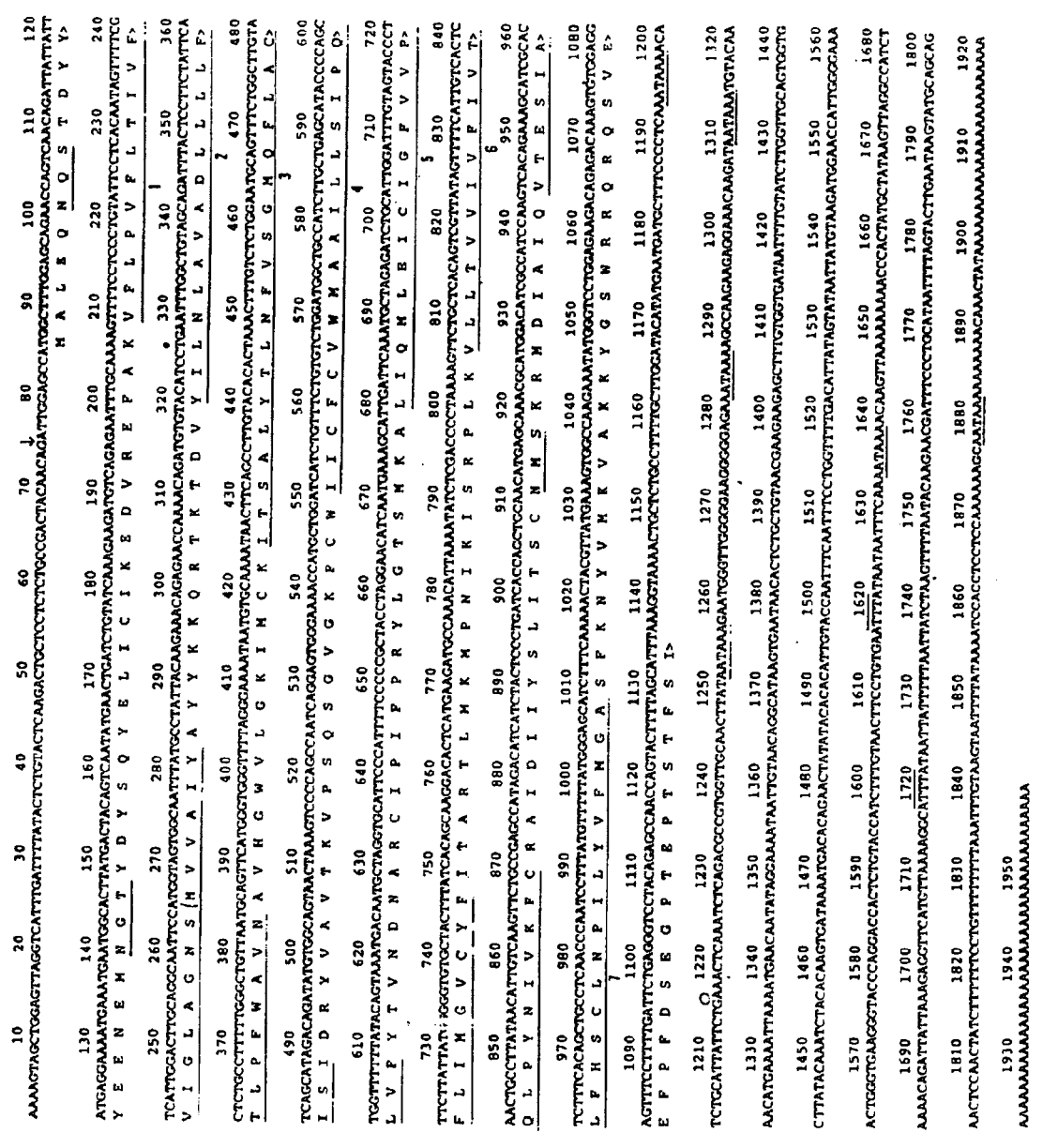
Figure 36:
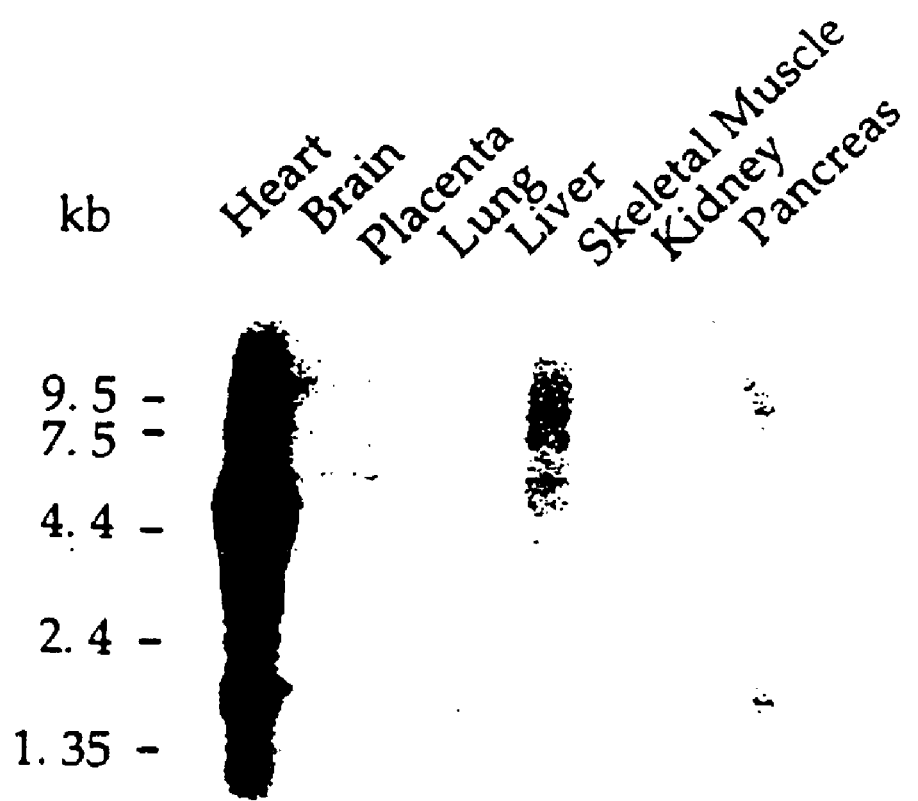
FIG. 36 depicts the results of Northern blot analysis of various human tissues using VSHK-1 polynucleotide encoding amino acids 114 to 223 of SEQ ID NO:72.

VSHK-1 cDNA was cloned and sequenced. As shown in FIG. 35 the cDNA sequence (SEQ ID NO:71) has two potential Met start codons, the first of which has a consensus Kozak sequence. Full-length VSHK-1 cDNA encodes a polypeptide of 350 amino acids (SEQ ID NO:72), with several conserved motifs typical of seven transmembrane receptors. In FIG. 36, the putative transmembrane domains are underlined and labeled 1 through 7. The amino acid sequence has three potential N-glycosylation sites, two in the amino terminal portion (underlined "NQS" and "NGT" in FIG. 35 and one in the third extracellular loop (underlined "NMS" in FIG. 35. EST H67224 (GenBank Accession No. H67224) provides a 328-nucleotide sequence which is identical (except for the "n", or unidentified, nucleotide in EST H67224) to nucleotides 324 through 651 of SEQ ID NO:71.

As shown in FIG. 36, VSHK-1 mRNA is found predominantly in heart tissue. Faint or undetectable hybridization was detected with RNA from brain, placenta, lung, liver, skeletal muscle, kidney, and pancreas. In heart, three RNA species were identified: a 1.3 kb; a 2.0 kb; and a 5.0 kb species. The cDNA depicted in FIG. 35 corresponds to the 2.0 kb form. Use of an alternative polyadenylation site could account for the 1.3 form.

Genomic analysis revealed an intron at nucleotide 74, with splice donor and acceptor sites being ACTACCAACAGgttggtacttta (SEQ ID NO:73) and ctttgccatctagAGTGGAGCC (SEQ ID NO:74), respectively. The 3.0 kb intron is transcribed, and could account for the 5.0 kb mRNA species.

The amino acid sequence of VSHK-1 was compared to known amino acid sequences available in GenBank. Using the Clustal W program with default parameters, sequences sharing amino acid identity with VSHK-1 were identified as CCR6, CCR7, and CXCR2. CCR6 and CCR7 share 32% and 37% amino acid sequence identity, respectively, with the sequence set forth in SEQ ID NO:72. The alignment is shown in FIG. 37. The highest amino acid sequence identity is found in transmembrane domain 2.

The VSHK-1 coding region was cloned into the mammalian expression vector pcDNA3 (Invitrogen). The construct, designated pHA-VSHK1, also includes a hemagluttinin (HA) epitope tag in-frame with VSHK-1 coding sequences. The insert was transcribed in vitro and translated in the presence and absence of canine pancreatic microsomal membranes. A major polypeptide of approximately 45 kDa was observed, which was modified in the presence of the membrane to a higher molecular weight form. The presence of the additional HA tag at the N-terminus increases the size of the polypeptide, confirming that the signal sequence is not processed.

Figure 38:
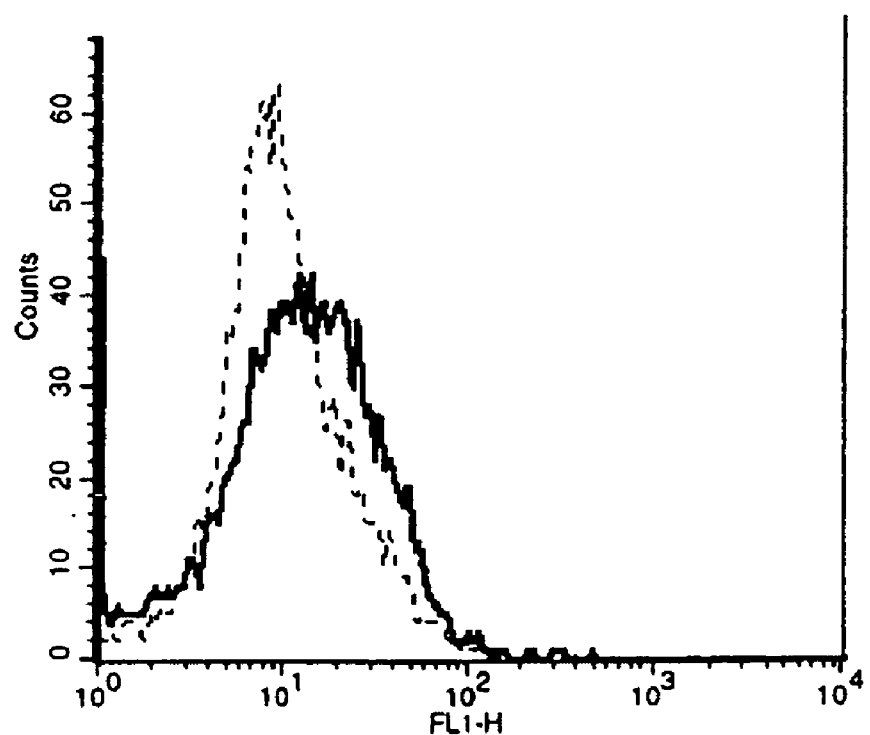
FIG. 38 depicts the results of FACS analysis of HEK293 cells expressing epitope-tagged VSHK-1. Epitope-specific antibody binding to mock-transfected cells (dashed lines) and to cells transfected with epitope-tagged VSHK-1-expression construct (solid lines) is shown.

HEK-293 cells were transiently transfected with either pHA-VSHK-1 or pcDNA-3 (vector control), using Translt-LT1. Shymala and Khoja (1998) *Biochem.* 37:15918-15924. Six hours post-transfection, the media was changed to DMEM containing 10% serum. 48 hours later, cells were released from the plates with $Ca^{2+}$ and $Mg^{2+}$-free phosphate buffered saline containing 5 mM EDTA. Intact cells were treated with mouse monoclonal 12CA5 anti-HA antibody (Boehringer), followed by incubation with FITC-conjugated anti-mouse antibody. The cell suspension was subjected to FACS (fluorescence-activated cell sorting) analysis. The results are shown in FIG. 38. Vector control (dashed lines) shows background binding, while pHA-VSHK-1 expressing cells (solid lines) showed expression of the epitope-tagged protein.

Example 29

Identification of Receptor Binding Agonists and Antagonists

VSHK-1 peptide ligands, agonists, and antagonists can be identified using the following methods. Construction of a phage library encoding random peptides is described in Devlin, WO91/18980. Such a construction consists of (1) Producing Oligonucleotides Encoding Random Peptides;
(2) Creating a Shuttle Vector, Plasmid M3LP67, for Recombination with the Wild Type Phage; and
(3) Production of Phage Encoding Random Peptides by Recombination.

Once the phage library is constructed, the library is screened using a VSHK-1 receptor polypeptide. From the phage library, peptides with the desired binding properties can be assayed for their receptor binding agonist or antagonist properties.

I. Producing Oligonucleotides Encoding Random Peptides

An oligonucleotide having the following structure was synthesized, and purified using methods known in the art, as described in Devlin, WO91/18980:

```
5' CTTTCTATTCTCACTCCGCTGAA(NNS)15CCG    (SEQ ID NO:75)
CCTCCACCTCCACC 3';
and 5' GGC CGG TGG AGG TGG AGG CGG          (SEQ ID NO:76)
(iii)15 TTC AGC GGA GTG AGA ATA GAA
AGG-TAC 3'.
```

During the synthesis of (NNS)15, a mixture consisting of equal amounts of the deoxy-nucleotides A, C and T, and about 30% more G was used for N, and an equal mixture of C and G for S. Deoxyinosine (i) was used because of its capacity to base pair with each of the four bases (A, G, C, and T) (J. F. Reidhaar-Olson et al., *Science*, (1988) 24:53). Alternatively, other base analogs may be used as described by J. Habener et al., *Proc Natl Acad Sci USA* (1988) 85:1735.

Immediately preceding the nucleotide sequence that encodes the random peptide sequence is a nucleotide sequence that encodes alanine and glutamic acid residues. These amino acids were included because they correspond to the first two amino terminal residues of the wild type mature gene III protein of M13, and thus may facilitate producing the fusion protein produced as described below.

Immediately following the random peptide sequence is a nucleotide sequence that encodes 6 proline residues. Thus, the oligonucleotide encodes the following amino acid sequence:

H₂N-Ala-Glu-Xaa₁₅-Pro₆(SEQ ID NO: 96).

Xaa denotes amino acids encoded by the random DNA sequence. As described below, the oligonucleotides were cloned into a derivative of M13 to produce a mature fusion protein having the above amino acid sequence, and following the proline residues, the entire wild type mature gene III.

II. Construction the Shuttle Vector, Plasmid M13LP67, for Recombination with the Wild Type Phage The plasmid M13LP67 was used to express the random peptide/gene III fusion protein construct. M13LP67 was derived from M13 mp19.

Briefly, M13mp19 was altered in two ways. The first alteration consisted of inserting the marker gene, β-lactamase, into the polylinker region of the virion. This consisted of obtaining the gene by PCR amplification from the plasmid pAc5. The oligonucleotide primers that were annealed to the pAc5 template have the following sequence:

```
5' GCT GCC CGA GAG ATC TGT ATA TAT    (SEQ ID NO:77)
GAG TAA ACT TGG 3';
and

5' GCA GGC TCG GGA ATT CGG GAA ATG    (SEQ ID NO:78)
TGC GCG AAA CCC 3'.
```

Amplified copies of the β-lactamase gene were digested with the restriction enzymes Bg/II and EcoRI, and the replicative form of the modified M13mp19 was digested with BamHI and EcoRI. The desired fragments were purified by gel electrophoresis, ligated, and transformed into *E. coli* strain DH5 alpha (BRL). *E. coli* transformed with phage that carried the insert were selected on ampicillin plates. The phage so produced were termed JD32.

The plasmid form of the phage, pJD32 (M13mp19Ampr), was mutagenized so that two restriction sites, EagI and KpnI, were introduced into gene III without altering the amino acids encoded in this region. The restriction sites were introduced using standard PCR in vitro mutagenesis techniques as described by M. Innis et al. in "PCR Protocols—A Guide to Methods and Applications" (1990), Academic Press, Inc.

The KpnI site was constructed by converting the sequence, TGTTCC, at position 1611 to GGTACC. The two oligonucleotides used to effect the mutagenesis have the following sequence:

```
LP159: AAACTTCCTCATGAAAAAGTC;         (SEQ ID NO:79)
and

LP162: AGAATAGAAAGGTACCACTAAAGGA.    (SEQ ID NO:80)
```

To construct the EagI restriction site, the sequence at position 1631 of pJD32, CCGCTG, was changed to CGGCCG using the following two oligonucleotides:

```
LP160: TTT AGT GGT ACC TTT CTA TTC    (SEQ ID NO:81)
       TCA CTC GGC CGA AAC TGT;
and

LP161: AAA GCG CAG TCT CTG AAT TTA    (SEQ ID NO:82)
       CCG.
```

More specifically, the PCR products obtained using the primers LP159, LP162 and LP160 and LP161 were digested with BspHI and KpnI, and KpnI and AlwNI, respectively. These were ligated with T4 ligase to M13mp19 previously cut with BspHI and AlwNI to yield M13mpLP66. This vector contains the desired EagI and KpnI restriction sites, but lacks the ampicillin resistance gene, β-lactamase. Thus, the vector M13mpLP67, which contains the EagI and KpnI restriction sites and β-lactamase was produced by removing the β-lactamase sequences from pJD32 by digesting the vector with XbaI and EcoRI. The β-lactamase gene was then inserted into the polylinker region of M13mpLP66 which was previously digested with XbaI and EcoRI. Subsequent ligation with T4 ligase produced M13mpLP67, which was used to generate the random peptide library. Schematics of the construction of M13mpLP67 are shown in Devlin et al., PCT WO91/18980.

Production of Phage Encoding Random Peptides

To produce phage having DNA sequences that encode random peptide sequences, M13LP67 was digested with EagI and KpnI, and ligated to the oligonucleotides. The ligation mixture consisted of digested M13LP67 DNA at 45 ng/µl, a 5-fold molar excess of oligonucleotides, 3.6 U/µl of T4 ligase (New England Biolabs), 25 mM Tris-HCl, pH 7.8, 10 mM MgCl₂, 2 mM DTT, 0.4 mM ATP, and 0.1 mg/ml BSA. Prior to being added to the ligation mixture, the individual oligonucleotides were combined and heated to 95° C. for 5 minutes, and subsequently cooled to room temperature in 15 µL aliquots. Next, the ligation mixture was incubated for 4 hours at room temperature and subsequently overnight at 15° C. This mixture was then electroporated into *E. coli* as described below.

M13LP67 DNA was electroporated into H249 cells prepared essentially as described by W. Dower et al.(1988) *Nucl. Acids Res.* 16:6127. H249 cells are a recA, sup°, F' kan$^R$ derivative of MM294. Briefly, 4×10⁹ H249 cells and 1 µg of M13LP67 DNA were combined in 85 µl of a low conductivity solution consisting of 1 mM HEPES. The cell/M13LP67DNA mixture was positioned in a chilled 0.56 mm gap electrode of a BTX electroporation device (BTX Corp.) and subjected to a 5 millisecond pulse of 560 volts.

Immediately following electroporation, the cells were removed from the electrode assembly, mixed with fresh H249 lawn cells, and plated at a density of about 2×10⁵ plaques per 400 cm² plate. The next day phage from each plate were eluted with 30 ml of fresh media, PEG precipitated, resuspended in 20% glycerol, and stored frozen at −70° C. About 2.8×10⁷ plaques were harvested and several hundred analyzed to determine the approximate number that harbor random peptide sequences.

Using the polymerase chain reaction to amplify DNA in the region that encodes the random peptide sequence, it was determined that about 50-90% of the phage contained a 69 base pair insert at the 5' end of gene III. This confirmed the presence of the oligonucleotides that encode the random peptides sequences. The PCR reaction was conducted using standard techniques and with the following oligonucleotides:

```
5' TCGAAAGCAAGCTGATAAACCG 3';    (SEQ ID NO:83) and

5' ACAGACAGCCCTCATAGTTAGCG 3'.   (SEQ ID NO:84)
```

The reaction was run for 40 cycles, after which the products were resolved by electrophoresis in a 2% agarose gel. Based on these results, it was calculated that phage from the 2.8×10⁷ plaques encode about 2×10⁷ different random amino acid sequences.

Panning for Receptor Binding Agonists and Antagonists

Peptides having an affinity for VSHK-1 receptor are identified as follows:

1.) 1 Smer phage ($2.5 \times 10^{10}$) prepared as described above are selected by coincubation with $10^6$ Sf9 (*Spodoptera frugiperda*) cells expressing native VSHK-1 in a baculovirus expression vector on the second day after infection. The coincubation is at room temperature for 60 minutes in Grace's medium with 2% nonfat milk. Binding phage are eluted with 6M urea (pH 2.2), the pH neutralized by adding 2 M Tris-HCl, and assayed. The phage are amplified on solid agar plates as plaques, eluted with Tris-buffered saline, and precipitated with polyethylene glycol.

2.) The phage resulting from round 1 are reselected on CHO cells expressing the native VSHK-1 on second day 2 after plating the cells at a density of $7.1 \times 10^5$, using $3.1 \times 10^{11}$ phage on in DMEM with 2% nonfat milk and 10 mM HEPES. The phage are bound, eluted, assayed, and amplified as described in round 1.

3.) The phage selected in round 2 are reselected on Sf9 cells expressing the native VSHK-1 receptor on day 2 post-infection as described for round 1 ($2.8 \times 10^{10}$ phage on $10^6$ Sf9 cells). Sample phage from the urea eluate are cloned, and their DNAs are isolated and sequenced.

Once the amino acid sequence of the putative agonists and antagonists is determined, synthetic oligopeptides can be produced and their signal transduction activity can be assayed by, for example, Amersham's inositol 1,4,5-trisphosphate assay system (Arlington Heights, Ill., U.S.A.).

CHO cells expressing the VSHK-1 receptor polypeptide are plated at a density of $1 \times 10^5$ cells/well in a 12-well plate. The cells are cultured for 2 days, and then, the cells are washed twice with PBS containing 0.2% BSA. Next, the cells are incubated in the same medium for 30 minutes at 37° C. The medium on the cells is changed to PBS containing 0.2% BSA and 10 mM LiCl, and the cells are incubated for another 30 minutes at 37° C.

Signal transduction is induced by changing the medium of the cells to PBS containing 0.2% BSA, 10 mM LiCl, and the desired concentration of the oligopeptide, as determined by the screening. The cells are incubated in this medium for 5 minutes and then the media is removed from the cells. Next, 0.2 volumes ice-cold 20% (v/v) perchloric acid (PCA) is added to the cells to quench the stimulation and to prepare the cells for the inositol phosphate assay. The cells are incubated on ice in PCA for 20 minutes. At the beginning of the incubation, the cells are dislodged from the plate with a rubber policeman. After the incubation, the cells are removed from the plate and centrifuged at 2,000×g for 15 minutes at 4° C. The supernatants are removed and titrated to pH 7.5 with 10 N KOH and kept on ice. The solution is centrifuged at 2,000×g for 15 minutes at 4° C. to remove the precipitate. The supernatant is then assayed to determine the amount of inositol trisphosphate present.

Amersham provides a kit containing the reagents for an inositol triphosphate competition assay. With the kit, an inositol 1,4,5-triphosphate binding protein is provided, which cross-reacts with inositol 1,3,4,5-tetrakisphosphate less than 10% and less than 1% with other inositol phosphates. The assay measures that amount of inositol triphosphate that competes for the binding protein with the radioactive labeled triphosphate.

1) Preparing the Standard

First allow all the reagents to thaw at 2-8° C. and then mix thoroughly. As this is occurring, eight poypropylene tubes (12×75 mm) are labeled "0.19," "0.38," "0.76," "1.5," "3.1," "6.2," "12.5," and "25 pmol." 1.5 ml of water are pipetted into the tube marked "25 pmol." Into the remaining marked standard tubes 500 µl of water are pipetted. Next, into the marked "25 pmol" tube, are added exactly 100 µl of the standard solution (3 nmol D-myo-inositol 1,4,5-trisphosphate in water). The solution is mixed completely. Five hundred µl of the 25 pmol solution are transferred to the 12.5 pmol tube, and the solution is vortexed throughly. Repeat this 1:2 dilution succesively with the remaining tubes. These working standards should be prepared immediately before each assay and not re-used. The standard solution from the kit should be recapped after use and immediately stored at −15° C. to −30° C.

2) Assay Protocol

First label duplicate polypropylene tubes (10×55 mm) "TC" for total counts; "NSB" for non-specific binding; "$B_o$" for zero standards; "0.19," "0.38," "0.76," "1.5," "3.1," 6.2, "12.5, " and "25" pmol for the standards; and whatever is desired for the samples. Next, into all the tubes 100 µl of the assay buffer (0.1 M Tris buffer pH 9.0, 4 mM EDTA and 4 mg/ml bovine serum albumin (BSA)) is pipetted. Into the Bo and TC tubes, 100 µl and 200 µl, respectively deionized water is added. Then, starting with the most dilute solution, 100 µl of each of the standard solutions, described above, is pipetted into the appropriately labelled tubes. A new pipette tip is used for each standard solution. Into the NSB tubes, 100 µl of stock standard solution (3 nmol D-myo-inositol 1,4,5-trisphosphate in water) are pipetted. One hundred microliters of the samples should be added to the appropriate sample tubes. A new pipette tip is used for each sample.

One hundred microliters of first the tracer (~1.0 µCi or ~37 kBq of D-myo-[$^3$H]inositol 1,4,5-trisphosphate in 1:1 (v/v) water:ethanol) and then binding protein is added to all the tubes. All the tubes are vortexed to mix all the contents throughly and then incubated for 15 minutes on ice. Then, the binding protein is isolated by the centrifugation procedure below.

All the tubes, except those labeled "TC", are centrifuged at 2,000×g for at least 10 minutes at 4° C. After centrifugation, the tubes are carefully placed into a suitable decantation rack and the supernatant is poured off and discarded. The tubes are kept inverted and placed on absorbent tissues and allowed to drain for 2 minutes. Next, the rims of the inverted tubes are firmly blotted on the tissue to remove any adhering droplets of liquid, and the inside of the tubes are carefully swapped for the same reason. This is done carefully to avoid disturbing the pellet at the bottom of the tube.

To each tube, 200 µl of water is added to resuspend the pellet except the "TC" labeled tubes. The tube is vortexed to mix the solution throughly. Then, 2 ml of scintillation fluid is added to the resuspended pellet. Before measuring the radioactivity of each sample for four minutes in a γ-scintillation counter, the samples are capped and mixed throughly.

Example 30

Purification of VSHK-1 Receptor Polypeptides from Nucleic Acids

The following protocol may be used for membrane preparation for ligand binding assay using COS-7, HEK293, or CHO cells transfected with an expression vector comprising VSHK-1 -encoding sequences. COS-7 cells, for example, are grown in 245 mm×245 mm tissue culture plates and transfected with 30 µg of VSHK-1 receptor encoding plasmid DNA. After two days, the cells are washed with PBS and released from the culture plates by scraping the cells into PBS containing 5 mM EDTA and a protease cocktail. The protease cocktail contains 0.5 mM PMSF, 5 μg/ml aprotinin, 5 μg/ml leupeptin, and 5 μg/ml pepstatin. Cells are harvested by centrifugation 2,500×g for 5 minutes at 4° C., and resuspended in 1 ml of the PBS-protease cocktail. The harvested cells are lysed by rapidly diluting the cells into 20 ml of ice-cold 20 mM HEPES buffer, pH 7.5 containing protease cocktail. The lysed cells are centrifuged at 30,000 g for 30 minutes. The pellet, containing the cell membranes, is separated from the aqueous phase, and then the pellet is resuspended in 50 mM HEPES, pH 7.5, 10 mM $MgCl_2$. The membranes can be frozen at −70° C. for future use.

Deposit Information:

The following materials were deposited with the American Type Culture Collection:

| Name | Deposit Date | Accession No. |
|---|---|---|
| VCT170 in E. coli host DH5a | Oct. 30, 1998 | 98968 |
| VCT181 in E. coli host DH5a | Oct. 30, 1998 | 98967 |

VCT 170 comprises full-length VSHK-1 coding sequence. VCT 181 comprises 5' untranslated region and partial coding sequence.

The above materials have been deposited with the American Type Culture Collection, Manassas, Va., U.S.A., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

Those skilled in the art will recognize, or be able to ascertain, using not more than routine experimentation, many equivalents to the specific embodiments of the invention described herein. Such specific embodiments and equivalents are intended to be encompassed by the following claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

That which is claimed is:

1. An isolated human polypeptide comprising the amino acid sequence of SEQ ID NO: 53 or SEQ ID NO: 55.

2. The isolated human polypeptide of claim 1, comprising the amino acid sequence of SEQ ID NO: 53.

3. The isolated human polypeptide of claim 1, comprising the amino acid sequence of SEQ ID NO: 55.

4. An isolated human polypeptide comprising amino acids 1-342 of SEQ ID NO: 53.

5. An isolated human polypeptide comprising amino acids 1-352 of SEQ ID NO: 55.

6. An isolated polypeptide encoded by a polynucleotide comprising a sequence selected from the group consisting of:
   (a) a polynucleotide sequence comprising SEQ ID NO: 52;
   (b) a polynucleotide sequence comprising nucleotides 1-1724 of SEQ ID NO: 52;
   (c) a polynucleotide sequence comprising nucleotides 698-1724 of SEQ ID NO: 52;
   (d) a polynucleotide sequence comprising SEQ ID NO: 54;
   (e) a polynucleotide sequence comprising nucleotides 1-1754 of SEQ ID NO: 54; and
   (f) a polynucleotide sequence comprising nucleotides 728-1754 of SEQ ID NO: 54.

7. The isolated polypeptide of claim 6, wherein said polynucleotide is overexpressed in an adenocarcinoma of a tissue selected from the group consisting of exocrine pancreas, breast, and colon.

8. The isolated polypeptide of claim 6, wherein said polynucleotide sequence comprises the polynucleotide sequence of SEQ ID NO: 52.

9. The isolated polypeptide of claim 6, wherein said polynucleotide sequence comprises the polynucleotide sequence of SEQ ID NO:54.

10. The isolated polypeptide of claim 6, wherein said polynucleotide sequence comprises nucleotides 1-1724 of SEQ ID NO:52.

11. The isolated polypeptide of claim 6, wherein said polynucleotide sequence comprises nucleotides 1-1754 of SEQ ID NO:54.

12. A composition comprising the polypeptide of any one of claim 1 or 6 and a pharmaceutically acceptable carrier.

13. An in vitro method for producing a polypeptide, the method comprising the steps of:
   a) culturing a recombinant host cell containing an isolated polynucleotide comprising a sequence selected from the group consisting of:

(i) a polynucleotide sequence comprising nucleotides 1-1724 of SEQ ID NO:52;
(ii) a polynucleotide sequence comprising nucleotides 698-1724 of SEQ ID NO:52;
(iii) a polynucleotide sequence comprising nucleotides 1-1754 of SEQ ID NO:54; and
(iv) a polynucleotide sequence comprising nucleotides 728-1754 of SEQ ID NO:54, wherein said culturing is under conditions suitable for the expression of the polypeptide; and b) recovering the polypeptide from the host cell culture.

* * * * *